(12) United States Patent
Edwards et al.

(10) Patent No.: US 11,814,429 B2
(45) Date of Patent: *Nov. 14, 2023

(54) SINGLE DOMAIN ANTIBODIES TO PROGRAMMED CELL DEATH (PD-1)

(71) Applicant: CRESCENDO BIOLOGICS LIMITED, Cambridge (GB)

(72) Inventors: Bryan Edwards, Cambridge (GB); Carolyn Edwards, Cambridge (GB); James Legg, Cambridge (GB); Martyna Lewandowska, Cambridge (GB); Daniela Sydoruk, Cambridge (GB); Colette Johnston, Cambridge (GB); Christine Rossant, Cambridge (GB); Yumin Teng, Cambridge (GB)

(73) Assignee: CRESCENDO BIOLOGICS LIMITED, Cambridge (GB)

( * ) Notice: Subject to any disclaimer, the term of this patent is extended or adjusted under 35 U.S.C. 154(b) by 189 days.

This patent is subject to a terminal disclaimer.

(21) Appl. No.: 16/475,590

(22) PCT Filed: Jan. 8, 2018

(86) PCT No.: PCT/GB2018/050035
§ 371 (c)(1),
(2) Date: Jul. 2, 2019

(87) PCT Pub. No.: WO2018/127709
PCT Pub. Date: Jul. 12, 2018

(65) Prior Publication Data
US 2020/0239570 A1    Jul. 30, 2020

(30) Foreign Application Priority Data

Jan. 6, 2017 (GB) ................................ 1700207
Jan. 6, 2017 (GB) ................................ 1700208
Jan. 6, 2017 (GB) ................................ 1700210

(51) Int. Cl.
| | |
|---|---|
| C07K 16/28 | (2006.01) |
| A61K 39/00 | (2006.01) |
| C07K 16/18 | (2006.01) |
| C12N 15/85 | (2006.01) |
| G01N 33/68 | (2006.01) |
| A61P 35/00 | (2006.01) |
| A01K 67/027 | (2006.01) |

(52) U.S. Cl.
CPC ...... *C07K 16/2818* (2013.01); *A01K 67/0278* (2013.01); *A61P 35/00* (2018.01); *C07K 16/2803* (2013.01); *C12N 15/85* (2013.01); *G01N 33/6803* (2013.01); *A01K 2227/105* (2013.01); *A61K 2039/505* (2013.01); *C07K 16/18* (2013.01); *C07K 2317/24* (2013.01); *C07K 2317/31* (2013.01); *C07K 2317/33* (2013.01); *C07K 2317/35* (2013.01); *C07K 2317/565* (2013.01); *C07K 2317/569*

(2013.01); *C07K 2317/70* (2013.01); *C07K 2317/76* (2013.01); *C07K 2317/92* (2013.01); *C07K 2317/94* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 7,728,114 B2 | 6/2010 | Mach et al. | |
| 7,851,598 B2 * | 12/2010 | Davis ...................... | C07K 7/08 530/387.1 |
| 9,872,852 B2 | 1/2018 | Chupak et al. | |
| 10,202,458 B2 | 2/2019 | Goetsch et al. | |
| 10,323,090 B2 | 6/2019 | Bowman et al. | |
| 10,975,161 B2 | 4/2021 | Balloi et al. | |
| 11,117,964 B2 | 9/2021 | Hsu et al. | |
| 11,236,174 B2 | 2/2022 | McGuinness et al. | |
| 11,312,771 B2 | 4/2022 | Edwards et al. | |
| 11,591,398 B2 | 2/2023 | Hayes et al. | |
| 2010/0122358 A1 | 5/2010 | Brüggemann et al. | |
| 2013/0202623 A1 | 8/2013 | Chomont et al. | |
| 2014/0356908 A1 | 12/2014 | Grosveld et al. | |
| 2015/0201769 A1 | 7/2015 | Freeman et al. | |
| 2015/0210796 A1 | 7/2015 | Kim et al. | |
| 2017/0240644 A1 | 8/2017 | Zhou et al. | |
| 2018/0362666 A1 | 12/2018 | Teng et al. | |
| 2019/0023807 A1 | 1/2019 | Balloi et al. | |
| 2019/0144561 A1 | 5/2019 | McGuinness et al. | |
| 2019/0322749 A1 | 10/2019 | Edwards et al. | |
| 2020/0131274 A1 | 4/2020 | Royle et al. | |
| 2020/0216540 A1 | 7/2020 | Geuijen et al. | |
| 2020/0227870 A1 | 7/2020 | Lollo et al. | |

(Continued)

FOREIGN PATENT DOCUMENTS

| | | |
|---|---|---|
| CN | 103087171 A | 5/2013 |
| CN | 105384825 A | 3/2016 |

(Continued)

OTHER PUBLICATIONS

Tzartos et al., Methods in Molecular Biology, 1996, 66:55-66.*

(Continued)

*Primary Examiner* — Marianne P Allen

(74) *Attorney, Agent, or Firm* — Sterne, Kessler, Goldstein & Fox P.L.L.C.

(57) ABSTRACT

The invention relates to PD-1 binding agents that do not block the interaction of PD-1 with its ligands, and the use of such binding agents in the treatment, prevention and detection of disease.

Figure 1A:
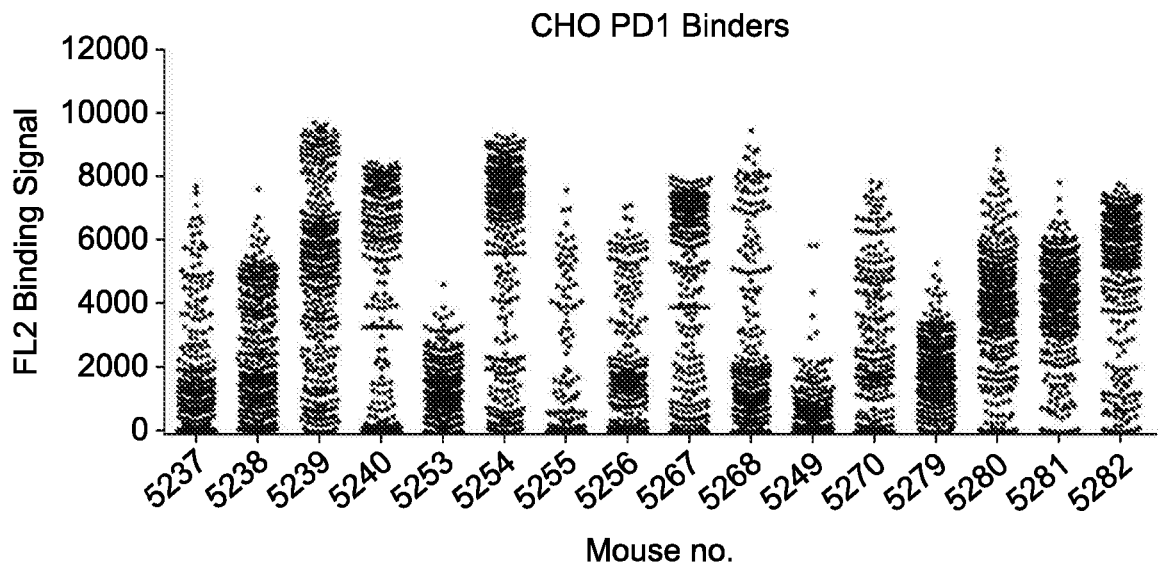

10 Claims, 9 Drawing Sheets
Specification includes a Sequence Listing.

(56) References Cited

U.S. PATENT DOCUMENTS

| | | | |
|---|---|---|---|
| 2020/0239573 A1* | 7/2020 | Hayes | C12N 15/85 |
| 2020/0362047 A1 | 11/2020 | Brucklacher-Waldert et al. | |
| 2020/0362051 A1 | 11/2020 | Brucklacher-Waldert et al. | |
| 2020/0392244 A1 | 12/2020 | Balloi et al. | |
| 2021/0015937 A1 | 1/2021 | Edwards et al. | |
| 2021/0340233 A1 | 11/2021 | Edwards et al. | |
| 2022/0112305 A1 | 4/2022 | McGuinness et al. | |
| 2022/0220215 A1 | 7/2022 | Enever et al. | |
| 2022/0227850 A1 | 7/2022 | Dunlevy et al. | |
| 2022/0306744 A1 | 9/2022 | Edwards et al. | |

FOREIGN PATENT DOCUMENTS

| | | |
|---|---|---|
| EP | 2363404 A2 | 9/2011 |
| EP | 2363404 B1 | 9/2016 |
| EP | 3470426 A1 | 4/2019 |
| WO | WO-2003000737 A2 | 1/2003 |
| WO | WO-2004076618 A2 | 9/2004 |
| WO | WO-2006089230 A2 | 8/2006 |
| WO | WO-2007117264 A2 | 10/2007 |
| WO | WO 2009/117335 | 9/2009 |
| WO | WO-2009114335 A2 | 9/2009 |
| WO | WO 2010/036959 | 4/2010 |
| WO | WO 2011/110621 | 9/2011 |
| WO | WO-2012072731 A2 | 6/2012 |
| WO | WO-2013126712 A1 | 8/2013 |
| WO | WO-2013167883 A1 | 11/2013 |
| WO | WO 2014/141192 | 9/2014 |
| WO | WO-2014198223 A1 | 12/2014 |
| WO | WO-2015034820 A1 | 3/2015 |
| WO | WO-2015112900 A1 | 7/2015 |
| WO | WO-2015116539 A1 | 8/2015 |
| WO | WO-2015142675 A2 | 9/2015 |
| WO | WO-2015143079 A1 | 9/2015 |
| WO | WO-2015200119 A1 | 12/2015 |
| WO | WO 2016/020856 | 2/2016 |
| WO | WO-2016025880 A1 | 2/2016 |
| WO | WO-2016062990 A1 | 4/2016 |
| WO | WO-2016073760 A1 | 5/2016 |
| WO | WO 2016/106159 | 6/2016 |
| WO | WO-2016184882 A1 | 11/2016 |
| WO | WO 2016/197497 | 12/2016 |
| WO | WO-2017019846 A1 | 2/2017 |
| WO | WO-2017020801 A1 | 2/2017 |
| WO | WO-2017060144 A1 | 4/2017 |
| WO | WO-2017087589 A2 | 5/2017 |
| WO | WO-2017122017 A1 | 7/2017 |
| WO | WO-2017122018 A1 | 7/2017 |
| WO | WO-2017122019 A1 | 7/2017 |
| WO | WO-2017123650 A2 | 7/2017 |
| WO | WO-2017191476 A1 | 11/2017 |
| WO | WO-2017201488 A1 | 11/2017 |
| WO | WO-2018104444 A1 | 6/2018 |
| WO | WO-2018127709 A1 | 7/2018 |
| WO | WO-2018127710 A1 | 7/2018 |
| WO | WO-2018127711 A1 | 7/2018 |
| WO | WO-2018224439 A1 | 12/2018 |
| WO | WO-2019012260 A1 | 1/2019 |
| WO | WO-2019092451 A1 | 5/2019 |
| WO | WO-2019092452 A1 | 5/2019 |
| WO | WO-2019158942 A1 | 8/2019 |
| WO | WO-2020099871 A1 | 5/2020 |
| WO | WO-2020229842 A1 | 11/2020 |
| WO | WO-2020229844 A1 | 11/2020 |

OTHER PUBLICATIONS

Goel, Manisha, et al. "Plasticity within the antigen-combining site may manifest as molecular mimicry in the humoral immune response." The Journal of Immunology 173(12): 7358-7367, American Association of Immunology, United States (2004).

Lloyd, C., et al. "Modelling the human immune response: performance of a $10^{11}$ human antibody repertoire against a broad panel of therapeutically relevant antigens." Protein Engineering, Design & Selection 22(3): 159-168, Oxford University Press, England (2009).

Edwards, Bryan M., et al. "The remarkable flexibility of the human antibody repertoire; isolation of over one thousand different antibodies to a single protein, BLyS." Journal of Molecular Biology 334(1): 103-118, Elsevier, Netherlands (2003).

Padlan, Eduardo A. "X-ray crystallography of antibodies." Advances in Protein Chemistry 49: 57-133, Academic Press, United States (1996).

Berglund, Lisa, et al. "The epitope space of the human proteome." Protein Science 17(4): 606-613, John Wiley, United States (2008).

Tzartos, Socrates J. "Epitope mapping by antibody competition." Epitope Mapping Protocols: in Methods in Molecular Biology, 66:55-66, Humana Press, United States (1996).

Chen, Longxin, et al. "Epitope-directed antibody selection by site-specific photocrosslinking," Science Advances 6(14): eaaz7825, 9 pages, American Association for the Advancement of Science, United States (2020).

Paul, "Fv Structure and Diversity in Three Dimensions," Fundamental Immunology, 3rd Edition, pp. 292-295, Oxford Academic, England (1993).

Muyldermans, Serge, "Nanobodies: natural single-domain antibodies." Annual Review Of Biochemistry 82: 17.1-17.23, 23 pages, Annual Reviews, United States (2013).

Zabetakis, Dan, et al. "Contributions of the complementarity determining regions to the thermal stability of a single-domain antibody." PloS one 8(10): e77678, 7 pages, Public Library of Science, United States (2013).

Vincke, Cecile, et al. "General strategy to humanize a camelid single-domain antibody and identification of a universal humanized nanobody scaffold." Journal of Biological Chemistry 284(5): 3273-3284, American Society for Biochemistry and Molecular Biology, United States (2009).

Saerens, Dirk, et al. "Identification of a universal VHH framework to graft non-canonical antigen-binding loops of camel single-domain antibodies." Journal of Molecular Biology 352(3): 597-607, Elsevier, Netherlands (2005).

Colman, P. M. "Effects of amino acid sequence changes on antibody-antigen interactions." Research in Immunology 145(1): 33-36, Elsevier, United States (1994).

Office Action dated Jun. 30, 2021, in U.S. Appl. No. 16/475,597, Hayes. et al., 371(c) Date: Jul. 2, 2019, 23 pages.

Office Action dated Jun. 11, 2021, in U.S. Appl. No. 16/475,599, Edwards, C. et al., 371(c) Date: Jul. 2, 2019, 10 pages.

Caldas, C., et al., "Humanization of the anti-CD18 antibody 6.7: an unexpected effect of a framework residue in binding to antigen," *Molecular Immunology* 39(15):941-952, Elsevier, Netherlands (May 2003).

Du, J., et al., "Molecular basis of recognition of human osteopontin by 23C3, a potential therapeutic antibody for treatment of rheumatoid arthritis," *Journal of Molecular Biology* 382(4):835-842, Elsevier, Netherlands (published online Jul. 2008, published in print Oct. 2008).

Kunik, V., et al., "Structural consensus among antibodies defines the antigen binding site," *PLoS Comput Biol* 8(2):e1002388, 12 pages, Public Library of Science, United States (published online Feb. 2012).

Geng, Yu, et al., "$2^{nd}$ International Conference on Antibodies and Therapeutics." Jul. 11-12, 2016, Philadelphia, USA.

UK Search Report issued in application No. GB 1700207.2, dated Nov. 24, 2017, 4 pages.

Wesolowski et al., 'Single domain antibodies: promising experimental and therapeutic tools . . . ' Medical Microbiology and Immunology, vol. 198 issue 3, 2009, pp. 157-174. Available online at https://www.ncbi.nlm.nih.gov/pmc/articles/PMC2714450/ [Accessed Oct. 27, 2017].

Matthias D'Huyvetter et al: "Radiolabeled nanobodies as theranostic tools in targeted radionu-clide therapy of cancer", Expert Opinion on Drug Delivery, vol. 1-6, 49-8111, No. 12,Jul. 18, 2014 (Jul. 18, 2014), pp. 1939-1954.

Holt J et al: "Domain antibodies: proteins for therapy", Trends in Biotechnology, Elsevier Publications, Cambridge, GB, vol. 21, No. 11, Nov. 1, 2003 (Nov. 1, 2003), pp. 484-490.

(56) References Cited

OTHER PUBLICATIONS

Roe, "Superior Human Single Domain VH Antibody Fragments from a Transgenic Mouse," Biopharmadealmakers, www.crescendobiologics.com p. B23, 2013.
Rudikoff et al., "Single Amino Acid Substitution Altering Antigen-Binding Specificity," Pro-ceedings of the National Academy of Sciences, v. 79, pp. 1979-1983, 1982.
Wong et al., "Structural Requirements for a Specificity Switch and for Maintenance of Affinity Using Mutational Analysis of a Phase-Displayed Anti-Arsonate Antibody of Fab Heavy Chain First Complementarily-Determining Region," The Journal of Immunology, 160, pp. 5990-5997, 1998.
Agata, Y., "Expression of the PD-1 antigen on the surface of stimulated mouse T and B lymphocytes," Int. Immunology, 8(5):765-772, Oxford University Press, United Kingdom (May 1996).
Bennett, F., et al., "Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses," Journal of Immunology 170(2):711-718, The American Association of Immunologists, Inc., United States (2003).
Bruschi, C.V., and Gjuracic, K., "Yeast Artifical Chromosomes" in the Encyclopedia of Life Sciences, pp. 1-6, Macmillan Publishers Ltd., United Kingdom (2002).
Callahan, M.K., and Wolchok, J.D., "At the bedside: CTLA-4- and PD-1-blocking antibodies in cancer immunotherapy," J Leukoc Biol 94(1):41-53, Society for Leukocyte Biology, United States (2013).
Castelli, C., et al., "Lymphocyte activation gene-3 (LAG-3, CD223) in plasmacytoid dendritic cells (pDCs): a molecular target for the restoration of active antitumor immunity," Oncoimmunology, 3(11):e967146, 4 pages, Landes Bioscience, United States (Nov. 2014).
Dietz, L.J., et al., "Volumetric capillary cytometry: a new method for absolute cell enumeration," Cytometry 23(3):177-186, John Wiley & Sons, United States (1996).
Francisco, L., et al., "The PD-1 pathway in tolerance and autoimmunity," Immunol. Rev., 236:219-242, Wiley-Blackwell Publishing Ltd., United Kingdom (Jul. 2010).
GenBank, "Alpha-synuclein," Accession No. P37840.1, accessed at https://www.ncbi.nlm.nih.gov/protein/P37840, accessed on Sep. 24, 2020, 13 pages.
GenBank, "C-type lectin domain family 4 member G isoform 1 [*Homo sapiens*]," Accession No. NP_940894.1, accessed at https://www.ncbi.nlm.nih.gov/protein/NP_940894, accessed on Sep. 24, 2020, 3 pages.
GenBank, "E3 ubiquitin-protein ligase CBL-B isoform b [*Homo sapiens*]," Accession No. NP_001308717.1, accessed at https://www.ncbi.nlm.nih.gov/protein/NP_001308717, accessed on Sep. 24, 2020, 4 pages.
GenBank, "galectin-3 [*Homo Sapiens*]," Accession No. BAA22164.1, accessed at https://www.ncbi.nlm.nih.gov/protein/BAA22164, accessed on Sep. 24, 2020, 2 pages.
GenBank, "*Homo sapiens* lymphocyte activating 3 (LAG3), mRNA," Accession No. NM_002286.6, accessed at https://www.ncbi.nlm.nih.gov/nuccore/NM_002286, accessed on Sep. 24, 2020, 5 pages.
GenBank, "Human hPD-1 (hPD-1) mRNA, complete cds," Accession No. U64863.1, accessed at https://www.ncbi.nlm.nih.gov/nuccore/U64863, accessed on Sep. 24, 2020, 3 pages.
GenBank, "Macaca fascicularis chromosome 11, Macaca_fascicularis_5.0, whole genome shotgun sequence," Accession No. NC_022282.1, accessed at https://www.ncbi.nlm.nih.gov/nuccore/NC_022282, accessed on Sep. 24, 2020, 2 pages.
GenBank, "Macaca mulatta lymphocyte activating 3 (LAG3), mRNA," Accession No. XM_001108923.4, accessed at https://www.ncbi.nlm.nih.gov/nuccore/XM_001108923, accessed on Sep. 24, 2020, 2 pages.
Grosso, J., et al., "LAG-3 regulates CD8+ T cell accumulation and effector function in murine self- and tumor-tolerance systems," J. Clin. Invest., 117(11):3383-92, American Society for Clinical Investigation, United States (Nov. 2007).
He, J., et al., "Development of PD-1/PD-L1 Pathway in Tumor Immune Microenvironment and Treatment for Non-Small Cell Lung Cancer," Scientific Reports 5:13110, 9 pages, Nature Publishing Group, United Kingdom (2015).
Huang, C., et al., "Role of LAG-3 in regulatory T cells," Immunity, 21(4):503-13, Cell Press, United States (Oct. 2004).
Huang, R., et al., "Compensatory upregulation of PD-1, LAG-3, and CTLA-4 limits the efficacy of single-agent checkpoint blockade in metastatic ovarian cancer," Oncoimmunol. 6(1):e1249561, 13 pages, Taylor and Francis Group, United Kingdom (Oct. 2016).
Huard, B., et al., "Characterization of the major histocompatibility complex class II binding site on LAG-3 protein," Proc. Natl. Acad. Sci., 94(11):5744-5749, National Academy of Sciences, United States (May 1997).
Huard, B., et al., "Lymphocyte-activation gene 3/major histocompatibility complex class II interaction modulates the antigenic response of CD4+ T lymphocytes," Eur. J. Immunol., 24(12):3216-21, Wiley-VCH Verlag, Germany (Dec. 1994).
Huard, B., et al., "T cell major histocompatibility complex class II molecules down-regulate CD4+ T cell clone responses following LAG-3 binding," Eur. J. Immunol., 26(5):1180-6, Wiley-VCH Verlag, Germany (May 1996).
International Preliminary Report on Patentability of the International Searching Authority directed to related International Patent Application No. PCT/GB2018/050035, dated Jul. 9, 2019, 11 pages.
International Preliminary Report on Patentability of the International Searching Authority directed to related International Patent Application No. PCT/GB2018/050036, dated Jul. 9, 2019, 11 pages.
International Preliminary Report on Patentability of the International Searching Authority directed to related International Patent Application No. PCT/GB2018/050037, dated Jul. 9, 2019, 12 pages.
International Preliminary Report on Patentability of the International Searching Authority directed to related International Patent Application No. PCT/GB2019/050425, dated Aug. 18, 2020, 7 pages.
International Search Report and Written Opinion of the International Searching Authority directed to related International Patent Application No. PCT/GB2018/050035, dated Apr. 25, 2018, 16 pages.
International Search Report and Written Opinion of the International Searching Authority directed to related International Patent Application No. PCT/GB2018/050036, dated May 3, 2018, 16 pages.
International Search Report and Written Opinion of the International Searching Authority directed to related International Patent Application No. PCT/GB2018/050037, dated Apr. 25, 2018, 18 pages.
International Search Report and Written Opinion of the International Searching Authority directed to related International Patent Application No. PCT/GB2019/050425, dated Apr. 17, 2019; 10 pages.
Ishida, Y., et al., "Induced expression of PD-1, a novel member of the immunoglobulin gene superfamily, upon programmed cell death," EMBO J., 11(11): 3887-3895, Nature Publishing Group on behalf of the European Molecular Biology Organization, United Kingdom (Nov. 1992).
Karwacz, K., et al., "PD-L1 co-stimulation contributes to ligand-induced T cell receptor down-modulation on CD8+ T cells," EMBO Mol. Med., 3(10): 581-592, Nature Publishing Group on behalf of the European Molecular Biology Organization, United Kingdom (Oct. 2011).
Keir, M.E., et al., "Programmed death-1 (PD-1):PD-ligand 1 interactions inhibit TCR-mediated positive selection of thymocytes," J Immunol 175(11):7372-7379, The American Association of Immunologists, Inc., United States (2005).
Kisielow, M., et al., "Expression of lymphocyte activation gene 3 (LAG-3) on B cells is induced by T cells," Eur. J. Immunol., 35(7):2081-8, Wiley-VCH Verlag, Germany (Jul. 2005).
Kouo, T., et al., "Galectin-3 Shapes Antitumor Immune Responses by Suppressing CD8+ T Cells via LAG-3 and Inhibiting Expansion of Plasmacytoid Dendritic Cells," Cancer Immunol. Res., 3(4):412-423, American Association for Cancer Research Inc., United States (Apr. 2015).

(56) References Cited

OTHER PUBLICATIONS

Kraman, M., et al., "A LAG-3/PD-L1 bispecific antibody inhibits tumor growth in two syngeneic colon carcinoma models," Society for Immunotherapy of Cancer (SITC) Conference, Poster 128, 1 page, BioMed Central Ltd., United Kingdom (Nov. 2016).

Lowther, D.E., et al., "PD-1 marks dysfunctional regulatory T cells in malignant gliomas," JCI Insight 1(5):e85935, 15 pages, The American Society for Clinical Investigation, United States (2016).

Main, S., et al., "A potent human anti-eotaxin1 antibody, CAT-213: isolation by phage display and in vitro and in vivo efficacy," J Pharmacol Exp Ther 319(3):1395-1404, American Society for Pharmacology and Experimental Therapeutics, United States (2006).

Marks, J.D., and Bradbury, A., "Chapter 8: Selection of Human Antibodies from Phage Display Libraries" in Methods in Molecular Biology, Antibody Engineering: Methods and Protocols, Lo, B., ed., V. 248, pp. 161-176, Springer Nature, Switzerland (2004).

Marks, J.D., "Chapter 19: Antibody Affinity Maturation by Chain Shuffling" in Methods in Molecular Biology, Antibody Engineering: Methods and Protocols, Lo, B., ed., V. 248, pp. 327-343, Springer Nature, Switzerland (2004).

Matsuzaki, J., et al., "Tumor-infiltrating NY-ESO-1-specific CD8+ T cells are negatively regulated by LAG-3 and PD-1 in human ovarian cancer," Proc. Natl. Acad. Sci., 107(17):7875-7880, National Academy of Science, United States (Apr. 2010).

Miraglia, S., et al., "Homogeneous Cell- and Bead-Based Assays for High Throughput Screening Using Fluorometric Microvolume Assay Technology," J Biomol Screening 4(4):193-204, SAGE Journals, United States (1999).

NCT02061761, "Safety Study of Anti-LAG-3 in Relapsed or Refractory Hematologic Malignancies," ClinicalTrials.gov, posted Feb. 13, 2014, accessed at https://www.clinicaltrials.gov/ct2/show/NCT02061761 on Dec. 14, 2020, 4 pages.

NCT02460224, "Safety and Efficacy of LAG525 Single Agent and in Combination With PDR001 in Patients With Advanced Malignancies," ClinicalTrials.gov, posted Jun. 2, 2015, accessed at https://www.clinicaltrials.gov/ct2/show/NCT02460224 on Dec. 14, 2020, 5 pages.

Nishimura, H., et al., "Autoimmune dilated cardiomyopathy in PD-1 receptor-deficient mice," Science, 291(5502):319-322, American Association for the Advancement of Science, United States (Jan. 2001).

Nishimura, H., et al., "Development of lupus-like autoimmune diseases by disruption of the PD-1 gene encoding an ITIM motif-carrying immunoreceptor," Immunity, 11(2):141-151, Cell Press, United States (Aug. 1999).

Posthumus, W.P., et al., "Analysis and simulation of a neutralizing epitope of transmissible gastroenteritis virus," J Virology 64(7):3304-3309, American Society for Microbiology, United States (1990).

Ren, L., et al., "Silencing of the immunoglobulin heavy chain locus by removal of all eight constant-region genes in a 200-kb region," Genomics, 84(4):686-695, Academic Press Inc., United States (Oct. 2004).

Riley, J., "PD-1 signaling in primary T cells," Immunol Rev., 229(1):114-125, Wiley-Blackwell Publishing Ltd., United Kingdom (May 2009).

Triebel, F., et al., "LAG-3, a novel lymphocyte activation gene closely related to CD4," J. Exp. Med., 171(5):1393-1405, Rockefeller University Press, United States (May 1990).

Tseng, S., et al., "B7-DC, a new dendritic cell molecule with potent costimulatory properties for T cells," J. Exp. Med., 193(7):839-45, Rockefeller University Press, United States (Apr. 2001).

UniParc, "UPI0000119BF0," accessed at https://www.uniprot.org/uniparc/UPI0000119BF0, accessed on Sep. 24, 2020, 1 page.

UniProt, "E3 ubiquitin-protein ligase CBL," Accession No. P22681, accessed at https://www.uniprot.org/uniprot/P22681, accessed on Sep. 24, 2020, 10 pages.

UniProt, "E3 ubiquitin-protein ligase CBL-B," Accession No. Q13191, accessed at https://www.uniprot.org/uniprot/Q13191, accessed on Sep. 24, 2020, 10 pages.

UniProt, "Programmed cell death protein 1," Accession No. Q15116, accessed at https://www.uniprot.org/uniprot/Q15116, accessed on Sep. 24, 2020, 7 pages.

Wang, C., et al., "In vitro characterization of the anti-PD-1 antibody nivolumab, BMS-936558, and in vivo toxicology in non-human primates," Cancer Immunol Res 2(9):846-856, American Association for Cancer Research, United States (2014).

Wang, W., et al., "PD1 blockade reverses the suppression of melanoma antigen-specific CTL by CD4+ CD25$^{Hi}$ regulatory T cells," Int Immunol 21(9):1065-1077, Oxford University Press, United Kingdom (2009).

Workman, C., et al., "Cutting edge: molecular analysis of the negative regulatory function of lymphocyte activation gene-3," J. Immunol., 169(10):5392-5395, American Association of Immunologists, United States (Nov. 2002).

Xu, F., et al., "LSECtin expressed on melanoma cells promotes tumor progression by inhibiting antitumor T-cell responses," Cancer Res., 74(13):3418-3428, American Association for Cancer Research, United States (Jul. 2014).

Yokosuka, T., et al., "Programmed cell death 1 forms negative costimulatory microclusters that directly inhibit T cell receptor signaling by recruiting phosphatase SHP2," J. Exp. Med., 209(6):1201-1217, Rockefeller University Press, United States (Jun. 2012).

Zhang, X., et al., "Structural and functional analysis of the costimulatory receptor programmed death-1," Immunity, 20(3):337-347, Cell Press, United States (Mar. 2004).

Zou, X., et al., "Block in development at the pre-B-II to immature B cell stage in mice without Ig kappa and Ig lambda light chain," J. Immunol., 170(3):1354-61, American Association of Immunologists, United States (Feb. 2003).

Holt, L.J., et al., "Anti-serum albumin domain antibodies for extending the half-lives of short lived drugs," Protein Eng. Des. Sel. 21(5):283-288, Oxford University Press, United Kingdom (2008).

Gordon, S.R., et al., "PD-1 expression by tumour-associated macrophages inhibits phagocytosis and tumour immunity," Nature 545(7655): 495-499, Nature Publishing Group, United Kingdom (May 2017).

Legg, J.W., et al., "CB307: A novel T-cell costimulatory Humabody® VH therapeutic for PSMA-positive tumors," retrieved from: https://www.crescendobiologics.com/wp-content/uploads/2019/08/20190412-CB307-A-novel-T-cell-costimulatory-Humabody%C2%AE-VH-therapeutic-for-PSMA-positive-tumors.pdf, 1 page, (Apr. 2019).

Perez-Ruiz, E., et al., "Anti-CD137 and PD-1/PD-L1 Antibodies En Route toward Clinical Synergy," Clinical Cancer Research 23(18):5326-5328, American Cancer Research, United States (Aug. 2017).

International Search Report and Written Opinion in Application No. PCT/GB2020/051201, E.P.O., Netherlands, dated Oct. 13, 2020, 23 pages.

Office action dated Nov. 15, 2021 in U.S. Appl. No. 16/475,597, inventor Hayes, P., et al., 371(c) date Jul. 2, 2019, 15 pages.

Japanese Office Action dated Dec. 13, 2021, in Japanese Patent Application No. 2019-536937, filed Jan. 18, 2018, 21 pages.

Japanese Office Action dated Dec. 6, 2021, in Japanese Patent Application No. 2019-536936, filed Jan. 8, 2018, 17 pages.

Drabek, D., et al., "Expression Cloning and Production of Human Heavy-Chain-Only Antibodies from Murine Transgenic Plasma Cells," Frontiers in Immunology 7(619): 1-10, Frontiers Media SA, United States (2016).

Trinklein, N., et al., "Abstract LB-090: Sequence-based discovery of fully human anti-CD3 and anti-PDL1 single domain antibodies using novel transgenic rats," Cancer Research 76(14):1-3, American Association of cancer Research, United States (Jul. 2016).

Crescendo Biologics, "Humabody Fragments: Small and Perfectly Formed," BioPharma Dealmakers: B12-B13, retrieved from: https://www.crescendobiologics.com/wp-content/uploads/2016/03/20150309-Crescendo0315.pdf, retrieved on Jan. 20, 2022, dated Mar. 2016, 2 pages.

An, Z., ed., "Section 3.4.3—Glycan Profiles of Recombinant IgG Produced in Rodent Cell Lines," in *Therapeutic Monoclonal Antibodies: From Bench to Clinic*, pp. 73-76, John Wiley & Sons, United States (2009).

Bahara, N.H.H., et al., "Construction of a Semisynthetic Human VH Single-Domain Antibody Library and Selection of Domain Anti-

(56) References Cited

OTHER PUBLICATIONS bodies against a-Crystalline of *Mycobacterium tuberculosis*," Journal of Biomolecular Screening 21(1):35-43, Sage Publications, United States (Jan. 2016).

Bander, N.H., et al., "Targeted Systemic Therapy of Prostate Cancer with a Monoclonal Antibody to Prostate-Specific Membrane Antigen," Seminars in Oncology 30(5):667-676, W.B. Saunders, United States (Oct. 2003).

Barve, A., et al., "Prostate Cancer Relevant Antigens and Enzymes For Targeted Drug Delivery," Journal of Control Release 187:118-132, Elsevier Science Publishers, Netherlands (Aug. 2014).

Bayachou, M., et al., "Catalytic Two-Electron Reductions of $N_2O$ and $N_3^-$ by Myglobin in Surfactant Films," Inorganic Chemistry 39(2):289-293, American Chemical Society, United States (Jan. 2000).

Bruggemann, M., et al., "A Repertoire of Monoclonal Antibodies With Human Heavy Chains From Transgenic Mice," Proc Natl Acad Sci USA 86(17):6709-6713, National Academy of Sciences, United States (Sep. 1989).

Bulliard, Y., et al., "OX40 Engagement Depletes Intratumoral Tregs via Activating FcγRs, Leading to Antitumor Efficacy," Immunology and Cell Biology 92(6):475-480, Nature Publishing Group, United Kingdom (2014).

Chalupny, N.J., et al., "T-cell Activation Molecule 4-1BB Binds to Extracellular Matrix Proteins," Proc Natl Acad Sci USA 89(21):10360-10364, National Academy of Sciences, United States (Nov. 1992).

Chatalic, K.L.S., et al.," A Novel $^{111}$In-Labeled Anti-Prostate-Specific Membrane Antigen Nanobody for Targeted SPECT/CT Imaging of Prostate Cancer," The Journal of Nuclear Medicine 56(7):1094-1099, Society of Nuclear Medicine and Molecular Imaging, United States (Jul. 2015).

Chen, L., et al., "Epitope-Directed Antibody Selection by Site-Specific Photocrosslinking," Science Advances 6(14):eaaz7825, pp. 1-9, American Association for the Advancement of Science, United States (Apr. 2020).

Chothia, C. and Lesk, A. M., "Canonical Structures for the Hypervariable Regions of Immunoglobulins," Journal of Molecular Biology 196(4):901-917, Elsevier, United Kingdom (Aug. 1987).

Cizeau, J., et al., "Abstract 5770: Engineering and Characterization of Anti-PSMA Humabody-deBouganin Fusion Proteins," Cancer Research 78(13_Suppl):5770, AACR Annual Meeting 2018 (Apr. 4-18, 2018), 2 pages, American Association for Cancer Research, United States (Jul. 2018).

ClinicalTrials.gov, "Safety Study of Anti-LAG-3 in CLL, HL and NHL," Identifier NCT02061761, accessed at https://clinicaltrials.gov/archive/NCT02061761/2014_08_28, last accessed on Jan. 13, 2015, 4 pages.

Communication from the Examining Division for EP Application No. EP 17 700 734.1, European Patent Office, Munich, Germany, dated Jul. 24, 2020, 10 pages.

Communication from the Examining Division for EP Application No. EP 17 701 006.3, European Patent Office, Munich, Germany, dated Jun. 5, 2019, 6 pages.

Communication from the Examining Division for EP Application No. EP 17 724 869.7, European Patent Office, Munich, Germany, dated Dec. 4, 2019, 6 pages.

Communication from the Examining Division for EP Application No. EP 19 707 094.9, European Patent Office, Munich, Germany, dated Nov. 22, 2021, 4 pages.

Conrath, E., et al., "Camel Single-Domain Antibodies as Modular Building Units in Bispecific and Bivalent Antibody Constructs," Journal of Biological Chemistry 276(10):7346-7350, American Society for Biochemistry and Molecular Biology, United States (Mar. 2001).

Dubrot, J., et al., "Treatment With Anti-CD137 mAbs Causes Intense Accumulations of Liver T Cells Without Selective Antitumor Immunotherapeutic Effects in This Organ," Cancer Immunology, Immunotherapy 59(8):1223-1233, Springer Verlag, Germany (2010).

Elsadek, B. and Kratz, F., "Impact of Albumin on Drug Delivery—New Applications on the Horizon," Journal of Controlled Release 157(1):4-28, Elsevier Science Publishers, Netherlands (Jan. 2012).

Evazalipour, M., et al., "Camel Heavy Chain Antibodies against Prostate-Specific Membrane Antigen," Hybridoma (Larchmt) 31(6):424-429, Mary Ann Liebert Inc., United States (Dec. 2012).

Evazalipour, M., et al., "Generation and Characterization of Nanobodies Targeting PSMA For Molecular Imaging of Prostate Cancer," Contrast Media & Molecular Imaging 9(3):211-220, Hindawi in collaboration with John Wiley & Sons, Inc, United Kingdom (May-Jun. 2014).

Fan, G., et al., "Bispecific Antibodies and their Applications," Journal of Hematology & Oncology 8, Article No. 130, 14 pages, BioMed Central: Part of Springer Nature, United Kingdom (Dec. 2015).

Fan, X., et al., "Ultrasonic Nanobubbles Carrying Anti-PSMA Nanobody: Construction and Application In Prostate Cancer-Targeted Imaging," PLoS One 10(6) :e0127419, 13 pages, Public Library of Science, United States (Jun. 2015).

Fisher, T.S., et al., "Targeting of 4-1BB by monoclonal antibody PF-05082566 enhances T-cell function and promotes anti-tumor activity," Cancer Immunology Immunotherapy, 61: 1721-1733, Springer Nature Limited, Germany (2012).

Gauttier, V., et al., "Agonistic anti-CD137 Antibody Treatment Leads to Antitumor Response in Mice with Liver Cancer," International Journal of Cancer 135(2):2857-2867, Wiley-Liss Inc., United States (Dec. 2014).

Genbank, "*Homo sapiens* TNF receptor superfamily member 9 (TNFRSF9), mRNA," NCBI Reference Sequence: NM_001561.6, https://www.ncbi.nlm.nih.gov/nuccore/NM001561, last accessed on May 19, 2020, 5 pages.

GenBank, "tumor necrosis factor receptor superfamily member 9 precursor [*Homo sapiens*]," Accession No. NP_001552.2, 4 pages, accessed on https://www.ncbi.nlm.nih.gov/protein/NP001552, Oct. 7, 2016.

Guo, Y., et al., "Chimeric Antigen Receptor-Modified T Cells for Solid Tumors: Challenges and Prospects," Journal of Immunology Research 2016:3850839, 11 pages, Hindawi Publishing Corporation, Egypt (2016).

Henry, K. A., et al., "Identification of Cross-reactive Single-domain Antibodies Against Serum Albumin Using Next-generation DNA Sequencing," Protein Engineering, Design & Selection 28(10):379-383, Oxford University Press, United Kingdom (Oct. 2015).

Holliger, P, and Hudson, P.J., "Engineered Antibody Fragments and the Rise of Single Domains," Nature Biotechnology 23(9):1126-1136, Nature America Publishing, United States (2005).

Homayouni, V., et al., "Preparation and characterization of novel nanobody against T-cell immunoglobulin and mucin-3 (TIM-3)," Iranian Journal of Basic Medical Sciences 19(11):1201-1208, Mashhad University of Medical Sciences, Iran (2016).

Houot, R., et al., "Therapeutic Effect of CD137 Immunomodulation in Lymphoma and Its Enhancement by Treg Depletion," Blood 114(16):3431-3438, American Society of Hematology, United States (2009).

International Preliminary Report on Patentability for International Application No. PCT/GB2017/050074, The International Bureau of WIPO, Switzerland, dated Jul. 17, 2018, 11 pages.

International Preliminary Report on Patentability for International Application No. PCT/GB2017/050075, The International Bureau of WIPO, Switzerland, dated Jul. 17, 2018, 7 pages.

International Preliminary Report on Patentability for International Application No. PCT/GB2017/051272, The International Bureau of WIPO, Switzerland, dated Nov. 6, 2018, 11 pages.

International Preliminary Report on Patentability for International Application No. PCT/GB2018/051941, The International Bureau of WIPO, Switzerland, dated Jan. 14, 2020, 6 pages.

International Preliminary Report on Patentability for International Application No. PCT/GB2018/053279, The International Bureau of WIPO, Switzerland, dated May 19, 2020, 11 pages.

International Preliminary Report on Patentability for International Application No. PCT/GB2018/053280, The International Bureau of WIPO, Switzerland, dated May 19, 2020, 12 pages.

(56) References Cited

OTHER PUBLICATIONS

International Preliminary Report on Patentability for International Application No. PCT/GB2019/053220, The International Bureau of WIPO, Switzerland, dated May 18, 2021, 11 pages.

International Preliminary Report on Patentability for International Application No. PCT/GB2020/051199, The International Bureau of WIPO, Switzerland, dated Nov. 16, 2021, 8 pages.

International Preliminary Report on Patentability for International Application No. PCT/GB2020/051201, The International Bureau of WIPO, Switzerland, dated Nov. 16, 2021, 17 pages.

International Search Report and Written Opinion for International Application No. PCT/GB2017/050074, European Patent Office, Netherlands, dated May 30, 2017, 17 pages.

International Search Report and Written Opinion for International Application No. PCT/GB2017/050075, European Patent Office, Netherlands, dated Mar. 23, 2017, 12 pages.

International Search Report and Written Opinion for International Application No. PCT/GB2017/051272, European Patent Office, Netherlands, dated Sep. 11, 2017, 17 pages.

International Search Report and Written Opinion for International Application No. PCT/GB2018/051941, European Patent Office, Netherlands, dated Sep. 14, 2018, 11 pages.

International Search Report and Written Opinion for International Application No. PCT/GB2018/053279, European Patent Office, Netherlands, dated Feb. 1, 2019, 15 pages.

International Search Report and Written Opinion for International Application No. PCT/GB2018/053280, European Patent Office, Netherlands, dated Feb. 11, 2019, 17 pages.

International Search Report and Written Opinion for International Application No. PCT/GB2019/050425, European Patent Office, Netherlands, dated Apr. 17, 2019, 10 pages.

International Search Report and Written Opinion for International Application No. PCT/GB2019/053220, European Patent Office, Netherlands, dated Apr. 3, 2020, 17 pages.

International Search Report and Written Opinion for International Application No. PCT/GB2020/051199, European Patent Office, Netherlands, dated Aug. 20, 2020, 13 pages.

Jamnani, F.R., et al., "T Cells Expressing VHH-Directed Oligoclonal Chimeric Her2 Antigen Receptors: Towards Tumor-Directed Oligoclonal T Cell Therapy," Biochimica et Biophysica Acta 1840(1):378-386, Elsevier Pub. Co, Netherlands (Jan. 2014).

Kabat, E.A. and Wu, T.T., "Attempts to Locate Complementarity-Determining Residues in the Variable Positions of Light and Heavy Chains," Annals of the New York Academy of Sciences 190:382-393, Blackwell, United States (1971).

Kabat, E.A., et al., "Sequences of proteins of immunological interest," 5th Edition, NIH publication No. 91-3242, 1-1137, U.S. Department of Public Health and Human Services, National Institutes of Health, United States (1991).

Kunik, V., et al., "The Indistinguishability of Epitopes From Protein Surface is Explained By the Distinct Binding Preferences of Each of the Six Antigen-Binding Loops," Protein Engineering, Design and Selection 26(10):599-609, Oxford University Press, United Kingdom (Oct. 2013).

Kwon, B.S., and Weissman, S.M., "cDNA Sequences of Two Inducible T-Cell Genes," Proc Natl Acad Sci USA 86(6):1963-1967, National Academy of Science, United States (Mar. 1989).

Lefranc, M.P., et al., "IMGT Unique Numbering for Immunoglobulin and T Cell Receptor Constant Domains and Ig Superfamily C-like Domains," Developmental and Comparative Immunology 29(3):185-203, Elsevier Science, United States (2005).

Madireddi, S., et al., "Galectin-9 Controls the Therapeutic Activity of 4-1BB-Targeting Antibodies," The Journal of Experimental Medicine 211(7): 1433-1448, The Rockefeller University Press, United States (Jun. 2014).

McGuinness, B., "Humabody fragments: Small and perfectly formed," Biopharmadealmakers, accessed at www.crescendobiologics.com, pp. B12-B13, 2 pages (2013).

McGuinness, B., et al., "Abstract 5766: Multifunctional biologies for targeted T-cell therapy based on in vivo matured fully human VH domains," Cancer Research 78(13_Suppl):5766, AACR Annual Meeting 2018 (Apr. 4-18, 2018), 2 pages, American Association for Cancer Research, United States (Jul. 2018).

Muyldermans, S., et al., "Nanobodies: Natural Single-domain Antibodies," Annual Review of Biochemistry, 82:17.1-17.23, Annual Reviews, United States (2013).

Muyldermans, S., et al., "Recognition of Antigens by Single-Domain Antibody Fragments: the Superfluous Luxury of Paired Domains," Trends in Biochemical Sciences 26(4):230-235, Elsevier Trends Journals, United Kingdom (Apr. 2001).

Muyldermans, S., "Single Domain Camel Antibodies: Current Status," Reviews in Molecular Biotechnology 74(4):277-302, Elsevier Science Publishers, Netherlands (2001).

Office Action for Japanese Patent Application No. 2018-537519, dated Feb. 5, 2021, Japan Patent Office, Japan, 9 pages.

Office Action for Japanese Patent Application No. 2018-537533, dated Feb. 16, 2021, Japan Patent Office, Japan, 6 pages.

Office Action dated Apr. 22, 2022, in U.S. Appl. No. 16/475,597, Hayes. et al., 371(c) Date: Jul. 2, 2019, 26 pages.

Office Action dated Aug. 11, 2020, in U.S. Appl. No. 16/069,495, Balloi, E., et al., filed Jul. 11, 2018, 18 pages.

Zare, H., et al., "Production of Nanobodies against Prostate-Specific Membrane Antigen (PSMA) Recognizing LnCaP Cells," Int J Bioi Markers 29(2):e169-e179, SAGE Publications, United States (Jun. 2014).

Office Action dated Nov. 15, 2021, in U.S. Appl. No. 16/475,597, Hayes. et al., 371(c) Date: Jul. 2, 2019, 15 pages.

Zapata, J.M., et al., "CD137 (4-1BB) Signalosome: Complexity Is a Matter of TRAFs," Frontiers in Immunology 9:2618, 12 pages, Frontiers Research Foundation, Switzerland (Nov. 2018).

Patel, T. P., et al., "Different Culture Methods Lead to Differences in Glycosylation of a Murine IgG Monoclonal Antibody," Biochemical Journal 285(Pt 3):839-845, Portland Press on behalf of the Biochemical Society, United Kingdom (1992).

Roovers, R.C., et al., "A Biparatopic Anti-EGFR Nanobody Efficiently Inhibits Solid Tumour Growth," International Journal of Cancer 129(8):2013-2024, Wiley-Liss Inc., United States (Oct. 2011).

Sanchez-Paulete, A.R., et al., "Deciphering CD137 (4-1BB) Signaling in T-cell Costimulation for Translation Into Successful Cancer Immunotherapy," European Journal of Immunology 46(3):513-522, Wiley-VCH Verlag GmbH & Co. KGaA, Germany (Mar. 2016).

Segal, N.H., et al., "Results from an Integrated Safety Analysis of Urelumab, an Agonist Anti-CD137 Monoclonal Antibody," Clinical Cancer Research 23(8): 1929-1936, American Association for Cancer Research, United States (Oct. 2016).

Strohl, W.R., "Fusion Proteins for Half-Life Extension of Biologies as a Strategy to Make Biobetters," BioDrugs 29(4):215-239, Springer International, New Zealand (Jul. 2015).

UniProtKB, "Glutamate carboxypeptidase 2," UniProtKB-Q04609 (FOLH1_HUMAN), https://www.uniprot.org/uniprot/Q04609, last accessed on May 19, 2020, 24 pages.

UniProtKB, "Tumor necrosis factor receptor superfamily member 9," UniProtKB-Q07011 (TNR9 Human), https://www.uniprot.org/uniprot/Q07011, last accessed on May 19, 2020, 12 pages.

Vinay, D. S., and Kwon, B. S., "Therapeutic Potential of Anti-CD137 (4-1BB) Monoclonal Antibodies," Expert Opinion on Therapeutic Targets 20(3):361-373, Informa Healthcare, United Kingdom (2016).

Vinay, D.S., and Kwon, B.S., "4-1BB (CD137), an Inducible Costimulatory Receptor, as a Specific Target For Cancer Therapy," BMB Reports 47(3):122-129, The Korean Society for Biochemistry and Molecular Biology, South Korea (Mar. 2014).

Vinay, D.S and Kwon, B.S., "Immunotherapy of cancer with 4-1BB," Molecular Cancer Therapeutics 11(5): 1062-1070, American Association for Cancer Research, United States (May 2012).

Vinay, D.S., and Kwon, B.S., "Role of 4-1BB in Immune Responses," Seminars in Immunology 10(6):481-489, Article No. si980157, Academic Press, United Kingdom (Dec. 1998).

Vincke, C., and Muyldermans, S., "Introduction to Heavy Chain Antibodies and Derived Nanobodies," Methods in Molecular Biology 911:15-26, Springer Science+Business Media, Germany (2012).

(56) References Cited

OTHER PUBLICATIONS

Viuff, D., et al., "Generation of a Double Transgenic Humanized Neonatal Fc Receptor (FcRn)/Albumin Mouse to Study the Pharmacokinetics of Albumin-Linked Drugs," Journal of Controlled Release 223:22-30, Elsevier Science Publishers, Netherlands (Feb. 2016).

Ward, E. S., et al., "Binding Activities of a Repertoire of Single Immunoglobulin Variable Domains Secreted from *Escherichia coli*," Nature 341(6242):544-546, Nature Publishing Group, United Kingdom (Oct. 1989).

Co-pending U.S. Appl. No. 17/610,328, inventors Dunlevy; G. et al., filed Nov. 10, 2021 (Not yet Published).

Co-pending U.S. Appl. No. 17/610,330, inventors Enever; C. et al., filed Nov. 10, 2021 (Not yet Published).

Co-pending U.S. Appl. No. 17/706,839, inventors Edwards; C. et al., filed Mar. 29, 2022 (Not yet Published).

Chen, C., et al., "Enhancement and destruction of antibody function by somatic mutation: unequal occurrence is controlled by V gene combinatorial associations," EMBO Journal 14(12):2784-2794, Oxford University Press, England (Jun. 1995).

Reeck, G. R., et al., "'Homology' in Proteins and Nucleic Acids: A Terminology Muddle and a Way out of It," Cell 50:667 (1 page), Cell Press, United States (Aug. 1987).

Steven, J., et al., "In Vitro Maturation of a Humanized Shark VNAR Domain to Improve Its Biophysical Properties to Facilitate Clinical Development," Front Immunol 8:1361(15 pages), Frontiers Media S.A., Switzerland (Oct. 2017).

Translation of Japanese Office Action dated Jul. 4, 2022, in Japanese Patent Application No. 2019-536936, filed Jan. 8, 2018, 5 pages.

Yan, J., et al., "Construction of a synthetic phage-displayed Nanobody library with CDR3 regions randomized by trinucleotide cassettes for diagnostic applications," J Transl Med 12:343, 12 pages, BioMed Central Ltd., United Kingdom (Dec. 2014).

Zak, K.M., et al., "Structural basis for small molecule targeting of the programmed death ligand 1 (PD-L1)," Oncotarget 7 (21):30323-30335, Impact Journals, United States (Apr. 2016).

Office Action dated Oct. 19, 2022, in U.S. Appl. No. 16/969,905, inventor Edwards, et al., 371(c) filing date Aug. 13, 2020, 17 pages.

Abdiche, Y.N., et al, "Assessing Kinetic and Epitopic Diversity Across Orthogonal Monoclonal Antibody Generation Platforms," mAbs, 8(2):264-277, Taylor & Francis Group, United States (Feb. 2016).

Boyd, S.D., et al, "Deep Sequencing and Human Antibody Repertoire Analysis," Current Opinion in Immunology 40:103-109, Elsevier, Netherlands (Apr. 2016).

Casset, F., et al., "A Peptide Mimetic of an Anti-CD4 Monoclonal Antibody By Rational Design," Biochemical and Biophysical Research Communications 307(1):198-205, Academic Press, United States (Jul. 2003).

Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, United Kingdom (Nov. 1999).

Conroy, P.J., et al, "Antibodies: From Novel Repertoires to Defining and Refining the Structure Of Biologically Important Targets," Methods 116:12-22, Elsevier, Netherlands (Jan. 2017).

Damschroder, M.M., et al, "Analysis of Human and Primate CD2 Molecules by Protein sequence and Epitope mapping with Anti-Human CD2 Antibodies," Molecular Immunology 41:985-1000, Elsevier, Netherlands (Jun. 2004).

De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).

Ferrara, F., et al, "Recombinant Renewable Polyclonal Antibodies," mAbs 7(1):32-41, Taylor & Francis Group, United States (Jan. 2015).

Kanyavuz, A., et al, "Breaking the Law: Unconventional Strategies for Antibody Diversification," Immunology 19:355-368, Nature Reviews, United Kingdom (Jun. 2019).

Khan, L., et al, "Cross-neutralizing Anti-HIV-1 Human Single Chain Variable Fragments (scFvs) Against CD4 Binding Site and N332 Glycan Identified From a Recombinant Phage Library," Scientific Reports 7:45163, 12 pages, Nature Publishing Group, United Kingdom (Mar. 2017).

Konitzer, J.D., et al, "Generation of a Highly Diverse Panel of Antagonistic Chicken Monoclonal Antibodies Against the GIP Receptor," mAbs 9(3):536-549, Taylor & Francis Group, United States (Feb. 2017).

Lamminmäki, U. and Kankare, J.A., "Crystal Structure of a Recombinant Anti-estradiol Fab Fragment in Complex With 17beta-estradiol," The Journal of Biological Chemistry 276(39):36687-36694, Elsevier Inc., United States (Sep. 2001).

Lee, J., et al, "Molecular-level Analysis of the Serum Antibody Repertoire In Young Adults Before and After Seasonal Influenza Vaccination," Nature Medicine 22(12):1456-1464, with Supplemental Methods and Data, Nature Publishing Group, United Kingdom (Nov. 2016).

MacCallum, R. M., et al., "Antibody-antigen Interactions: Contact Analysis and Binding Site Topography," Journal of Molecular Biology 262(5):732-745, Academic Press, United Kingdom (Oct. 1996).

Office Action dated Apr. 10, 2023, in U.S. Appl. No. 16/099,099, inventors McGuinness, B., et al., 371(c) date: Nov. 5, 2018, 10 pages.

Office Action dated Apr. 25, 2023, in U.S. Appl. No. 16/763,063, inventors Brucklacher-Waldert, V., et al., 371(c) date: May 11, 2020, 11 pages.

Padlan, E. A., et al., "Structure of an Antibody-antigen Complex: Crystal Structure of the HyHEL-10 Fab-lysozyme Complex," Proceedings of the National Academy of Sciences of the United States of America 86(15):5938-5942, National Academy of Sciences, United States (Aug. 1989).

Parola, C., et al, "Integrating High-throughput Screening and Sequencing for Monoclonal Antibody Discovery and Engineering," Immunology 153:31-41, John Wiley & Sons Ltd., United States (Sep. 2017).

Sheehan, J., et al, "Phage and Yeast Display," Microbiology Spectrum 3(1):1-17, American Society for Microbiology Press, United States (Feb. 2015).

Vajdos, F. F., et al., "Comprehensive Functional Maps of The Antigen-binding Site of an Anti-ErbB2 Antibody Obtained with Shotgun Scanning Mutagenesis," Journal of Molecular Biology 320(2):415-428, Academic Press, United Kingdom (Jul. 2002).

Van Regenmortel, M.H. V., "Development of a Preventive HIV Vaccine Requires Solving Inverse Problems Which Is Unattainable by Rational Vaccine Design," Hypothesis and Theory 8: Article 2009, 11 pages, Frontiers in Immunology, United Kingdom (Jan. 2018).

Wu, H., et al., "Humanization of a Murine Monoclonal Antibody by Simultaneous Optimization of Framework and CDR Residues," Journal of Molecular Biology 294(1):151-162, Elsevier, United Kingdom (Nov. 1999).

Zhou, T., et al, "Structural Repertoire of HIV-1-Neutralizing Antibodies Targeting the CD4 Supersite in 14 Donors," Cell 161:1280-1292, Elsevier, Netherlands (Jun. 2015).

Office action dated Jan. 24, 2023, in U.S. Appl. No. 16/763,059, inventors Brucklacher-Waldert, V., et al., 371(c) date: May 11, 2020, 25 pages.

Office action dated Apr. 11, 2023, in U.S. Appl. No. 16/969,905, inventors Edwards, C., et al., 371(c) date: Aug. 13, 2020, 9 pages.

Co-Pending U.S. Appl. No. 18/167,318, filed Feb. 10, 2023, inventor Hayes, P. et al. (Unpublished).

* cited by examiner

```
Human:  NGRDFHMSVVRARR
        |  ||||      ||
Mouse:  NRHDFHMNILDTRR
```

SINGLE DOMAIN ANTIBODIES TO PROGRAMMED CELL DEATH (PD-1)

CROSS REFERENCE TO RELATED APPLICATIONS

This application is a national phase entry of International Application No. PCT/GB2018/050035, filed Jan. 8, 2018, which claims foreign priority to GB Application Nos. 1700207.2, filed Jan. 6, 2017, 1700208.0, filed Jan. 6, 2017, and 1700210.6, filed Jan. 6, 2017, each of which is hereby incorporated by reference herein in its entirety.

REFERENCE TO A SEQUENCE LISTING SUBMITTED ELECTRONICALLY VIA EFS-WEB

The content of the electronically submitted sequence listing in ASCII text file format (Name: U.S. Ser. No. 16/475,590.txt; Size: 273,051 bytes; and Date of Creation: Oct. 7, 2019) is herein incorporated by reference in its entirety.

FIELD OF THE INVENTION

The invention relates to PD-1 binding agents, in particular PD-1 binding $V_H$ single domain antibodies (sdAb), and the use of such binding agents in the treatment, prevention and detection of disease.

INTRODUCTION

Antibody-based therapeutics have emerged as important components of therapies for an increasing number of human diseases in such fields as oncology, inflammatory and infectious diseases. Indeed, antibodies are one of the best-selling classes of drugs today; five of the top ten best selling drugs are antibodies.

The Programmed Death 1 (PD-1) protein is encoded by the PDCD1 gene and expressed as a 55 kDa type I transmembrane protein (Agata 1996 Int Immunol 8(5):765-72). PD-1 is an immunoglobulin superfamily member (Ishida 1992 EMBO 11(11):3887-95) and it is an inhibitory member of the extended CD28/CTLA-4 family of T cell regulators. Other members of this family include CD28, CTLA-4, ICOS and BTLA. PD-1 exists as a monomer, lacking the unpaired cysteine residue characteristic of other CD28 family members (Zhang 2004 Immunity 20:337-47). Its cytoplasmic domain contains an immunoreceptor tyrosine-based inhibitory motif (ITIM) and an immunoreceptor tyrosine-based switch motif (ITSM) that are phosphorylated during signal transduction (Riley 2009 Immunol Rev 229(1):114-25).

PD-1 is expressed on B cells, T cells, and monocytes (Agata 1996). The role of PD-1 in maintaining immunologic self-tolerance was demonstrated in PDCD1−/− mice, which develop autoimmune disorders (Nishimura 1999 Immunity 11:141-51, Nishimura 2001 Science 291(5502):319-22). The PD-1 pathway therefore regulates antigen responses, balancing autoimmunity and tolerance.

There are two ligands for PD-1 that mediate its regulatory function. PD-L1 (B7-H1) is normally expressed on dendritic cells, macrophages, resting B cells, bone marrow-derived mast cells and T cells as well as non-hematopoietic cell lineages (reviewed in Francisco 2010 Immunol Rev 236: 219-42). PD-L2 (B7-DC) is largely expressed on dendritic cells and macrophages (Tseng 2001 J Exp Med 193(7):839-45). Ligand expression is influenced by local mediators and can be upregulated by inflammatory cytokines.

PD-1 is known as an immunoinhibitory protein that negatively regulates TCR signals. The interaction between PD-1 and PD-L1 can act as an immune checkpoint, which can lead to, e.g., a decrease in tumour infiltrating lymphocytes, a decrease in T-cell receptor mediated proliferation, and/or immune evasion by cancerous cells. Immune suppression can be reversed by inhibiting the local interaction of PD-1 with PD-L1 or PD-L2; the effect is additive when the interaction of PD-1 with both PD-L1 and PD-L2 is blockedl.

As T cells become activated and co-stimulated by antigen-presenting cells (APCs), T cell expression of PD-1 is induced. PD-1 engagement with ligand on the APC cross-links PD-1 and clusters it into the T cell receptor (TCR) complex within the immunological synapse (Yokosuka 2012 J Exp Med 209(9):1201-17). Within the T cell cytoplasm, PD-1 signalling domains ITIM and ITSM are phosphorylated. This induces Src-homology-2 domain-containing tyrosine phosphatase (SHP1/2) that attenuates various components of the T cell receptor (TCR) signalling. T cell activation is dampened, which leads to a reduction in cytokine response, proliferation and cytolytic activity. This downregulation of T cell function serves to prevent over-stimulation, tolerising cells against weakly immunogenic self-antigen.

The PD-1 pathway can be exploited in cancer or infection, whereby tumours or viruses can evade effective immune recognition and T cells demonstrate an 'exhausted' phenotype. PD-L1 has also been shown to be expressed in many tumour types including urothelial, ovarian, breast, cervical, colon, pancreatic, gastric, melanoma, glioblastoma and non-small cell lung carcinoma (reviewed in Callahan 2014 J Leukoc Biol 94(1):41-53). The cytokines produced by cancer stromal cells can further upregulate PD-L1 in the tumour microenvironment (He 2015 Nature Scientific Reports 5:13110). As a result, tumour-specific T cells become unresponsive through PD-1 signalling and therefore fail to eliminate their target. T regulatory cells (T regs) have also been shown to express high levels of PD-1 and they suppress the anti-tumour response further (Lowther 2016 JCI Insight 1(5):85935).

Disruption of the PD-1:PD-L1 interaction enhances T cell activity. An anti-PD-1 monoclonal antibody demonstrates blockade of the interaction between PD-1 and its ligands (Wang 2014 Cancer Immunol Res 2(9):846-56). T cell function in-vitro can be enhanced by PD-1 blockade, as demonstrated by improved proliferation and cytokine responses in mixed lymphocyte reactions of T cells and dendritic cells. cytotoxic lymphocytes (CTLs) derived from melanoma patients has also been shown to be enhanced by PD-1 blockade in vitro using the antibody OPDIVO (nivolumab), and can become resistant to Treg suppression (Wang 2009 Int Immunol 21(9):1065-1077). This antibody has been tested in clinical dose escalation studies in melanoma, non-small cell lung carcinoma (NSCLC), renal cell cancer (RCC) and others. It shows improved overall survival rates compared to chemotherapy in NSCLC patients. Another PD-1 blocking antibody, KEYTRUDA® (pembrolizumab), demonstrates responses in NSCLC patients refractory to CTLA-4 blockade. OPDIVO® and KEYTRUDA® both functionally block the interaction of human PD-1 with its ligands.

It is possible to induce PD-1 signalling by cross-linking it on the membrane with a combination of anti-PD-1 plus anti-CD3 antibodies (Bennett 2003 J Immunol 170:711-18, Keir 2005 J Immunol 175:7372-7379). This function could be detrimental during an anti-tumour response because T cell activity would be suppressed. If suppression of T cell responses were desired, agonistic anti-PD-1 antibodies or those with effector functions could be used to treat immune-related diseases such as rheumatoid arthritis.

The aim of the present invention is to address the need of alternative antibody-based treatments for use in the treatment of disease, in particular in the treatment of cancer.

SUMMARY OF THE INVENTION

The invention relates to an isolated human variable single domain antibody or an isolated human heavy chain only antibody that binds to human PD-1 and related methods for treating disease.

The inventors have surprisingly identified human variable single domain antibodies generated in vivo in transgenic mice that bind to human PD-1, but do not block the functional interaction between human PD-1 and its ligands.

Thus, the anti-PD-1 $V_H$ single domain antibodies of the invention bind an epitope that is distant from the part of the PD-1 protein that interacts with its ligands PD-L1 and PD-L2 and that is therefore outside the region of binding of known therapeutics targeting PD-1. As further described below, this renders a human variable single domain antibodies of the invention particularly useful in anchoring binding molecules to human PD-1 when used in combination with other binding domains. For example, the human variable single domain antibodies can be used in combination therapies with antibodies or antibody fragments that bind to human PD-1 and block the interaction of PD-1 with its ligands PD-L1 and PDL-2. Furthermore, the human variable single domain antibodies can also be used in combination therapies with antibodies or antibody fragments that target other immune checkpoint inhibitors.

The small size of the $V_H$ domains makes it possible to format the $V_H$ domain in a multivalent format, for example by linking a $V_H$ single domain antibody as described herein to another binding agent, such as another $V_H$ single domain antibody. The second binding agent, such as another $V_H$ single domain antibody, may bind to another epitope on PD-1, and may block the functional interaction PD-1 and PD-L1 and/or PD-L2. Alternatively, the second binding agent, such as another $V_H$ single domain antibody, may bind another epitope on PD-1 and not block functional ligand interaction, may cross-link or cluster multiple PD-1 monomers to effect PD-1 signalling and functions.

As demonstrated herein, providing an isolated single domain antibody that binds to human PD-1 but does not block the interaction of human PD-1 with human PD-L1 and/or PD-L2 together with a inhibitor single domain antibody blocks the interaction of human PD-1 with human PD-L1 and/or PD-L2 in a bivalent format is advantageous. In this format, the inhibitory effect is increased by 10 to 25 fold compared to the blocker in monovalent format.

In one aspect, the invention relates to an isolated single domain antibody that binds to human PD-1 but does not block the interaction of human PD-1 with human PD-L1 and/or PD-L2.

In one aspect, the invention relates to an isolated $V_H$ single domain antibody that binds to an epitope comprising one or more residue selected from $R^{104}$, $D^{105}$, $F^{106}$, $H^{107}$, $M^{108}$, $S^{109}$ and $V^{110}$ of human PD-1.

In one aspect, the invention relates to an isolated single $V_H$ domain antibody that binds to human PD-1 comprising a CDR3 sequence as shown Table 1 or 2 below or a sequence with at least 60%, 70%, 80%, 90%, 95% or more sequence identity thereto.

In one aspect, the invention relates to an isolated single domain antibody comprising a sequence selected from SEQ ID Nos. 4, 8, 12, 16, 20, 24, 28, 32, 36, 40, 44, 48, 52, 56, 60, 64, 68, 72, 76, 80, 104, 108, 112, 116, 120, 124, 128, 132, 136, 140, 144, 148, 152, 156, 160, 164, 168, 172, 176, 180, 184, 188, 192, 196, 200, 204, 208, 212, 216, 220, 254, 258, 262, 266, 270, 274, 278, 282, 286, 290, 294, 298, 302, 306, 310, 314, 318, 322, 326, 330, 334, 338, 342, 346, 350, 354, 358, 362, 366, 370, 374, 378, 382, 386, 390, 394, 398, 402, 406, 410, 414, 418, 422, 426, 430, 434, 438, 442, 446, 450, 454, 458 or 462 or a sequence with at least 60%, 70%, 80% or 90% homology thereto.

In preferred embodiments, the single domain is a human heavy chain variable domain. Human heavy chain variable domains are commonly designated $V_H$.

In one embodiment, the isolated single domain antibody wherein said single domain antibody is conjugated to a toxin, enzyme, radioisotope, half-life extending moiety, label, therapeutic molecule or other chemical moiety.

In another aspect, the invention relates to an isolated single domain antibody that does not compete with an antibody that blocks the functional interaction of PD-1 with PD-L1 and/or the interaction of PD-1 with PD-L2.

In another aspect, the invention relates to a binding agent that binds to essentially the same epitope as the single domain antibody described herein.

In another aspect, the invention relates to an isolated binding agent that competes for binding to human PD-1 with the single domain antibody as described herein.

In another aspect, the invention relates to an isolated binding agent comprising a single domain antibody as described herein. In one embodiment, said single domain antibody is linked to a second binding molecule that does not bind to PD-1. In one embodiment, said second single domain antibody binds to an immunooncology target. In one embodiment, said single domain antibody is linked to a second binding molecule that binds to PD-1. In one embodiment, said binding molecule blocks the interaction of PD-1 with PD-L1 and/or PD-L2.

In one embodiment, the isolated binding agent is conjugated to a toxin, enzyme, radioisotope, half-life extending moiety, therapeutic molecule or other chemical moiety.

In another aspect, the invention relates to the use of a single domain antibody described herein in a multispecific or multivalent binding agent.

In another aspect, the invention relates to an immunoconjugate comprising a single domain antibody as described herein or a binding molecule as described herein linked to a therapeutic agent.

In another aspect, the invention relates to a pharmaceutical composition comprising a single domain antibody, a binding agent or an immunoconjugate as described herein and a pharmaceutical carrier.

In another aspect, the invention relates to a method for treating a cancer, an immune disorder, neurological disease, inflammatory disorder, allergy, transplant rejection, viral infection, immune deficiency or other immune system-related disorder comprising administering a therapeutically effective amount of a comprising a single domain, a binding agent, an immunoconjugate or a pharmaceutical composition as described herein.

In another aspect, the invention relates to the use of a single domain, a binding agent, an immunoconjugate or a pharmaceutical composition as described herein in the manufacture of a medicament for the treatment of a cancer, an immune disorder, neurological disease, inflammatory disorder, allergy, transplant rejection, viral infection, immune deficiency or other immune system-related disorder.

In another aspect, the invention relates to a single domain antibody, a binding agent, an immunoconjugate or a pharmaceutical composition as described herein for use as medicament.

In another aspect, the invention relates to a single domain antibody, a binding agent, an immunoconjugate or a pharmaceutical composition as described herein for use in the treatment of a cancer, an immune disorder, neurological disease, inflammatory disorder, allergy, transplant rejection, viral infection, immune deficiency, and other immune system-related disorder.

In another aspect, the invention relates to a method of modulating an immune response comprising administering a single domain antibody, a binding agent, an immunoconjugate or a pharmaceutical composition as described herein.

In another aspect, the invention relates to an isolated nucleic acid molecule comprising a nucleotide sequence selected from SEQ ID Nos. 81 to 100, 221 to 250 or 463 to 515.

In another aspect, the invention relates to a vector comprising a nucleic acid sequence selected from SEQ ID Nos. 81 to 100, 221 to 250, or 463 to 515.

In another aspect, the invention relates to a host cell comprising a vector comprising a nucleic acid sequence selected from SEQ ID Nos. 81 to 100, 221 to 250, or 463 to 515.

In another aspect, the invention relates to a method for producing a single domain antibody as described herein comprising expressing a nucleic acid encoding said binding molecule in a host cell and isolating the binding molecule from the host cell.

In another aspect, the invention relates to a kit comprising a single domain antibody, a binding agent, an immunoconjugate or a pharmaceutical composition as described herein.

In another aspect, the invention relates to a method for detecting the presence of human PD-1 in a test sample comprising contacting said sample with a single domain antibody as described herein and at least one detectable label and detecting binding of said single domain antibody to human PD-1.

In another aspect, the invention relates to a method for producing a $V_H$ single domain antibody that binds to human PD-1 but does not block the interaction of PD-1 with PD-L1 and/or PD-L2 said method comprising
  a) immunising a transgenic animal that expresses a nucleic acid construct comprising human heavy chain V genes and that is not capable of making functional endogenous light or heavy chains with an PD-1 antigen,
  b) generating a library from said animal
  c) isolating $V_H$ single domain antibodies from said libraries,
  d) identifying a $V_H$ single domain antibody that binds to human PD-1 but does not block the interaction of PD-1 with PD-L1 and/or PD-L2 and
  e) isolating said antibody.

In another aspect, the invention relates to a $V_H$ single domain antibody obtained or obtainable by the method described above.

In another aspect, the invention relates to a human $V_H$ single domain antibody that exhibits one or more of the following properties:
  (a) binds to human PD-1 with a KD as shown in the examples;
  (b) does not block the functional interaction of PD-1 with its ligands;
  (c) binds to human PD-1 and cynomolgus monkey PD-1;
  (d) does not bind to mouse PD-1;
  (e) is capable of enhancing antagonistic action of an antagonistic human $V_H$ single domain antibody when linked to such antibody;
  (f) does not enhance T cell activation;
  (g) has EC50 or IC50 values as shown in the examples.

In another aspect, the invention relates to an isolated heavy chain only antibody comprising a $V_H$ domain that binds to human PD-1 but does not block the interaction of PD-1 with PD-L1 and/or PD-L2.

In another aspect, the invention relates to a transgenic rodent that produces a heavy chain only antibody as described herein.

In another aspect, the invention relates to a heavy chain only antibody comprising a $V_H$ domain that binds to human PD-1 but does not block the interaction of PD-1 with PD-L1 and/or PD-L2 obtained or obtainable from a transgenic mouse which expresses human V, D and J loci and does not produce functional endogenous lambda and kappa light chains and heavy chains.

Another aspect relates to an isolated heavy chain only antibody comprising a $V_H$ domain that binds to human PD-1 but does not block the interaction of PD-1 with PD-L1 and/or PD-L2 for use as an agonist.

FIGURES

The invention is further described in the following non-limiting figures.

Figure 1B:
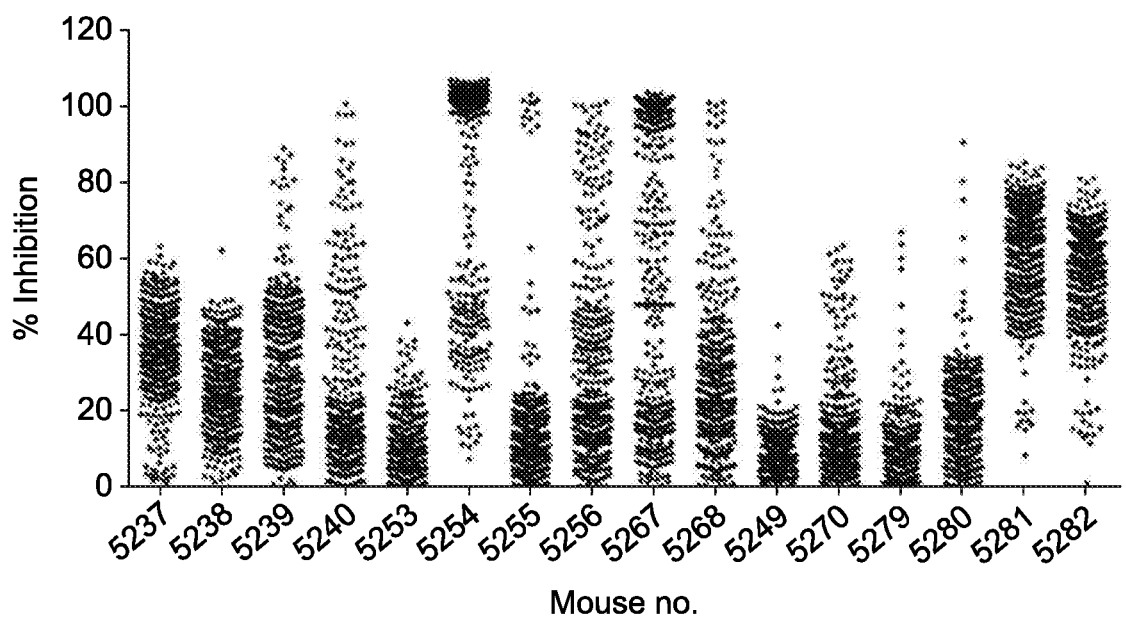

FIG. 1. a) Binding Assay and b) Inhibition Assay.

Figure 2A:
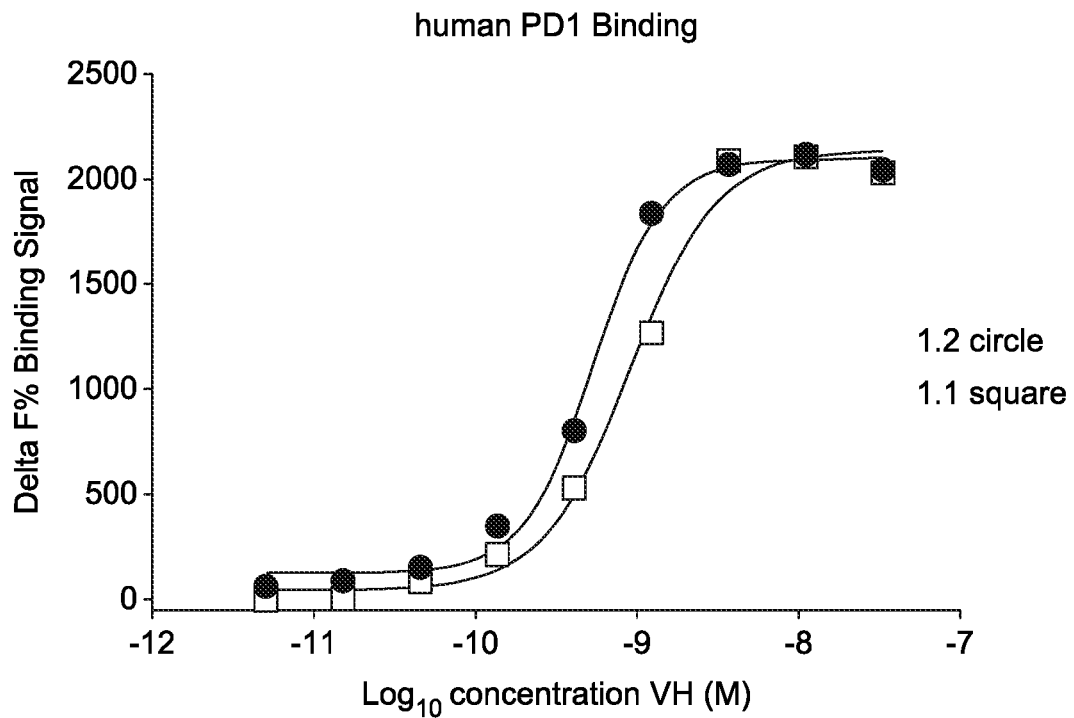
Figure 2B:
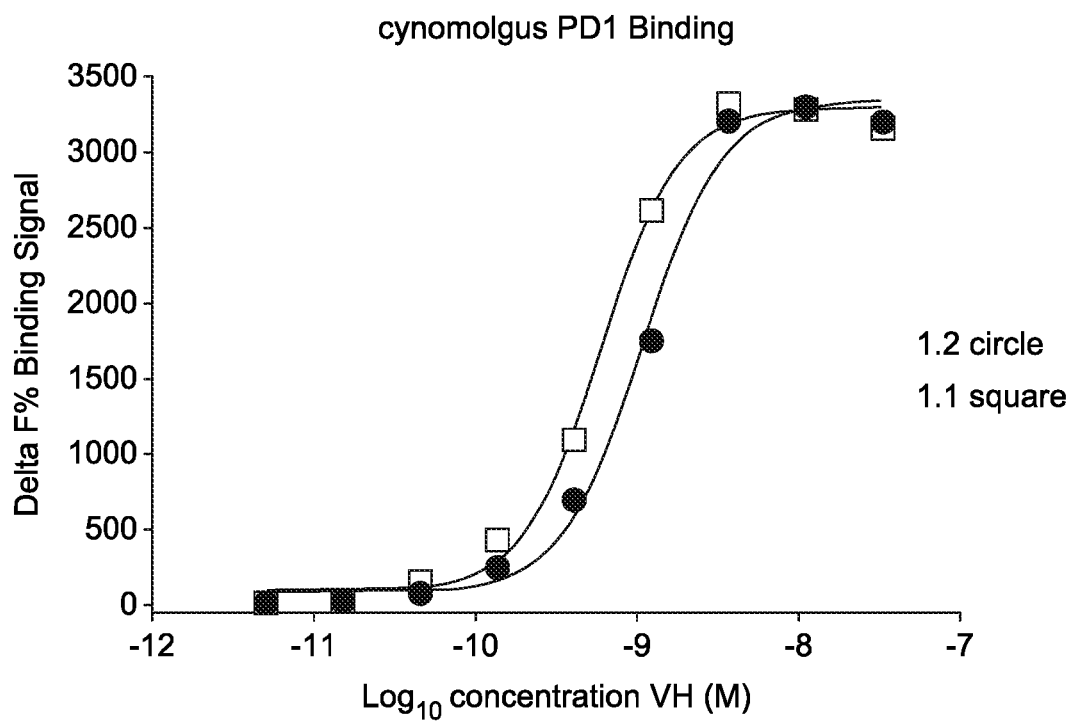

FIG. 2. a) $V_H$ single domain antibody 1.2 and 1.1 binding to human recombinant PD-1 protein b) $V_H$ single domain antibody 1.2 and 1.1 binding to cynomolgus PD-1 recombinant protein c) $V_H$ single domain antibody 1.2 and 1.1 do not bind to mouse PD-1.

Figure 3A:
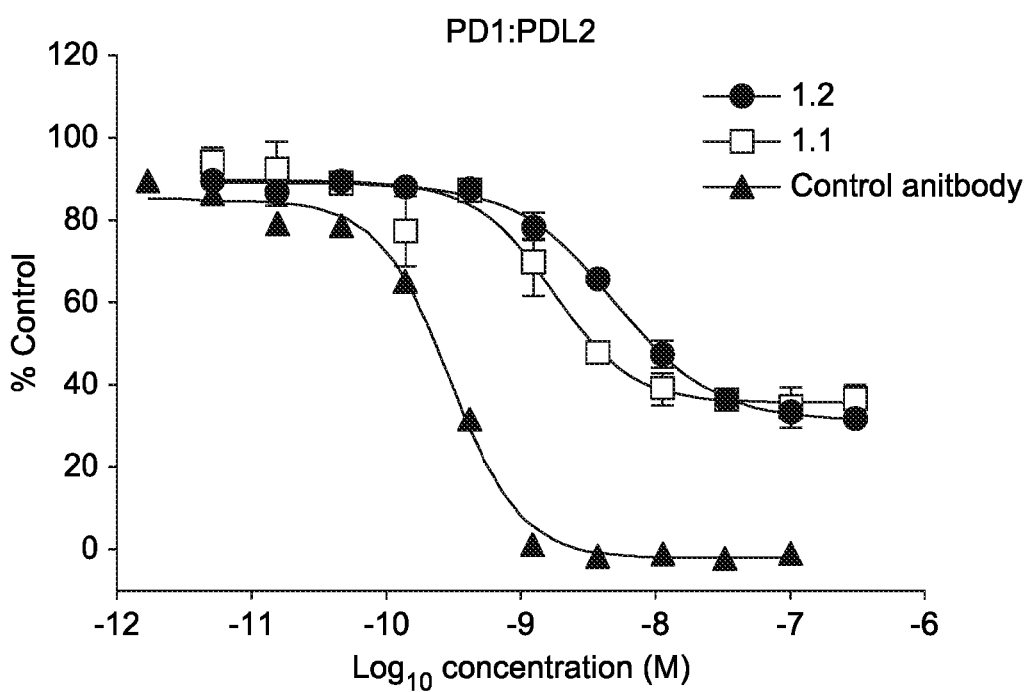
Figure 3B:
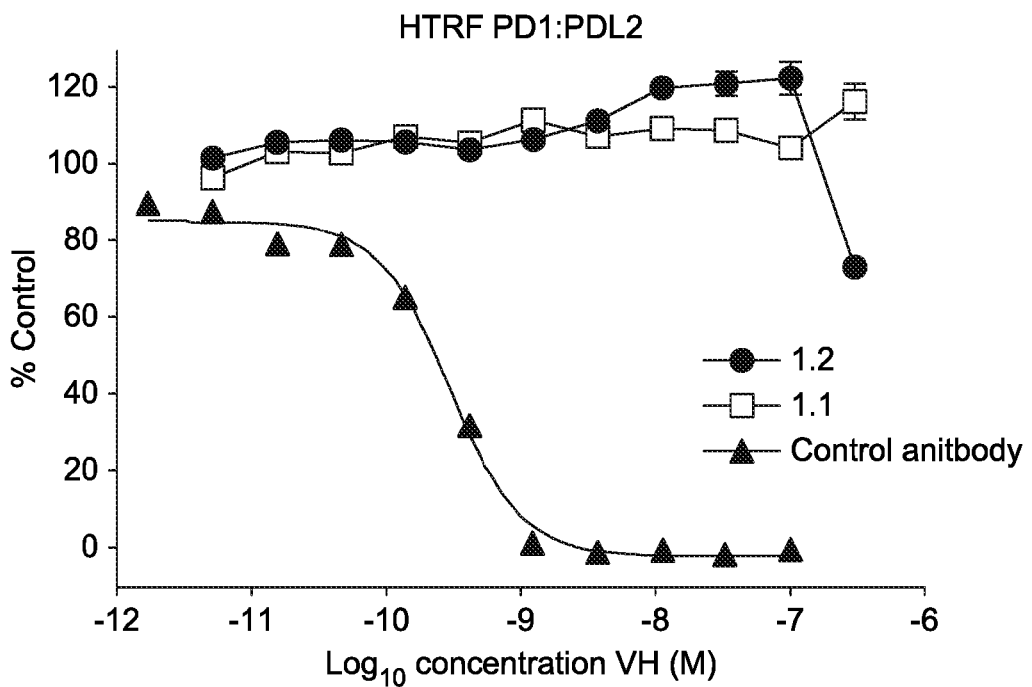

FIG. 3. Inhibition of human PD-L1 (3a) and PD-L2 (3b) binding to recombinant human PD-1 protein using $V_H$ domain antibodies 1.2 and 1.1 in HTRF assay.

FIG. 4. Binding of VHs to CHO human PD-1 cells and testing whether binding inhibits PD-L1 interaction. a) CHO-PD-1 binding b) CHO-PD-1 PD-L1 inhibition.

Figure 5A:
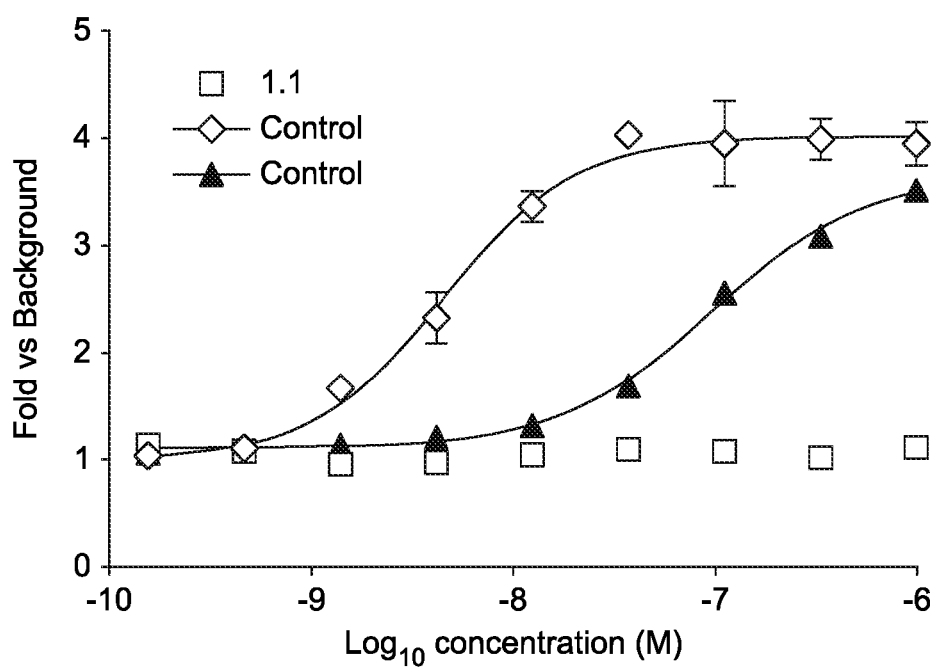
Figure 5B:
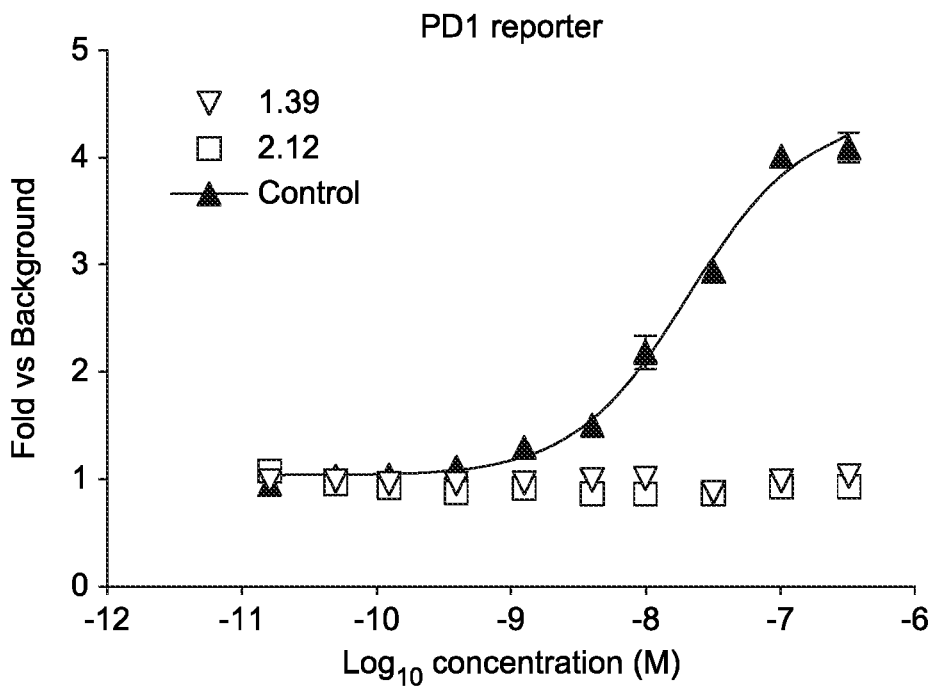
Figure 5C:
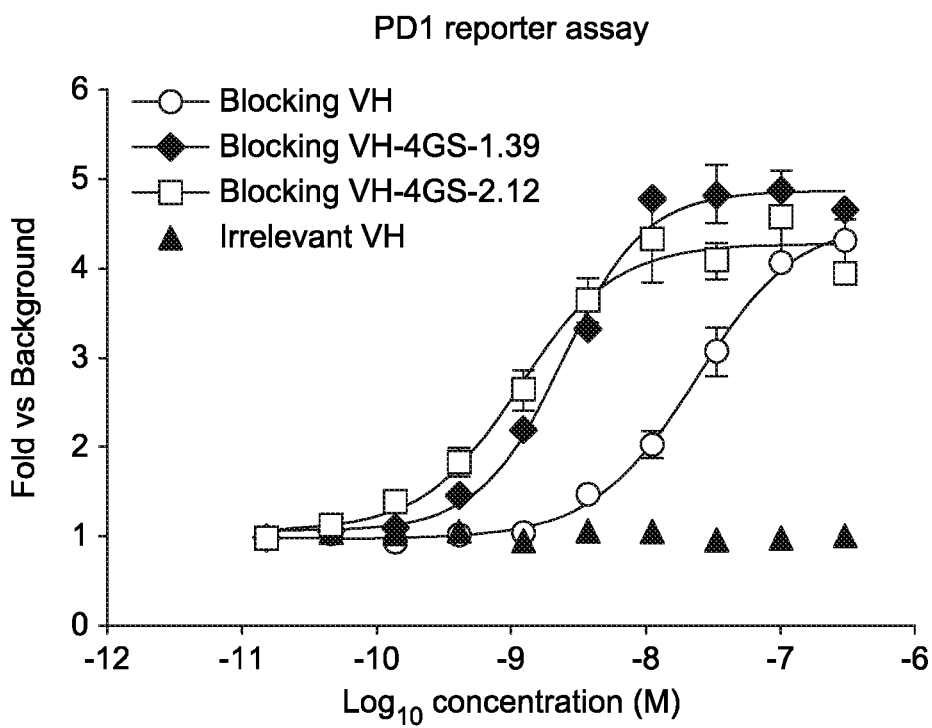

FIG. 5. Functional reporter gene assay. Different single domain antibodies as well as biparatopic format were tested together with a control $V_H$ in the functional reporter assay.

Figure 6:
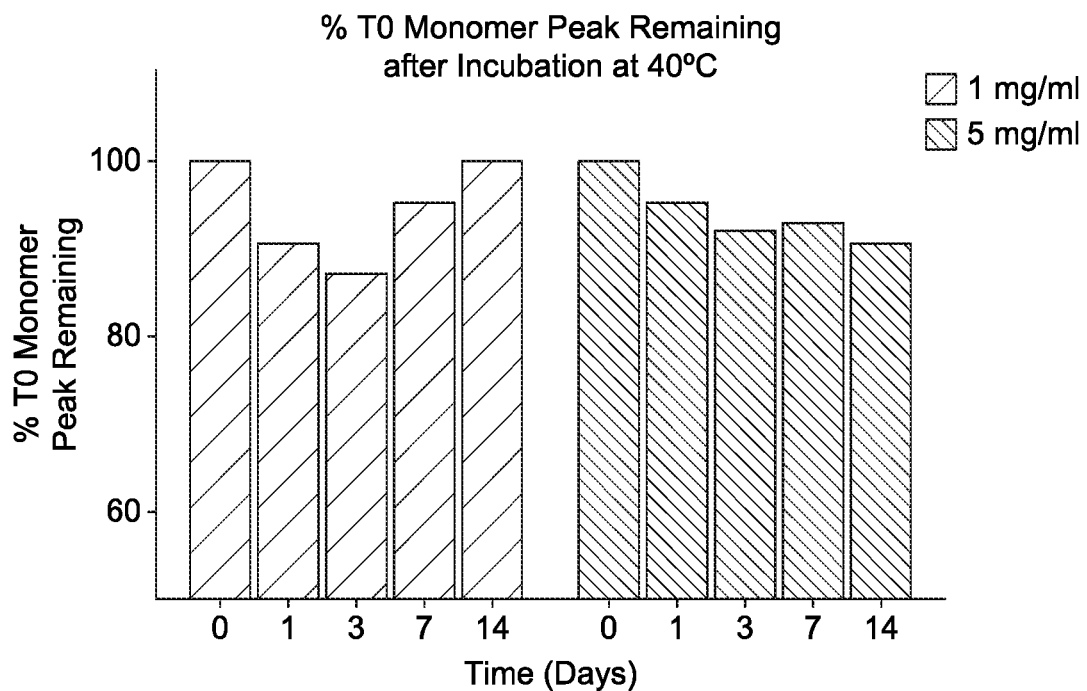

FIG. 6. Stability of $V_H$ single domain antibody 1.1 at 40° C. for 0-14 days.

Figure 7:
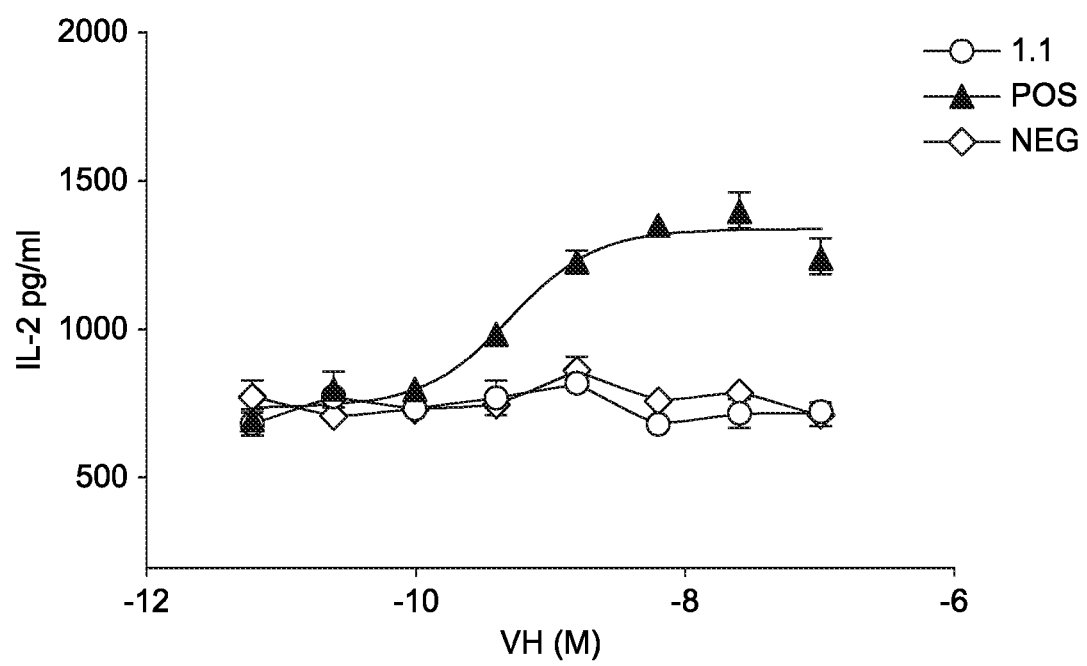

FIG. 7. $V_H$ single domain antibody 1.1 has no impact on IL-2 secretion from allogeneic dendritic cell/T cell co-culture. Positive control (POS) is a Humabody® $V_H$ that functionally blocks PD-1:PD-L1 interaction. Negative control (NEG) is an irrelevant Humabody® $V_H$. IL-2 levels were determined after 2 days by Homogenous Time Resolved Fluorescence assay (HTRF).

FIG. 8. a) 1.1 and 2.1 common epitope residues on human PD-1 (PDB code: 4ZQK) based on Pepscan analysis. The residues common to both the 1.1 and 2.1 epitope are shown in black. b) alignment of residues of human PD-1 involved in binding $V_H$ single domain antibody 1.1 with PD-1 mouse sequence.

FIG. 9. a) Mouse serum stability of $V_H$ single domain antibody 2.12 and b) human serum stability of $V_H$ single domain antibody 2.12.

DETAILED DESCRIPTION

Various aspects and embodiments will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Generally, nomenclatures used in connection with, and techniques of, cell and tissue culture, pathology, oncology, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g., Green and Sambrook et al., Molecular Cloning: A Laboratory Manual, 4th ed., Cold Spring Harbor Laboratory Press, Cold Spring Harbor, N.Y. (2012); Therapeutic Monoclonal Antibodies: From Bench to Clinic, Zhiqiang An (Editor), Wiley, (2009); and Antibody Engineering, 2nd Ed., Vols 1 and 2, Ontermann and Dubel, eds., Springer-Verlag, Heidelberg (2010).

Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The inventors have surprisingly identified human $V_H$ single domain antibodies that bind to human PD-1, but do not block the functional interaction between human PD-1 and its ligands as demonstrated in the functional assays in the examples (see also FIGS. 5 and 7). The inventors have further shown that the human $V_H$ single domain antibodies of the invention bind to an epitope that is distinct from the binding site of human PD-1 to PDL-1 or PDL-2.

The invention thus provides isolated single domain antibodies that bind human PD-1, but do not block the interaction of PD-1 with PD-L1 and/or the interaction of PD-1 with PD-L2, pharmaceutical compositions comprising such binding molecules, as well as isolated nucleic acids, isolated recombinant expression vectors and isolated host cells for making such binding proteins. Also provided are methods of using the single domain antibodies disclosed herein to detect human PD-1 and methods of treating disease. In another aspect, the invention provides binding molecules comprising a single domain antibody that binds human PD-1, but does not block the interaction of PD-1 with PD-L1 and/or the interaction of PD-1 with PD-L2 as described herein. In another aspect, the invention provides binding molecules comprising a single domain antibody that binds to an epitope on human PD-1 as defined herein.

In preferred embodiments, the single domain antibody is a single domain antibody wherein the domain is a human variable heavy chain ($V_H$) domain. Thus, in certain embodiments, the we provide isolated single domain antibodies that bind human PD-1, wherein the domain is a variable heavy chain domain, preferably a $V_H$ domain and wherein said single domain antibodies bind to human PD-1 and do not block the interaction of PD-1 with PD-L1 and/or the interaction of PD-1 with PD-L2.

As used herein, the term "do not block or do not inhibit the interaction of human PD-1 with its ligands" refers to the functional interaction of human PD-1 with its ligands. In other words, the binding of the single domain antibodies of the invention does not abolish or reduce the functional interaction of human PD-1 with its ligands. This can for example be measured in a PD-1 signaling assay and is not defined as blocking ligand binding. Thus, the binding of the single domain antibodies of the invention to human PD-1 does not affect the biological function of the interaction of human PD-1 with its ligands. In one embodiment, the ligand is PD-L1. In one embodiment, the ligand is PD-L2.

The single domain antibodies of the invention bind to PD-1 with high affinity and specificity.

The properties of the single domain antibodies of the invention as described above can be exploited in therapeutic methods and uses. Compounds of the invention are particularly useful in anchoring, associating or bringing into proximity a therapeutic molecule to human PD-1, for example in a targeted therapy to recruit the therapeutic compound to the cell or tissue of interest or to a region of the cell associated with PD-1 localisation. This makes the compounds of the invention particularly suitable for delivery together with other compounds, for example those that block the interaction of PD-1 with its ligands or other immunomoldulators. For example, the single domain antibodies of the invention can be linked, for example using peptide linkers, to a compound that antagonises human PD-1 binding to its ligands PD-L1 and/or PD-L2 thereby up-modulating the immune response. Such a compound can be selected from an antibody or fragment thereof, including a $V_H$ single domain antibody.

Thus, one aspect relates to the use of a single domain antibody as disclosed herein in a multivalent binding agent, for example in combination with a $V_H$ single domain antibody that blocks binding of PD-1 to its ligands PD-L1 and/or PD-L2. In one embodiment, this can be combined with a mAb or an Fc region of an antibody e.g. a Humabody® mAb fusion. This could enable longer half-life and or Fc effector function to deplete PD-1 positive cells for application in treating autoimmune diseases. In one embodiment, multivalent molecules find use as antagonists. In In one embodiment, multivalent molecules find use as agonists.

In another embodiment, the single domain antibodies can be co-administered together with a compound that blocks the interaction of PD-1 with its ligands or other immunomoldulators.

This can be done in the same medicament, or by sequential administration of separate compositions. In another aspect, the single domain can also be combined with another compound that down regulates immune response.

The single domain antibodies of the invention can further be used as depleting antibodies for example for targeting cells for depletion by NK cells or via delivery of a toxic payload. Furthermore, single domain antibodies of the invention can be used as imaging agents, for example in methods for diagnosing cancer or other biomarker related methods. Applications include a method of predicting clinical response of a patient affected by cancer to a treatment, for example with an immune checkpoint pathway inhibitor.

In particular, as explained below, the single domain antibodies of the invention can be used in a multivalent or multispecific format. Thus, the invention also relates to multifunctional binding agents comprising a single domain antibody as described herein.

Molecules of the invention bind specifically to wild type human PD-1 (UniProt Accession No. Q15116, GenBank Accession No. U64863, SEQ ID No. 518). Residues 1-20 correspond to the pre-sequence, residues 171 and beyond make up the transmembrane helix and the intracellular domain of PD-1.

Unless otherwise specified, the term PD-1 as used herein refers to human PD-1. The terms "Programmed Death 1," "Programmed Cell Death 1," "Protein PD-1," "PD-1," PD1," "PDCD1," "hPD-1" and "hPD-1" are used interchangeably, and include variants, isoforms, species homologs of human PD-1

The terms "PD-1 binding molecule/protein/polypeptide/ agent", "PD-1 antigen binding molecule protein/polypeptide/agent", "anti-PD-1 single domain antibody", "anti-PD-1 single immunoglobulin variable domain", "anti-PD1 heavy chain only antibody" or "anti-PD-1 antibody" all refer to a molecule capable of specifically binding to the human PD-1 antigen. The binding reaction may be shown by standard methods, for example with reference to a negative control test using an antibody of unrelated specificity. The term "PD-1 binding molecule/agent" includes a PD-1 binding protein.

An antibody or binding molecule of the invention, including a single domain antibody and multivalent or multispecific binding agent described herein, "which binds" or is "capable of binding" an antigen of interest, e.g. PD-1, is one that binds the antigen with sufficient affinity such that the antibody is useful as a therapeutic agent in targeting a cell or tissue expressing the antigen.

Binding molecules of the invention, including the single domain antibodies and multivalent or multispecific binding agents described herein, bind specifically to human PD-1. In other words, binding to the PD-1 antigen is measurably different from a non-specific interaction. As demonstrated in the examples, the single domain antibodies of the invention do not cross react with mouse PD-1. Preferably, the single domain antibodies of the invention bind to human PD-1 and also bind to cyno PD-1.

The term "specific binding" or "specifically binds to" or is "specific for" a particular polypeptide or an epitope on a particular polypeptide target as used herein can be exhibited, for example, by a molecule having a KD for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

The term "antibody" broadly refers to any immunoglobulin (Ig) molecule, or antigen binding portion thereof, comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art.

In a full-length antibody, each heavy chain is comprised of a heavy chain variable region or domain (abbreviated herein as HCVR) and a heavy chain constant region. The heavy chain constant region is comprised of three domains, $C_H1$, $C_H2$ and $C_H3$. Each light chain is comprised of a light chain variable region or domain (abbreviated herein as LCVR) and a light chain constant region. The light chain constant region is comprised of one domain, $C_L$.

The heavy chain and light chain variable regions can be further subdivided into regions of hypervariability, termed complementarity determining regions (CDR), interspersed with regions that are more conserved, termed framework regions (FR). Each heavy chain and light chain variable region is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "CDR" refers to the complementarity-determining region within antibody variable sequences. There are three CDRs in each of the variable regions of the heavy chain and the light chain, which are designated CDR1, CDR2 and CDR3, for each of the variable regions.

The term "CDR set" refers to a group of three CDRs that occur in a single variable region capable of binding the antigen. The exact boundaries of these CDRs can be defined differently according to different systems known in the art. The Kabat Complementarity Determining Regions (CDRs) are based on sequence variability and are the most commonly used (Kabat et al., (1971) Ann. NY Acad. Sci. 190:382-391 and Kabat, et al., (1991) Sequences of Proteins of Immunological Interest, Fifth Edition, U.S. Department of Health and Human Services, NIH Publication No. 91-3242). Chothia refers instead to the location of the structural loops (Chothia and Lesk J. Mol. Biol. 196:901-917 (1987)). The Kabat numbering system is generally used when referring to a residue in the variable domain (approximately residues 1-107 of the light chain and residues 1-113 of the heavy chain).

The system described by Kabat is used herein unless otherwise specified. The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion.

A chimeric antibody is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, are transferred from the heavy and light variable chains of the rodent antibody into human heavy and light variable domains (e.g., framework region sequences). The constant domains of the antibody molecule are derived from those of a human antibody. In certain embodiments, a limited number of framework region amino acid residues from the parent (rodent) antibody may be substituted into the human antibody framework region sequences.

The term "antigen binding site" refers to the part of the antibody or antibody fragment that comprises the area that specifically binds to an antigen. An antigen binding site may be provided by one or more antibody variable domains. Preferably, an antigen binding site is comprised within the associated $V_H$ and $V_L$ of an antibody or antibody fragment.

An antibody fragment is a portion of an antibody, for example as F(ab')$_2$, Fab, Fv, sFv and the like. Functional fragments of a full length antibody retain the target specificity of a full length antibody. Recombinant functional antibody fragments, such as Fab (Fragment, antibody), scFv (single chain variable chain fragments) and single domain antibodies (dAbs) have therefore been used to develop therapeutics as an alternative to therapeutics based on mAbs.

scFv fragments (~25 kDa) consist of the two variable domains, $V_H$ and $V_L$. Naturally, $V_H$ and $V_L$ domain are non-covalently associated via hydrophobic interaction and tend to dissociate. However, stable fragments can be engineered by linking the domains with a hydrophilic flexible linker to create a single chain Fv (scFv).

The smallest antigen binding fragment is the single variable fragment, namely the $V_H$ or $V_L$ domain. Binding to a light chain/heavy chain partner respectively is not required for target binding. Such fragments are used in single domain antibodies. A single domain antibody (~12 to 15 kDa) therefore consists of or comprises either the $V_H$ or $V_L$ domain.

In one aspect, the invention relates to an isolated single domain antibody, an isolated variable single domain or an isolated immunoglobulin single variable domain wherein said isolated single domain antibody, isolated variable single domain or isolated immunoglobulin single variable domain binds to human PD-1, but does not block the interaction of PD-1 and PD-L1 or PD-L2.

The terms "single domain antibody, variable single domain or immunoglobulin single variable domain (ISV)" are all well known in the art and describe the single variable fragment of an antibody that binds to a target antigen. These terms are used interchangeably herein. As explained below, some embodiments relate to single heavy chain variable domain antibodies/immunoglobulin heavy chain single variable domains which bind a PD-1 antigen in the absence of light chain. Some embodiments relate to human heavy chain variable domain antibodies. Such binding molecules are also termed Humabody® herein. Humabody® is a registered trademark of Crescendo Biologics Ltd.

Thus, in some embodiments, the isolated binding agents/molecules of the invention comprise or consist of at least one single domain antibody wherein said domain is a human heavy chain variable domain. Thus, in one aspect, the binding agents of the invention comprise or consist of at least one immunoglobulin single variable heavy chain domain that has a $V_H$ domain, and they are devoid of $V_L$ domains.

The term "isolated" single domain antibody refers to a single domain antibody that is substantially free of other single domain antibodies, antibodies or antibody fragments having different antigenic specificities. Moreover, an isolated single domain antibody may be substantially free of other cellular material and/or chemicals.

Each single $V_H$ domain antibody comprises three CDRs and four FRs, arranged from amino-terminus to carboxy-terminus in the following order: FR1-CDR1-FR2-CDR2-FR3-CDR3-FR4. Thus, in one embodiment of the invention, the domain is a human variable heavy chain ($V_H$) domain with the following formula FR1-CDR1-FR2-CDR2-FR3-CDR3-FR4.

Modifications to the C or N-terminal $V_H$ framework sequence may be made to the single domain antibodies of the invention to improve their properties. For example, the $V_H$ domain may comprise C or N-terminal extensions or deletions. C-terminal extensions can be added to the C terminal end of a $V_H$ domain which terminates with the residues VTVSS (SEQ ID No. 516).

In one embodiment, the single domain antibodies of the invention comprise C-terminal extensions or deletions of from 1 to 50, or more residues, for example 1 to 25, e.g. 1, 2, 3, 4, 5, 6, 7, 8, 9 or 10 additional amino acids. In one embodiment, the single domain antibodies of the invention comprise additional amino acids of the human $C_H1$ domain thus that the C terminal end extends into the $C_H1$ domain. In one embodiment, said extension comprises at least 1 alanine residue, for example a single alanine residue, a pair of alanine residues or a triplet of alanine residues.

Additional C or N-terminal residues can be linkers that are used to conjugate the single domain antibodies of the invention to another moiety, or tags that aid the detection of the molecule. Such tags are well known in the art and include for, example linker His tags, e.g., hexa-His (HHHHHH, SEQ ID No. 517) or myc tags.

As used herein, the term "homology" generally refers to the percentage of amino acid residues in a sequence that are identical with the residues of the reference polypeptide with which it is compared, after aligning the sequences and in some embodiments after introducing gaps, if necessary, to achieve the maximum percent homology, and not considering any conservative substitutions as part of the sequence identity. Thus, the percent homology between two amino acid sequences is equivalent to the percent identity between the two sequences. Neither N- or C-terminal extensions, tags or insertions shall be construed as reducing identity or homology. Methods and computer programs for the alignment are well known. The percent identity between two amino acid sequences can be determined using well known mathematical algorithms.

According to the various aspects and embodiments of the invention, the variable domain of the single domain antibodies of the invention is preferably a human variable domain ($V_H$). As used herein, a human $V_H$ domain includes a fully human or substantially fully human $V_H$ domain. As used herein, the term human $V_H$ domain also includes $V_H$ domains that are isolated from heavy chain only antibodies made by transgenic mice expressing fully human immunoglobulin heavy chain loci, in particular in response to an immunisation with an antigen of interest, for example as described in WO2016/062990 and in the examples. In one embodiment, a human $V_H$ domain can also include a $V_H$ domain that is derived from or based on a human $V_H$ domain amino acid or nucleic acid sequence encoding such $V_H$ domain. Thus, the term includes variable heavy chain regions derived from or encoded by human germline immunoglobulin sequences. A substantially human $V_H$ domain or $V_H$ domain that is derived from or based on a human $V_H$ domain may include amino acid residues not encoded by human germline immunoglobulin sequences (e.g., mutations introduced in vitro, e.g. by random or site-specific mutagenesis, or introduced by somatic mutation in vivo). The term "human $V_H$ domain" therefore also includes a substantially human $V_H$ domain wherein one or more amino acid residue has been modified. For example, a substantially human $V_H$ domain may include up to 10, for example 1, 2, 3, 4 or 5 or up to 20 amino acid modifications compared to a fully human sequence.

However, the term "human $V_H$ domain" or "substantially human $V_H$ domain", as used herein, is not intended to include antibodies in which CDR sequences derived from the germline of another mammalian species, such as a mouse, have been grafted onto human framework sequences. Preferably, the term "human $V_H$ domain", as used herein, is also not intended to include camelized $V_H$ domains, that is human $V_H$ domains that have been specifically modified, for example in vitro by conventional mutagenesis methods to select predetermined positions in the $V_H$ domains sequence and introduce one or more point mutation at the predetermined position to change one or more predetermined residue to a specific residue that can be found in a camelid $V_{HH}$ domain.

As shown in the examples, the inventors have identified $V_H$ domains that bind to PD-1 at common residues of PD-1, namely $R^{104}$, $D^{105}$, $F^{106}$, $H^{107}$, $M^{108}$, $S^{109}$ and $V^{110}$ of human PD-1.

In one embodiment, the invention relates thus to an isolated single domain antibody that binds to an epitope, epitope part, domain, subunit or conformation of human PD-1 comprising one or more or all of the residues selected from $R^{104}$, $D^{105}$, $F^{106}$, $H^{107}$, $M^{108}$, $S^{109}$ and $V^{110}$ of human PD-1.

In one embodiment, said epitope, epitope part, domain, subunit or conformation further comprises one or more or all of $G^{103}$, $V^{111}$, $R^{112}$ and $A^{113}$. In one embodiment, said epitope, epitope part, domain, subunit or conformation comprises $G^{103}$. In one embodiment, said epitope, epitope part, domain, subunit or conformation comprises $R^{104}$. In one embodiment, said epitope, epitope part, domain, subunit or conformation comprises $S^{109}$. In one embodiment, said epitope, epitope part, domain, subunit or conformation comprises $V^{110}$. In one embodiment, said epitope, epitope part, domain, subunit or conformation comprises $V^{111}$. In one embodiment, said epitope, epitope part, domain, subunit or conformation comprises $R^{112}$. In one embodiment, said epitope, epitope part, domain, subunit or conformation comprises $A^{113}$. As shown in the examples, the single domain antibodies described herein do have binding to these residues in common. In one embodiment, said epitope, epitope part, domain, subunit or conformation comprises all of $G^{103}$, $R^{104}$, $S^{109}$, $V^{110}$, $V^{111}$, $R^{112}$ and $A^{113}$ of human PD-1.

In one embodiment, said epitope, epitope part, domain, subunit or conformation described above further comprises one or more or all of residues $N^{102}$, $D^{105}$, $F^{106}$, $H^{107}$, $M^{108}$, $R^{114}$ and $R^{115}$ of human PD-1. Said epitope further comprises one or more or all of residues selected from $N^{33}$, $P^{34}$, $P^{35}$, $T^{36}$, $F^{37}$, $S^{38}$, $C^{54}$, $F^{55}$, $S^{56}$, $N^{57}$, $T^{58}$, $S^{59}$, $E^{60}$, $S^{61}$, $F^{62}$, $V^{63}$, $L^{64}$, $N^{65}$, $W^{66}$, $P^{101}$ and $G^{103}$. In one embodiment, said epitope, epitope part, domain, subunit or conformation comprises $N^{102}$. In one embodiment, said epitope, epitope part, domain, subunit or conformation comprises $D^{105s}$. In one embodiment, said epitope, epitope part, domain, subunit or conformation comprises $F^{106}$. In one embodiment, said epitope, epitope part, domain, subunit or conformation comprises $H^{107}$. In one embodiment, said epitope, epitope part, domain, subunit or conformation further comprises $M^{108}$. In one embodiment, said epitope, epitope part, domain, subunit or conformation comprises $R^{114}$. In one embodiment, said epitope, epitope part, domain, subunit or conformation comprises $R^{115}$.

In another embodiment, the single domain antibody binds to an epitope comprising one or more or all residues selected from $R^{104}$, $D^{105}$, $F^{106}$, $H^{107}$, $M^{108}$, $S^{109}$ and $V^{110}$ of human PD-1 and further to one or more or all of $S^{60}$, $E^{61}$, $S^{62}$, $F^{63}$, $V^{64}$, $L^{65}$, $N^{66}$, $W^{67}$, $Y^{68}$, $R^{69}$, $M^{70}$, $S^{71}$, $G^{90}$, $Q^{91}$, $D^{92}$, $C^{93}$, $R^{94}$, $F^{95}$, $R^{96}$, $V^{97}$, $T^{98}$, $V^{111}$, $R^{112}$, $A^{113}$ and $R^{11}$. As shown in the examples, the VHs of Family 2 bind to these residues.

The term "epitope" or "antigenic determinant" refers to a site on the surface of an antigen (e.g., PD-1) to which an immunoglobulin, antibody or antibody fragment, including a $V_H$ single domain antibody specifically binds. Generally, an antigen has several or many different epitopes and reacts with many different antibodies. The term specifically includes linear epitopes and conformational epitopes.

Epitopes within protein antigens can be formed both from contiguous amino acids (usually a linear epitope) or non-contiguous amino acids juxtaposed by tertiary folding of the protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody or antibody fragment (i.e., epitope mapping) are well known in the art and include, for example, immunoblotting and immunoprecipitation assays, wherein overlapping or contiguous peptides from are tested for reactivity with a given antibody or antibody fragment.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in different formats, using either labelled antigen or labelled antibody.

In one embodiment, the invention relates to an isolated single $V_H$ domain antibody that binds to human PD-1 comprising a CDR3 sequence as shown Table 1 below or a sequence with at least 60%, 70%, 80%, 90%, 95% or more sequence identity thereto. In one embodiment, said sequence homology is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. In one embodiment, said sequence homology is at least 90%, 91%, 92%, 93%, 94%, 95%, 96%, 97%, 98% or 99%.

In one embodiment, the $V_H$ single domain antibody has a CDR3 sequence comprising SEQ ID No. 3 or a sequence having at least 70%, at least 80%, at least 90%, or at least 95% homology to SEQ ID No. 3. In one embodiment, said sequence homology is at least 90%, 91%, 92%, 93%, 94%, 95%, 96%, 97%, 98% or 99%.

In one embodiment, the $V_H$ single domain antibody has a CDR1 as shown in SEQ ID No. 1 or SEQ ID No. 1 with 1 or 2 amino acid substitutions, a CDR2 as shown in SEQ ID No. 2 or SEQ ID No. 2 with 1 to 5 amino acid substitutions and a CDR3 as shown in SEQ ID No. 3 or SEQ ID No. 3 with 1 to 5 amino acid substitutions.

In one embodiment, the $V_H$ single domain antibody comprises a combination of CDR1, 2 and 3 sequences selected from the CDR1, 2 and 3 sequences in Table 1 or combinations thereof. In one embodiment, the $V_H$ single domain antibody comprises a set of CDR1, 2 and 3 sequences selected from the sets of CDR1, 2 and 3 sequences as shown for the any of the clones in Table 1. Thus, in one aspect, the isolated single domain antibody comprises a CDR1, CDR2 and CDR3 selected from CDRs1-3 of full length sequences SEQ ID No: 4, 8, 12, 16, 20, 24, 28, 32, 36, 40, 44, 48, 52, 56, 60, 64, 68, 72, 76, 80, 104, 108, 112, 116, 120, 124, 128, 132, 136, 140, 144, 148, 152, 156, 160, 164, 168, 172, 176, 180, 184, 188, 192, 196, 200, 204, 208, 212, 216 or 220. Accordingly, in one embodiment, the $V_H$ single domain antibody comprises CDR1 having SEQ ID No. 1, CDR2 having SEQ ID No. 2 and CDR3 having SEQ ID No. 3 (CDRs of SEQ ID NO. 4), CDR1 having SEQ ID No. 5, CDR2 having SEQ ID No. 6 and CDR3 having SEQ ID No. 7 (CDRs of SEQ ID NO. 8) and so forth. Thus, the $V_H$ single domain antibody comprises one of the following CDR combinations: SEQ ID Nos. 1, 2, 3; SEQ ID Nos. 5, 6, 7; SEQ ID Nos. 9, 10, 11; SEQ ID Nos. 13, 14, 15; SEQ ID Nos. 17, 18, 19; SEQ ID Nos. 21, 22, 23; SEQ ID Nos. 25, 26, 27; SEQ ID Nos. 29, 30, 31; SEQ ID Nos.333, 34, 35; SEQ ID Nos. 37, 38, 39; SEQ ID Nos. 41, 42, 43, SEQ ID Nos. 45, 46, 47; SEQ ID Nos. 49, 50, 51; SEQ ID Nos. 53, 54, 55; SEQ ID Nos. 57, 58, 59; SEQ ID Nos. 61, 62, 63; SEQ ID Nos.65, 66, 67; SEQ ID Nos. 69, 70, 71; SEQ ID Nos.73. 74. 75; SEQ ID Nos. 77. 78, 79; SEQ ID Nos. 101, 102, 103; SEQ ID Nos. 105, 106, 107; SEQ ID Nos. 109, 110, 111; SEQ ID Nos. 113, 114, 115; SEQ ID Nos. 117, 118, 119; SEQ ID Nos. 121, 122, 123; SEQ ID Nos. 125, 126, 127; SEQ ID Nos. 129; 130; 131; SEQ ID Nos. 133, 134, 15; SEQ ID Nos. 137, 18, 139; SEQ ID Nos. 141, 142, 143; SEQ ID Nos. 145, 146, 147; SEQ ID Nos. 149, 150, 151; SEQ ID Nos. 153, 154, 155; SEQ ID Nos. 157, 158, 159; SEQ ID Nos. 161, 162, 163; SEQ ID Nos. 165, 166, 167; SEQ ID Nos. 169, 170, 171; SEQ ID Nos. 173, 174, 175; SEQ ID Nos. 177, 178, 179; SEQ ID Nos. 181, 182, 183; SEQ ID Nos. 185, 186, 187; SEQ ID Nos. 189, 190, 191; SEQ ID Nos. 193, 194, 195; SEQ ID Nos. 197, 198, 199; SEQ ID Nos. 201, 202, 203; SEQ ID Nos. 205, 206, 207; SEQ ID Nos. 209, 210, 211; SEQ ID Nos. 213, 214, 215; SEQ ID Nos. 217, 218, 219.

In another embodiment, said CDR1 comprises or consists of the amino acid sequence SEQ ID NO. 1 or a sequence with at least at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto. In one embodiment, said CDR2 comprises or consists of the amino acid sequence SEQ ID No. 2 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto. In one embodiment, said CDR3 comprises or consists of the amino acid sequence SEQ ID No. 3 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto.

In another embodiment, the $V_H$ single domain antibody comprises or consists of a polypeptide sequence as shown for any one of $V_H$ single domain antibodies 1.1 to 1.50 as shown in Table 1 or a sequence with at least 60%, 70%, 80%, 90%, 95% or more sequence homology thereto. Thus, the $V_H$ single domain antibody comprises or consists of an amino acid sequence selected from SEQ ID Nos. 4, 8, 12, 16, 20, 24, 28, 32, 36, 40, 44, 48, 52, 56, 60, 64, 68, 72, 76, 80, 104, 108, 112, 116, 120, 124, 128, 132, 136, 140, 144, 148, 152, 156, 160, 164, 168, 172, 176, 180, 184, 188, 192, 196, 200, 204, 208, 212, 216 or 220 or a sequence with at least 60%, 70%, 80%, 90%, 95% or more sequence homology thereto. In one embodiment, the $V_H$ single domain antibody comprises or consists of SEQ ID No. 104, 108, 112, 116, 120, 124, 128, 132, 136, 140, 144, 148, 152, 156, 160, 164, 168, 172, 176, 180, 184, 188, 192, 196, 200, 204, 208, 212, 216 or 220 or a sequence with at least 60%, 70%, 80%, 90%, 95% or more sequence homology thereto. In one embodiment, the $V_H$ single domain antibody comprises or consists of SEQ ID No. 4 or SEQ ID No. 176 or a sequence with at least 60%, 70%, 80%, 90%, 95% or more sequence homology thereto. In one embodiment, said sequence homology is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

TABLE 1

Full length sequences and CDR sequences of $V_H$ single domain antibodies

| Name | CDR1 sequence of $V_H$ | CDR2 sequence of $V_H$ | CDR3 sequence of $V_H$ | Full length $V_H$ sequence with formula 1: FR1 - CDR1 - FR2 - CDR2 - FR3 - CDR3 - FR4 |
|---|---|---|---|---|
| 1.1 | SEQ ID NO: 1 DHAMH | SEQ ID NO: 2 GISWNS GSMGYA DSVKD | SEQ ID NO: 3 EKGPGLT GSTADYY GLDV | SEQ ID NO: 4 EVQLLESGGGSVQPGRSLRLSCAASG FTFDDHAMHWVRQAPGKGLEWVSGI SWNSGSMGYADSVKDRFTISRDNAKS SLYLQMNSLRAEDTALYYCVREKGPG LTGSTADYYGLDVWGQGTMVTVSS |
| 1.2 | SEQ ID NO: 5 DYAMH | SEQ ID NO: 6 GISWNG GSMGYA ASVKG | SEQ ID NO: 7 DKGPGLIG STADYYGL DV | SEQ ID NO: 8 EVQLVESGGGLVQPGRSLRLSCAASG FTFDDYAMHWVRQAPGKDLEWVSGIS WNGGSMGYAASVKGRFTISRDNAKN SLYLQMNSLRAEDTALYYCVKDKGPG LIGSTADYYGLDVWGQGTTVTVSS |
| 1.3 | SEQ ID NO: 9 DYAMH | SEQ ID NO: 10 GISWNS GSMGYA DSVKD | SEQ ID NO: 11 DKGPGLIG STADYHGL DV | SEQ ID NO: 12 EVQLLESGGGLVQPGRSLRLSCAASG FTFDDYAMHWVRQAPGKGREWVSGI SWNSGSMGYADSVKDRFTISRDNAKN SLYLQMNSLRAEDTALYYCVKDKGPG LIGSTADYHGLDVWGQGTTVTVSS |

TABLE 1-continued

Full length sequences and CDR sequences of $V_H$ single domain antibodies

| Name | CDR1 sequence of $V_H$ | CDR2 sequence of $V_H$ | CDR3 sequence of $V_H$ | Full length $V_H$ sequence with formula 1: FR1 - CDR1 - FR2 - CDR2 - FR3 - CDR3 - FR4 |
|---|---|---|---|---|
| 1.4 | SEQ ID NO: 13 DYAMH | SEQ ID NO: 14 GISWNGGSMGYAESVKG | SEQ ID NO: 15 DKGPGLTGTTADYYGMDV | SEQ ID NO: 16 EVQLLESGGGLVQPGRSLRLSCAASG FTFADYAMHWVRQAPGKGREWVSGI SWNGGSMGYAESVKGRFTISRDNAK NSLYLQMNSLRAEDSALYYCVKDKGP GLTGTTADYYGMDVWGQGTTVTVSS |
| 1.5 | SEQ ID NO: 17 DYAMH | SEQ ID NO: 18 GISWNGGSMGYADSVKD | SEQ ID NO: 19 DKGPGLIGSTADYHGLDV | SEQ ID NO: 20 EVQLVESGGGLVQPGRSLRLSCAASG FTFDDYAMHWVRQAPGKGLEWVSGI SWNGGSMGYADSVKDRFTISRDNAK NSLYLQMNRLRAEDTALYYCVKDKGP GLIGSTADYHGLDVWGQGTTVTVSS |
| 1.6 | SEQ ID NO: 21 SYAMH | SEQ ID NO: 22 GISWNSGSMGYAESVKG | SEQ ID NO: 23 DKGPGLTGTTADYYGMDV | SEQ ID NO: 24 EVQLVESGGGVVQPGRSLRLSCAASG FTFSSYAMHWVRQAPGKGREWVSGI SWNSGSMGYAESVKGRFTISRDNAKN SLYLQMNSLRAEDSALYYCVKDKGPG LTGTTADYYGMDVWGQGTTVTVSS |
| 1.7 | SEQ ID NO: 25 DYAMH | SEQ ID NO: 26 GISWNGGSMGYAESVKG | SEQ ID NO: 27 DKGPGLTGTTADYYGMDV | SEQ ID NO: 28 EVQLVESGGGVIQPGRSLRLSCAASG FTFDDYAMHWVRQAPGKGREWVSGI SWNGGSMGYAESVKGRFTISRDNAQ NSLYLQMNSLRAEDSALYYCVKDKGP GLTGTTADYYGMDVWGQGTTVTVSS |
| 1.8 | SEQ ID NO: 29 DYAMH | SEQ ID NO: 30 GISWNSGSMGYADSVKD | SEQ ID NO: 31 DKGPGLIGSTADYHGLDV | SEQ ID NO: 32 EVQLVESGGGLVQPGRSLRLSCAASG FTFDDYAMHWVRQAPGKGLEWVSGI SWNSGSMGYADSVKDRFTISRDNAKN SLYLQMNSLRAEDTALYYCVKDKGPG LIGSTADYHGLDVWGQGTTVTVSS |
| 1.9 | SEQ ID NO: 33 DYAMH | SEQ ID NO: 34 GISWNGGSMGYAESVKG | SEQ ID NO: 35 DKGPGLIGSTADYYGMDV | SEQ ID NO: 36 EVQLVESGGGCVQPGRSLRISCAASG FTFDDYAMHWVRQAPGKGREWVSGI SWNGGSMGYAESVKGRFTISRDNAK NSLYLQMNSLRAEDSALYYCVKDKGP GLIGSTADYYGMDVWGQGTTVTVSS |
| 1.10 | SEQ ID NO: 37 DYAMH | SEQ ID NO: 38 GISWNGGSMGYAESVKG | SEQ ID NO: 39 DKGPGLTGTTADYYGMDV | SEQ ID NO: 40 EVQLVESGGGLVQPGRSLRLSCAASG FTFADYAMHWVRQAPGKGREWVSGI SWNGGSMGYAESVKGRFTISRDNAK NSLYLQMNSLRAEDSALYYCVKDKGP GLTGTTADYYGMDVWGQGTTVTVSS |
| 1.11 | SEQ ID NO: 41 DYAMH | SEQ ID NO: 42 GISWNGGSMGYAESVKG | SEQ ID NO: 43 DKGPGLIGSTADYYGLDV | SEQ ID NO: 44 EVQLLESGGGFVQPGRSLRISCAASG FTFDDYAMHWVRQAPGKDLEWVSGIS WNGGSMGYAESVKGRFTISRDNAKN SLYLKMNSLRVEDTALYYCVKDKGPG LIGSTADYYGLDVWGQGTTVTVSS |
| 1.12 | SEQ ID NO: 45 DYAMH | SEQ ID NO: 46 GISWNGGSMGYADSVKD | SEQ ID NO: 47 DKGPGLTGSTADYHGMDV | SEQ ID NO: 48 QVQLVESGGGLVQPGRSLRLSCAASG FTFDDYAMHWVRQAPGKGREWVSGI SWNGGSMGYADSVKDRFTISRDNAK NSLYLQMNSLRAEDTALYYCVKDKGP GLTGSTADYHGMDVWGQGTTVTVSS |
| 1.13 | SEQ ID NO: 49 DYAMH | SEQ ID NO: 50 GISWNGGSMGYAASVKG | SEQ ID NO: 51 DKGPGLIGSTADYYGLDV | SEQ ID NO: 52 QVQLVESGGGLVQPGRSLRLSCAASG FTFDDYAMHWVRQAPGKDLEWVSGIS WNGGSMGYAASVKGRFTISRDNAQN SLYLQMNSLRAEDTALYYCVKDKGPG LIGSTADYYGLDVWGQGTTVTVSS |

TABLE 1-continued

Full length sequences and CDR sequences of $V_H$ single domain antibodies

| Name | CDR1 sequence of $V_H$ | CDR2 sequence of $V_H$ | CDR3 sequence of $V_H$ | Full length $V_H$ sequence with formula 1: FR1 - CDR1 - FR2 - CDR2 - FR3 - CDR3 - FR4 |
|---|---|---|---|---|
| 1.14 | SEQ ID NO: 53 GYAMH | SEQ ID NO: 54 GISWNSGSMGYAESVKG | SEQ ID NO: 55 DKGPGLTGSTADYYGMDV | SEQ ID NO: 56 EVQLVESGGGLVQPGRSLRLSCAASGFTFDGYAMHWVRQAPGKGREWVSGISWNSGSMGYAESVKGRFTISRDNAKNSLYLQMNSLRAEDSALYYCVKDKGPGLTGSTADYYGMDVWGQGTTVTVSS |
| 1.15 | SEQ ID NO: 57 DYAMH | SEQ ID NO: 58 GISWNSGSMGYAESVKG | SEQ ID NO: 59 DKGPGLIGSTADYYGMDV | SEQ ID NO: 60 EVQLLESGGGLVQPGRSLRLSCTASGFTFDDYAMHWVRQAPGKGREWVSGISWNSGSMGYAESVKGRFTISRDNAKNSLYLQMNSLRAEDSALYYCVKDKGPGLIGSTADYYGMDVWGQGTTVTVSS |
| 1.16 | SEQ ID NO: 61 DYAMH | SEQ ID NO: 62 GISWNGGSMGYAESVKG | SEQ ID NO: 63 DKGPGLIGSTADYYGMDV | SEQ ID NO: 64 QVQLVESGGGLVQPGRSLRLSCAASGFTFDDYAMHWVRQAPGKGREWVSGISWNGGSMGYAESVKGRFTISRDNAKNSLYLQMNSLRAEDSALYYCVKDKGPGLIGSTADYYGMDVWGQGTTVTVSS |
| 1.17 | SEQ ID NO: 65 DYAMH | SEQ ID NO: 66 GISWNSGSMGYAASVKD | SEQ ID NO: 67 DKGPGLIGSTADYHGLDV | SEQ ID NO: 68 EVQLLESGGGLVQPGGSLRLSCAASGFTFDDYAMHWVRQAPGKGLEWVSGISWNSGSMGYAASVKDRFTISRDNAKNSLYLQMNSLTTEDTALYYCVKDKGPGLIGSTADYHGLDVWGQGTTVTVSS |
| 1.18 | SEQ ID NO: 69 DYAMH | SEQ ID NO: 70 GISWNGGSMGYAASVKG | SEQ ID NO: 71 DKGPGLIGSTADYYGLDV | SEQ ID NO: 72 QVQLVESGGGLVQPGRSLRLSCAASGFTFDDYAMHWVRQAPGKDLEWVSGISWNGGSMGYAASVKGRFTISRDNAKNSLYLQMNSLRAEDTALYYCVKDKGPGLIGSTADYYGLDVWGQGTTVTVSS |
| 1.19 | SEQ ID NO: 73 DYAMH | SEQ ID NO: 74 GISWNGGSMGYADSVKG | SEQ ID NO: 75 EKGPGLTGSTADYYGLDV | SEQ ID NO: 76 EVQLVESGGGLVQPGRSLRLSCAASGFTFDDYAMHWVRQAPGKDLEWVSGISWNGGSMGYADSVKGRFTISRDNAKNSLYLQMNSLRAEDTALYYCVREKGPGLTGSTADYYGLDVWGQGMVTVSS |
| 1.20 | SEQ ID NO: 77 DYAMH | SEQ ID NO: 78 GISWNGGSMGYADSVKG | SEQ ID NO: 79 EKGPGLTGSTADYYGLDV | SEQ ID NO: 80 EVQLVESGGGLVQPGRSLRLSCAASGFTFDDYAMHWVRQAPGKDLEWVSGISWNGGSMGYADSVKGRFTISRDNAKNSLYLQMNSLRAEDTALYYCVREKGPGLTGSTADYYGLDVWGQGMVTVSS |
| 1.21 | SEQ ID NO: 101 DYAMH | SEQ ID NO: 102 GISWNGGSMGYAASVKG | SEQ ID NO: 103 EKGPGLTGSTADYYGLDV | SEQ ID NO: 104 EVQLVESGGGLVQPGRSLRLSCAASGFTFDDYAMHWVRQAPGKDLEWVSGISWNGGSMGYAASVKGRFTISRDNAKNSLYLQMNSLRAEDTALYYCVREKGPGLTGSTADYYGLDVWGQGMVTVSS |
| 1.22 | SEQ ID NO: 105 DYAMH | SEQ ID NO: 106 GISWNGGSMGYAASVKG | SEQ ID NO: 107 EKGPGLTGSTADYYGLDA | SEQ ID NO: 108 EVQLVESGGGLVQPGRSLRLSCAASGFTFDDYAMHWVRQAPGKDLEWVSGISWNGGSMGYAASVKGRFTISRDNAKNSLYLQMNSLRAEDTALYYCVREKGPGLTGSTADYYGLDAWGQGMVTVSS |
| 1.23 | SEQ ID NO: 109 DYAMH | SEQ ID NO: 110 GISWNSGSMGYAASVKG | SEQ ID NO: 111 EKGPGLTGSTADYYGLDV | SEQ ID NO: 112 EVQLVESGGGLVQPGRSLRLSCAASGFTFDDYAMHWVRQAPGKDLEWVSGISWNSGSMGYAASVKGRFTISRDNAKNSLYLQMNSLRAEDTALYYCVREKGPGLTGSTADYYGLDVWGQGMVTVSS |

TABLE 1-continued

Full length sequences and CDR sequences of $V_H$ single domain antibodies

| Name | CDR1 sequence of $V_H$ | CDR2 sequence of $V_H$ | CDR3 sequence of $V_H$ | Full length $V_H$ sequence with formula 1: FR1 - CDR1 - FR2 - CDR2 - FR3 - CDR3 - FR4 |
|---|---|---|---|---|
| 1.24 | SEQ ID NO: 113 DYAMH | SEQ ID NO: 114 GISWNS GSMGYA ASVKG | SEQ ID NO: 115 EKGPGLT GSTADYY GLDA | SEQ ID NO: 116 EVQLVESGGGLVQPGRSLRLSCAASG FTFDDYAMHWVRQAPGKDLEWVSGIS WNSGSMGYAASVKGRFTISRDNAKNS LYLQMNSLRAEDTALYYCVREKGPGL TGSTADYYGLDAWGQGTMVTSS |
| 1.25 | SEQ ID NO: 117 DYAMH | SEQ ID NO: 118 GISWNG GSQGYA ASVKG | SEQ ID NO: 119 EKGPGLT GSTADYY GLDA | SEQ ID NO: 120 EVQLVESGGGLVQPGRSLRLSCAASG FTFDDYAMHWVRQAPGKDLEWVSGIS WNGGSQGYAASVKGRFTISRDNAKNS LYLQMNSLRAEDTALYYCVREKGPGL TGSTADYYGLDAWGQGTMVTSS |
| 1.26 | SEQ ID NO: 121 DYAMH | SEQ ID NO: 122 GISWNG GSMGYA DSVKG | SEQ ID NO: 123 EKGPGLT GSTADYY GLDA | SEQ ID NO: 124 EVQLVESGGGLVQPGRSLRLSCAASG FTFDDYAMHWVRQAPGKDLEWVSGIS WNGGSMGYADSVKGRFTISRDNAKN SLYLQMNSLRAEDTALYYCVREKGPG LTGSTADYYGLDAWGQGTMVTSS |
| 1.27 | SEQ ID NO: 125 DYAMH | SEQ ID NO: 126 GISWNG GSRGYA ASVKG | SEQ ID NO: 127 EKGPGLT GSTADYY GLDA | SEQ ID NO: 128 EVQLVESGGGLVQPGRSLRLSCAASG FTFDDYAMHWVRQAPGKDLEWVSGIS WNGGSRGYAASVKGRFTISRDNAKNS LYLQMNSLRAEDTALYYCVREKGPGL TGSTADYYGLDAWGQGTMVTSS |
| 1.28 | SEQ ID NO: 129 DYAMH | SEQ ID NO: 130 GISWNA GSMGYA ASVKG | SEQ ID NO: 131 EKGPGLT GSTADYY GLDA | SEQ ID NO: 132 EVQLVESGGGLVQPGRSLRLSCAASG FTFDDYAMHWVRQAPGKDLEWVSGIS WNAGSMGYAASVKGRFTISRDNAKNS LYLQMNSLRAEDTALYYCVREKGPGL TGSTADYYGLDAWGQGTMVTSS |
| 1.29 | SEQ ID NO: 133 DYAMH | SEQ ID NO: 134 GISWNS GSMGYA DSVKG | SEQ ID NO: 135 EKGPGLT GSTADYY GLDV | SEQ ID NO: 136 EVQLVESGGGLVQPGRSLRLSCAASG FTFDDYAMHWVRQAPGKDLEWVSGIS WNSGSMGYADSVKGRFTISRDNAKNS LYLQMNSLRAEDTALYYCVREKGPGL TGSTADYYGLDVWGQGTMVTSS |
| 1.30 | SEQ ID NO: 137 DYAGH | SEQ ID NO: 138 GISWNG GSMGYA ASVKG | SEQ ID NO: 139 EKGPGLT GSTADYY GLDA | SEQ ID NO: 140 EVQLVESGGGLVQPGRSLRLSCAASG FTFDDYAGHWVRQAPGKDLEWVSGIS WNGGSMGYAASVKGRFTISRDNAKN SLYLQMNSLRAEDTALYYCVREKGPG LTGSTADYYGLDAWGQGTMVTSS |
| 1.31 | SEQ ID NO: 141 DYALH | SEQ ID NO: 142 GISWNG GSMGYA ASVKG | SEQ ID NO: 143 EKGPGLT GSTADYY GLDA | SEQ ID NO: 144 EVQLVESGGGLVQPGRSLRLSCAASG FTFDDYALHWVRQAPGKDLEWVSGIS WNGGSMGYAASVKGRFTISRDNAKN SLYLQMNSLRAEDTALYYCVREKGPG LTGSTADYYGLDAWGQGTMVTSS |
| 1.32 | SEQ ID NO: 145 DYAMH | SEQ ID NO: 146 GISWNS GSMGYA DSVKG | SEQ ID NO: 147 EKGPGLT GSTADYY GLDA | SEQ ID NO: 148 EVQLVESGGGLVQPGRSLRLSCAASG FTFDDYAMHWVRQAPGKDLEWVSGIS WNSGSMGYADSVKGRFTISRDNAKNS LYLQMNSLRAEDTALYYCVREKGPGL TGSTADYYGLDAWGQGTMVTSS |
| 1.33 | SEQ ID NO: 149 DYAMH | SEQ ID NO: 150 GISWNG GSYGYA DSVKG | SEQ ID NO: 151 EKGPGLT GSTADYY GLDA | SEQ ID NO: 152 EVQLVESGGGLVQPGRSLRLSCAASG FTFDDYAMHWVRQAPGKDLEWVSGIS WNGGSYGYADSVKGRFTISRDNAKNS LYLQMNSLRAEDTALYYCVREKGPGL TGSTADYYGLDAWGQGTMVTSS |

TABLE 1-continued

Full length sequences and CDR sequences of V$_H$ single domain antibodies

| Name | CDR1 sequence of V$_H$ | CDR2 sequence of V$_H$ | CDR3 sequence of V$_H$ | Full length V$_H$ sequence with formula 1: FR1 - CDR1 - FR2 - CDR2 - FR3 - CDR3 - FR4 |
|---|---|---|---|---|
| 1.34 | SEQ ID NO: 153 DYAMH | SEQ ID NO: 154 GISWNG GSQGYA DSVKG | SEQ ID NO: 155 EKGPGLT GSTADYY GLDA | SEQ ID NO: 156 EVQLVESGGGLVQPGRSLRLSCAASG FTFDDYAMHWVRQAPGKDLEWVSGIS WNGGSQGYADSVKGRFTISRDNAKN SLYLQMNSLRAEDTALYYCVREKGPG LTGSTADYYGLDAWGQGTMVTVSS |
| 1.35 | SEQ ID NO: 157 DYAMH | SEQ ID NO: 158 GISWNG GSKGYA DSVKG | SEQ ID NO: 159 EKGPGLT GSTADYY GLDA | SEQ ID NO: 160 EVQLVESGGGLVQPGRSLRLSCAASG FTFDDYAMHWVRQAPGKDLEWVSGIS WNGGSKGYADSVKGRFTISRDNAKNS LYLQMNSLRAEDTALYYCVREKGPGL TGSTADYYGLDAWGQGTMVTVSS |
| 1.36 | SEQ ID NO: 161 DYAMH | SEQ ID NO: 162 GISWNA GSMGYA DSVKG | SEQ ID NO: 163 EKGPGLT GSTADYY GLDA | SEQ ID NO: 164 EVQLVESGGGLVQPGRSLRLSCAASG FTFDDYAMHWVRQAPGKDLEWVSGIS WNAGSMGYADSVKGRFTISRDNAKNS LYLQMNSLRAEDTALYYCVREKGPGL TGSTADYYGLDAWGQGTMVTVSS |
| 1.37 | SEQ ID NO: 165 DYAFH | SEQ ID NO: 166 GISWNG GSMGYA DSVKG | SEQ ID NO: 167 EKGPGLT GSTADYY GLDA | SEQ ID NO: 168 EVQLVESGGGLVQPGRSLRLSCAASG FTFDDYAFHWVRQAPGKDLEWVSGIS WNGGSMGYADSVKGRFTISRDNAKN SLYLQMNSLRAEDTALYYCVREKGPG LTGSTADYYGLDAWGQGTMVTVSS |
| 1.38 | SEQ ID NO: 169 DYALH | SEQ ID NO: 170 GISWNG GSMGYA DSVKG | SEQ ID NO: 171 EKGPGLT GSTADYY GLDA | SEQ ID NO: 172 EVQLVESGGGLVQPGRSLRLSCAASG FTFDDYALHWVRQAPGKDLEWVSGIS WNGGSMGYADSVKGRFTISRDNAKN SLYLQMNSLRAEDTALYYCVREKGPG LTGSTADYYGLDAWGQGTMVTVSS |
| 1.39 | SEQ ID NO: 173 DYALH | SEQ ID NO: 174 GISWNG GSYGYA DSVKG | SEQ ID NO: 175 EKGPGLT GSTADYY GLDA | SEQ ID NO: 176 EVQLVESGGGLVQPGRSLRLSCAASG FTFDDYALHWVRQAPGKDLEWVSGIS WNGGSYGYADSVKGRFTISRDNAKNS LYLQMNSLRAEDTALYYCVREKGPGL TGSTADYYGLDAWGQGTMVTVSS |
| 1.40 | SEQ ID NO: 177 DYALH | SEQ ID NO: 178 GISWNG GSQGYA DSVKG | SEQ ID NO: 179 EKGPGLT GSTADYY GLDA | SEQ ID NO: 180 EVQLVESGGGLVQPGRSLRLSCAASG FTFDDYALHWVRQAPGKDLEWVSGIS WNGGSQGYADSVKGRFTISRDNAKN SLYLQMNSLRAEDTALYYCVREKGPG LTGSTADYYGLDAWGQGTMVTVSS |
| 1.41 | SEQ ID NO: 181 DYAFH | SEQ ID NO: 182 GISWNG GSYGYA DSVKG | SEQ ID NO: 183 EKGPGLT GSTADYY GLDA | SEQ ID NO: 184 EVQLVESGGGLVQPGRSLRLSCAASG FTFDDYAFHWVRQAPGKDLEWVSGIS WNGGSYGYADSVKGRFTISRDNAKNS LYLQMNSLRAEDTALYYCVREKGPGL TGSTADYYGLDAWGQGTMVTVSS |
| 1.42 | SEQ ID NO: 185 DYAFH | SEQ ID NO: 186 GISWNG GSQGYA DSVKG | SEQ ID NO: 187 EKGPGLT GSTADYY GLDA | SEQ ID NO: 188 EVQLVESGGGLVQPGRSLRLSCAASG FTFDDYAFHWVRQAPGKDLEWVSGIS WNGGSQGYADSVKGRFTISRDNAKN SLYLQMNSLRAEDTALYYCVREKGPG LTGSTADYYGLDAWGQGTMVTVSS |
| 1.43 | SEQ ID NO: 189 DYAFH | SEQ ID NO: 190 GISWNA GSYGYA DSVKG | SEQ ID NO: 191 EKGPGLT GSTADYY GLDA | SEQ ID NO: 192 EVQLVESGGGLVQPGRSLRLSCAASG FTFDDYAFHWVRQAPGKDLEWVSGIS WNAGSYGYADSVKGRFTISRDNAKNS LYLQMNSLRAEDTALYYCVREKGPGL TGSTADYYGLDAWGQGTMVTVSS |

TABLE 1-continued

Full length sequences and CDR sequences of $V_H$ single domain antibodies

| Name | CDR1 sequence of $V_H$ | CDR2 sequence of $V_H$ | CDR3 sequence of $V_H$ | Full length $V_H$ sequence with formula 1: FR1 - CDR1 - FR2 - CDR2 - FR3 - CDR3 - FR4 |
|---|---|---|---|---|
| 1.44 | SEQ ID NO: 193 DYALH | SEQ ID NO: 194 GISWNS GSYGYA DSVKG | SEQ ID NO: 195 EKGPGLT GSTADYY GLDA | SEQ ID NO: 196 EVQLVESGGGLVQPGRSLRLSCAASG FTFDDYALHWVRQAPGKDLEWVSGIS WNSGSYGYADSVKGRFTISRDNAKNS LYLQMNSLRAEDTALYYCVREKGPGL TGSTADYYGLDAWGQGTMVTVSS |
| 1.45 | SEQ ID NO: 197 DYALH | SEQ ID NO: 198 GISWNA GSQGYA DSVKG | SEQ ID NO: 199 EKGPGLT GSTADYY GLDA | SEQ ID NO: 200 EVQLVESGGGLVQPGRSLRLSCAASG FTFDDYALHWVRQAPGKDLEWVSGIS WNAGSQGYADSVKGRFTISRDNAKNS LYLQMNSLRAEDTALYYCVREKGPGL TGSTADYYGLDAWGQGTMVTVSS |
| 1.46 | SEQ ID NO: 201 DYALH | SEQ ID NO: 202 GISWNA GSYGYA DSVKG | SEQ ID NO: 203 EKGPGLT GSTADYY GLDA | SEQ ID NO: 204 EVQLVESGGGLVQPGRSLRLSCAASG FTFDDYALHWVRQAPGKDLEWVSGIS WNAGSYGYADSVKGRFTISRDNAKNS LYLQMNSLRAEDTALYYCVREKGPGL TGSTADYYGLDAWGQGTMVTVSS |
| 1.47 | SEQ ID NO: 205 DYAFH | SEQ ID NO: 206 GISWNS GSYGYA DSVKG | SEQ ID NO: 207 EKGPGLT GSTADYY GLDA | SEQ ID NO: 208 EVQLVESGGGLVQPGRSLRLSCAASG FTFDDYAFHWVRQAPGKDLEWVSGIS WNSGSYGYADSVKGRFTISRDNAKNS LYLQMNSLRAEDTALYYCVREKGPGL TGSTADYYGLDAWGQGTMVTVSS |
| 1.48 | SEQ ID NO: 209 DYALH | SEQ ID NO: 210 GISWNS GSQGYA DSVKG | SEQ ID NO: 211 EKGPGLT GSTADYY GLDA | SEQ ID NO: 212 EVQLVESGGGLVQPGRSLRLSCAASG FTFDDYALHWVRQAPGKDLEWVSGIS WNSGSQGYADSVKGRFTISRDNAKNS LYLQMNSLRAEDTALYYCVREKGPGL TGSTADYYGLDAWGQGTMVTVSS |
| 1.49 | SEQ ID NO: 213 DYAFH | SEQ ID NO: 214 GISWNS GSQGYA DSVKG | SEQ ID NO: 215 EKGPGLT GSTADYY GLDA | SEQ ID NO: 216 EVQLVESGGGLVQPGRSLRLSCAASG FTFDDYAFHWVRQAPGKDLEWVSGIS WNSGSQGYADSVKGRFTISRDNAKNS LYLQMNSLRAEDTALYYCVREKGPGL TGSTADYYGLDAWGQGTMVTVSS |
| 1.50 | SEQ ID NO: 217 DYAFH | SEQ ID NO: 218 GISWNA GSQGYA DSVKG | SEQ ID NO: 219 EKGPGLT GSTADYY GLDA | SEQ ID NO: 220 EVQLVESGGGLVQPGRSLRLSCAASG FTFDDYAFHWVRQAPGKDLEWVSGIS WNAGSQGYADSVKGRFTISRDNAKNS LYLQMNSLRAEDTALYYCVREKGPGL TGSTADYYGLDAWGQGTMVTVSS |

In one embodiment, the invention relates to an isolated single $V_H$ domain antibody that binds to human PD-1 comprising a CDR3 sequence as shown Table 2 below or a sequence with at least 60%, 70%, 80%, 90%, 95% or more sequence identity thereto. In one embodiment, said sequence homology is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. In one embodiment, said sequence homology is at least 90%, 91%, 92%, 93%, 94%, 95%, 96%, 97%, 98% or 99%. In one embodiment, the $V_H$ single domain antibody has a CDR3 sequence comprising SEQ ID No. 253 or a sequence having at least 70%, at least 80%, at least 90%, or at least 95% homology to SEQ ID No. 253. In one embodiment, said sequence homology is at least 90%, 91%, 92%, 93%, 94%, 95%, 96%, 97%, 98% or 99%.

In one embodiment, the $V_H$ single domain antibody has a CDR1 as shown in SEQ ID No. 251 or SEQ ID No. 251 with 1 or 2 amino acid substitutions, a CDR2 as shown in SEQ ID No. 252 or SEQ ID No. 252 with 1 to 5 amino acid substitutions and a CDR3 as shown in SEQ ID No. 253 or SEQ ID No. 253 with 1 to 5 amino acid substitutions.

In one embodiment, the $V_H$ single domain antibody comprises a combination of CDR1, 2 and 3 sequences selected from the CDR1, 2 and 3 sequences in Table 2 or combinations thereof. In one embodiment, the $V_H$ single domain antibody comprises a set of CDR1, 2 and 3 sequences selected from the sets of CDR1, 2 and 3 sequences as shown for the any of the clones in Table 2. Thus, in one aspect, the isolated single domain antibody comprises a CDR1, CDR2 and CDR3 selected from CDRs 1-3 of full length sequences SEQ ID Nos: 254, 258, 262, 266, 270, 274, 278, 282, 286, 290, 294, 298, 302, 306, 310, 314, 318, 322, 326, 330, 334, 338, 342, 346, 350, 354, 358, 362, 366, 370, 374, 378, 382, 386, 390, 394, 398, 402, 406, 410, 414, 418, 422, 426, 430, 434, 438, 442, 446, 450, 454, 458 or 462.

Accordingly, in one embodiment, the V$_H$ single domain antibody comprises CDR1 having SEQ ID No. 251, CDR2 having SEQ ID No. 252 and CDR3 having SEQ ID No. 253 (CDRs of SEQ ID NO. 254) and so forth. Thus, the V$_H$ single domain antibody comprises one of the following CDR combinations: SEQ ID Nos. 251, 252, 253; SEQ ID Nos. 255, 256, 257; SEQ ID Nos. 259, 260, 261; SEQ ID Nos. 263, 264, 265; SEQ ID Nos. 267, 268, 269; SEQ ID Nos. 271, 272, 273; SEQ ID Nos. 275, 276, 277; SEQ ID Nos. 279, 280, 281; SEQ ID Nos. 283, 284, 285; SEQ ID Nos. 287, 288, 289; SEQ ID Nos. 291, 292, 293; SEQ ID Nos. 295, 296, 297; SEQ ID Nos. 299, 300, 301; SEQ ID Nos. 303, 304, 305; SEQ ID Nos. 307, 308, 309; SEQ ID Nos. 311, 312, 313; SEQ ID Nos. 315, 316, 317; SEQ ID Nos. 319, 320, 321, SEQ ID Nos. 323, 324, 325; SEQ ID Nos. 327, 328, 329; SEQ ID Nos. 331, 332, 333; SEQ ID Nos. 335, 336, 337; SEQ ID Nos. 339, 340, 341; SEQ ID Nos. 343, 344, 345; SEQ ID Nos. 347, 348, 349; SEQ ID Nos. 351, 352, 353; SEQ ID Nos. 355, 356, 357; SEQ ID Nos. 359, 360, 361; SEQ ID Nos. 363, 364, 365; SEQ ID Nos. 367, 368, 369; SEQ ID Nos. 371. 372, 373; SEQ ID Nos. 275, 376, 377; SEQ ID Nos. 379, 380, 381; SEQ ID Nos. 383, 384, 385; SEQ ID Nos. 387, 388, 389; SEQ ID Nos. 391, 392, 393; SEQ ID Nos. 395, 396, 397; SEQ ID Nos. 399, 400, 401; SEQ ID Nos. 403, 404, 405; SEQ ID Nos. 407, 408, 409; SEQ ID Nos. 411, 412, 413; SEQ ID Nos. 415, 416, 417; SEQ ID Nos. 419, 420, 421; SEQ ID Nos. 423, 424, 425; SEQ ID Nos. 427, 428, 429; SEQ ID Nos. 431, 432, 433; SEQ ID Nos. 435, 436, 437; SEQ ID Nos. 439, 440, 441; SEQ ID Nos. 443, 444, 445; SEQ ID Nos. 447, 448, 449; SEQ ID Nos. 451, 452, 453; SEQ ID Nos. 455, 456, 457 or SEQ ID Nos. 459, 460, 461.

In another embodiment, said CDR1 comprises or consists of the amino acid sequence SEQ ID NO. 251 or a sequence with at least at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto. In one embodiment, said CDR2 comprises or consists of the amino acid sequence SEQ ID No. 252 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto. In one embodiment, said CDR3 comprises or consists of the amino acid sequence SEQ ID No. 253 or a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology thereto.

In another embodiment, the V$_H$ single domain antibody comprises or consists of a polypeptide sequence as shown for any one of V$_H$ single domain antibodies 2.1 to 2.53 as shown in Table 2 or a sequence with at least 60%, 70%, 80%, 90%, 95% or more sequence homology thereto. Thus, the V$_H$ single domain antibody comprises or consists of an amino acid sequence selected from SEQ ID Nos. 254, 258, 262, 266, 270, 274, 278, 282, 286, 290, 294, 298, 302, 306, 310, 314, 318, 322, 326, 330, 334, 338, 342, 346, 350, 354, 358, 362, 366, 370, 374, 378, 382, 386, 390, 394, 398, 402, 406, 410, 414, 418, 422, 426, 430, 434, 438, 442, 446, 450, 454, 458 or 462 or a sequence with at least 60%, 70%, 80%, 90%, 95% or more sequence homology thereto. In one embodiment, the V$_H$ single domain antibody comprises or consists of SEQ ID No. 298, 302, 306, 310, 314, 318, 322, 326, 330, 334, 338, 342, 346, 350, 354, 358, 362, 366, 370, 374, 378, 382, 386, 390, 394, 398, 402, 406, 410, 414, 418, 422, 426, 430, 434, 438, 442, 446, 450, 454, 458 or 462 or a sequence with at least 60%, 70%, 80%, 90%, 95% or more sequence homology thereto. In one embodiment, the V$_H$ single domain antibody comprises or consists of 254 or 298 or a sequence with at least 60%, 70%, 80%, 90%, 95% or more sequence homology thereto. In one embodiment, said sequence homology is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

TABLE 2

Full length sequences and CDR sequences of V$_H$ single domain antibodies

| Name | CDR1 sequence of VH | CDR2 sequence of VH | CDR3 sequence of VH | Full length VH sequence |
|---|---|---|---|---|
| 2.1 | SEQ ID NO: 251 DYAMS | SEQ ID NO: 252 GITWNG GSTGYA DSVKD | SEQ ID NO: 253 DKYSYA WSYDGF DI | SEQ ID NO: 254 EVQLVESGGGVVRPGGSLRLSCAASGFTF DDYAMSWVRQAPGKGLEWVSGITWNGG STGYADSVKDRFTISRDNAKNSLYLQMNSL RAEDTALYYCVRDKYSYAWSYDGFDIWG QGTMVTVSS |
| 2.2 | SEQ ID NO: 255 DYGMS | SEQ ID NO: 256 GISRNGG SAGYSD SAKD | SEQ ID NO: 257 EKYSSG WSYDDF DI | SEQ ID NO: 258 EVQLLESGGGVVRPGGSLRLSCAASGFTF DDYGMSWVRQPPGKGLEWVSGISRNGGS AGYSDSAKDRFTISRDNAKNSLYLQMNSL RADDTAMYYCAREKYSSGWSYDDFDIWG QGTMVTVSS |
| 2.3 | SEQ ID NO: 259 DYGMS | SEQ ID NO: 260 GISRNGG SAGYSD SAKD | SEQ ID NO: 261 EKYSSG WSYDDF DI | SEQ ID NO: 262 QVQLVESGGGVVRPGGSLRLSCAASGFTF DDYGMSWVRQSPGKGLEWVSGISRNGGS AGYSDSAKDRFTISRDNAKNSLYLQMNSL RADDTAMYYCAREKYSSGWSYDDFDIWG QGTMVTVSS |

TABLE 2-continued

Full length sequences and CDR sequences of V_H single domain antibodies

| Name | CDR1 sequence of VH | CDR2 sequence of VH | CDR3 sequence of VH | Full length VH sequence |
|---|---|---|---|---|
| 2.4 | SEQ ID NO: 263 DYGMS | SEQ ID NO: 264 GISRNGG SAGYSD SAKD | SEQ ID NO: 265 EKYSSG WSYDDF DI | SEQ ID NO: 266 QVQLVESGGGVVRPGGSLRLSCAASGFTF DDYGMSWVRQPPGKGLEWVSGISRNGGS AGYSDSAKDRFTISRDNAKNSLYLQMNSL RADDTAMYYCAREKYSSGWSYDDFDIWG QGTMVTVSS |
| 2.5 | SEQ ID NO: 267 DYGMS | SEQ ID NO: 268 GISRNGG SAGYSD SAKD | SEQ ID NO: 269 EKYSSG WSYDDF DI | SEQ ID NO: 270 EVQLVESGGGVVRPGGSLRLSCAASGFTF DDYGMSWVRQPPGKGLEWVSGISRNGGS AGYSDSAKDRFTISRDNAKNSLYLQMNSL RADDTAMYYCAREKYSSGWSYDDFDIWG QGTMVTVSS |
| 2.6 | SEQ ID NO: 271 DYGMS | SEQ ID NO: 272 GISRNGG STGYADS VKD | SEQ ID NO: 273 DPYSSG WSYDSF DI | SEQ ID NO: 274 QVQLVESGGGVVRLGGSLRLSCAASGFSF VDYGMSWVRQAPGQGLEWVSGISRNGG STGYADSVKDRFTISRDNAKNTLYLQMNSL RAEDTALYYCARDPYSSGWSYDSFDIWG QGTMVTVSS |
| 2.7 | SEQ ID NO: 275 DYGMS | SEQ ID NO: 276 GISRNGG STGYTAS VKD | SEQ ID NO: 277 EKYSSG WSYDDF DI | SEQ ID NO: 278 QVQLVESGGGVVRPGGSLRLSCAASGFTF DDYGMSWVRQAPGKGLEWVSGISRNGGS TGYTASVKDRFTISRDNAKNSLYLQMNSLR ADDTAMYYCAREKYSSGWSYDDFDIWGQ GTMVTVSS |
| 2.8 | SEQ ID NO: 279 DYAMS | SEQ ID NO: 280 GISWNG GSAGYA DSVKD | SEQ ID NO: 281 DPHSSA WSYDAF DI | SEQ ID NO: 282 QVQLVESGGGLVQPGGSLRLSCAASGFTF DDYAMSWVRQAPGKGLEWVSGISWNGG SAGYADSVKDRFTISRDNAKNSLYLQMNS LRAEDTALYYCARDPHSSAWSYDAFDIWG QGTMVTVSS |
| 2.9 | SEQ ID NO: 283 DYAMS | SEQ ID NO: 284 GISWNG GSKGYA DSVKD | SEQ ID NO: 285 DPYSGA WSYDAF DI | SEQ ID NO: 286 QVQLVESGGGVVRPGGSLRLSCAASGFTF DDYAMSWVRQAPGKGLEWVSGISWNGG SKGYADSVKDRFTISRDNAKNSLYLQMNS LRAEDTALYYCARDPYSGAWSYDAFDIWG QGTMVTVSS |
| 2.10 | SEQ ID NO: 287 DYAMS | SEQ ID NO: 288 GISWNG GSTGYA DSVKD | SEQ ID NO: 289 DPYSGA WSYDAF DI | SEQ ID NO: 290 QVQLVESGGGVVRPGGSLRLSCAASGFTF DDYAMSWVRQAPGKGLEWVSGISWNGG STGYADSVKDRFTISRDNAKNSLYLQMNSL RAEDTALYYCARDPYSGAWSYDAFDIWG QGTMVTVSS |
| 2.11 | SEQ ID NO: 291 NYAMS | SEQ ID NO: 292 GITWNG GSTGYA DSVKD | SEQ ID NO: 293 DKYSYA WSYDTF DI | SEQ ID NO: 294 QVQLVESGGGVVRPGGSLRLSCAASGFTF DNYAMSWVRQAPGKGLEWVSGITWNGG STGYADSVKDRFTISRDNAKNSLYLQMNSL RAEDTALYYCARDKYSYAWSYDTFDIRGQ GTMVTVSS |
| 2.12 | SEQ ID NO: 295 DYAMS | SEQ ID NO: 296 GITWNAG STGYADS VKG | SEQ ID NO: 297 DKYSYA WSYDDF DI | SEQ ID NO: 298 EVQLVESGGGVVRPGGSLRLSCAASGFTF DDYAMSWVRQAPGKGLEWVSGITWNAGS TGYADSVKGRFTISRDNAKNSLYLQMNSL RAEDTALYYCVRDKYSYAWSYDDFDIWGQ GTMVTVSS |
| 2.13 | SEQ ID NO: 299 DYAMS | SEQ ID NO: 300 GITWNR GSTGYA DSVKG | SEQ ID NO: 301 DKYSYA WSYDDF DI | SEQ ID NO: 302 EVQLVESGGGVVRPGGSLRLSCAASGFTF DDYAMSWVRQAPGKGLEWVSGITWNRGS TGYADSVKGRFTISRDNAKNSLYLQMNSL RAEDTALYYCVRDKYSYAWSYDDFDIWGQ GTMVTVSS |

TABLE 2-continued

Full length sequences and CDR sequences of $V_H$ single domain antibodies

| Name | CDR1 sequence of VH | CDR2 sequence of VH | CDR3 sequence of VH | Full length VH sequence |
|---|---|---|---|---|
| 2.14 | SEQ ID NO: 303 DYAFS | SEQ ID NO: 304 GITWNG GSTGYA DSVKG | SEQ ID NO: 305 DKYSYA WSYDGF DI | SEQ ID NO: 306 EVQLVESGGGVVRPGGSLRLSCAASGFTF DDYAFSWVRQAPGKGLEWVSGITVVNGGS TGYADSVKGRFTISRDNAKNSLYLQMNSL RAEDTALYYCVRDKYSYAWSYDGFDIWG QGTMVTVSS |
| 2.15 | SEQ ID NO: 307 DYAQS | SEQ ID NO: 308 GITWNG GSTGYA DSVKG | SEQ ID NO: 309 DKYSYA WSYDGF DI | SEQ ID NO: 310 EVQLVESGGGVVRPGGSLRLSCAASGFTF DDYAQSWVRQAPGKGLEWVSGITWNGGS TGYADSVKGRFTISRDNAKNSLYLQMNSL RAEDTALYYCVRDKYSYAWSYDGFDIWG QGTMVTVSS |
| 2.16 | SEQ ID NO: 311 DYANS | SEQ ID NO: 312 GITWNG GSTGYA DSVKG | SEQ ID NO: 313 DKYSYA WSYDGF DI | SEQ ID NO: 314 EVQLVESGGGVVRPGGSLRLSCAASGFTF DDYANSWVRQAPGKGLEWVSGITWNGGS TGYADSVKGRFTISRDNAKNSLYLQMNSL RAEDTALYYCVRDKYSYAWSYDGFDIWG QGTMVTVSS |
| 2.17 | SEQ ID NO: 315 DYAGS | SEQ ID NO: 316 GITWNG GSTGYA DSVKG | SEQ ID NO: 317 DKYSYA WSYDGF DI | SEQ ID NO: 318 EVQLVESGGGVVRPGGSLRLSCAASGFTF DDYAGSWVRQAPGKGLEWVSGITWNGGS TGYADSVKGRFTISRDNAKNSLYLQMNSL RAEDTALYYCVRDKYSYAWSYDGFDIWG QGTMVTVSS |
| 2.18 | SEQ ID NO: 319 DYAES | SEQ ID NO: 320 GITWNG GSTGYA DSVKG | SEQ ID NO: 321 DKYSYA WSYDGF DI | SEQ ID NO: 322 EVQLVESGGGVVRPGGSLRLSCAASGFTF DDYAESWVRQAPGKGLEWVSGITWNGGS TGYADSVKGRFTISRDNAKNSLYLQMNSL RAEDTALYYCVRDKYSYAWSYDGFDIWG QGTMVTVSS |
| 2.19 | SEQ ID NO: 323 DYAWS | SEQ ID NO: 324 GITWNG GSTGYA DSVKG | SEQ ID NO: 325 DKYSYA WSYDGF DI | SEQ ID NO: 326 EVQLVESGGGVVRPGGSLRLSCAASGFTF DDYAWSWVRQAPGKGLEWVSGITWNGG STGYADSVKGRFTISRDNAKNSLYLQMNS LRAEDTALYYCVRDKYSYAWSYDGFDIWG QGTMVTVSS |
| 2.20 | SEQ ID NO: 327 DYAVS | SEQ ID NO: 328 GITWNG GSTGYA DSVKG | SEQ ID NO: 329 DKYSYA WSYDGF DI | SEQ ID NO: 330 EVQLVESGGGVVRPGGSLRLSCAASGFTF DDYAVSWVRQAPGKGLEWVSGITWNGGS TGYADSVKGRFTISRDNAKNSLYLQMNSL RAEDTALYYCVRDKYSYAWSYDGFDIWG QGTMVTVSS |
| 2.21 | SEQ ID NO: 331 DYALS | SEQ ID NO: 332 GITWNG GSTGYA DSVKG | SEQ ID NO: 333 DKYSYA WSYDGF DI | SEQ ID NO: 334 EVQLVESGGGVVRPGGSLRLSCAASGFTF DDYALSWVRQAPGKGLEWVSGITWNGGS TGYADSVKGRFTISRDNAKNSLYLQMNSL RAEDTALYYCVRDKYSYAWSYDGFDIWG QGTMVTVSS |
| 2.22 | SEQ ID NO: 335 DYASS | SEQ ID NO: 336 GITWNG GSTGYA DSVKG | SEQ ID NO: 337 DKYSYA WSYDGF DI | SEQ ID NO: 338 EVQLVESGGGVVRPGGSLRLSCAASGFTF DDYASSWVRQAPGKGLEWVSGITWNGGS TGYADSVKGRFTISRDNAKNSLYLQMNSL RAEDTALYYCVRDKYSYAWSYDGFDIWG QGTMVTVSS |
| 2.23 | SEQ ID NO: 339 DYARS | SEQ ID NO: 340 GITWNG GSTGYA DSVKG | SEQ ID NO: 341 DKYSYA WSYDGF DI | SEQ ID NO: 342 EVQLVESGGGVVRPGGSLRLSCAASGFTF DDYARSWVRQAPGKGLEWVSGITWNGGS TGYADSVKGRFTISRDNAKNSLYLQMNSL RAEDTALYYCVRDKYSYAWSYDGFDIWG QGTMVTVSS |

TABLE 2-continued

Full length sequences and CDR sequences of V$_H$ single domain antibodies

| Name | CDR1 sequence of VH | CDR2 sequence of VH | CDR3 sequence of VH | Full length VH sequence |
|---|---|---|---|---|
| 2.24 | SEQ ID NO: 343 DYAMS | SEQ ID NO: 344 GITWNSGSTGYADSVKD | SEQ ID NO: 345 DKYSYAWSYDDFDI | SEQ ID NO: 346 EVQLVESGGGVVRPGGSLRLSCAASGFTFDDYAMSWVRQAPGKGLEWVSGITWNSGSTGYADSVKDRFTISRDNAKNSLYLQMNSLRAEDTALYYCVRDKYSYAWSYDDFDIWGQGTMVTVSS |
| 2.25 | SEQ ID NO: 347 DYAMS | SEQ ID NO: 348 GITWNQGSTGYADSVKD | SEQ ID NO: 349 DKYSYAWSYDDFDI | SEQ ID NO: 350 EVQLVESGGGVVRPGGSLRLSCAASGFTFDDYAMSWVRQAPGKGLEWVSGITWNQGSTGYADSVKDRFTISRDNAKNSLYLQMNSLRAEDTALYYCVRDKYSYAWSYDDFDIWGQGTMVTVSS |
| 2.26 | SEQ ID NO: 351 DYAMS | SEQ ID NO: 352 GITWNHGSTGYADSVKD | SEQ ID NO: 353 DKYSYAWSYDVFDI | SEQ ID NO: 354 EVQLVESGGGVVRPGGSLRLSCAASGFTFDDYAMSWVRQAPGKGLEWVSGITWNHGSTGYADSVKDRFTISRDNAKNSLYLQMNSLRAEDTALYYCVRDKYSYAWSYDVFDIWGQGTMVTVSS |
| 2.27 | SEQ ID NO: 355 DYAMS | SEQ ID NO: 356 GITWNAGSTGYADSVKD | SEQ ID NO: 357 DKYSYAWSYDDFDI | SEQ ID NO: 358 EVQLVESGGGVVRPGGSLRLSCAASGFTFDDYAMSWVRQAPGKGLEWVSGITWNAGSTGYADSVKDRFTISRDNAKNSLYLQMNSLRAEDTALYYCVRDKYSYAWSYDDFDIWGQGTMVTVSS |
| 2.28 | SEQ ID NO: 359 DYAMS | SEQ ID NO: 360 GITWNGGSTGYADSVKG | SEQ ID NO: 361 DKYSYAWSYDVFDI | SEQ ID NO: 362 EVQLVESGGGVVRPGGSLRLSCAASGFTFDDYAMSWVRQAPGKGLEWVSGITWNGGSTGYADSVKGRFTISRDNAKNSLYLQMNSLRAEDTALYYCVRDKYSYAWSYDVFDIWGQGTMVTVSS |
| 2.29 | SEQ ID NO: 363 DYAMS | SEQ ID NO: 364 GITWNGGSTGYADSVKG | SEQ ID NO: 365 DKYSYAWSYDDFDI | SEQ ID NO: 366 EVQLVESGGGVVRPGGSLRLSCAASGFTFDDYAMSWVRQAPGKGLEWVSGITWNGGSTGYADSVKGRFTISRDNAKNSLYLQMNSLRAEDTALYYCVRDKYSYAWSYDDFDIWGQGTMVTVSS |
| 2.30 | SEQ ID NO: 367 DYAMS | SEQ ID NO: 368 GITWNKGSTGYADSVKD | SEQ ID NO: 369 DKYSYAWSYDDFDI | SEQ ID NO: 370 EVQLVESGGGVVRPGGSLRLSCAASGFTFDDYAMSWVRQAPGKGLEWVSGITWNKGSTGYADSVKDRFTISRDNAKNSLYLQMNSLRAEDTALYYCVRDKYSYAWSYDDFDIWGQGTMVTVSS |
| 2.31 | SEQ ID NO: 371 DYAMS | SEQ ID NO: 372 GITWNRGSTGYADSVKD | SEQ ID NO: 373 DKYSYAWSYDDFDI | SEQ ID NO: 374 EVQLVESGGGVVRPGGSLRLSCAASGFTFDDYAMSWVRQAPGKGLEWVSGITWNRGSTGYADSVKDRFTISRDNAKNSLYLQMNSLRAEDTALYYCVRDKYSYAWSYDDFDIWGQGTMVTVSS |
| 2.32 | SEQ ID NO: 375 DYAIS | SEQ ID NO: 376 GITWNGGSTGYADSVKD | SEQ ID NO: 377 DKYSYAWSYDGFDI | SEQ ID NO: 378 EVQLVESGGGVVRPGGSLRLSCAASGFTFDDYAISWVRQAPGKGLEWVSGITWNGGSTGYADSVKDRFTISRDNAKNSLYLQMNSLRAEDTALYYCVRDKYSYAWSYDGFDIWGQGTMVTVSS |
| 2.33 | SEQ ID NO: 379 DYATS | SEQ ID NO: 380 GITWNGGSTGYADSVKD | SEQ ID NO: 381 DKYSYAWSYDGFDI | SEQ ID NO: 382 EVQLVESGGGVVRPGGSLRLSCAASGFTFDDYATSWVRQAPGKGLEWVSGITWNGGSTGYADSVKDRFTISRDNAKNSLYLQMNSLRAEDTALYYCVRDKYSYAWSYDGFDIWGQGTMVTVSS |

TABLE 2-continued

Full length sequences and CDR sequences of V$_H$ single domain antibodies

| Name | CDR1 sequence of VH | CDR2 sequence of VH | CDR3 sequence of VH | Full length VH sequence |
|---|---|---|---|---|
| 2.34 | SEQ ID NO: 383 DYANS | SEQ ID NO: 384 GITWNG GSTGYA DSVKD | SEQ ID NO: 385 DKYSYA WSYDGF DI | SEQ ID NO: 386 EVQLVESGGGVVRPGGSLRLSCAASGFTF DDYANSWVRQAPGKGLEWVSGITWNGGS TGYADSVKDRFTISRDNAKNSLYLQMNSL RAEDTALYYCVRDKYSYAWSYDGFDIWG QGTMVTVSS |
| 2.35 | SEQ ID NO: 387 DYADS | SEQ ID NO: 388 GITWNG GSTGYA DSVKD | SEQ ID NO: 389 DKYSYA WSYDGF DI | SEQ ID NO: 390 EVQLVESGGGVVRPGGSLRLSCAASGFTF DDYADSWVRQAPGKGLEWVSGITWNGGS TGYADSVKDRFTISRDNAKNSLYLQMNSL RAEDTALYYCVRDKYSYAWSYDGFDIWG QGTMVTVSS |
| 2.36 | SEQ ID NO: 391 DYASS | SEQ ID NO: 392 GITWNG GSTGYA DSVKD | SEQ ID NO: 393 DKYSYA WSYDGF DI | SEQ ID NO: 394 EVQLVESGGGVVRPGGSLRLSCAASGFTF DDYASSWVRQAPGKGLEWVSGITWNGGS TGYADSVKDRFTISRDNAKNSLYLQMNSL RAEDTALYYCVRDKYSYAWSYDGFDIWG QGTMVTVSS |
| 2.37 | SEQ ID NO: 395 DYALS | SEQ ID NO: 396 GITWNG GSTGYA DSVKD | SEQ ID NO: 397 DKYSYA WSYDGF DI | SEQ ID NO: 398 EVQLVESGGGVVRPGGSLRLSCAASGFTF DDYALSWVRQAPGKGLEWVSGITWNGGS TGYADSVKDRFTISRDNAKNSLYLQMNSL RAEDTALYYCVRDKYSYAWSYDGFDIWG QGTMVTVSS |
| 2.38 | SEQ ID NO: 399 DYAGS | SEQ ID NO: 400 GITWNG GSTGYA DSVKD | SEQ ID NO: 401 DKYSYA WSYDGF DI | SEQ ID NO: 402 EVQLVESGGGVVRPGGSLRLSCAASGFTF DDYAGSWVRQAPGKGLEWVSGITWNGGS TGYADSVKDRFTISRDNAKNSLYLQMNSL RAEDTALYYCVRDKYSYAWSYDGFDIWG QGTMVTVSS |
| 2.39 | SEQ ID NO: 403 DYAES | SEQ ID NO: 404 GITWNG GSTGYA DSVKD | SEQ ID NO: 405 DKYSYA WSYDGF DI | SEQ ID NO: 406 EVQLVESGGGVVRPGGSLRLSCAASGFTF DDYAESWVRQAPGKGLEWVSGITWNGGS TGYADSVKDRFTISRDNAKNSLYLQMNSL RAEDTALYYCVRDKYSYAWSYDGFDIWG QGTMVTVSS |
| 2.40 | SEQ ID NO: 407 DYAWS | SEQ ID NO: 408 GITWNG GSTGYA DSVKD | SEQ ID NO: 409 DKYSYA WSYDGF DI | SEQ ID NO: 410 EVQLVESGGGVVRPGGSLRLSCAASGFTF DDYAWSWVRQAPGKGLEWVSGITWNGG STGYADSVKDRFTISRDNAKNSLYLQMNSL RAEDTALYYCVRDKYSYAWSYDGFDIWG QGTMVTVSS |
| 2.41 | SEQ ID NO: 411 DYARS | SEQ ID NO: 412 GITWNG GSTGYA DSVKD | SEQ ID NO: 413 DKYSYA WSYDGF DI | SEQ ID NO: 414 EVQLVESGGGVVRPGGSLRLSCAASGFTF DDYARSWVRQAPGKGLEWVSGITWNGGS TGYADSVKDRFTISRDNAKNSLYLQMNSL RAEDTALYYCVRDKYSYAWSYDGFDIWG QGTMVTVSS |
| 2.42 | SEQ ID NO: 415 DYAFS | SEQ ID NO: 416 GITWNG GSTGYA DSVKD | SEQ ID NO: 417 DKYSYA WSYDGF DI | SEQ ID NO: 418 EVQLVESGGGVVRPGGSLRLSCAASGFTF DDYAFSWVRQAPGKGLEWVSGITWNGGS TGYADSVKDRFTISRDNAKNSLYLQMNSL RAEDTALYYCVRDKYSYAWSYDGFDIWG QGTMVTVSS |
| 2.43 | SEQ ID NO: 419 DYAVS | SEQ ID NO: 420 GITWNG GSTGYA DSVKD | SEQ ID NO: 421 DKYSYA WSYDGF DI | SEQ ID NO: 422 EVQLVESGGGVVRPGGSLRLSCAASGFTF DDYAVSWVRQAPGKGLEWVSGITWNGGS TGYADSVKDRFTISRDNAKNSLYLQMNSL RAEDTALYYCVRDKYSYAWSYDGFDIWG QGTMVTVSS |

TABLE 2-continued

Full length sequences and CDR sequences of V_H single domain antibodies

| Name | CDR1 sequence of VH | CDR2 sequence of VH | CDR3 sequence of VH | Full length VH sequence |
|---|---|---|---|---|
| 2.44 | SEQ ID NO: 423 DYAMS | SEQ ID NO: 424 GITWTGG STGYADS VKD | SEQ ID NO: 425 DKYSYA WSYDGF DI | SEQ ID NO: 426 EVQLVESGGGVVRPGGSLRLSCAASGFTF DDYAMSWVRQAPGKGLEWVSGITWTGGS TGYADSVKDRFTISRDNAKNSLYLQMNSL RAEDTALYYCVRDKYSYAWSYDGFDIWG QGTMVTVSS |
| 2.45 | SEQ ID NO: 427 DYAMS | SEQ ID NO: 428 GITWSG GSTGYA DSVKD | SEQ ID NO: 429 DKYSYA WSYDGF DI | SEQ ID NO: 430 EVQLVESGGGVVRPGGSLRLSCAASGFTF DDYAMSWVRQAPGKGLEWVSGITWSGGS TGYADSVKDRFTISRDNAKNSLYLQMNSL RAEDTALYYCVRDKYSYAWSYDGFDIWG QGTMVTVSS |
| 2.46 | SEQ ID NO: 431 DYAMS | SEQ ID NO: 432 GITWPG GSTGYA DSVKD | SEQ ID NO: 433 DKYSYA WSYDGF DI | SEQ ID NO: 434 EVQLVESGGGVVRPGGSLRLSCAASGFTF DDYAMSWVRQAPGKGLEWVSGITWPGGS TGYADSVKDRFTISRDNAKNSLYLQMNSL RAEDTALYYCVRDKYSYAWSYDGFDIWG QGTMVTVSS |
| 2.47 | SEQ ID NO: 435 DYAMS | SEQ ID NO: 436 GITWIGG STGYADS VKD | SEQ ID NO: 437 DKYSYA WSYDGF DI | SEQ ID NO: 438 EVQLVESGGGVVRPGGSLRLSCAASGFTF DDYAMSWVRQAPGKGLEWVSGITWIGGS TGYADSVKDRFTISRDNAKNSLYLQMNSL RAEDTALYYCVRDKYSYAWSYDGFDIWG QGTMVTVSS |
| 2.48 | SEQ ID NO: 439 DYAMS | SEQ ID NO: 440 GITWLGG STGYADS VKD | SEQ ID NO: 441 DKYSYA WSYDGF DI | SEQ ID NO: 442 EVQLVESGGGVVRPGGSLRLSCAASGFTF DDYAMSWVRQAPGKGLEWVSGITWIGGS TGYADSVKDRFTISRDNAKNSLYLQMNSL RAEDTALYYCVRDKYSYAWSYDGFDIWG QGTMVTVSS |
| 2.49 | SEQ ID NO: 443 DYAMS | SEQ ID NO: 444 GITWNG GSTGYA DSVKG | SEQ ID NO: 445 DKYSYA WSYDGF DI | SEQ ID NO: 446 EVQLVESGGGVVRPGGSLRLSCAASGFTF DDYAMSWVRQAPGKGLEWVSGITWNGG STGYADSVKGRFTISRDNAKNSLYLQMNS LRAEDTALYYCVRDKYSYAWSYDGFDIWG QGTMVTVSS |
| 2.50 | SEQ ID NO: 447 DYAMS | SEQ ID NO: 448 GITWKG GSTGYA DSVKD | SEQ ID NO: 449 DKYSYA WSYDGF DI | SEQ ID NO: 450 EVQLVESGGGVVRPGGSLRLSCAASGFTF DDYAMSWVRQAPGKGLEWVSGITWKGGS TGYADSVKDRFTISRDNAKNSLYLQMNSL RAEDTALYYCVRDKYSYAWSYDGFDIWG QGTMVTVSS |
| 2.51 | SEQ ID NO: 451 DYAMS | SEQ ID NO: 452 GITWRG GSTGYA DSVKD | SEQ ID NO: 453 DKYSYA WSYDGF DI | SEQ ID NO: 454 EVQLVESGGGVVRPGGSLRLSCAASGFTF DDYAMSWVRQAPGKGLEWVSGITWRGG STGYADSVKDRFTISRDNAKNSLYLQMNSL RAEDTALYYCVRDKYSYAWSYDGFDIWG QGTMVTVSS |
| 2.52 | SEQ ID NO: 455 DYAMS | SEQ ID NO: 456 GITWNG GSTGYA DSVKD | SEQ ID NO: 457 DKYSYA WSYDVF DI | SEQ ID NO: 458 EVQLVESGGGVVRPGGSLRLSCAASGFTF DDYAMSWVRQAPGKGLEWVSGITWNGG STGYADSVKDRFTISRDNAKNSLYLQMNSL RAEDTALYYCVRDKYSYAWSYDVFDIWGQ GTMVTVSS |
| 2.53 | SEQ ID NO: 459 DYAMS | SEQ ID NO: 460 GITWNG GSTGYA DSVKD | SEQ ID NO: 461 DKYSYA WSYDDF DI | SEQ ID NO: 462 EVQLVESGGGVVRPGGSLRLSCAASGFTF DDYAMSWVRQAPGKGLEWVSGITWNGG STGYADSVKDRFTISRDNAKNSLYLQMNSL RAEDTALYYCVRDKYSYAWSYDDFDIWGQ GTMVTVSS |

In some embodiments, the invention provides a $V_H$ single domain antibody that is a variant of any of the above single $V_H$ domain antibodies having one or more amino acid substitutions, deletions, insertions or other modifications, and which retains a biological function of the single domain antibody. Thus, variant $V_H$ single domain antibody can be sequence engineered. Modifications include at least one substitution, deletion or insertion of one or more codons encoding the single domain antibody or polypeptide that results in a change in the amino acid sequence as compared with the native sequence $V_H$ single domain antibody or polypeptide. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 10, for example 1, 2, 3, 4, 5, 6, 7, 8, 9 or 10 amino acids or 1 to 20 amino acids. The variation allowed may be determined by systematically making insertions, deletions or substitutions of amino acids in the sequence and testing the resulting variants for activity exhibited by the full-length or mature native sequence. A variant of a $V_H$ single domain antibody described herein has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology to the non-variant molecule, preferably at least 95%, 96%, 97%, 98% or 99% sequence homology.

In one embodiment, the modification is a conservative sequence modification. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of a single domain antibody of the invention can be replaced with other amino acid residues from the same side chain family and the altered antibody can be tested for retained function (i.e., the functions set forth in (c) through (I) above) using the functional assays described herein.

In some embodiments, the invention provides a $V_H$ single domain antibody that is a variant of a single domain antibody selected from those shown in Table 1 or 2 that comprises one or more sequence modification and has improvements in one or more of a property such as binding affinity, specificity, thermostability, expression level, effector function, glycosylation, reduced immunogenicity, or solubility as compared to the unmodified single domain antibody.

In one embodiment, modifications can be made to decrease the immunogenicity of the single domain antibody. For example, one approach is to revert one or more framework residues to the corresponding human germline sequence. More specifically, a single domain antibody that has undergone somatic mutation may contain framework residues that differ from the germline sequence from which the single domain antibody is derived. Such residues can be identified by comparing the single domain antibody framework sequences to the germline sequences from which the single domain antibody is derived.

To return one or more of the amino acid residues in the framework region sequences to their germline configuration, the somatic mutations can be "backmutated" to the germline sequence by, for example, site-directed mutagenesis or PCR-mediated mutagenesis.

Another type of framework modification involves mutating one or more residues within the framework region, or even within one or more CDR regions, to remove T cell epitopes to thereby reduce the potential immunogenicity of the antibody.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen.

A skilled person will know that there are different ways to identify, obtain and optimise the antigen binding molecules as described herein, including in vitro and in vivo expression libraries. This is further described in the examples. Optimisation techniques known in the art, such as display (e.g., ribosome and/or phage display) and/or mutagenesis (e.g., error-prone mutagenesis) can be used. The invention therefore also comprises sequence optimised variants of the single domain antibodies described herein.

In one embodiment, the variant $V_H$ single domain antibody is selected from any one of SEQ ID Nos. 4, 8, 12, 16, 20, 24, 28, 32, 36, 40, 44, 48, 52, 56, 60, 64, 68, 72, 76, 80, 104, 108, 112, 116, 120, 124, 128, 132, 136, 140, 144, 148, 152, 156, 160, 164, 168, 172, 176, 180, 184, 188, 192, 196, 200, 204, 208, 212, 216, 220 or 254, 258, 262, 266, 270, 274, 278, 282, 286, 290, 294, 298, 302, 306, 310, 314, 318, 322, 326, 330, 334, 338, 342, 346, 350, 354, 358, 362, 366, 370, 374, 378, 382, 386, 390, 394, 398, 402, 406, 410, 414, 418, 422, 426, 430, 434, 438, 442, 446, 450, 454, 458 or 462, but comprises one or more amino acid substitutions, for example 1, 2, 3, 4, 5, 6, 7, 8, 9 or 10 amino acid substitutions compared to these sequences. In one embodiment, the one or more amino acid substitution is in one or more of the framework areas. In another embodiment, the one or more amino acid substitution is in one or more of the CDRs. In one embodiment, the amino acid substitutions are in the framework and in the CDR sequences. In one embodiment, the single domain antibody comprises or consists of SEQ ID No. 4 or 136 or a sequence which comprises one or more amino acid substitutions, for example 1, 2, 3, 4, 5, 6, 7, 8, 9 or 10 amino acid substitutions.

In one embodiment, the $V_H$ single domain antibody comprises SEQ ID No. 4 with amino acid substitutions at one or more or all of the following positions: 5L, 32H, 44G, 55S, 66D, 77S and/or 105T. In one embodiment, the V$_H$ single domain antibody comprises SEQ ID No. 4 with amino acid substitutions selected from one of the following:
  a) 5L→V, 11S→L, 32H→Y, 44G→D, 55S→G, 62D→A, 66D→G and 77S→N or
  b) 5L→V, 11S→L, 32H→Y, 44G→D, 55S→G, 66D→G and 77S→N or
  c) 1E→Q, 5L→V, 11S→L, 32H→Y, 44G→D, 55S→G, 66D→G, 77S→N, 98R→K, 99E→D, 105T→I and 102M→T.

In one embodiment, the V$_H$ single domain antibody comprises SEQ ID No. 136 with amino acid substitutions at one or more or all of the following positions: M34, M58, V102, V116. In one embodiment, the V$_H$ single domain antibody comprises SEQ ID No 136 with amino acid substitutions selected from one of the following:
  a) M34→L, M58→Y, V116A (Humabody® 1.39);
  b) M34→F, G54→A, M58→Q, V102A (Humabody®1.50);
  c) V116A (Humabody®1.26);
  d) M34→L, M58→Q, V116A (Humabody®1.40).

In one embodiment, the V$_H$ single domain antibody comprises SEQ ID No. 254 with amino acid substitutions at one or more or all of the following positions: G 109, D66, G55. In one embodiment, the V$_H$ single domain antibody comprises SEQ ID No 254 with amino acid substitutions selected from one of the following:
  a) G109→D, D66→G, G55→A (Humabody® 2.12);
  b) G109→D, G55→A (Humabody® 2.27);
  c) G109→D (Humabody® 2.53);
  d) G109→D, D66→G (Humabody® 2.29);
  e) G109→V, D66→G (Humabody® 2.28).

In one embodiment, when Q is found at position 1, it is changed to E or another residue.

The numbering used above is based on the actual position of the residue in the molecule.

Thus, these amino acid changes can typically be made without altering the biological activity, function, or other desired property of the polypeptide, such as its affinity or its specificity for antigen. In general, single amino acid substitutions in nonessential regions of a polypeptide do not substantially alter biological activity. Furthermore, substitutions of amino acids that are similar in structure or function are less likely to disrupt the polypeptides' biological activity. Abbreviations for the amino acid residues that comprise polypeptides and peptides described herein, and conservative substitutions for these amino acid residues are shown in the Table below.

Amino Acid Residues and Examples of Conservative Amino Acid Substitutions

| Original residue Three letter code, single letter code | Conservative substitution |
| --- | --- |
| Alanine, Ala, A | Gly, Ser |
| Arginine, Arg, R | Lys, His |
| Asparagine, Asn, N | Gln, His |
| Aspartic acid Asp, D | Glu, Asn |
| Cysteine, Cys, C | Ser, Ala |
| Glutamine, Gln, Q | Asn |
| Glutamic acid, Glu, E | Asp, Gln |
| Glycine, Gly, G | Ala |
| Histidein, His, H | Asn, Gln |
| isoleucine, Ile, I | Leu, Val |
| Leucine, Leu, L | Ile, Val |
| Lysine, lys, K | Ar, His |
| Methionine, Met, M | Leu, Ile, Tyr |
| Phenylalanine, Phe, F | Tyr, Met, Leu |
| Proline, Pro, P | Ala |
| Serine, Ser, S | Thr |
| Threonine, Thr, T | Ser |
| Tryptophan, Trp, W | Tyr, Phe |
| Tyrosine, Tyr, Y | Try, Phe |
| Valine, Val, V | Ile, Leu |

V$_H$ single domain antibodies of the invention have shown excellent stability. Furthermore, V$_H$ single domain antibodies of the invention also show high specificity for human PD-1 and fast on rates (see examples).

The V$_H$ single domain antibodies of the invention preferably have KD and EC$_{50}$ values as further described herein and as shown in the examples. In one embodiment, the V$_H$ single domain antibodies specifically binding to a human PD-1 with a binding affinity of KD $10^{-8}$ to $10^{-10}$. In another embodiment, the single domain antibody has an EC50 value in the subnanomolar range as determined in binding to CHO-PD-1 cell line.

The term "KD" refers to the "equilibrium dissociation constant" and refers to the value obtained in a titration measurement at equilibrium, or by dividing the dissociation rate constant (Koff) by the association rate constant (Kon). "KA" refers to the affinity constant.

The association rate constant, the dissociation rate constant and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used. In one embodiment, a single domain antibody has a KD value in the nanomolar or subnanomaolar range.

The present invention further provides an isolated nucleic acid encoding a single domain antibody of the present invention. Nucleic acid may include DNA and/or RNA. In one aspect, the present invention provides a nucleic acid that codes for a CDR, for example CDR3, a set of two or three CDRs or a V$_H$ single domain antibody of the invention as shown in Table 1 or 2.

In one aspect, the invention thus also relates to a nucleic acid sequences comprising or consisting of a sequence selected from SEQ ID Nos. 81 to 100 or 221 to 250. These encode V$_H$ single domain antibody as shown in Table 1.

In one aspect, the invention thus also relates to a nucleic acid sequences comprising or consisting of a sequence selected from SEQ ID Nos. 463 to 515. These encode V$_H$ single domain antibody as shown in Table 2.

In one embodiment, the nucleic acid sequence has at least 60%, 70%, 80%, 90%, 95% or more sequence homology to one of the nucleic acid sequences described above selected from Table 2. In one embodiment, said sequence homology is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%.

A nucleic acid according to the present invention may comprise DNA or RNA and may be wholly or partially synthetic or recombinantly produced. Reference to a nucleotide sequence as set out herein encompasses a DNA molecule with the specified sequence, and encompasses a RNA molecule with the specified sequence in which U is substituted for T, unless context requires otherwise.

Furthermore, the invention relates to a nucleic acid construct comprising at least one nucleic acid as defined above. The construct may be in the form of a plasmid, vector, transcription or expression cassette.

The invention also relates to an isolated recombinant host cell comprising one or more nucleic acid construct as described above. The host cell may be a bacterial, viral, insect, plant, mammalian or other suitable host cell. In one embodiment, the cell is an *E. coli* cell. In another embodiment, the cell is a yeast cell. In another embodiment, the cell is a Chinese Hamster Ovary (CHO) cell.

In an embodiment, a method of making an anti-PD-1 single domain antibody as described herein is provided, wherein the method comprises culturing the host cell under conditions suitable for expression of the polynucleotide encoding the single domain antibody, and isolating the single domain antibody.

In another aspect, the invention provides antibodies or fragments thereof that bind to the same epitope on human PD-1 as any of the PD-1 single domain antibodies of the invention (i.e., antibodies that have the ability to cross-compete for binding to PD-1 with any of the single domain antibodies of the invention). In preferred embodiments, the reference antibody for cross-competition studies can be single domain antibody 1.1 (SEQ ID No. 4) or 2.1 (SEQ ID No. 254).

Such cross-competing antibodies can be identified based on their ability to cross-compete with any of single domain antibodies 1.1 to 1.50 or 2.1 to 2.53 in standard PD-1 binding assays. For example, BIAcore analysis, ELISA assays or flow cytometry may be used to demonstrate cross-competition with the single domain antibodies of the current invention.

In one embodiment, the invention provides a binding agent capable of binding human PD-1 wherein any one of the single domain antibodies described above displaces the binding agent in a competitive assay. In one embodiment, said is single domain antibody SEQ ID No. 4. In some embodiments, the binding agent is an antibody, a functional fragment thereof, for example a single domain antibody, or an antibody mimetic protein. In another aspect, invention provides a binding agent capable of binding human PD-1 wherein the binding agent displaces any one of the single domain antibodies described above in a competitive assay. In one embodiment, said single domain antibody comprises SEQ ID No. 4, 176, 254 or 298. In another aspect, invention provides a binding agent capable of binding human PD-1 wherein the binding agent binds to essentially the same epitope as the single domain antibody of the invention.

In another aspect, the invention provides an isolated heavy chain only antibody comprising a $V_H$ domain as described herein and set out in Table 1 or 2.

In one aspect, the invention relates to a binding agent comprising a single domain antibody according to the invention and at least a second moiety. Thus, the invention provides multifunctional molecules. In one embodiment, the at least second moiety is a binding molecule, for example selected from an antibody or antibody fragment (e.g., a Fab, F(ab')2, Fv, a single chain Fv fragment (scFv) or single domain antibody, for example a $V_H$ domain) or antibody mimetic protein. In one embodiment, the at least second moiety is a $V_H$ domain.

In one embodiment, the single domain antibody of the invention can be linked to an antibody Fc region or fragment thereof, comprising one or both of $C_H2$ and $C_H3$ domains, and optionally a hinge region.

The binding agent may be multivalent, for example bivalent, or multiparatopic, for example biparatopic. Thus, the binding molecule may comprise a first $V_H$ single domain antibody and $V_H(A)$ and a second $V_H$ single domain antibody and $V_H(B)$ and thus has the following formula: $V_H(A)$-$V_H(B)$.

Each $V_H$ comprises CDR and FR regions. Thus, the binding molecule may have the following formula: FR1(A)-CDR1(A)-FR2(A)-CDR2(A)-FR3(A)-CDR3(A)-FR4(A)-FR1(B)-CDR1(B)-FR2(B)-CDR2(BA)-FR3(B)-CDR3(B)-FR4(B). The order of the immunoglobulin single variable domains A and B is not particularly limited, so that, within a polypeptide of the invention, immunoglobulin single variable domain A may be located N-terminally and immunoglobulin single variable domain B may be located C-terminally, or vice versa. The $V_H$ domain antibodies are typically connected via a linker.

In one embodiment, the binding molecule is biparatopic. In one embodiment, the binding molecule is bispecific. Thus, in one aspect, the invention relates to a bispecific molecule comprising the single domain antibody described herein linked to a second functional moiety having a different binding specificity than said single domain antibody.

In one embodiment, biparatopic binding molecules are provided that comprise a first and a second binding molecule that bind to the target protein PD-1, but on different or overlapping sites. Complete or partial blocking can be seen in epitope binning studies. The first binding molecule is a single domain antibody according to the invention. In one embodiment, the second binding molecule is a PD-1 inhibitor that blocks the interaction of human PD-1 with one of its ligands. In one embodiment, the second binding molecule blocks the interaction of PD-1 with PD-L1. In one embodiment, the second binding molecule blocks the interaction of PD-1 with PD-L2. In one embodiment, the second binding molecule blocks the interaction of PD-1 with PD-L1 and PD-L2. The order of the first and second is binding molecule not particularly limited and can be reversed.

In one embodiment, the PD-1 inhibitor is an anti-PD-1 antibody chosen from Nivolumab®, Pembrolizumab® or Pidilizumab®. In some embodiments, the anti-PD-1 antibody is Nivolumab®. Alternative names for Nivolumab® include MDX-1106, MDX-1106-04, ONO-4538, or BMS-936558. In other embodiments, the anti-PD-1 antibody is Pembrolizumab®. Pembrolizumab® (Trade name KEYTRUDA® formerly Lambrolizumab®, also known as Merck 3745, MK-3475 or SCH-900475) is a humanized IgG4 monoclonal antibody that binds to PD-1. In some embodiments, the anti-PD-1 antibody is Pidilizumab®. Pidilizumab® (CT-011; Cure Tech) is a humanized IgG1k monoclonal antibody that binds to PD-1.

In one embodiment, the PD-1 inhibitor is a $V_H$ single domain antibody. Thus, another aspect relates to a binding molecule has the following formula: $V_H(A)$-L-$V_H(B)$ or $V_H(B)$-L-$V_H(A)$ wherein $V_H(A)$- is a $V_H$ single domain antibody as disclosed herein and wherein $V_H(B)$ is a $V_H$ single domain antibody that blocks binding of PD-1 to PD-L1 and/or PD-L2. L is a linker. Suitable linkers include for example a linker with GS residues such as $(Gly_4Ser)n$, where n=from 1 to 20, e.g. 1 to 10, e.g. 1, 2, 3, 4, 5, 6, 7, 8, 9 or 10. In one embodiment, the linker is $(Gly_4Ser)n$, where n=4 or more.

As shown in the examples, we have surprisingly shown that a binding molecule has the following formula: $V_H(A)$-L-$V_H(B)$ as described above provides an enhanced inhibitory effect compared to a $V_H$ single domain antibody that blocks binding of PD-1 to PD-L1 and/or PD-L2 and is not linked to a non-blocking $V_H$ single domain antibody. Thus, the $V_H$ single domain antibodies described herein find particular use for combination with a $V_H$ single domain antibody that blocks binding of PD-1 to PD-L1 and/or PD-L2 or that binds to another epitope in a biparatopic molecule. In another embodiment, the orientation is $V_H(B)$-L-$V_H(A)$. In one embodiment, L is (Gly$_4$Ser)n wherein n is 4 or more.

In one embodiment, the binding molecule is multivalent, for example bivalent. Bivalent binding molecules comprise two $V_H$ single domain antibodies that bind to the same target protein; e.g. human PD-1, at the same sites. In one embodiment, such molecules may comprise the same Humabody® $V_H$. In another embodiment, such molecules may comprise two $V_H$ single domain antibodies that are part of the same family, i.e. selected from the sequences shown in Table 1 or 2. In another embodiment, such molecules may comprise two $V_H$ single domain antibodies that are not part of the same family, but bind to the same site on human PD-1, for example a $V_H$ single domain antibody as shown in table 1 linked to a $V_H$ single domain antibody as shown in table 2.

Biparatopic and bivalent binding molecules of the present invention can be constructed using methods known in the art.

In certain embodiments, the binding agent is in the form of a multispecific, for example bispecific, binding agent providing multiple functionalities. Such multispecific agent comprises a single domain antibody according to the invention that has a first binding specificity to PD-1 and at least one further binding molecule with a second binding specificity. Said further binding molecule can be selected from an antibody, an antibody fragment or antibody mimetic. In one embodiment, said antibody fragment is selected from F(ab')$_2$, Fab, Fv, sFv or domain antibody. In one embodiment, said antibody fragment is a $V_H$ single domain antibody.

In one embodiment, the binding agent is bispecific and comprises a single domain antibody according to the invention that has a first binding specificity to PD-1 and a second binding molecule with a second binding specificity. In one embodiment, the second binding molecule binds to an immunomodulatory agent, a checkpoint modulator, an agent involved in T-cell activation, a tumor microenvironment modifier (TME) or a tumour-specific target.

For example, the immunomodulator can be an inhibitor of an immune checkpoint molecule selected from an inhibitor of one or more of PD-L1, PD-L2, CTLA-4, TIM-3, LAG-3, CEACAM, VISTA, BTLA, TIGIT, LAIR1, CD160, 2B4 or TGFR beta. In another embodiment, the immunomodulator can be an activator of a costimulatory molecule selected from an agonist of one or more of IL-2, 11-12, OX40, OX40L, CD2, CD3, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, B7-H4 or CD83 ligand, CD3, CD8, CD28, CD4 or ICAM-1.

In one embodiment, the binding agent described above comprises further binding molecules. Thus, the binding agent can be trispecific or tetraspecific. Additional specificities are also envisaged. Any combination of the aforesaid molecules can be made in a multispecific binding agent, for example, a trispecific binding agent that includes a single domain antibody of the invention and a second and third binding specificity.

In another embodiment, the at least second moiety may serve to prolong the half-life of the binding molecule. The second moiety may comprise a protein, for example an antibody, or part thereof that binds a serum albumin, e.g., human serum albumin (HSA) or mouse serum albumin (MSA). The second moiety may comprise a $V_H$ domain that binds serum albumin, e.g., human serum albumin (HSA) or mouse serum albumin (MSA).

The second moiety may comprise a serum albumin, e.g. a human serum albumin (HSA) or a variant thereof such as HSA C34S. Further provided is a binding molecule as described herein comprising a $V_H$ domain and an Fc domain, e.g., wherein the $V_H$ domain is fused to an Fc domain. Further provided is a binding molecule that comprises a second variable domain that specifically binds a second antigen, where the second antigen is an antigen other than human PD-1. The second antigen may be a cluster of differentiation (CD) molecule or a Major Histocompatibility Complex (MHC) Class II molecule.

In one embodiment, the anti-PD-1 single domain antibodies or multivalent binding agents of the invention are labelled with a detectable or functional label. A label can be any molecule that produces or can be induced to produce a signal, including but not limited to fluorophores, fluorescers, radiolabels, enzymes, chemiluminescers, a nuclear magnetic resonance active label or photosensitizers. Thus, the binding may be detected and/or measured by detecting fluorescence or luminescence, radioactivity, enzyme activity or light absorbance.

In still other embodiments, the anti-PD-1 single domain antibodies or multivalent binding agents of the invention are coupled to at least one therapeutic moiety, such as a drug, an enzyme or a toxin. In one embodiment, the therapeutic moiety is a toxin, for example a cytotoxic radionuclide, chemical toxin or protein toxin.

In another aspect, the anti-PD-1 single domain antibodies or multivalent binding agents of the invention are modified to increase half-life, for example by a chemical modification, especially by PEGylation, or by incorporation in a liposome or using a serum albumin protein.

Half-life may be increased by at least 1.5 times, preferably at least 2 times, such as at least 5 times, for example at least 10 times or more than 20 times, greater than the half-life of the corresponding $V_H$ single domain antibodies of the invention. For example, increased half-life may be more than 1 hours, preferably more than 2 hours, more preferably more than 6 hours, such as more than 12 hours, or even more than 24, 48 or 72 hours, compared to the corresponding $V_H$ single domain antibodies of the invention.

To generate a multivalent binding agents as described above, two binding molecules are connected by a linker, for example a polypeptide linker. Suitable linkers include for example a linker with GS residues such as (Gly$_4$Ser)n, where n=from 1 to 20, e.g., 1 to 10, e.g. 1, 2, 3, 4, 5, 6, 7, 8, 9 or 10.

In one embodiment, the anti-PD1 single domain antibodies can also be formatted to induce PD-1 agonism, for example in a bivalent or biparatopic format. PD-1 signalling is induced by PD-L1 and leads to downregulation of T cell activity. One could say that something that induces PD-1 signalling is a 'PD1 agonist', which has contrasting effect to a T cell agonist.

We provide evidence of a PD-1 engager that is capable of causing PD-1 agonism in absence of a CD3 or T cell receptor clustering antibody An exemplary system to measure PD-1 agonism is a reporter cell line that shows a response when PD-1 signalling occurs. Ligand drives this response (PD- L1). Multivalent Humabody® $V_H$ are capable of a mild agonism and biparatopic format enhances this. Thus, a $V_H$ single domain antibody selected from table 1 can be combined with another $V_H$ single domain antibody selected from table 1 to provide agonistic function. In another embodiment, a $V_H$ single domain antibody selected from table 2 can be combined with another $V_H$ single domain antibody selected from table 2 to provide agonistic function. In another embodiment, a $V_H$ single domain antibody selected from table 1 can be combined with another $V_H$ single domain antibody selected from table 2 to provide agonistic function.

A biparatopic format has the formula: $V_H(A)$-L-$V_H(B)$ or $V_H(B)$-L-$V_H(A)$ wherein $V_H(A)$- is a $V_H$ single domain antibody as disclosed herein (i.e. selected from table 1 or 2) and wherein $V_H(B)$ is a $V_H$ single domain antibody that blocks binding of PD-1 to PD-L1 and/or PD-L2. In another embodiment, the orientation is $V_H(B)$-L-$V_H(A)$. L is a linker. Suitable linkers include for example a linker with GS residues such as (Gly4Ser)n, where n=from 1 to 10, e.g., 1, 2, 3, 4, 5, 6, 7, 8, 9 or 10. In one embodiment, the linker is Gly4Ser)n, where n=less than 4, for example 1, 2 or 3.

A biparatopic molecule can enhance receptor cross-linking. A biparatopic molecule binds two epitopes on a single PD1 monomer. Alternatively, it can engage one arm with one PD1 molecule and the other arm with a second molecule. The second molecule still has an available epitope for a further biparatopic to engage and so a 'chain' of PD1 molecules can be clustered together. A shorter linker than $(Gly_4Ser)_4$ can prevent binding to a single molecule and can encourage cross-linking, thereby permitting PD1 agonism. The preferred embodiment for this function is a multivalent molecule, ideally with non-antagonistic function, joined by linkers of less than $(Gly_4Ser)_4$, preferably with at least 2 epitopes. In one embodiment, L $(Gly_4Ser)_n$ wherein n is 1, 2, 3 or 4.

Our data shows a biparatopic format containing an antagonist and an anchor. Although this can induce PD1 signalling, there is sufficient masking of the ligand-binding epitope to allow it to block ligand-induced signalling and have an antagonistic function.

A PD-1 agonist as described above is useful in the treatment of autoimmune and/or inflammatory and/or infectious diseases. Thus, another aspect relates to a PD-1 agonist as described above for use in the treatment of autoimmune and/or inflammatory and/or infectious diseases as well as methods for use in the treatment of autoimmune and/or inflammatory and/or infectious diseases comprising administration of a PD-1 agonist as described above. Another aspect thus relates to an agonistic multivalent or multiparatopic molecule comprising single domain antibody as described herein combined with another single domain antibody as described herein (for example one of the single domain antibody of table 1 combined with another single domain antibody of table 1) or combined with a PD-1 blocker.

A single domain antibody described herein can be obtained from a transgenic rodent that expresses heavy chain only antibodies upon stimulation with a PD-1 antigen. The transgenic rodent, for example a mouse, preferably has a reduced capacity to express endogenous antibody genes. Thus, in one embodiment, the rodent has a reduced capacity to express endogenous light and/or heavy chain antibody genes. The rodent may therefore comprise modifications to disrupt expression of endogenous kappa and lambda light and/or heavy chain antibody genes so that no functional light and/or heavy chains are produced, for example as further explained below.

The invention also relates to a method for producing human heavy chain only antibodies capable of binding human PD-1 which do not block the interaction of PD-1 with PD-L1 and/or PD-L2 said method comprising
  a) immunising a transgenic rodent with an PD-1 antigen wherein said rodent expresses a nucleic acid construct comprising un-rearranged human heavy chain V genes and is not capable of making functional endogenous light or heavy chains,
  b) isolating human heavy chain only antibodies
  c) identifying heavy chain only antibodies that bind to human PD-1 but do not block the interaction of PD-1 with PD-L1 and/or PD-L2.

Further steps may include isolating a $V_H$ domain from said human heavy chain only antibodies or generating a library of sequences comprising $V_H$ domain sequences from said mouse and isolating sequences comprising $V_H$ domain sequences from said libraries.

The invention also relates to a method for producing a single $V_H$ domain antibody capable of binding human PD-1 said method comprising
  a) immunising a transgenic rodent with an PD-1 antigen wherein said rodent expresses a nucleic acid construct comprising un-rearranged human heavy chain V genes and is not capable of making functional endogenous light or heavy chains,
  b) generating a library of sequences comprising $V_H$ domain sequences from said mouse
  c) isolating sequences comprising $V_H$ domain sequences from said libraries
  d) identifying $V_H$ domains that bind to human PD-1 but do not block the interaction of PD-1 with PD-L1 and/or PD-L2.

Functional assays for example as shown in the examples may be used to assess if a heavy chain only antibody or $V_H$ domain binds to PD-1 but does not block the interaction of PD-1 with PD-L1 and/or PD-L2.

Methods for preparing or generating the polypeptides, nucleic acids, host cells, products and compositions described herein using in vitro expression libraries can comprise the steps of:
  a) providing a set, collection or library of nucleic acid sequences encoding amino acid sequences; and
  b) screening said set, collection or library for amino acid sequences that can bind to/have affinity for PD-1 and does not block the interaction of PD-1 with PD-L1 and/or PD-L2
  c) isolating the amino acid sequence(s) that can bind to/have affinity for PD-1.

In the above method, the set, collection or library of amino acid sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art (see for example Phage Display of Peptides and Proteins: A Laboratory Manual, Academic Press; 1st edition (Oct. 28, 1996) Brian K. Kay, Jill Winter, John McCafferty).

Libraries, for example phage libraries, are generated by isolating a cell or tissue expressing an antigen-specific, heavy chain-only antibody, cloning the sequence encoding the VH domain(s) from mRNA derived from the isolated cell or tissue and displaying the encoded protein using a library.

The $V_H$ domain(s) can be expressed in bacterial, yeast, insect, plant mammalian or other expression systems.

The invention also relates to an isolated $V_H$ single domain antibody or an isolated heavy chain only antibody comprising a $V_H$ domain binding to PD-1 comprising an amino acid product of or derived from a human $V_H$ germline sequence. The heavy chain only antibody may be fully human or comprise mouse sequences.

In the various aspects and embodiment of the invention as out herein, the term rodent may relate to a mouse or a rat.

In one embodiment, the rodent is a mouse. The mouse may comprise a non-functional endogenous lambda light chain locus. Thus, the mouse does not make a functional endogenous lambda light chain. In one embodiment, the lambda light chain locus is deleted in part or completely or rendered non-functional through insertion, inversion, a recombination event, gene editing or gene silencing. For example, at least the constant region genes C1, C2 and C3 may be deleted or rendered non-functional through insertion or other modification as described above. In one embodiment, the locus is functionally silenced so that the mouse does not make a functional lambda light chain.

Furthermore, the mouse may comprise a non-functional endogenous kappa light chain locus. Thus, the mouse does not make a functional endogenous kappa light chain. In one embodiment, the kappa light chain locus is deleted in part or completely or rendered non-functional through insertion, inversion, a recombination event, gene editing or gene silencing. In one embodiment, the locus is functionally silenced so that the mouse does not make a functional kappa light chain.

The mouse having functionally-silenced endogenous lambda and kappa L-chain loci may, for example, be made as disclosed in WO 2003/000737, which is hereby incorporated by reference in its entirety.

Furthermore, the mouse may comprise a non-functional endogenous heavy chain locus. Thus, the mouse does not make a functional endogenous heavy chain. In one embodiment, the heavy chain locus is deleted in part or completely or rendered non-functional through insertion, inversion, a recombination event, gene editing or gene silencing. In one embodiment, the locus is functionally silenced so that the mouse does not make a functional heavy chain.

For example, as described in WO 2004/076618 (hereby incorporated by reference in its entirety), all 8 endogenous heavy chain constant region immunoglobulin genes (μ, δ, γ3, γ1, γ2a, γ2b, ε and α) are absent in the mouse, or partially absent to the extent that they are non-functional, or genes δ, γ3, γ1, γ2a, γ2b and ε are absent and the flanking genes and α are partially absent to the extent that they are rendered non-functional, or genes μ, δ, γ3, γ1, γ2a, γ2b and ε are absent and α is partially absent to the extent that it is rendered non-functional, or δ, γ3, γ1, γ2a, γ2b, ε and α are absent and μ is partially absent to the extent that it is rendered non-functional. By deletion in part is meant that the endogenous locus gene sequence has been deleted or disrupted, for example by an insertion, to the extent that no functional endogenous gene product is encoded by the locus, i.e., that no functional product is expressed from the locus. In another embodiment, the locus is functionally silenced.

In one embodiment, the mouse comprises a non-functional endogenous heavy chain locus, a non-functional endogenous lambda light chain locus and a non-functional endogenous kappa light chain locus. The mouse therefore does not produce any functional endogenous light or heavy chains. Thus, the mouse is a triple knockout (TKO) mouse.

The transgenic mouse may comprise a vector, for example a Yeast Artificial Chromosome (YAC) for expressing a heterologous, preferably a human, heavy chain locus. YACs are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K. Yeast Artificial Chromosomes, Encyclopedia of Life Sciences, 2002 Macmillan Publishers Ltd, Nature Publishing Group).

For example, the YAC may comprise a plethora of unrearranged human $V_H$, D and J genes in combination with mouse immunoglobulin constant region genes lacking $C_H1$ domains, mouse enhancer and regulatory regions. The human $V_H$, D and J genes are human $V_H$, D and J loci and they are unrearranged genes that are fully human. An example of such a YAC is provided in the example section.

Alternative methods known in the art may be used for deletion or inactivation of endogenous mouse or rat immunoglobulin genes and introduction of human $V_H$, D and J genes in combination with mouse immunoglobulin constant region genes lacking $C_H1$ domains, mouse enhancer and regulatory regions.

Transgenic mice can be created according to standard techniques as illustrated in the examples. The two most characterised routes for creating transgenic mice are via pronuclear microinjection of genetic material into freshly fertilised oocytes or via the introduction of stably transfected embryonic stem cells into morula or blastocyst stage embryos.

Regardless of how the genetic material is introduced, the manipulated embryos are transferred to pseudo-pregnant female recipients where pregnancy continues and candidate transgenic pups are born.

The main differences between these broad methods are that ES clones can be screened extensively before their use to create a transgenic animal. In contrast, pronuclear microinjection relies on the genetic material integrating to the host genome after its introduction and, generally speaking, the successful incorporation of the transgene cannot be confirmed until after pups are born.

There are many methods known in the art to both assist with and determine whether successful integration of transgenes occurs. Transgenic animals can be generated by multiple means including random integration of the construct into the genome, site-specific integration, or homologous recombination. There are various tools and techniques that can be used to both drive and select for transgene integration and subsequent modification including the use of drug resistance markers (positive selection), recombinases, recombination-mediated cassette exchange, negative selection techniques, and nucleases to improve the efficiency of recombination. Most of these methods are commonly used in the modification of ES cells. However, some of the techniques may have utility for enhancing transgenesis mediated via pronuclear injection.

Further refinements can be used to give more efficient generation of the transgenic line within the desired background. As described above, in preferred embodiments, the endogenous mouse immunoglobulin expression is silenced to permit sole use of the introduced transgene for the expression of the heavy-chain only repertoire that can be exploited for drug discovery. Genetically-manipulated mice, for example TKO mice that are silenced for all endogenous immunoglobulin loci (mouse heavy chain, mouse kappa chain and mouse lambda chain) can be used as described above. The transfer of any introduced transgene to this TKO background can be achieved via breeding, either conventional or with the inclusion of an IVF step to give efficient scaling of the process. However, it is also possible to include the TKO background during the transgenesis procedure. For example, for microinjection, the oocytes may be derived from TKO donors. Similarly, ES cells from TKO embryos can be derived for use in transgenesis.

Triple knock-out mice into which transgenes have been introduced to express immunoglobulin loci are referred to herein as TKO/Tg.

In one embodiment, the mouse is as described in WO2016/062990.

The invention also relates to a rodent, preferably a mouse which expresses a human heavy chain locus and which has been immunized with a PD-1 antigen. The invention also relates to a rodent as described above, preferably a mouse which expresses a heavy chain only antibody comprising a human $V_H$ domain that binds to human PD-1. Preferably, said rodent is not capable of making functional endogenous kappa and lambda light and/or heavy chains. The human heavy chain locus is located on a transgene which can be as described above.

The invention also relates to an anti-human PD-1 heavy chain only antibody comprising a human $V_H$ domain or an anti-human PD-1 single $V_H$ domain antibody obtained or obtainable from a rodent, preferably a mouse, immunised with a human PD-1 antigen and which expresses a human heavy chain locus. Preferably, said rodent is not capable of making functional endogenous kappa and lambda light and/or heavy chains. The human heavy chain locus is located on a transgene which can be as described above.

In another aspect of the present invention, there is provided a pharmaceutical composition comprising a single domain antibody according to the present invention and optionally a pharmaceutically acceptable carrier. A single domain antibody of the present invention or the pharmaceutical composition of the invention can be administered by any convenient route, including but not limited to oral, topical, parenteral, sublingual, rectal, vaginal, ocular, intranasal, pulmonary, intradermal, intravitrial, intramuscular, intraperitoneal, intravenous, subcutaneous, intracerebral, transdermal, transmucosal, by inhalation, or topical, particularly to the ears, nose, eyes, or skin or by inhalation.

Parenteral administration includes, for example, intravenous, intramuscular, intraarterial, intraperitoneal, intranasal, rectal, intravesical, intradermal, topical or subcutaneous administration. Preferably, the compositions are administered parenterally.

The pharmaceutically acceptable carrier or vehicle can be particulate, so that the compositions are, for example, in tablet or powder form. The term "carrier" refers to a diluent, adjuvant or excipient, with which a drug antibody conjugate of the present invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to an animal, the single domain antibody of the present invention or compositions and pharmaceutically acceptable carriers are sterile. Water is a preferred carrier when the drug antibody conjugates of the present invention are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The pharmaceutical composition of the invention can be in the form of a liquid, e.g., a solution, emulsion or suspension. The liquid can be useful for delivery by injection, infusion (e.g., IV infusion) or sub-cutaneously.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent. When the composition is in the form of a capsule (e. g. a gelatin capsule), it can contain, in addition to materials of the above type, a liquid carrier such as polyethylene glycol, cyclodextrin or a fatty oil.

The composition can be in the form of a liquid, e. g. an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

Compositions can take the form of one or more dosage units.

In specific embodiments, it can be desirable to administer the composition locally to the area in need of treatment, or by intravenous injection or infusion.

The amount of the single domain antibody of the present invention that is effective/active in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances. Factors like age, body weight, sex, diet, time of administration, rate of excretion, condition of the host, drug combinations, reaction sensitivities and severity of the disease shall be taken into account.

Typically, the amount is at least about 0.01% of a single domain antibody of the present invention by weight of the composition. When intended for oral administration, this amount can be varied to range from about 0.1% to about 80% by weight of the composition. Preferred oral compositions can comprise from about 4% to about 50% of the single domain antibody of the present invention by weight of the composition.

Preferred compositions of the present invention are prepared so that a parenteral dosage unit contains from about 0.01% to about 2% by weight of the single domain antibody of the present invention.

For administration by injection, the composition can comprise from about typically about 0.1 mg/kg to about 250 mg/kg of the animal's body weight, preferably, between about 0.1 mg/kg and about 20 mg/kg of the animal's body weight, and more preferably about 1 mg/kg to about 10 mg/kg of the animal's body weight. In one embodiment, the composition is administered at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks.

The invention provides methods of treating PD-1-mediated diseases or disorders in a mammal, e.g., a human patient, comprising administering an effective amount of an antibody of the present invention to a mammal in need thereof. In particular, the invention furthermore relates to a method for the prevention and/or treatment of a disorder selected from cancer, an immune disorder, neurological disease, inflammatory disorder, allergy, transplant rejection, viral infection, immune deficiency, and other immune system-related disorder said method comprising administering, to a subject in need thereof, a pharmaceutically active amount of a single domain antibody or pharmaceutical composition of the invention, or of a pharmaceutical composition of the invention.

As used herein, "treat", "treating" or "treatment" means inhibiting or relieving a disease or disorder. For example, treatment can include a postponement of development of the symptoms associated with a disease or disorder, and/or a reduction in the severity of such symptoms that will, or are expected, to develop with said disease. The terms include ameliorating existing symptoms, preventing additional symptoms, and ameliorating or preventing the underlying causes of such symptoms. Thus, the terms denote that a beneficial result is being conferred on at least some of the mammals, e.g., human patients, being treated. Many medical treatments are effective for some, but not all, patients that undergo the treatment.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

As used herein, the term "effective amount" means an amount of an anti-PD-1 antibody, that when administered alone or in combination with an additional therapeutic agent to a cell, tissue, or subject, is effective to achieve the desired therapeutic or prophylactic effect under the conditions of administration The invention also relates to a single domain antibody or pharmaceutical composition of the invention for use in the treatment or prevention of a disease.

In another aspect, the invention relates to a single domain antibody or pharmaceutical composition of the invention for use in the treatment or prevention of cancer, an immune disorder, neurological disease, inflammatory disorder, allergy, transplant rejection, viral infection, immune deficiency, and other immune system-related disorder.

In another aspect, the invention relates to the use of a single domain antibody or pharmaceutical composition of the invention in the treatment or prevention of a disease.

In another aspect, the invention relates to the use of a single domain antibody or pharmaceutical composition of the invention in the manufacture of a medicament for the treatment or prevention of cancer, an immune disorder, neurological disease, inflammatory disorder, allergy, transplant rejection, viral infection, immune deficiency, and other immune system-related disorder.

The cancer can be selected from a solid or non-solid tumor. For example, the cancer may be selected from bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, breast cancer, brain cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, kidney cancer, sarcoma of soft tissue, cancer of the urethra, cancer of the bladder, renal cancer, lung cancer, non-small cell lung cancer, thymoma, urothelial carcinoma leukemia, prostate cancer, mesothelioma, adrenocortical carcinoma, lymphomas, such as such as Hodgkin's disease, non-Hodgkin's, gastric cancer, and multiple myelomas.

In one embodiment, the tumor is a solid tumor. Examples of solid tumors which may be accordingly treated include breast carcinoma, lung carcinoma, colorectal carcinoma, pancreatic carcinoma, glioma and lymphoma. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kaposi's sarcoma, CNS, neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma. Examples of vascularized skin cancers for which the antagonists of this invention are effective include squamous cell carcinoma, basal cell carcinoma and skin cancers that can be treated by suppressing the growth of malignant keratinocytes, such as human malignant keratinocytes.

In one embodiment, the tumor is a non-solid tumor. Examples of non-solid tumors include leukemia, multiple myeloma and lymphoma.

In one aspect, the cancer is identified as a PD-L1 positive cancer. In one aspect, the cancer is locally advanced unresectable, metastatic, or recurrent cancer.

Preferred cancers whose growth may be inhibited using the antibodies of the invention include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer).

In one embodiment, the cancer has progressed after another treatment, for example chemotherapy.

The single domain antibodies and pharmaceutical compositions of the present invention are particularly useful for the treatment of cancers that are associated with cells (e.g., exhausted T cells, B cells, monocytes, etc.) that express abnormally high levels of PD-1. Other preferred cancers include those characterized by elevated expression of PD-1 and/or its ligands PD-L1 and/or PD-L2. In one embodiment, the cancer is selected from a cancer that has high levels of cancer-associated genetic mutations and/or high levels of expression of tumour antigens. In another embodiment, the cancer is selected from a cancer known to be immunogenic or that is able to become immunogenic upon treatment with other cancer therapies.

The immune disorder can be selected from auto-immune diseases, graft vs. host disease, arthritis, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, Neuromyelitis optica (NMO), type 1 or immune-mediated diabetes mellitus, myasthenia gravis, pemphigus vulgaris, pernicious anemia, polyarteritis *nodosa*, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, transverse myelitis, ulcerative colitis, uveitis, vasculitides such as dermatitis herpetiformis vasculitis, vitiligo, and Wegener's granulomatosis.

The neurological disease can be selected from Alzheimer's disease, epilepsy, Parkinson's disease, dementia, multiple sclerosis, peripheral neuropathy or post-herpetic neuralgia.

The single domain antibody or pharmaceutical composition of the invention may be administered as the sole active ingredient or in combination with one or more other therapeutic agent. A therapeutic agent is a compound or molecule which is useful in the treatment of a disease. Examples of therapeutic agents include antibodies, antibody fragments, drugs, toxins, nucleases, hormones, immunomodulators, pro-apoptotic agents, anti-angiogenic agents, boron compounds, photoactive agents or dyes and radioisotopes. An antibody molecule includes a full antibody or fragment thereof (e.g., a Fab, F(ab')2, Fv, a single chain Fv fragment (scFv) or a single domain antibody, for example a $V_H$ domain) or antibody mimetic protein.

In one embodiment, the single domain antibody is used in combination with an existing therapy or therapeutic agent, for example an anti-cancer therapy. Thus, in another aspect, the invention also relates to a combination therapy comprising administration of a single domain antibody or pharmaceutical composition of the invention and an anti-cancer therapy. The anti-cancer therapy may include a therapeutic agent or radiation therapy and includes gene therapy, viral therapy, RNA therapy bone marrow transplantation, nanotherapy, targeted anti-cancer therapies or oncolytic drugs. Examples of other therapeutic agents include other checkpoint inhibitors, antineoplastic agents, immunogenic agents, attenuated cancerous cells, tumor antigens, antigen presenting cells such as dendritic cells pulsed with tumor-derived antigen or nucleic acids, immune stimulating cytokines (e.g., IL-2, IFNa2, GM-CSF), targeted small molecules and biological molecules (such as components of signal transduction pathways, e.g. modulators of tyrosine kinases and inhibitors of receptor tyrosine kinases, and agents that bind to tumor-specific antigens, including EGFR antagonists), an anti-inflammatory agent, a cytotoxic agent, a radiotoxic agent, or an immunosuppressive agent and cells transfected with a gene encoding an immune stimulating cytokine (e.g., GM-CSF), chemotherapy. In one embodiment, the single domain antibody is used in combination with surgery.

In one embodiment, the single domain antibody or pharmaceutical composition of the invention is administered together with an immunomodulator, a checkpoint modulator, an agent involved in T-cell activation, a tumor microenvironment modifier (TME) or a tumour-specific target. For example, the immunomodulator can be an inhibitor of an immune checkpoint molecule selected from an inhibitor of one or more of PD-1, PD-L1, PD-L2, CTLA-4, TIM-3, LAG-3, CEACAM, VISTA, BTLA, TIGIT, LAIR1, CD160, 2B4 or TGFR beta. In another embodiment, the immunomodulator can be an activator of a costimulatory molecule selected from an agonist of one or more of OX40, OX40L, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand, CD3, CD8, CD28, CD4 or ICAM-1.

In one embodiment, the PD-1 inhibitor is an anti-PD-1 antibody chosen from Nivolumab®, Pembrolizumab® or Pidilizumab®.

In a specific embodiment of the present invention, the composition is administered concurrently with a chemotherapeutic agent or with radiation therapy. In another specific embodiment, the chemotherapeutic agent or radiation therapy is administered prior or subsequent to administration of the composition of the present invention, preferably at least an hour, five hours, 12 hours, a day, a week, a month, more preferably several months (e. g. up to three months), prior or subsequent to administration of composition of the present invention.

In some embodiments, the single domain antibodies of the invention may be administered with two or more therapeutic agents. In some embodiments, the binding agents of the invention may be administered with two or more therapeutic agents.

The single domain antibody or pharmaceutical composition of the invention may be administered at the same time or at a different time as the other therapy or therapeutic compound or therapy, e.g., simultaneously, separately or sequentially.

In another aspect, the invention relates to an immunoconjugate comprising a single domain antibody of the invention conjugated to at least one therapeutic and/or diagnostic agent.

In another aspect, the invention provides a kit for the treatment or prevention of a disease or an immune response and/or for detecting PD-1 for diagnosis, prognosis or monitoring disease comprising a single domain antibody of the invention. Such a kit may contain other components, packaging, instructions, or material to aid in the detection of PD-1 protein. The kit may include a labeled single domain antibody of the invention as described above and one or more compounds for detecting the label.

The invention in another aspect provides a single domain antibody of the invention packaged in lyophilized form, or packaged in an aqueous medium.

The invention also relates to a single domain antibody as described herein with reference to the figures, examples and/or tables 1 and 2.

In another aspect, antibodies of the invention are used for non-therapeutic purposes, such as diagnostic tests and assays. A method for detecting the presence of human PD-1 in a test sample comprises contacting said sample with a single domain antibody according to the invention and at least one detectable label and detecting binding of said single domain antibody to human PD-1.

In one embodiment, the invention relates to a method of diagnosing a PD-1-mediated adaptive immune resistance in a patient who has cancer. The method comprises contacting a sample with a compound disclosed herein that has been labelled with a detectable moiety; and detecting expression of PD-1 on immune cells, e.g., CD8+ T cells; B cells; and macrophages. The sample may be tumor tissue.

Modifications of antibodies for diagnostic purposes are well known in the art. For example, antibodies may be modified with a ligand group such as biotin, or a detectable marker group such as a fluorescent group, a radioisotope, or an enzyme. Compounds of the invention can be labelled using conventional techniques. Suitable detectable labels include but are not limited to fluorophores, chromophores, radioactive atoms, electron-dense reagents, enzymes, and ligands having specific binding partners.

Unless otherwise defined herein, scientific and technical terms used in connection with the present disclosure shall have the meanings that are commonly understood by those of ordinary skill in the art. While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification are incorporated herein by reference in their entirety, including references to gene accession numbers and references to patent publications.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

The invention is further described in the non-limiting examples.

EXAMPLES

Example 1. Construction of Tg/TKO Mice

Mice carrying a human heavy-chain antibody transgenic locus in germline configuration within a background that is silenced for endogenous heavy and light chain antibody expression (triple knock-out, or TKO) were created as previously described (WO2004/076618, WO2003/000737, Ren et al., Genomics, 84, 686, 2004; Zou et al., J. Immunol., 170, 1354, 2003 and WO2016/062990). Briefly, transgenic mice were derived following pronuclear microinjection of freshly fertilised oocytes with a yeast artificial chromosome (YAC) comprising a plethora of human $V_H$, D and J genes in combination with mouse immunoglobulin constant region genes lacking $C_H1$ domains, mouse enhancer and regulatory regions. Yeast artificial chromosomes (YACs) are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K. Yeast Artificial Chromosomes, Encyclopedia of Life Sciences, 2002, Macmillan Publishers Ltd., Nature Publishing Group/www.els.net).

The YAC used comprised multiple human heavy chain V genes, multiple human heavy chain D and J genes, a murine $C_H1$ gene and a murine 3' enhancer gene. It lacks the $C_H1$ exon.

The transgenic founder mice were back crossed with animals that lacked endogenous immunoglobulin expression to create the Tg/TKO lines used in the immunisation studies described.

Example 2. Antigen for Immunisation

The immunisations used recombinant human PD-1 Fc chimera purchased from R&D, catalogue number 1086-PD, lot number FVQ081502B.

Example 3. Immunisation Protocol

Tg/TKO mice aged 8-12 weeks of age each received an initial prime dose of either 50 ug or 10 ug of recombinant purified human PD-1 protein emulsified in Complete Freund's Adjuvant and delivered subcutaneously, followed by three boosts of 10 µg of the recombinant protein, emulsified in Incomplete Freund's Adjuvant, also administered subcutaneously, given at various intervals following the initial priming. A final dose of 10 µg recombinant purified human PD-1 protein antigen was administered intraperitoneally, in phosphate buffered saline, in the absence of adjuvant.

Example 4. Serum ELISA

Serum was collected from mice before and after immunisation, and checked by ELISA for the presence of serum PD-1/Fc reactive heavy chain antibodies in response to PD-1/Fc immunisation using Nunc Maxisorp plates (Nunc cat. no. 443404) coated overnight with recombinant huPD-1-Fc solution in PBS. Plates were washed using PBS. To block non-specific protein interactions, a solution of 3% (w/v) skimmed milk powder (Marvel®) in PBS was added to the wells and the plate was incubated for at least one hour at room temperature, then discarded.

Whole blood samples were centrifuged at 13000 rpm for 5 mins to separate blood from serum. Dilutions of serum were prepared in 3% Marvel™/PBS in polypropylene tubes or plates, pre-incubated for at least one hour at room temperature then transferred to the blocked ELISA plate and incubated for at least one hour. Unbound protein was removed by repetitive washing with PBS/Tween 20 followed by PBS. A 1:10000 solution of biotin-conjugated, goat anti-mouse IgG, Fcgamma subclass 1 specific antibody (Jackson cat. no. 115-065-205), prepared in PBS/3% Marvel was added to each well and incubated at room temperature for at least one hour. Unbound detection antibody was removed by repeated washing using PBS/Tween 20 and PBS. Neutravidin-HRP solution (Pierce cat. no. 31030) in 3% Marvel/PBS was added to the ELISA plates and allowed to bind for 30 minutes, then washed as above.

Mice were checked by ELISA for the presence of antibody in serum. All mice showed a robust immune response.

Example 5. Generation of Libraries from Immunised Mice

Generation of libraries from immunised mice described above followed standard protocols of library generation as summarised below.

Tissue Collection and Homogenisation

Total spleen, inguinal and brachial lymph nodes were used according to standard protocols.

RNA Extraction and RT-PCR

Spleen: 400 µl supernatant was used for preparation of total RNA. RNA was extracted from total spleen using Qiagen RNeasy® kit (cat. no. 74104) following the manufacturer's protocol.

Lymph nodes: prepared by essentially the same process on the Kingfisher $V_H$ sequences were mined from the RNA samples using Superscript III RT-PCR high-fidelity kit (Invitrogen cat. no. 12574-035) according to the manufacturer's protocol. For each spleen and LN RNA sample, RT-PCR reactions were performed using a single $J_H$ primer in combination with primers for $V_H1$, $V_{H2}$, $V_{H3}$, $V_{H4}$ or $V_{H6}$ families.

Products in the range of 370 bp were confirmed by gel electrophoresis RT-PCR products were pooled so that products from lymph nodes and spleen were combined. Amplified material was purified using the GeneJet™ purification kit (cat # K0702) according to the manufacturer's protocol.

Cloning into Phagemid Vector

The phagemid vector, pUCG3, was employed in these studies. A conventional PCR-based method was used to construct the $V_H$ phagemid libraries from the amplified $V_H$ sequences.

Purified $V_H$ RT-PCR products were used to prime a PCR reaction from the linearised pUCG3 resulting in a heterogeneous population of $V_H$ cloned into pUCG3.

PCR products were analysed on a 1% (w/v) agarose gel.

Generation of Phagemid Library $V_H$/phagemid PCR products were pooled by animal-of-origin and purified using Fermentas PCR purification kit (cat. no. K0702) according to the manufacturer's instructions. Eluted DNA was used to transform TG1 E. coli (Lucigen, cat. no. 60502-2) by electroporation using the Bio-Rad GenePulser Xcell. Electroporated cells were pooled.

A 10-fold dilution series of the transformations was plated on 2×TY agar petri plates with 2% (w/v) glucose and 100 µg/ml ampicillin. Resulting colonies on these dishes were used to estimate library size. The remainder of the transformation was plated on large format 2×TY agar Bioassay dishes supplemented with 2% (w/v) glucose and 100 µg/ml ampicillin. All agar plates were incubated overnight at 30° C.

Libraries were harvested by adding 10 ml of 2×TY broth to the large format bioassay dishes. Bacterial colonies were gently scraped and OD600 recorded. Aliquots were stored at −80° C. in cryovials after addition of an equal volume of 50% (v/v) glycerol solution or used directly in a phage selection process Example 6. Selection Strategies for Isolation of PD-1 Binding $V_H$ Preparation of library phage stocks and phage display selections were performed according to published methods (Antibody Engineering, edited by Benny Lo, chapter 8, p 161-176, 2004). In most cases, phage display combined with a panning approach was used to isolate binding $V_H$ domains. However, a variety of different selection methods are well described in the art, including soluble selection and selections performed under stress (e.g., heat).

Example 7. Screening of Periplasmic Extracts for Binding to CHO Human PD-1 Cells and Inhibition of PD-L1 Binding PD-1

Following selections of the libraries, specific $V_H$ that bound to CHO cells expressing human PD-1 and either partially inhibited or did not inhibit the interaction between recombinant human PD-1 protein and recombinant human PD-L1 protein were identified by single point screening of bacterial periplasmic extracts. Small-scale bacterial periplasmic extracts were prepared from 1 ml cultures, grown in deep well plates. Starter cultures were used to inoculate 96-well deep well plates (Fisher, cat. no. MPA-600-030X) containing 2×TY broth (Melford cat. no. M2130), supplemented with 0.1% (w/v) glucose and 100 µg/ml ampicillin at 37° C. with 250 rpm shaking. When $OD_{600}$ had reached 0.6-1, $V_H$ production was induced by adding 100 µl of 2XTY, supplemented with 0.5 mM IPTG and ampicillin and the cultures were grown overnight at 30° C. with shaking at 220 rpm. E. coli were pelleted by centrifugation at 3200 rpm for 10 mins and supernatants discarded. Cell pellets were resuspended in 120 µl of ice cold extraction buffer (50 mM MOPs, 0.5 mM EDTA, 0.5M Sucrose), then 180 µl of 1:5 diluted ice cold extraction buffer added. Cells were incubated on ice for 30 minutes and then centrifuged at 4500 rpm for 15 mins at 4° C. Supernatants were transferred to polypropylene plates for testing in assays.

Binding of His-tagged $V_H$ in the supernatants to CHO cell expressed human PD-1 was assessed using Fluorescence Microvolume Assay Technology (FMAT), a fluorescence-based platform that detects fluorescence localized to beads or cells settled at the bottom of microwells (Dietz et al., Cytometry 23:177-186 (1996), Miraglia et al., J. Biomol. Screening 4:193-204 (1999). A CHO TREX human PD1 cell line was generated in-house using full-length human PD-1 sequence by standard procedures. All reagents were prepared in FMAT assay buffer (pH 7.4) containing PBS, 0.1%

Bovine Serum Albumin, 0.01% Sodium Azide. Peripreps were transferred into 384 well black clear-bottomed assay plates (Costar cat. no. 3655) and incubated for a minimum of 2 hours at room temperature with 1.5 nM Anti-His (Millipore cat. no. 05-949)/3 nM Goat Anti-Mouse Alexa Fluor-488 (Jackson Immunolabs cat. no. 115-545-071) and 2000 CHO human PD-1 cells pre-stained with DRAQ5 (Thermo Scientific cat. no. 62251). Plates were read in the FL2 (502 nm-537 nm) and FL5 (677-800 nm) channels on the TTP Mirrorball plate reader following excitation at 488 nm and 640 nm. Data was gated on FL5 perimeter and peak intensity and the FL2 median mean fluorescence intensity of the gated data used for determination of $V_H$ binding.

In parallel to the CHO PD-1 binding assay periplasmic extracts were tested for inhibition of the interaction of PD-L1 protein with PD-1 protein by single point screening in an HTRF inhibition assay. All samples and reagents were prepared in HTRF assay buffer containing PBS, 0.1% (w/v) BSA and 0.4M Potassium Fluoride. Periplasmic extracts were incubated with 25 nM strep tagged human PD-L1 (Acro Biosystems cat no. PD1-H5282), 1.5 nM Anti human-Fc Cryptate PAb (Cisbio cat. no. 61HFCKLB), 10 nM StrepMAB-Oyster 645 conjugate in black 384-shallow-well plates (Costar cat. no. 3676) for a minimum of 3 hours at room temperature. Total binding controls containing periplasmic extract sample buffer and non-specific binding controls containing excess untagged competitor were set up on each plate for data normalisation. Time-resolved fluorescent emission at 620 nm and 665 nm was measured following excitation at 337 nm on the BMG PHERAstar plate reader. Data was expressed as a % of the total binding control (% control) after subtraction of the background signal determined from the non-specific binding control wells. $V_H$ were identified that bound to the CHO human PD-1 cells with FL2 fluorescence >1000 and showed partial or no inhibition of PD-1 binding to PD-L1 (FIGS. 1a and b).

Example 8. Sequencing

Each individual $V_H$ clone as identified above was sequenced from the phagemid and grouped based on $V_H$ germline and CDR3 amino acid similarity. Representative clones were further characterised. Further clones were generated by sequence optimisation of clone 1.1 or 2.1. Standard methods were used for optimisation. Clones 1.1 to 1.18 as shown in table 1 were isolated as above and grouped into a single family. Clones 1.19-1.50 are sequence optimised clones of clone 1.1. Clones 2.1 to 2.11 as shown in table 2 were isolated as above and grouped into a single family. Clones 2.12-2.53 are sequence optimised clones of clone 2.1.

Example 9. Preparation and Characterisation of Purified $V_H$ Single Domain Antibody a) Preparation of Purified $V_H$ Purified $V_H$ were obtained by using the $V_H$ C-terminal 6×HIS tag for nickel-agarose affinity chromatographic purification of the periplasmic extracts. A starter culture of each $V_H$ was grown overnight in 2XTY media (2XTY broth (Melford cat. no. M2103) supplemented with 2% (w/v) glucose and 100 µg/ml ampicillin at 30° C. with 250 rpm shaking. This overnight culture was then used to inoculate 50 ml-200 ml 2XTY media and incubated at 37° C. with 250 rpm shaking for approximately 6-8 hours (until $OD_{600}$=0.6-1.0). Cultures were centrifuged at 3200 rpm for 10 mins and the cell pellets resuspended in fresh 2XTY broth containing 100 µg/ml ampicillin/1 mM IPTG. Shake flasks were incubated overnight at 30° C. and 250 rpm. Cultures were again centrifuged at 3200 rpm for 10 mins and supernatants discarded. Cell pellets were resuspended in ice cold extraction buffer (20% (w/v) sucrose, 1 mM EDTA, 50 mM Tris-HCl pH 8.0 or 50 mM MOPS) by gently pipetting then diluted further with 1:5 diluted ice cold extraction buffer. Cells were incubated on ice for 30 minutes then centrifuged at 4500 rpm for 15 mins at 4° C. Supernatants were transferred to tubes containing 10 mM imidazole (Sigma cat. no. 12399) and pre-equilibrated nickel agarose beads (Qiagen, Ni-NTA 50% soln, cat. no. 30210). $V_H$ binding was allowed to proceed for 2 hours at 4° C. with gentle shaking. The beads were transferred to a polyprep column (BioRad cat. no. 731-1550) and the supernatant discarded by gravity flow. Columns were washed 3 times with PBS/0.05% Tween® followed by 3 washes with 5 ml of PBS/20 mM Imidazole. $V_H$ were eluted from the columns using PBS/250 mM imidazole. The imidazole was removed from the purified $V_H$ preparations by buffer exchange with NAP-5 columns (GE Healthcare, 17-0853-01) and elution with PBS. Yields of purified $V_H$ were estimated spectrophotometrically and purity was assessed using SDS PAGE.

Alternatively, $V_H$ were purified from the supernatants of W3110 *E. coli* with pJExpress vector. For this procedure up to 400 ml cultures were grown at 37° C. with 250 rpm shaking in TB media before being induced overnight with 1 mM IPTG overnight. The resulting supernatants were harvested and $V_H$ purified on AKTA Pure using a Ni-Sepharose excel column (HiScale 16, GE Healthcare). Yields of purified $V_H$ were estimated spectrophotometrically and purity was assessed using SDS PAGE.

b) Species Cross Reactivity Testing

Purified $V_H$ were tested for their ability to bind to human PD-1 (R&D Systems cat no. 1086-PD), cynomolgus PD-1 (Acro Biosystems cat no. PD1-C5254) and mouse PD1 (R&D Systems cat no. 1021-PD) in an HTRF Binding assay format. All reagents and serially diluted $V_H$ were prepared in assay buffer containing PBS, 0.1% BSA and 0.4M Potassium Fluoride. Samples or assay buffer (non-specific binding) were incubated with 2 nM human/cynomolgus or mouse PD-1, 1 nM Anti human-Fc Cryptate PAb (Cisbio cat. no. 61HFCKLB) and 30 nM anti His-D2 (CisBio cat no 61HISDLA) in black 384-shallow well assay plates for a minimum of 3 hours at room temperature. Time-resolved fluorescent emission at 620 nm and 665 nm was measured following excitation at 337 nm on the BMG PHERAstar plate reader. The HTRF ratio were calculated ((665 nm emission/620 nm emission)*10000) and the data corrected for (non-specific binding) to give the specific binding signal.

Figure 2C:
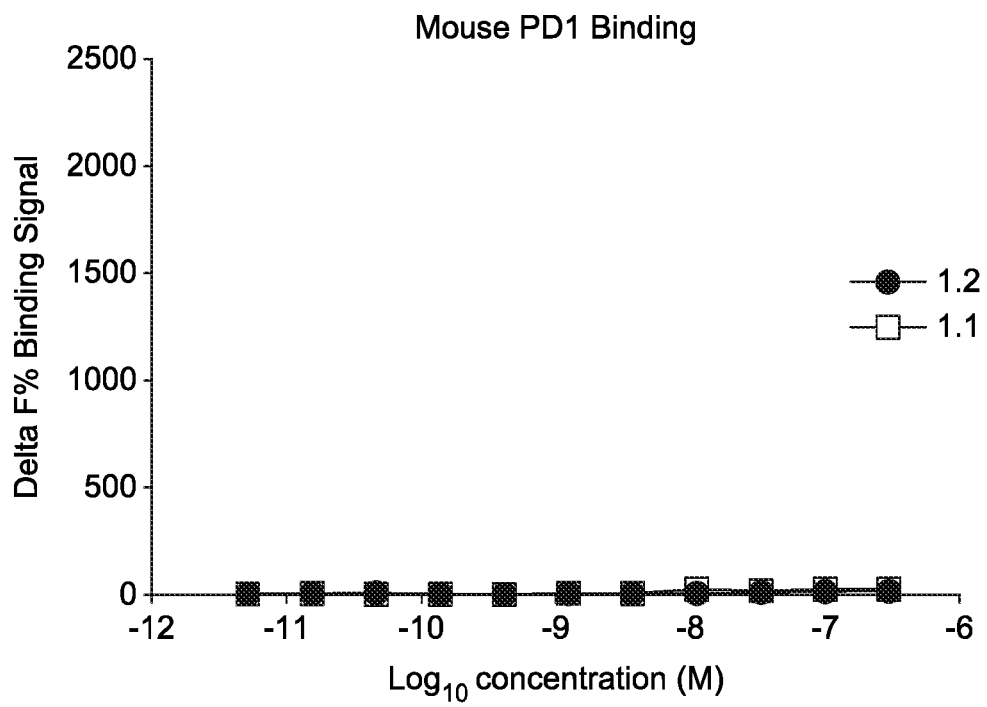

$V_H$ single domain antibodies generated as explained above showed binding to human (FIG. 2a) and cynomolgus PD-1 (FIG. 2b) recombinant protein, but no binding to mouse PD-1 protein (FIG. 2c).

Table 3 shows EC50 values obtained.

| $V_H$ single domain antibodies | human PD-1 $EC_{50}$ (M) | cyno PD-1 $EC_{50}$ (M) | mouse PD-1 $EC_{50}$ (M) |
|---|---|---|---|
| 1.2 | 9.0E−10 | 1.1E−9 | No binding |
| 1.1 | 5.0E−10 | 6.0E−10 | No binding |
| 2.1 | 3.3E−09 | 6.3E−09 | No binding |
| 1.39 | 2.6E−09 | 6.0E−09 | No binding |
| 2.12 | 1.3E−08 | 1.8E−08 | No binding | c) Inhibition of Human PD-L1 and PD-L2 Binding to Recombinant Human PD-1 Protein Purified $V_H$ were serially diluted in HTRF assay buffer and tested in the HTRF PD-1:PD-L1 Inhibition assay as described above.

For the PD-L2 inhibition assay, recombinant human PD-1 protein was labelled with Europium Trisbipyridine Cryptate (Cisbio cat no. 62EUSPEA) according to the manufacturer's protocol and PD-L2-Fc (Acro Biosystems cat no. PD2-H882R) was biotinylated according to EZ-link kit protocol (Thermo 21327). Serial dilutions of $V_H$ were incubated with 10 nM Streptavidin AlexaFluor-647 (Life Technologies cat no. S32357), 3 nM biotinylated PD-L2-Fc and Europium Cryptate labelled PD-1-Fc (167-fold dilution) for a minimum of 3 hours at room temperature. $V_H$ showed a partial inhibition profile in the PD-L1 inhibition assay, but did not inhibit binding of PD-L2 to human PD-1 protein (FIG. 3 showing $V_H$ single domain antibodies 1.1 and 1.2).

d) Inhibition of Human PD-L1 and Human PD-L2 to CHO Human PD-1 Cells

Purified $V_H$ were serially diluted in FMAT assay buffer and tested for binding to CHO human PD-1 cells as described above and for inhibition of human PD-L1/PD-L2 binding to CHO human PD-1 cells.

For the inhibition assay all reagents were prepared in FMAT assay buffer. $V_H$, buffer (total binding controls) or excess competitor (non-specific binding control) were incubated with 400 pM human Fc tagged human PDL-1 (or 100 pM human Fc tagged human PD-L2), 4 nM anti human Fc-Alexa Fluor-488 and 2000 per well CHO human PD1 DRAQ5 stained cells in 384 well black clear-bottomed assay plates. Plates were incubated for 2 hours at room temperature then fluorescence measured in the FL2 (502 nm-537 nm) and FL5 (677-800 nm) channels on the Mirrorball plate reader (TTP) following excitation at 488 nm and 640 nm. Data was expressed as a % of the total binding control (i.e. % control) after subtraction of the background signal determined from the non-specific binding control wells.

Figure 4A:
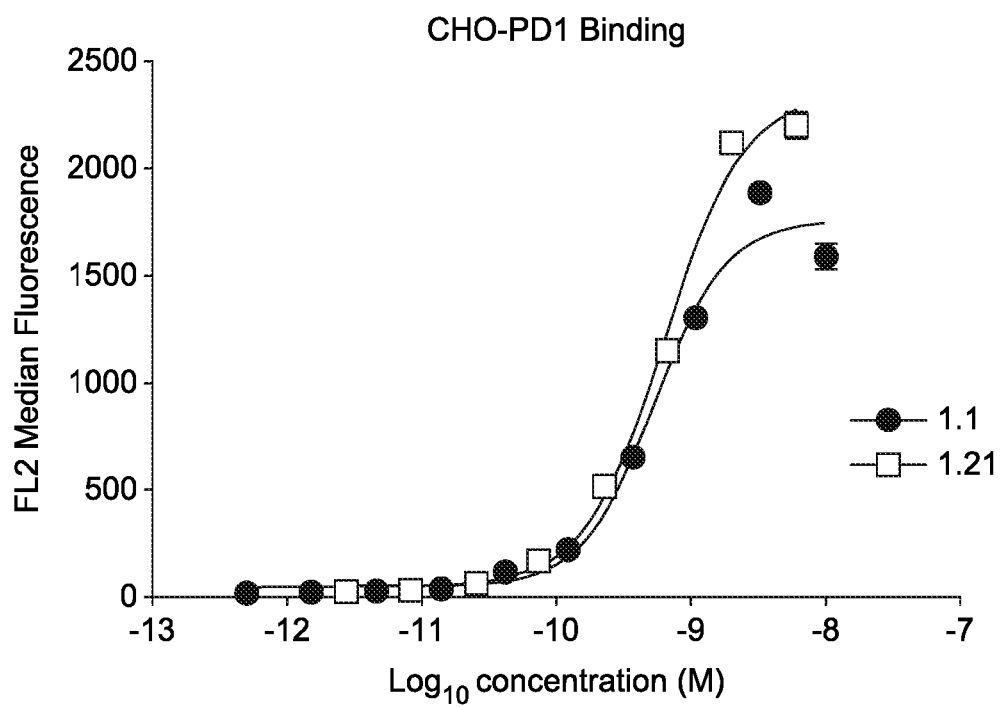
Figure 4B:
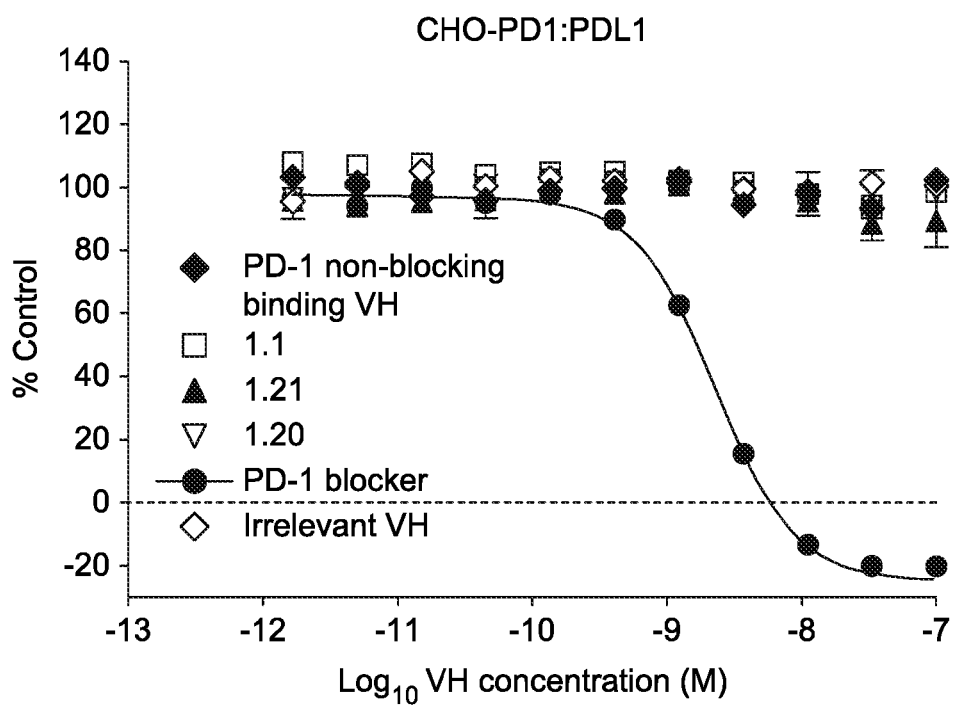

Example data for binding to CHO-human PD-1 cells and inhibition of binding of human PDL-1 to the CHO human PD-1 cells is shown in FIGS. 4a and 4b respectively. The Humabody® 1.1 and 1.20 showed concentration dependent binding to CHO human PD1 cells (FIG. 4a) but did not inhibit PD-L1 (FIG. 4b) and PD-L2 binding to CHO human PD-1 cells (Table 4).

TABLE 4

| Humabody ® VH | CHO PD-1 binding EC50 (M) | CHO PD-1: PD-L1 IC$_{50}$ (M) | CHO PD-1: PD-L2 IC$_{50}$ (M) |
|---|---|---|---|
| 1.39 | 0.6E−09 | No inhibition | No inhibition |
| 2.12 | 1.3E−09 | No inhibition | No inhibition |
| 2.1 | 0.7E−09 | No inhibition | | e) Reporter Gene Assays

The ability of $V_H$ single domain antibodies to inhibit functional responses in transfected Jurkat cells as a result of PD-1:PD-L1 blockade was assessed using an NFAT-Luciferase Reporter Gene assay. A Jurkat reporter cell line expressing human PD-1 and a luciferase reporter gene under the control of a promoter with an NFAT response element and a CHO cell line expressing a T-Cell Receptor activator and human PD-L1 under the control of a tetracycline inducible promotor were generated by standard methods. Cells were prepared in bulk, then frozen and stored in liquid nitrogen.

CHO human PD-L1/TCR activator cells were thawed in a 37° C. water bath, washed once with PBS, resuspended in (Hams F12/10% FBS/1 μg/ml tetracycline) and plated at 10000 cells/well in a 96 well white TC treated assay plate. Plates were incubated at 37° C. overnight in a CO2 incubator.

Samples were serially diluted in assay medium (RPMI+ 2% FBS). Jurkat PD-1 reporter cells were thawed in a 37° C. water bath, washed once with medium, then diluted into assay medium at 5e5 cells/ml. The media was removed from the CHO cells and 50 μl diluted sample or assay media (background control) added to the plates followed by 50 μl of the diluted Jurkat reporter cells. The plates were incubated for 6 hours at 37° C. overnight in a CO2 incubator, then removed from the incubator and equilibrated to room temperature for 20 mins. NanoGlo substrate (100 μl of substrate diluted 1:50 in NanGlo buffer (Promega cat no. N1120) was added and the plates incubated for 20 mins at room temperature prior to measurement of luminescence signal (RLU). Data was expressed as fold/background signal. Humabody® $V_H$ 1.39, 2.12, 2.1 and 1.1 were tested together with control PD-1 single blocking $V_H V_H$(A) (SEQ ID NO. 528) and biparatopic (Blocking VH(A)-4GS-1.39, Blocking VH(A)-4GS-2.12) (PD-1 antagonists).

Example data for activity of $V_H$ in the reporter assay is shown in FIGS. 5a, b and c. Tested Humabody® $V_H$ showed no activity in the assay demonstrating that Humabody® $V_H$ 1.39, 2.12 and 1.1 do not block PD-1: PD-L1 functional interaction. The biparatopic molecule shows an increased blocking activity (10 to 25 fold compared to monovalent blocker).

f) Measurement of Binding Kinetics Using Octet

Binding kinetics of clones to human PD-1-huFc were measured in real-time bio-layer interferometer based biosensor Octet (ForteBio). Recombinant human PD-1-huFc was either immobilized by standard amine coupling to amine reactive biosensors in 10 mM sodium acetate at pH 5.0 or capture by protein G biosensors (ForteBio). All the binding studies were performed in HBS-ET Octet kinetics buffer. Biosensors were always washed in Octet kinetics buffer in between different steps. A seven point, two-fold dilution series of each Humabody® $V_H$ was made with a top concentration in range 100-30 nM. The contact time for each of the association steps was varied between 180-300 seconds and the dissociation step was varied between 400-600 seconds. Kinetic association ($k_a$) and dissociation ($k_d$) rate constants were determined by processing and fitting the data to a 1:1 binding model using ForteBio Analysis software. The calculated affinity and kinetic constants are shown in Table 5 and the KD is in the nanomolar range.

TABLE 5

| Humabody ® $V_H$ | ka (1/Ms) | kd (1/s) | KD (M) |
|---|---|---|---|
| 1.1 | 4.5E+05 | 9.01E−04 | 1.9E−9 |
| 2.1 | 5.9E+05 | 1.5E−03 | 2.6E−9 |
| 2.39 | 3.7E+5 | 5.9E−04 | 1.6E−9 |
| 2.52 | 6.7E+05 | 2.2E−03 | 3.3E−09 |
| 2.53 | 1.0E+06 | 1.7E−02 | 1.6E−08 |
| 2.13 | 1.3E+06 | 3.5E−02 | 2.5E−08 |
| 2.37 | 4.5E+05 | 1.5E−03 | 3.4E−09 |
| 1.34 | 1.9E+05 | 7E−04 | 3.6E−09 |
| 1.33 | 3.7E+05 | 7.4E−04 | 2.0E−09 |
| 1.37 | 2.4E+05 | 1.3E−05 | 5.5E−09 | g) Binding Kinetics to Human PD-1 Using Surface Plasmon Resonance

Binding kinetics of certain $V_H$ single domain antibodies binding to human PD-1-huFc were measured by surface plasmon resonance (SPR) technology using Biacore T200 instrument (GE Healthcare). Recombinant human PD-1-huFc was immobilized by standard amine coupling to CM5 sensorschip (GE Healthcare) using 0.01 mg/ml solution of antigen in 10 mM sodium acetate at pH 5.5. For the reference flow cell, a blank immobilisation was carried out. Single cycle kinetics assays were used to study the interaction, a five point, three-fold dilution series of each Humabody® was made with a top concentration of 30 nM. The binding kinetics were followed by flowing the Humabody® over the chip surface in HBS EP+ buffer at a flow rate of 30 µl/min. The contact time for each of the association steps was 180 seconds and the dissociation step was varied between 1200-3600 seconds. The data was fitted to a 1:1 binding model after double reference subtraction using the Biacore T200 Evaluation software. The calculated affinity and kinetic constants are shown in Table 6 below

TABLE 6

| Humabody ® $V_H$ | ka (1/Ms) | kd (1/s) | KD (M) |
|---|---|---|---|
| 1.48 | 1.80E+05 | 2.91E−03 | 1.62E−08 |
| 1.39 | 3.16E+05 | 1.34E−03 | 4.24E−09 |
| 1.40 | 2.43E+05 | 1.45E−03 | 5.98E−09 |
| 1.44 | 2.24E+05 | 2.04E−03 | 9.10E−09 |
| 1.26 | 2.65E+05 | 2.11E−03 | 7.94E−09 |
| 1.47 | 2.48E+05 | 2.54E−03 | 1.02E−08 |
| 1.50 | 1.60E+05 | 2.29E−03 | 1.43E−08 |
| 2.12 | 5.5E+6 | 0.03848 | 6.89E−9 | h) Serum Stability

Figure 9A:
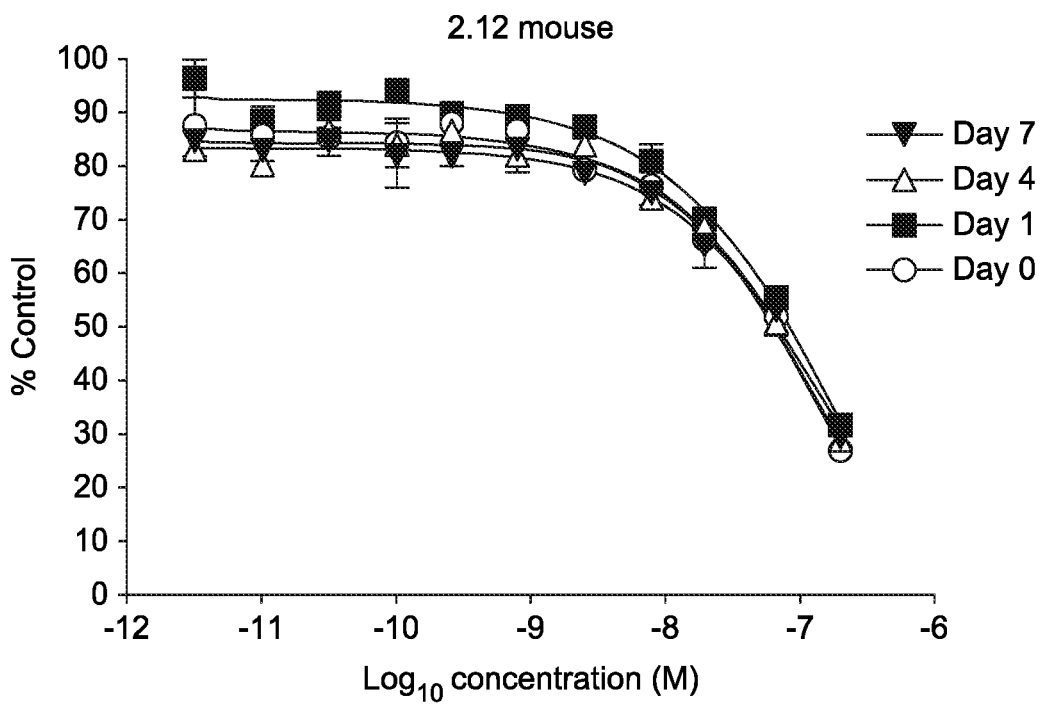
Figure 9B:
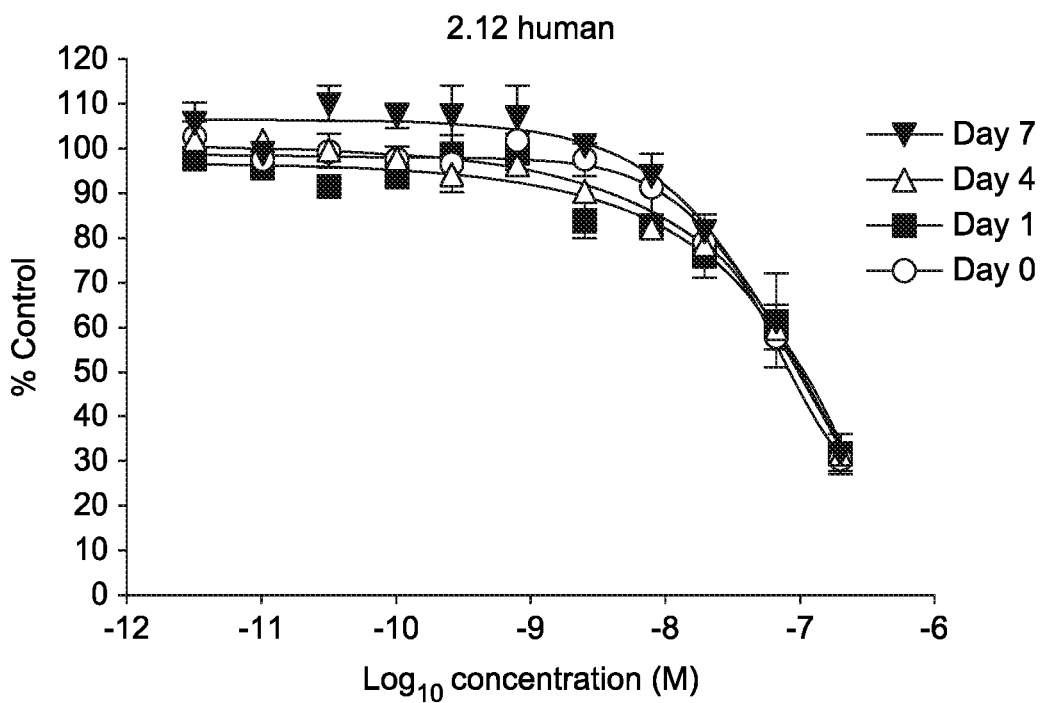

Serum stability of $V_H$ was assessed by measurement of its activity following incubation for 0, 1, 4 or 7 days in both human and mouse serum (Sigma M5905). The pre-incubated samples were serially diluted and tested in the 2.1 epitope competition assay. On incubation at 37° C. in the presence of either mouse or human serum no significant change in the activity was seen (Table 7). Example binding curve data is shown in FIGS. 9a and 9b.

TABLE 7

| | IC 50 (M) | | | | | | | |
|---|---|---|---|---|---|---|---|---|
| | Day 0 | | Day 1 | | Day 4 | | Day 7 | |
| Constructs | Human | Mouse | Human | Mouse | Human | Mouse | Human | Mouse |
| 1.39 | 12.9E−09 | 8.7E−09 | 10.1E−09 | 9.3E−09 | 10.2E−09 | 11.1E−09 | 9.3E−09 | 11.6E−09 | i) $V_H$ Single Domain Antibodies Demonstrate Good Stability

Purified $V_H$ were subjected to size exclusion chromatography. Briefly, purified $V_H$ were stored at 1 or 5 mg/ml in PBS buffer for 0-14 days at either 4° C. or 40° C., and then analysed at various time points using a Waters H-Class Bio UPLC containing a PDA detector (detection at 280 nm) with separation on a Waters ACQUITY BEH 125A SEC column. Samples were injected in 10 µl volumes and were run in a mobile phase containing 200 mM NaCl, 100 mM sodium phosphate, pH 7.4+5% propan-1-ol at a flow rate of 0.4 ml/min. Data were collected for 6 minutes and the area of the monomer peak remaining after storage as compared to that present at the start (T=0) was calculated. Examples of an anti-PD-1 $V_H$ single domain antibody 1.1 incubated at 40° C. for 14 days is illustrated in FIG. 6 and in Table 8. At incubation at 4° C. for 14 days, no significant change was seen.

TABLE 8

Stability of VH single domain antibody. This shows the percentage of monomer present after 0, 1, 3, 7 and 14 days.

| Name | 0 days | 1 days | 4 days | 7 days | 14 days |
|---|---|---|---|---|---|
| 1.1 | 100 | 90.19 | 87.04 | 94.93 | 100.10 |
| 1.1 | 100 | 95.01 | 91.79 | 92.55 | 90.46 |
| 1.21 | 100.00 | 100.44 | 104.46 | 106.95 | 111.95 |
| 1.29 | 100.00 | 99.20 | 101.18 | 108.35 | 115.06 |
| 1.39 | 100.00 | 102.25 | 101.71 | 104.41 | 96.61 |
| 2.12 | 100.00 | 99.26 | 99.10 | 93.94 | 90.35 |
| 2.1 | 100.00 | 99.20 | 100.15 | 100.40 | 100.78 |
| 2.29 | 100.00 | 99.99 | 101.03 | 93.96 | 96.03 |
| 2.52 | 100.00 | 100.80 | 100.79 | 96.70 | 99.58 |
| 2.28 | 100.00 | 101.41 | 101.04 | 99.40 | 100.46 |
| 2.53 | 100.00 | 99.79 | 101.12 | 100.00 | 101.06 | j) 1.1 and 2.1 Epitope Competition Assays

Sequence optimised single domain antibodies with improved activity and/or expression levels over that of the parental (non-optimised) single domain antibodies were initially identified by testing of bacterial periplasmic extracts for their ability to compete with the binding of the parental clone 1.1 or a 2.1 to CHO human PD-1 cells in an FMAT epitope competition assay.

Humabody® 1.1 or 2.1 $V_H$ sequence was amplified by PCR and sub-cloned into a vector enabling expression with a C terminally fused Strep tag. TG1 bacterial cultures transformed with the expression vector were cultured, periplasmic extracts prepared using extraction buffer (20% w/v sucrose, 1 mM EDTA, 50 mM Tris-HCl pH8.0) then Strep-tagged $V_H$ purified from the periplasm using Strep-Tactin affinity resin (Qiagen 30002).

For the epitope competition assay reagents were prepared in FMAT assay buffer. Bacterial periplasmic extracts, buffer (total binding controls) or excess His tagged $V_H$ competitor (non-specific binding control) were incubated with 2 nM 1.1-Strep tagged protein or 2 nM 2.1-Strep tagged protein, 1.5 nM Strep-Tag® II monoclonal antibody (Millipore 71590), 2.5 nM Goat anti mouse Fc-Alexa Fluor 488 and 2000 CHO human PD-1 DRAQ5 stained cells per well in a 384 well black clear-bottomed assay plate. Plates were incubated for a minimum of 1.5 hours at room temperature then fluorescence measured in the FL2 (502 nm-537 nm) and FL5 (677-800 nm) channels on the Mirrorball plate reader (TTP) following excitation at 488 nm and 640 nm. Data was expressed as a % of the total binding control (i.e. % control) after subtraction of the background signal determined from the non-specific binding control wells. Clones that showed improved activity compared to the parent $V_H$ were purified and tested multipoint in the Epitope Competition Assay for $IC_{50}$ determination or were tested directly in the reporter gene assay described below (data shown in Table 10).

TABLE 10

| Names | 1.1 EC IC50 (M) | 2.1 EC IC50 (M) |
|---|---|---|
| 1.39 | 8.9E−09 | 9.7E−09 |
| 1.34 | 6.5E−09 | |
| 1.26 | 8E−09 | |
| 1.33 | 2.5E−09 | |
| 1.37 | 7.5E−09 | |
| 2.27 | 9E−09 | 1.3E−08 |
| 2.53 | 7E−09 | 1.4E−08 |
| 2.52 | 6.5E−09 | 2.1E−08 |
| 1.1 | 3.5E−09 | 3.6E−09 |
| 2.1 | 9.2E−09 | 9.4E−09 | k) Effects of PD-1 Specific $V_H$ Single Domain Antibody on Human T Cell Activation in a Mixed Lymphocyte Reaction PD-1 specific $V_H$ single domain antibody $V_H$ 1.1 does not block the functional interaction of PD-1 with PD-L1 and therefore does not affect T cell activation in a Mixed Lymphocyte Reaction. Monocytes were isolated from human peripheral blood mononuclear cells (PBMCs) and differentiated into dendritic cells for 7 days using GM-CSF and IL-4. Dendritic cells were cultured with allogeneic CD4+ T cells, isolated from PBMCs via magnetic separation. Co-cultures were incubated for 2-7 days in the presence of PD-1-specific $V_H$ single domain antibody or control. T cell stimulation was measured by proliferation assay or cytokine quantification from the cell supernatant. IL-2 levels were determined after 3 days by Homogenous Time Resolved Fluorescence assay (HTRF, CisBio).

$V_H$ single domain antibody 1.1 does not enhance T cell activation (FIG. 7).

Example 10. Epitope Mapping of $V_H$ Single Domain Antibodies

The binding epitopes on PD-1 of $V_H$ single domain antibodies 1.1 and 2.1 were determined using peptide scanning analysis (PepScan). 1.1 in monovalent format was screened against arrays of PD-1 linear peptides and PD-1 peptides constrained to mimic loops and β-strands, with one residue offset between peptides in each set. 1.1 and 2.1 in bivalent format were screened against arrays combining discontinuous peptides.

Synthesis of peptides: To reconstruct continuous epitopes of huPD-1 extracellular domain, a library of peptides was synthesized. An amino functionalized polypropylene support was obtained by grafting with a proprietary hydrophilic polymer formulation, followed by reaction with t-butyloxy-carbonyl-hexamethylenediamine (BocHMDA) using dicyclohexylcarbodiimide (DCC) with Nhydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer). Synthesis of structural mimics was done using Pepscan's proprietary Chemically Linked Peptides on Scaffolds (CLIPS) technology. CLIPS technology allows to structure peptides into single loops, double loops, triple loops, sheet-like folds, helix-like folds and combinations thereof. CLIPS templates are coupled to cysteine residues. The side-chains of multiple cysteines in the peptides are coupled to one or two CLIPS templates. For example, a 0.5 mM solution of the P2 CLIPS (2,6-bis (bromomethyl)pyridine) is dissolved in ammonium bicarbonate (20 mM, pH 7.8)/acetonitrile (1:3(v/v)). This solution is added onto the peptide arrays. The CLIPS template will bind to side-chains of two cysteines as present in the solid-phase bound peptides of the peptide-arrays (455 wells plate with 3 μl wells). The peptide arrays are gently shaken in the solution for 30 to 60 minutes while completely covered in solution. Finally, the peptide arrays are washed extensively with excess of H2O and sonicated in disrupt-buffer containing 1% SDS/0.1% beta-mercaptoethanol in PBS (pH 7.2) at 70° C. for 30 minutes, followed by sonication in H2O for another 45 minutes. The T3 CLIPS carrying peptides were made in a similar way but now with three cysteines.

ELISA screening: The binding of antibody to each of the synthesized peptides was tested in a PEPSCAN-based ELISA. The peptide arrays were incubated with anti-His Tag monoclonal antibody (R&D) (overnight at 4° C.). After washing, the peptide arrays were incubated with a 1/1000 dilution of rabbit anti-mouse IgG (H+L) HRP conjugate (Southern Biotech) for one hour at 25° C. After washing, the peroxidase substrate 2,2'-azino-di-3-ethylbenzthiazoline sulfonate (ABTS) and 20 μl/ml of 3 percent $H_2O_2$ were added. After one hour, the colour development was measured. The colour development was quantified with a charge coupled device (CCD)—camera and an image processing system.

Data processing: The values obtained from the CCD camera range from 0 to 3000 mAU, similar to a standard 96-well plate ELISA-reader. The results are quantified and stored into the Peplab database. Occasionally a well contains an air-bubble resulting in a false-positive value, the cards are manually inspected, and any values caused by an air-bubble are scored as 0.

Synthesis quality control: To verify the quality of the synthesized peptides, a separate set of positive and negative control peptides was synthesized in parallel. These were screened with antibody 57.9 (Posthumus et al., J. Virology, 1990, 64:3304-3309).

When screened against linear peptides and peptides constrained to mimic loops and 3-strands peptides, 1.1 shows consistent binding to a subset of peptides comprising the motif 102-NGRDFHMSVVRARR-115 (SEQ ID No. 519). Binding to this epitope was observed over all sets of peptides tested and was independent of the structural restraints imposed upon the peptides.

Screened against discontinuous peptides, 1.1 displays binding to a subset of peptides comprising the motifs 33-NPPTFS-38 (SEQ ID No. 520), 54-CSFSNTS-ESFVLNW-67 (SEQ ID No. 521) and 101-PN-GRDFHMSV-110 (SEQ ID No. 522). The data is consistent with binding to the epitope identified in the linear peptides and also identifies additional residues which are proximal to the linear epitope in the tertiary structure. 2.1 displayed affinity for a discontinuous set of peptides comprising the motifs 60-SESFVLNWYRMS-71 (SEQ ID No. 523), 90-GQDCRFRVT-98 (SEQ ID No. 524) and 104-RDFHMSVVRAR-114 (SEQ ID No. 525). The identified sequences are proximal in the tertiary structure consistent with a discontinuous epitope.

Figures 8A, 8B:
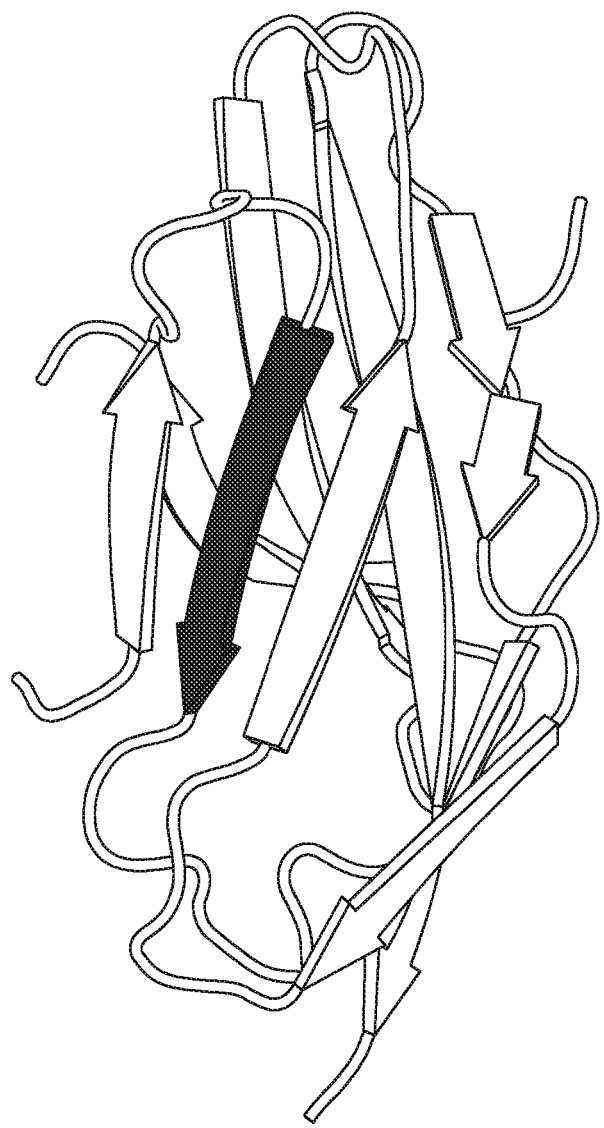

Analysis of the huPD-1 structure (PDB code: 4ZQK) indicates that the identified epitopes for both 1.1 and 2.1 are located on the opposing face of the huPD-1 extracellular domain to that of the PD-L1 binding interface, consistent with binding to huPD-1 without interrupting native ligand binding (see FIG. 8A).

The sequence 104-RDFHMSV-110 (SEQ ID No.526) (see FIG. 8A) is consistent within the epitopes identified for both Humabody® VH. The partial overlap of epitopes is consistent with the two Humabody® VH displaying competitive binding.

Example 11. PD-1 Stimulation

Experiments were performed using DiscoverX Path-Hunter Checkpoint assay, which measures PD-1 signalling. Cells expressed PD-1 linked to an intracellular enzyme fragment and SH2-domain containing phosphatase linked to another enzyme fragment. Upon dimerization of receptor, complementation of the enzyme occurs. Substrate addition leads to chemiluminescent signal. PD-1 dimerization occurs in response to a PD-L1+ cell line. In absence of ligand, this dimerization could be induced by antibodies. PD-1+ cells were incubated with a dilution series of Humabody® VH for 3 hours before addition of detection reagent. Chemiluminescence was read as relative light units and EC50 was calculated from curve fit. Maximum response was calculated as percentage increase in RLU above basal response. Table 11 Biparatopic Humabody (1GS) enhances PD-1 signalling.

Bivalent 1.1 induces low level PD-1 signalling, when formatted as a biparatopic it is capable of PD1 agonism. A shorter linker increases this further, which is likely to be caused by enhanced cross-linking. $V_H(B)$ is a blocking single $V_H$ domain that blocks ligand binding (SEQ ID No. 529). When measured in this assay, a bivalent molecule using 2.1 shows no agonistic effect.

TABLE 11

|  | EC50 uM | Max. % increase in response over baseline |
|---|---|---|
| VH (B)-1GS-1.21 | 0.00059 | 1332 |
| VH (B)-4GS-1.21 | 0.0005 | 253.2 |
| 1.1a-4GS-1.1a | 0.001 | 57.77 |

The invention claimed is:

1. An isolated single domain antibody that binds to human PD-1 but does not block the interaction of human PD-1 with human PD-L1 and/or PD-L2, wherein said single domain antibody is a human heavy chain variable domain (VH) comprising a CDR1, 2, and 3 having the following sequences SEQ ID NOs: 173, 174, and 175, respectively.

2. The isolated single domain antibody according to claim 1, wherein said isolated single domain antibody comprises the following $V_H$ sequence of SEQ ID NO.

3. The isolated single domain antibody according to claim 1, wherein said single domain antibody is conjugated to a toxin, enzyme, radioisotope, half-life extending moiety, label, therapeutic molecule or other chemical moiety, optionally wherein said half-life extending moiety is selected from the group consisting of an albumin binding moiety, a transferrin binding moiety, a polyethylene glycol molecule, a recombinant polyethylene glycol molecule, human serum albumin, a fragment of human serum albumin, and an albumin binding peptide or single domain antibody that binds to human serum albumin.

4. The isolated single domain antibody according to claim 1 that does not compete with an antibody that blocks the interaction of PD-1 with PD-L1 and/or the interaction of PD-1 with PD-L2, and/or wherein the isolated single domain antibody is obtained or obtainable from a transgenic rodent that expresses a transgene comprising human V, D and J regions, optionally wherein said rodent does not produce any functional endogenous light and heavy chains.

5. An isolated binding agent comprising a single domain antibody according to claim 1, wherein said single domain antibody is linked to a second binding molecule that does not bind to PD-1, optionally wherein said second binding molecule binds to an immunooncology target, or wherein said single domain antibody is linked to a second binding molecule that binds to PD-1, optionally wherein said second binding molecule blocks the interaction of PD-1 with PD-L1 and/or PD-L2 or wherein said single domain antibody is conjugated to a toxin, enzyme, radioisotope, half-life extending moiety, therapeutic molecule or other chemical moiety, optionally wherein said half-life extending moiety is selected from the group consisting of an albumin binding moiety, a transferrin binding moiety, a polyethylene glycol molecule, a recombinant polyethylene glycol molecule, human serum albumin, a fragment of human serum albumin, or an albumin binding peptide or single domain antibody that binds to human serum albumin.

6. An immunoconjugate comprising the single domain antibody of claim 1, wherein the single domain antibody is linked to a therapeutic agent, optionally wherein said therapeutic agent is a toxin, enzyme, radioisotope or other chemical moiety.

7. A pharmaceutical composition comprising a single domain antibody of claim 1 and a pharmaceutical carrier.

8. A kit comprising a single domain antibody according to claim 1 and instructions for use.

9. A bispecific molecule comprising the single domain antibody of claim 1 linked to a second functional moiety having a different binding specificity than said single domain antibody, optionally, wherein said second moiety is an antibody, an antibody fragment or antibody mimetic, optionally wherein said second moiety binds to an immunooncology target.

10. A multivalent binding agent comprising a single domain antibody, wherein said binding agent comprises two single domain antibodies wherein a first single domain antibody is according to claim 1, and wherein the second single domain antibody that binds to human PD-1 also blocks the interaction with human PD-L1 and/or PD-L2 and wherein said first single domain antibody is linked to the second single domain antibody.

* * * * *

UNITED STATES PATENT AND TRADEMARK OFFICE
CERTIFICATE OF CORRECTION

| | | |
|---|---|---|
| PATENT NO. | : 11,814,429 B2 | Page 1 of 1 |
| APPLICATION NO. | : 16/475590 | |
| DATED | : November 14, 2023 | |
| INVENTOR(S) | : Bryan Edwards et al. | |

It is certified that error appears in the above-identified patent and that said Letters Patent is hereby corrected as shown below:

In the Claims

In Claim 2, Column 350, Line 67, delete "SEQ ID NO.", and replace it with "SEQ ID NO: 176."

Signed and Sealed this
Thirteenth Day of February, 2024

*Katherine Kelly Vidal*

Katherine Kelly Vidal
*Director of the United States Patent and Trademark Office*

SEQUENCE LISTING

```
<160> NUMBER OF SEQ ID NOS: 529

<210> SEQ ID NO 1
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 4"

<400> SEQUENCE: 1

Asp His Ala Met His
1               5

<210> SEQ ID NO 2
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 4"

<400> SEQUENCE: 2

Gly Ile Ser Trp Asn Ser Gly Ser Met Gly Tyr Ala Asp Ser Val Lys
1               5                   10                  15

Asp

<210> SEQ ID NO 3
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 4"

<400> SEQUENCE: 3

Glu Lys Gly Pro Gly Leu Thr Gly Ser Thr Ala Asp Tyr Tyr Gly Leu
1               5                   10                  15

Asp Val

<210> SEQ ID NO 4
<211> LENGTH: 127
```

```
<212> TYPE: PRT
<213> ORGANISM: Homo sapiens
<220> FEATURE:
<221> NAME/KEY: source
<223> OTHER INFORMATION: /note="VH 1.1"

<400> SEQUENCE: 4

Glu Val Gln Leu Leu Glu Ser Gly Gly Gly Ser Val Gln Pro Gly Arg
1               5                   10                  15

Ser Leu Arg Leu Ser Cys Ala Ala Ser Gly Phe Thr Phe Asp Asp His
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Met Gly Tyr Ala Asp Ser Val
    50                  55                  60

Lys Asp Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Val Trp Gly Gln Gly Thr Met Val Thr Val Ser Ser
        115                 120                 125

<210> SEQ ID NO 5
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 8"

<400> SEQUENCE: 5

Asp Tyr Ala Met His
1               5

<210> SEQ ID NO 6
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 8"

<400> SEQUENCE: 6

Gly Ile Ser Trp Asn Gly Gly Ser Met Gly Tyr Ala Ala Ser Val Lys
1               5                   10                  15

Gly

<210> SEQ ID NO 7
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 8"

<400> SEQUENCE: 7

Asp Lys Gly Pro Gly Leu Ile Gly Ser Thr Ala Asp Tyr Tyr Gly Leu
1               5                   10                  15

Asp Val
```

```
<210> SEQ ID NO 8
<211> LENGTH: 127
<212> TYPE: PRT
<213> ORGANISM: Homo sapiens
<220> FEATURE:
<221> NAME/KEY: source
<223> OTHER INFORMATION: /note="VH 1.2"

<400> SEQUENCE: 8

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Asp Leu Glu Trp Val
            35                  40                  45

Ser Gly Ile Ser Trp Asn Gly Ser Met Gly Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Asp Lys Gly Pro Gly Leu Ile Gly Ser Thr Ala Asp Tyr Tyr
                100                 105                 110

Gly Leu Asp Val Trp Gly Gln Gly Thr Thr Val Thr Val Ser Ser
            115                 120                 125

<210> SEQ ID NO 9
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 12"

<400> SEQUENCE: 9

Asp Tyr Ala Met His
1               5

<210> SEQ ID NO 10
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 12"

<400> SEQUENCE: 10

Gly Ile Ser Trp Asn Ser Gly Ser Met Gly Tyr Ala Asp Ser Val Lys
1               5                   10                  15

Asp

<210> SEQ ID NO 11
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 12"

<400> SEQUENCE: 11

Asp Lys Gly Pro Gly Leu Ile Gly Ser Thr Ala Asp Tyr His Gly Leu
1               5                   10                  15

Asp Val
```

```
<210> SEQ ID NO 12
<211> LENGTH: 127
<212> TYPE: PRT
<213> ORGANISM: Homo sapiens
<220> FEATURE:
<221> NAME/KEY: source
<223> OTHER INFORMATION: /note="VH 1.3"

<400> SEQUENCE: 12

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Arg Glu Trp Val
        35                  40                  45

Ser Gly Ile Ser Trp Asn Ser Gly Ser Met Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Asp Lys Gly Pro Gly Leu Ile Gly Ser Thr Ala Asp Tyr His
            100                 105                 110

Gly Leu Asp Val Trp Gly Gln Gly Thr Thr Val Thr Val Ser Ser
        115                 120                 125

<210> SEQ ID NO 13
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 16"

<400> SEQUENCE: 13

Asp Tyr Ala Met His
1               5

<210> SEQ ID NO 14
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 16"

<400> SEQUENCE: 14

Gly Ile Ser Trp Asn Gly Gly Ser Met Gly Tyr Ala Glu Ser Val Lys
1               5                   10                  15

Gly

<210> SEQ ID NO 15
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 16"

<400> SEQUENCE: 15

Asp Lys Gly Pro Gly Leu Thr Gly Thr Thr Ala Asp Tyr Tyr Gly Met
1               5                   10                  15
```

Asp Val

```
<210> SEQ ID NO 16
<211> LENGTH: 127
<212> TYPE: PRT
<213> ORGANISM: Homo sapiens
<220> FEATURE:
<221> NAME/KEY: source
<223> OTHER INFORMATION: /note="VH 1.4"

<400> SEQUENCE: 16
```

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Ala Asp Tyr
            20                  25                  30

Ala Met His Trp Val Arg Gln Ala Pro Gly Lys Gly Arg Glu Trp Val
        35                  40                  45

Ser Gly Ile Ser Trp Asn Gly Gly Ser Met Gly Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ser Ala Leu Tyr Tyr Cys
                85                  90                  95

Val Lys Asp Lys Gly Pro Gly Leu Thr Gly Thr Thr Ala Asp Tyr Tyr
            100                 105                 110

Gly Met Asp Val Trp Gly Gln Gly Thr Thr Val Thr Val Ser Ser
        115                 120                 125

```
<210> SEQ ID NO 17
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 20"

<400> SEQUENCE: 17
```

Asp Tyr Ala Met His
1               5

```
<210> SEQ ID NO 18
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 20"

<400> SEQUENCE: 18
```

Gly Ile Ser Trp Asn Gly Gly Ser Met Gly Tyr Ala Asp Ser Val Lys
1               5                   10                  15

Asp

```
<210> SEQ ID NO 19
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 20"

<400> SEQUENCE: 19
```

-continued

Asp Lys Gly Pro Gly Leu Ile Gly Ser Thr Ala Asp Tyr His Gly Leu
1               5                   10                  15

Asp Val

<210> SEQ ID NO 20
<211> LENGTH: 127
<212> TYPE: PRT
<213> ORGANISM: Homo sapiens
<220> FEATURE:
<221> NAME/KEY: source
<223> OTHER INFORMATION: /note="VH 1.5"

<400> SEQUENCE: 20

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Gly Ser Met Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Arg Leu Arg Ala Glu Asp Thr Ala Leu Tyr Tyr Cys
                85                  90                  95

Val Lys Asp Lys Gly Pro Gly Leu Ile Gly Ser Thr Ala Asp Tyr His
            100                 105                 110

Gly Leu Asp Val Trp Gly Gln Gly Thr Thr Val Thr Val Ser Ser
        115                 120                 125

<210> SEQ ID NO 21
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 24"

<400> SEQUENCE: 21

Ser Tyr Ala Met His
1               5

<210> SEQ ID NO 22
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 24"

<400> SEQUENCE: 22

Gly Ile Ser Trp Asn Ser Gly Ser Met Gly Tyr Ala Glu Ser Val Lys
1               5                   10                  15

Gly

<210> SEQ ID NO 23
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 24"

-continued

```
<400> SEQUENCE: 23

Asp Lys Gly Pro Gly Leu Thr Gly Thr Thr Ala Asp Tyr Tyr Gly Met
1               5                   10                  15

Asp Val

<210> SEQ ID NO 24
<211> LENGTH: 127
<212> TYPE: PRT
<213> ORGANISM: Homo sapiens
<220> FEATURE:
<221> NAME/KEY: source
<223> OTHER INFORMATION: /note="VH 1.6"

<400> SEQUENCE: 24

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Arg Glu Trp Val
        35                  40                  45

Ser Gly Ile Ser Trp Asn Ser Gly Ser Met Gly Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ser Ala Leu Tyr Tyr Cys
                85                  90                  95

Val Lys Asp Lys Gly Pro Gly Leu Thr Gly Thr Thr Ala Asp Tyr Tyr
            100                 105                 110

Gly Met Asp Val Trp Gly Gln Gly Thr Thr Val Thr Val Ser Ser
        115                 120                 125

<210> SEQ ID NO 25
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 28"

<400> SEQUENCE: 25

Asp Tyr Ala Met His
1               5

<210> SEQ ID NO 26
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 28"

<400> SEQUENCE: 26

Gly Ile Ser Trp Asn Gly Gly Ser Met Gly Tyr Ala Glu Ser Val Lys
1               5                   10                  15

Gly

<210> SEQ ID NO 27
<211> LENGTH: 18
<212> TYPE: PRT
<213> ORGANISM: Homo sapiens
<220> FEATURE:
<221> NAME/KEY: source
```

```
<223> OTHER INFORMATION: /note="CDR3 sequence of SEQ ID NO: 28"

<400> SEQUENCE: 27

Asp Lys Gly Pro Gly Leu Thr Gly Thr Thr Ala Asp Tyr Tyr Gly Met
1               5                   10                  15
Asp Val

<210> SEQ ID NO 28
<211> LENGTH: 127
<212> TYPE: PRT
<213> ORGANISM: Homo sapiens
<220> FEATURE:
<221> NAME/KEY: source
<223> OTHER INFORMATION: /note="VH 1.7"

<400> SEQUENCE: 28

Glu Val Gln Leu Val Glu Ser Gly Gly Val Ile Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Arg Glu Trp Val
            35                  40                  45

Ser Gly Ile Ser Trp Asn Gly Ser Met Gly Tyr Ala Glu Ser Val
        50                  55                  60

Lys Gly Arg Phe Thr Ile Ser Arg Asp Asn Ala Gln Asn Ser Leu Tyr
65                  70                  75                  80

Leu Gln Met Asn Ser Leu Arg Ala Glu Asp Ser Ala Leu Tyr Tyr Cys
                85                  90                  95

Val Lys Asp Lys Gly Pro Gly Leu Thr Gly Thr Thr Ala Asp Tyr Tyr
                100                 105                 110

Gly Met Asp Val Trp Gly Gln Gly Thr Thr Val Thr Val Ser Ser
            115                 120                 125

<210> SEQ ID NO 29
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 32"

<400> SEQUENCE: 29

Asp Tyr Ala Met His
1               5

<210> SEQ ID NO 30
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 32"

<400> SEQUENCE: 30

Gly Ile Ser Trp Asn Ser Gly Ser Met Gly Tyr Ala Asp Ser Val Lys
1               5                   10                  15
Asp

<210> SEQ ID NO 31
<211> LENGTH: 18
<212> TYPE: PRT
<213> ORGANISM: Homo sapiens
```

```
<220> FEATURE:
<221> NAME/KEY: source
<223> OTHER INFORMATION: /note="CDR3 sequence of SEQ ID NO: 32"

<400> SEQUENCE: 31
```

Asp Lys Gly Pro Gly Leu Ile Gly Ser Thr Ala Asp Tyr His Gly Leu
1               5                   10                  15

Asp Val

```
<210> SEQ ID NO 32
<211> LENGTH: 127
<212> TYPE: PRT
<213> ORGANISM: Homo sapiens
<220> FEATURE:
<221> NAME/KEY: source
<223> OTHER INFORMATION: /note="VH 1.8"

<400> SEQUENCE: 32
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Met Gly Tyr Ala Asp Ser Val
        50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Asp Lys Gly Pro Gly Leu Ile Gly Ser Thr Ala Asp Tyr His
            100                 105                 110

Gly Leu Asp Val Trp Gly Gln Gly Thr Thr Val Thr Val Ser Ser
        115                 120                 125

```
<210> SEQ ID NO 33
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 36"

<400> SEQUENCE: 33
```

Asp Tyr Ala Met His
1               5

```
<210> SEQ ID NO 34
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 36"

<400> SEQUENCE: 34
```

Gly Ile Ser Trp Asn Gly Gly Ser Met Gly Tyr Ala Glu Ser Val Lys
1               5                   10                  15

Gly

```
<210> SEQ ID NO 35
<211> LENGTH: 18
```

```
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 36"

<400> SEQUENCE: 35

Asp Lys Gly Pro Gly Leu Ile Gly Ser Thr Ala Asp Tyr Tyr Gly Met
1               5                   10                  15

Asp Val

<210> SEQ ID NO 36
<211> LENGTH: 127
<212> TYPE: PRT
<213> ORGANISM: Homo sapiens
<220> FEATURE:
<221> NAME/KEY: source
<223> OTHER INFORMATION: /note="VH 1.9"

<400> SEQUENCE: 36

Glu Val Gln Leu Val Glu Ser Gly Gly Gly Cys Val Gln Pro Gly Arg
1               5                   10                  15

Ser Leu Arg Ile Ser Cys Ala Ala Ser Gly Phe Thr Phe Asp Asp Tyr
            20                  25                  30

Ala Met His Trp Val Arg Gln Ala Pro Gly Lys Gly Arg Glu Trp Val
        35                  40                  45

Ser Gly Ile Ser Trp Asn Gly Gly Ser Met Gly Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ser Ala Leu Tyr Tyr Cys
                85                  90                  95

Val Lys Asp Lys Gly Pro Gly Leu Ile Gly Ser Thr Ala Asp Tyr Tyr
            100                 105                 110

Gly Met Asp Val Trp Gly Gln Gly Thr Thr Val Thr Val Ser Ser
        115                 120                 125

<210> SEQ ID NO 37
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 40"

<400> SEQUENCE: 37

Asp Tyr Ala Met His
1               5

<210> SEQ ID NO 38
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 40"

<400> SEQUENCE: 38

Gly Ile Ser Trp Asn Gly Gly Ser Met Gly Tyr Ala Glu Ser Val Lys
1               5                   10                  15

Gly
```

```
<210> SEQ ID NO 39
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 40"

<400> SEQUENCE: 39

Asp Lys Gly Pro Gly Leu Thr Gly Thr Thr Ala Asp Tyr Tyr Gly Met
1               5                   10                  15

Asp Val

<210> SEQ ID NO 40
<211> LENGTH: 127
<212> TYPE: PRT
<213> ORGANISM: Homo sapiens
<220> FEATURE:
<221> NAME/KEY: source
<223> OTHER INFORMATION: /note="VH 1.10"

<400> SEQUENCE: 40

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ala Asp Tyr
            20                  25                  30

Ala Met His Trp Val Arg Gln Ala Pro Gly Lys Gly Arg Glu Trp Val
        35                  40                  45

Ser Gly Ile Ser Trp Asn Gly Gly Ser Met Gly Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ser Ala Leu Tyr Tyr Cys
                85                  90                  95

Val Lys Asp Lys Gly Pro Gly Leu Thr Gly Thr Thr Ala Asp Tyr Tyr
            100                 105                 110

Gly Met Asp Val Trp Gly Gln Gly Thr Thr Val Thr Val Ser Ser
        115                 120                 125

<210> SEQ ID NO 41
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 44"

<400> SEQUENCE: 41

Asp Tyr Ala Met His
1               5

<210> SEQ ID NO 42
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 44"

<400> SEQUENCE: 42

Gly Ile Ser Trp Asn Gly Gly Ser Met Gly Tyr Ala Glu Ser Val Lys
1               5                   10                  15

Gly
```

```
<210> SEQ ID NO 43
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 44"

<400> SEQUENCE: 43

Asp Lys Gly Pro Gly Leu Ile Gly Ser Thr Ala Asp Tyr Tyr Gly Leu
1               5                   10                  15

Asp Val

<210> SEQ ID NO 44
<211> LENGTH: 127
<212> TYPE: PRT
<213> ORGANISM: Homo sapiens
<220> FEATURE:
<221> NAME/KEY: source
<223> OTHER INFORMATION: /note="VH 1.11"

<400> SEQUENCE: 44

Glu Val Gln Leu Leu Glu Ser Gly Gly Gly Phe Val Gln Pro Gly Arg
1               5                   10                  15

Ser Leu Arg Ile Ser Cys Ala Ala Ser Gly Phe Thr Phe Asp Asp Tyr
                20                  25                  30

Ala Met His Trp Val Arg Gln Ala Pro Gly Lys Asp Leu Glu Trp Val
            35                  40                  45

Ser Gly Ile Ser Trp Asn Gly Gly Ser Met Gly Tyr Ala Glu Ser Val
        50                  55                  60

Lys Gly Arg Phe Thr Ile Ser Arg Asp Asn Ala Lys Asn Ser Leu Tyr
65                  70                  75                  80

Leu Lys Met Asn Ser Leu Arg Val Glu Asp Thr Ala Leu Tyr Tyr Cys
                85                  90                  95

Val Lys Asp Lys Gly Pro Gly Leu Ile Gly Ser Thr Ala Asp Tyr Tyr
            100                 105                 110

Gly Leu Asp Val Trp Gly Gln Gly Thr Thr Val Thr Val Ser Ser
        115                 120                 125

<210> SEQ ID NO 45
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 48"

<400> SEQUENCE: 45

Asp Tyr Ala Met His
1               5

<210> SEQ ID NO 46
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 48"

<400> SEQUENCE: 46

Gly Ile Ser Trp Asn Gly Gly Ser Met Gly Tyr Ala Asp Ser Val Lys
1               5                   10                  15
```

Asp

<210> SEQ ID NO 47
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 48"

<400> SEQUENCE: 47

Asp Lys Gly Pro Gly Leu Thr Gly Ser Thr Ala Asp Tyr His Gly Met
1               5                   10                  15

Asp Val

<210> SEQ ID NO 48
<211> LENGTH: 127
<212> TYPE: PRT
<213> ORGANISM: Homo sapiens
<220> FEATURE:
<221> NAME/KEY: source
<223> OTHER INFORMATION: /note="VH 1.12"

<400> SEQUENCE: 48

Gln Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Arg Glu Trp Val
        35                  40                  45

Ser Gly Ile Ser Trp Asn Gly Gly Ser Met Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Asp Lys Gly Pro Gly Leu Thr Gly Ser Thr Ala Asp Tyr His
            100                 105                 110

Gly Met Asp Val Trp Gly Gln Gly Thr Thr Val Thr Val Ser Ser
        115                 120                 125

<210> SEQ ID NO 49
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 52"

<400> SEQUENCE: 49

Asp Tyr Ala Met His
1               5

<210> SEQ ID NO 50
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 52"

<400> SEQUENCE: 50

```
Gly Ile Ser Trp Asn Gly Gly Ser Met Gly Tyr Ala Ala Ser Val Lys
1               5                   10                  15

Gly
```

<210> SEQ ID NO 51
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 52"

<400> SEQUENCE: 51

```
Asp Lys Gly Pro Gly Leu Ile Gly Ser Thr Ala Asp Tyr Tyr Gly Leu
1               5                   10                  15

Asp Val
```

<210> SEQ ID NO 52
<211> LENGTH: 127
<212> TYPE: PRT
<213> ORGANISM: Homo sapiens
<220> FEATURE:
<221> NAME/KEY: source
<223> OTHER INFORMATION: /note="VH 1.13"

<400> SEQUENCE: 52

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Gly Gly Ser Met Gly Tyr Ala Ala Ser Val
    50                  55                  60

Lys Gly Arg Phe Thr Ile Ser Arg Asp Asn Ala Gln Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Asp Lys Gly Pro Gly Leu Ile Gly Ser Thr Ala Asp Tyr Tyr
            100                 105                 110

Gly Leu Asp Val Trp Gly Gln Gly Thr Thr Val Thr Val Ser Ser
        115                 120                 125
```

<210> SEQ ID NO 53
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 56"

<400> SEQUENCE: 53

```
Gly Tyr Ala Met His
1               5
```

<210> SEQ ID NO 54
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 56"

```
<400> SEQUENCE: 54

Gly Ile Ser Trp Asn Ser Gly Ser Met Gly Tyr Ala Glu Ser Val Lys
1               5                   10                  15

Gly

<210> SEQ ID NO 55
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 56"

<400> SEQUENCE: 55

Asp Lys Gly Pro Gly Leu Thr Gly Ser Thr Ala Asp Tyr Tyr Gly Met
1               5                   10                  15

Asp Val

<210> SEQ ID NO 56
<211> LENGTH: 127
<212> TYPE: PRT
<213> ORGANISM: Homo sapiens
<220> FEATURE:
<221> NAME/KEY: source
<223> OTHER INFORMATION: /note="VH 1.14"

<400> SEQUENCE: 56

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Gly Tyr
            20                  25                  30

Ala Met His Trp Val Arg Gln Ala Pro Gly Lys Gly Arg Glu Trp Val
        35                  40                  45

Ser Gly Ile Ser Trp Asn Ser Gly Ser Met Gly Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ser Ala Leu Tyr Tyr Cys
                85                  90                  95

Val Lys Asp Lys Gly Pro Gly Leu Thr Gly Ser Thr Ala Asp Tyr Tyr
            100                 105                 110

Gly Met Asp Val Trp Gly Gln Gly Thr Thr Val Thr Val Ser Ser
        115                 120                 125

<210> SEQ ID NO 57
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 60"

<400> SEQUENCE: 57

Asp Tyr Ala Met His
1               5

<210> SEQ ID NO 58
<211> LENGTH: 17
<212> TYPE: PRT
<213> ORGANISM: Homo sapiens
<220> FEATURE:
<221> NAME/KEY: source
```

```
<223> OTHER INFORMATION: /note="CDR2 sequence of SEQ ID NO: 60"

<400> SEQUENCE: 58

Gly Ile Ser Trp Asn Ser Gly Ser Met Gly Tyr Ala Glu Ser Val Lys
1               5                   10                  15

Gly

<210> SEQ ID NO 59
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 60"

<400> SEQUENCE: 59

Asp Lys Gly Pro Gly Leu Ile Gly Ser Thr Ala Asp Tyr Tyr Gly Met
1               5                   10                  15

Asp Val

<210> SEQ ID NO 60
<211> LENGTH: 127
<212> TYPE: PRT
<213> ORGANISM: Homo sapiens
<220> FEATURE:
<221> NAME/KEY: source
<223> OTHER INFORMATION: /note="VH 1.15"

<400> SEQUENCE: 60

Glu Val Gln Leu Leu Glu Ser Gly Gly Gly Leu Val Gln Pro Gly Arg
1               5                   10                  15

Ser Leu Arg Leu Ser Cys Thr Ala Ser Gly Phe Thr Phe Asp Asp Tyr
            20                  25                  30

Ala Met His Trp Val Arg Gln Ala Pro Gly Lys Gly Arg Glu Trp Val
        35                  40                  45

Ser Gly Ile Ser Trp Asn Ser Gly Ser Met Gly Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ser Ala Leu Tyr Tyr Cys
                85                  90                  95

Val Lys Asp Lys Gly Pro Gly Leu Ile Gly Ser Thr Ala Asp Tyr Tyr
            100                 105                 110

Gly Met Asp Val Trp Gly Gln Gly Thr Thr Val Thr Val Ser Ser
        115                 120                 125

<210> SEQ ID NO 61
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 64"

<400> SEQUENCE: 61

Asp Tyr Ala Met His
1               5

<210> SEQ ID NO 62
<211> LENGTH: 17
<212> TYPE: PRT
<213> ORGANISM: Homo sapiens
```

```
<220> FEATURE:
<221> NAME/KEY: source
<223> OTHER INFORMATION: /note="CDR2 sequence of SEQ ID NO: 64"

<400> SEQUENCE: 62

Gly Ile Ser Trp Asn Gly Gly Ser Met Gly Tyr Ala Glu Ser Val Lys
1               5                   10                  15

Gly

<210> SEQ ID NO 63
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 64"

<400> SEQUENCE: 63

Asp Lys Gly Pro Gly Leu Ile Gly Ser Thr Ala Asp Tyr Tyr Gly Met
1               5                   10                  15

Asp Val

<210> SEQ ID NO 64
<211> LENGTH: 127
<212> TYPE: PRT
<213> ORGANISM: Homo sapiens
<220> FEATURE:
<221> NAME/KEY: source
<223> OTHER INFORMATION: /note="VH 1.16"

<400> SEQUENCE: 64

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Arg Glu Trp Val
        35                  40                  45

Ser Gly Ile Ser Trp Asn Gly Gly Ser Met Gly Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ser Ala Leu Tyr Tyr Cys
                85                  90                  95

Val Lys Asp Lys Gly Pro Gly Leu Ile Gly Ser Thr Ala Asp Tyr Tyr
            100                 105                 110

Gly Met Asp Val Trp Gly Gln Gly Thr Thr Val Thr Val Ser Ser
        115                 120                 125

<210> SEQ ID NO 65
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 68"

<400> SEQUENCE: 65

Asp Tyr Ala Met His
1               5

<210> SEQ ID NO 66
<211> LENGTH: 17
```

```
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 68"

<400> SEQUENCE: 66

Gly Ile Ser Trp Asn Ser Gly Ser Met Gly Tyr Ala Ala Ser Val Lys
1               5                   10                  15

Asp

<210> SEQ ID NO 67
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 68"

<400> SEQUENCE: 67

Asp Lys Gly Pro Gly Leu Ile Gly Ser Thr Ala Asp Tyr His Gly Leu
1               5                   10                  15

Asp Val

<210> SEQ ID NO 68
<211> LENGTH: 127
<212> TYPE: PRT
<213> ORGANISM: Homo sapiens
<220> FEATURE:
<221> NAME/KEY: source
<223> OTHER INFORMATION: /note="VH 1.17"

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Met Gly Tyr Ala Ala Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Thr Thr Glu Asp Thr Ala Leu Tyr Tyr Cys
                85                  90                  95

Val Lys Asp Lys Gly Pro Gly Leu Ile Gly Ser Thr Ala Asp Tyr His
            100                 105                 110

Gly Leu Asp Val Trp Gly Gln Gly Thr Thr Val Thr Val Ser Ser
        115                 120                 125

<210> SEQ ID NO 69
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 72"

<400> SEQUENCE: 69

Asp Tyr Ala Met His
1               5
```

-continued

<210> SEQ ID NO 70
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 72"

<400> SEQUENCE: 70

Gly Ile Ser Trp Asn Gly Gly Ser Met Gly Tyr Ala Ala Ser Val Lys
1               5                   10                  15
Gly

<210> SEQ ID NO 71
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 72"

<400> SEQUENCE: 71

Asp Lys Gly Pro Gly Leu Ile Gly Ser Thr Ala Asp Tyr Tyr Gly Leu
1               5                   10                  15
Asp Val

<210> SEQ ID NO 72
<211> LENGTH: 127
<212> TYPE: PRT
<213> ORGANISM: Homo sapiens
<220> FEATURE:
<221> NAME/KEY: source
<223> OTHER INFORMATION: /note="VH 1.18"

<400> SEQUENCE: 72

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Gly Gly Ser Met Gly Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Asp Lys Gly Pro Gly Leu Ile Gly Ser Thr Ala Asp Tyr Tyr
            100                 105                 110

Gly Leu Asp Val Trp Gly Gln Gly Thr Thr Val Thr Val Ser Ser
        115                 120                 125

<210> SEQ ID NO 73
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 76"

<400> SEQUENCE: 73

Asp Tyr Ala Met His
1               5

<210> SEQ ID NO 74
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 76"

<400> SEQUENCE: 74

Gly Ile Ser Trp Asn Gly Gly Ser Met Gly Tyr Ala Asp Ser Val Lys
1               5                   10                  15

Gly

<210> SEQ ID NO 75
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 76"

<400> SEQUENCE: 75

Glu Lys Gly Pro Gly Leu Thr Gly Ser Thr Ala Asp Tyr Tyr Gly Leu
1               5                   10                  15

Asp Val

<210> SEQ ID NO 76
<211> LENGTH: 127
<212> TYPE: PRT
<213> ORGANISM: Homo sapiens
<220> FEATURE:
<221> NAME/KEY: source
<223> OTHER INFORMATION: /note="VH 1.19"

<400> SEQUENCE: 76

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Asp Leu Glu Trp Val
            35                  40                  45

Ser Gly Ile Ser Trp Asn Gly Gly Ser Met Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Val Trp Gly Gln Gly Thr Met Val Thr Val Ser Ser
        115                 120                 125

<210> SEQ ID NO 77
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 80"

<400> SEQUENCE: 77

```
Asp Tyr Ala Met His
1               5

<210> SEQ ID NO 78
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 80"

<400> SEQUENCE: 78

Gly Ile Ser Trp Asn Gly Gly Ser Met Gly Tyr Ala Asp Ser Val Lys
1               5                   10                  15

Gly

<210> SEQ ID NO 79
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 80"

<400> SEQUENCE: 79

Glu Lys Gly Pro Gly Leu Thr Gly Ser Thr Ala Asp Tyr Tyr Gly Leu
1               5                   10                  15

Asp Val

<210> SEQ ID NO 80
<211> LENGTH: 127
<212> TYPE: PRT
<213> ORGANISM: Homo sapiens
<220> FEATURE:
<221> NAME/KEY: source
<223> OTHER INFORMATION: /note="VH 1.20"

<400> SEQUENCE: 80

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Gly Gly Ser Met Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Val Trp Gly Gln Gly Thr Met Val Thr Val Ser Ser
        115                 120                 125

<210> SEQ ID NO 81
<211> LENGTH: 381
<212> TYPE: DNA
<213> ORGANISM: Homo sapiens
<220> FEATURE:
<221> NAME/KEY: source
<223> OTHER INFORMATION: /note="VH 1.1"
```

-continued

<400> SEQUENCE: 81

```
gaggtgcagc tgttggagtc tgggggaggc tcggtacagc ctggcaggtc cctgagactc    60
tcctgtgcag cctctggatt cacctttgac gatcatgcca tgcactgggt ccggcaagct   120
ccagggaagg gcctggaatg ggtctcaggt attagttgga atagtggcag tatgggctat   180
gcggactctg tgaaggaccg attcaccatc tccagagaca acgccaagag ctccctgtat   240
ctccaaatga acagtctgag agctgaggac acggccttgt attattgtgt aagagaaaag   300
gggcccggct taactggaag tacggccgat tactacggtt tggacgtctg ggggccaaggg   360
accatggtca ccgtctcttc a                                              381
```

<210> SEQ ID NO 82
<211> LENGTH: 381
<212> TYPE: DNA
<213> ORGANISM: Homo sapiens
<220> FEATURE:
<221> NAME/KEY: source
<223> OTHER INFORMATION: /note="VH 1.2"

<400> SEQUENCE: 82

```
gaggtgcagc tggtggagtc tgggggaggc ttggtacagc ctggcaggtc cctgagactc    60
tcctgtgcag cctctggatt cacctttgac gattatgcca tgcactgggt ccggcaagct   120
ccggggaagg acctggagtg ggtctcaggt attagttgga atggtggtag catgggctac   180
gcggcctctg tgaagggccg attcaccatc tccagagaca acgccaagaa ctccctgtat   240
ctgcaaatga acagtctgag agctgaggac acggccttgt attattgtgt aaaagataag   300
gggcccggct taattggaag tacggccgat tactacggtt tggacgtctg ggggccaaggg   360
accacggtca ctgtctcctc a                                              381
```

<210> SEQ ID NO 83
<211> LENGTH: 381
<212> TYPE: DNA
<213> ORGANISM: Homo sapiens
<220> FEATURE:
<221> NAME/KEY: source
<223> OTHER INFORMATION: /note="VH 1.3"

<400> SEQUENCE: 83

```
gaggtgcagc tgttggagtc tgggggaggc ttggtacagc ctggcaggtc cctgagactc    60
tcctgtgcag cctctggatt cacctttgac gattatgcca tgcactgggt ccggcaagct   120
ccagggaagg gccgggagtg ggtctcaggt attagttgga atagtggtag catgggctat   180
gcggactctg tgaaggaccg cttcaccatc tccagagaca acgccaagaa ctccctgtat   240
ctgcaaatga acagtctgag agcagaggac acggccctgt attattgtgt gaaagataag   300
gggcccggct taattggaag tacggccgat taccacggtt tggacgtctg ggggccaaggg   360
accacggtca ccgtctcttc a                                              381
```

<210> SEQ ID NO 84
<211> LENGTH: 381
<212> TYPE: DNA
<213> ORGANISM: Homo sapiens
<220> FEATURE:
<221> NAME/KEY: source
<223> OTHER INFORMATION: /note="VH 1.4"

<400> SEQUENCE: 84

```
gaggtgcagc tgttggagtc tgggggaggc ttggtacagc ctggcaggtc cctgagactc    60
```

```
tcctgtgcag cctctggatt cacctttgcc gattatgcca tgcactgggt ccggcaggct    120
ccagggaagg gccgggagtg ggtctcagga attagttgga atggtggtag catgggctat    180
gcggagtctg tgaagggccg attcaccatc tccagagaca cgccaagaa ttccctgtat     240 ctgcaaatga acagtctgag agctgaggac tcggccttgt attattgtgt aaaagataag    300
gggcccggct taactggaac tacggccgat tactacggta tggacgtctg ggggccaaggg   360 accacggtca ccgtctcttc a                                              381
```

<210> SEQ ID NO 85
<211> LENGTH: 381
<212> TYPE: DNA
<213> ORGANISM: Homo sapiens
<220> FEATURE:
<221> NAME/KEY: source
<223> OTHER INFORMATION: /note="VH 1.5"

<400> SEQUENCE: 85

```
gaggtgcagc tggtggagtc tgggggaggc ttggtacagc ctggcaggtc cctgagactc    60
tcctgtgcag cctctggatt cacctttgac gattatgcca tgcactgggt ccggcaagct   120
ccaggaaagg gcctggagtg ggtctcaggt attagttgga atggtggttc catgggctat   180
gcggactctg tgaaggaccg cttcaccatc tccagagaca cgccaagaa ctccctgtat    240 ctgcaaatga acagactgag agctgaggac acggccttgt attattgtgt gaaagataag   300
gggcccggct taattggaag tacggccgat taccacggtt tggacgtctg ggggccaaggg  360 accacggtca ctgtctcttc a                                             381
```

<210> SEQ ID NO 86
<211> LENGTH: 381
<212> TYPE: DNA
<213> ORGANISM: Homo sapiens
<220> FEATURE:
<221> NAME/KEY: source
<223> OTHER INFORMATION: /note="VH 1.6"

<400> SEQUENCE: 86

```
gaggtgcagc tggtggagtc tgggggaggc gtggtccagc ctgggaggtc cctgagactc    60
tcctgtgcag cctctggatt caccttcagt agctatgcca tgcactgggt ccggcaggct   120
ccagggaagg gccgggagtg ggtctcagga attagttgga atagtggtag tatgggctat   180
gcggagtctg tgaagggccg attcaccatc tccagagaca cgccaagaa ctccctgtat    240 ctgcaaatga acagtctgag agctgaggac tcggccttgt attattgtgt aaaagataag   300
gggcccggcc taactggaac tacggccgat tattacggta tggacgtctg ggggccaaggg  360 accacggtca ccgtctcctc a                                             381
```

<210> SEQ ID NO 87
<211> LENGTH: 381
<212> TYPE: DNA
<213> ORGANISM: Homo sapiens
<220> FEATURE:
<221> NAME/KEY: source
<223> OTHER INFORMATION: /note="VH 1.7"

<400> SEQUENCE: 87

```
gaagtgcagc tggtggagtc tgggggaggc gtgatacagc ctggcaggtc cctgagactc    60
tcctgtgcag cctctggatt cacctttgac gattatgcca tgcactgggt ccggcaggct   120
ccagggaagg gccgggagtg ggtctcagga attagttgga atggtggtag catgggctat   180
```

```
gcggagtctg tgaagggccg attcaccatc tccagagaca acgcccagaa ttccctgtat    240
ctgcaaatga acagtctgag agctgaggac tcggccttgt attattgtgt aaaagataag    300
gggcccggct taactggaac tacggccgat tactacggta tggacgtctg gggccaaggg    360
accacggtca ctgtctcctc a                                              381
```

<210> SEQ ID NO 88
<211> LENGTH: 381
<212> TYPE: DNA
<213> ORGANISM: Homo sapiens
<220> FEATURE:
<221> NAME/KEY: source
<223> OTHER INFORMATION: /note="VH 1.8"

<400> SEQUENCE: 88

```
gaggtgcagc tggtggagtc tgggggaggc ttggtacagc ctggcaggtc cctgagactc     60
tcctgtgcag cctctggatt cacctttgac gattatgcca tgcactgggt ccggcaagct    120
ccagggaagg gcctggagtg ggtctcaggt attagttgga atagtggtag catgggctat    180
gcggactctg tgaaggaccg cttcaccatc tccagagaca acgccaagaa ctccctgtat    240
ctgcaaatga acagtctgag agctgaggac acggccttgt attattgtgt aaaagataag    300
gggcccggct taattggaag tacggccgat taccacggtt tggacgtctg gggccaaggg    360
accacggtca ctgtctcctc a                                              381
```

<210> SEQ ID NO 89
<211> LENGTH: 381
<212> TYPE: DNA
<213> ORGANISM: Homo sapiens
<220> FEATURE:
<221> NAME/KEY: source
<223> OTHER INFORMATION: /note="VH 1.9"

<400> SEQUENCE: 89

```
gaagtgcagc tggtggagtc tgggggaggc tgtgtacagc ctggcaggtc cctgagaatt     60
tcctgtgcag cctctggatt cacctttgac gattatgcca tgcactgggt ccggcaggct    120
ccagggaagg gccgggagtg ggtctcagga attagttgga atggtggtag catgggctat    180
gcggagtctg ttaagggccg attcaccatc tccagagaca acgccaagaa ctccctgtat    240
ctacaaatga acagtctgag agctgaggac tcggccttgt attattgtgt aaaagataag    300
gggcccggct taattggaag tacggccgat tactacggta tggacgtctg gggccaaggg    360
accacggtca ccgtctcctc a                                              381
```

<210> SEQ ID NO 90
<211> LENGTH: 381
<212> TYPE: DNA
<213> ORGANISM: Homo sapiens
<220> FEATURE:
<221> NAME/KEY: source
<223> OTHER INFORMATION: /note="VH 1.10"
<220> FEATURE:
<221> NAME/KEY: modified_base
<222> LOCATION: (226)..(226)
<223> OTHER INFORMATION: a, c, t, g, unknown or other

<400> SEQUENCE: 90

```
gaggtgcagc tgttggagtc tgggggaggc tcggtacagc ctggcaggtc cctgagactc     60
tcctgtgcag cctctggatt cacctttgac gatcatgcca tgcactgggt ccggcaagct    120
ccagggaagg gcctggaatg ggtctcaggt attagttgga atagtggcag tatgggctat    180
```

```
gcggactctg tgaaggaccg attcaccatc tccagagaca acgccnagag ctccctgtat      240
ctccaaatga acagtctgag agctgaggac acggccttgt attattgtgt aagagaaaag      300
gggcccggct taactggaag tacggccgat tactacggtt tggacgtctg ggggccaaggg      360 accatggtca ccgtctcttc a                                                381
```

<210> SEQ ID NO 91
<211> LENGTH: 381
<212> TYPE: DNA
<213> ORGANISM: Homo sapiens
<220> FEATURE:
<221> NAME/KEY: source
<223> OTHER INFORMATION: /note="VH 1.11"

<400> SEQUENCE: 91

```
gaggtgcagc tgttggagtc tggggggaggc tttgtacagc ctggcaggtc cctgagaatt      60
tcctgtgcag cctctggatt cacctttgac gattatgcca tgcactgggt ccggcaagct     120
ccagggaagg acctgagtg gtctcaggt attagttgga atggtggtag catgggctat       180
gcggagtctg tgaagggccg attcaccatc tccagagaca acgccaagaa ttccctatat     240
ctgaaaatga acagtctgag agttgaggac acggccttgt attattgtgt aaaagataag      300
gggcccgggt taattggaag tacggccgat tactacggtt tggacgtctg ggggccaaggg     360 accacggtca ctgtctcttc a                                                381
```

<210> SEQ ID NO 92
<211> LENGTH: 381
<212> TYPE: DNA
<213> ORGANISM: Homo sapiens
<220> FEATURE:
<221> NAME/KEY: source
<223> OTHER INFORMATION: /note="VH 1.12"

<400> SEQUENCE: 92

```
caggtgcagc tggtggagtc tggggggaggc ttggtacagc ctggcaggtc cctgagactc     60
tcctgtgcag cctctggatt cacctttgac gactatgcca tgcactgggt ccggcaggct    120
ccagggaagg gccgggagtg gtctcagga attagttgga atggtggtag catgggctat     180
gcggactctg tgaaggaccg cttcaccatc tccagagaca acgccaagaa ctcactatat     240
ctgcaaatga acagtctgag agctgaggac acggccttgt attattgtgt gaaagataag    300
gggcccggct taactggaag tacggccgat taccacggta tggacgtctg ggggccaaggg   360 accacggtca ccgtctcctc a                                                381
```

<210> SEQ ID NO 93
<211> LENGTH: 381
<212> TYPE: DNA
<213> ORGANISM: Homo sapiens
<220> FEATURE:
<221> NAME/KEY: source
<223> OTHER INFORMATION: /note="VH 1.13"

<400> SEQUENCE: 93

```
caggtgcagc tggtggagtc tggggggaggc ttggtacagc ctggcaggtc cctgagactc     60
tcctgtgcag cctctggatt cacctttgac gattatgcca tgcactgggt ccggcaagct    120
ccagggaagg acctgagtg gtctcaggt attagttgga atggtggtag catgggctac      180
gcggcctctg tgaagggccg attcaccatc tccagagaca acgccagaa ctccctgtat     240 ctgcaaatga acagtctgag agctgaggac acggccttgt attattgtgt aaaagataag    300
```

```
gggcccggct taattggaag tacggccgat tactacggtt tggacgtctg gggccaaggg    360
accacggtca ctgtctcttc a                                              381
```

<210> SEQ ID NO 94
<211> LENGTH: 381
<212> TYPE: DNA
<213> ORGANISM: Homo sapiens
<220> FEATURE:
<221> NAME/KEY: source
<223> OTHER INFORMATION: /note="VH 1.14"

<400> SEQUENCE: 94

```
gaggtgcagc tggtggagtc tgggggaggc ttggtacagc ctggcaggtc cctgagactc    60
tcctgtgcag cctctggatt cacctttgac ggttatgcca tgcactgggt ccggcaggct    120
ccagggaagg gccgggagtg ggtctcagga attagttgga atagtggtag catgggctat    180
gcggagtctg tgaagggccg attcaccatc tccagagaca acgccaagaa ctccctgtat    240
ctgcaaatga acagtctgag agctgaggac tcggccttgt attattgtgt aaaagataag    300
gggcccggct aactggaag tacggccgat tactacggta tggacgtctg gggccaaggg    360
accacggtca ccgtctcctc a                                              381
```

<210> SEQ ID NO 95
<211> LENGTH: 381
<212> TYPE: DNA
<213> ORGANISM: Homo sapiens
<220> FEATURE:
<221> NAME/KEY: source
<223> OTHER INFORMATION: /note="VH 1.15"

<400> SEQUENCE: 95

```
gaggtgcagc tgttggagtc tgggggaggc ttggtacagc ctggcaggtc cctgagactc    60
tcctgtacag cctctggatt cacctttgac gattatgcca tgcactgggt ccggcaggct    120
ccagggaagg gccgggagtg ggtctcagga attagttgga atagtggtag catgggctat    180
gcggagtctg tgaagggccg attcaccatc tccagagaca acgccaagaa ctccctgtat    240
ctgcaaatga acagtctgag agctgaggac tcggccttgt attattgtgt aaaagataag    300
gggcccggct taattggaag tacggccgat tactacggta tggacgtctg gggccaaggg    360
accacggtca ccgtctcctc a                                              381
```

<210> SEQ ID NO 96
<211> LENGTH: 381
<212> TYPE: DNA
<213> ORGANISM: Homo sapiens
<220> FEATURE:
<221> NAME/KEY: source
<223> OTHER INFORMATION: /note="VH 1.16"

<400> SEQUENCE: 96

```
caggtgcagc tggtggagtc tgggggaggc ttggtacagc ctggcaggtc cctgagactc    60
tcctgtgcag cctctggatt cacctttgac gactatgcca tgcactgggt ccggcaggct    120
ccagggaagg gccgggagtg ggtctcagga attagttgga atggtggtag catgggctat    180
gcggagtctg ttaagggccg attcaccatc tccagagaca acgccaagaa ctccctgtat    240
ctacaaatga acagtctgag agctgaggac tcggccttgt attattgtgt aaaagataag    300
gggcccggct taattggaag tacggccgat tactacggta tggacgtctg gggccaaggg    360
accacggtca ctgtctcctc a                                              381
```

<210> SEQ ID NO 97
<211> LENGTH: 381
<212> TYPE: DNA
<213> ORGANISM: Homo sapiens
<220> FEATURE:
<221> NAME/KEY: source
<223> OTHER INFORMATION: /note="VH 1.17"

<400> SEQUENCE: 97
gaggtgcagc tgttggagtc tgggggaggc ttggtccagc ctgggggtc cctgagactc      60 tcctgtgcag cctctggatt cacctttgac gattatgcca tgcactgggt ccggcaagct    120
ccagggaagg gcctggagtg ggtctcaggt attagttgga atagtggtag catgggctat    180
gcggcctctg tgaaggaccg cttcaccatc tccagagaca acgccaagaa ctccctgtat    240
ctgcaaatga acagtctgac aactgaggac acggccttgt attattgtgt gaaagataag    300
gggcccggct taattggaag tacggccgat tatcacggtt tggacgtctg ggggccaaggg   360 accacggtca ctgtctcctc a                                              381

<210> SEQ ID NO 98
<211> LENGTH: 381
<212> TYPE: DNA
<213> ORGANISM: Homo sapiens
<220> FEATURE:
<221> NAME/KEY: source
<223> OTHER INFORMATION: /note="VH 1.18"

<400> SEQUENCE: 98
caggtgcagc tggtggagtc tgggggaggc cttgtacagc ctggcaggtc cctgagactt      60
tcctgtgcag cctctggatt cacctttgac gattatgcca tgcactgggt ccggcaagct    120
ccagggaagg acctggagtg ggtctcaggt attagttgga atggtggtag catgggctat    180
gcggcgtctg tgaagggccg attcaccatc tccagagaca acgccaagaa ttccctatat    240
ctgcaaatga acagtctgag agctgaggac acggccttgt attattgtgt aaaagataag    300
gggcccgggt taattggaag tacggccgat tactacggtt tggacgtctg ggggccaaggg   360 accacggtca ctgtctcttc a                                              381

<210> SEQ ID NO 99
<211> LENGTH: 381
<212> TYPE: DNA
<213> ORGANISM: Homo sapiens
<220> FEATURE:
<221> NAME/KEY: source
<223> OTHER INFORMATION: /note="VH 1.19"

<400> SEQUENCE: 99
caggtgcagc tggtggagtc tgggggaggc cttgtacagc ctggcaggtc cctgagactt      60
tcctgtgcag cctctggatt cacctttgac gattatgcca tgcactgggt ccggcaagct    120
ccagggaagg acctggagtg ggtctcaggt attagttgga atggtggtag catgggctat    180
gcggcgtctg tgaagggccg attcaccatc tccagagaca acgccaagaa ttccctatat    240
ctgcaaatga acagtctgag agctgaggac acggccttgt attattgtgt aaaagataag    300
gggcccgggt taattggaag tacggccgat tactacggtt tggacgtctg ggggccaaggg   360 accacggtca ctgtctcttc a                                              381

<210> SEQ ID NO 100
<211> LENGTH: 381
<212> TYPE: DNA

```
<213> ORGANISM: Homo sapiens
<220> FEATURE:
<221> NAME/KEY: source
<223> OTHER INFORMATION: /note="VH 1.20"

<400> SEQUENCE: 100
gaggtgcagc tggtggagtc tgggggaggc ttggtacagc ctggcaggtc cctgagactc      60
tcctgtgcag cctctggatt cacctttgac gattatgcca tgcactgggt ccggcaagct     120
ccagggaagg acctggagtg ggtctcaggt attagttgga atggtggtag catgggctac     180
gcggactctg tgaagggccg attcaccatc tccagagaca acgccaagaa ctccctgtat     240
ctgcaaatga acagtctgag agctgaggac acggccttgt attattgtgt aagagaaaag     300
gggcccggct aactggaag tacggccgat tactacggtt tggacgtctg gggccaaggg     360
accatggtca ccgtctcctc a                                               381

<210> SEQ ID NO 101
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 104"

<400> SEQUENCE: 101

Asp Tyr Ala Met His
1               5

<210> SEQ ID NO 102
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 104"

<400> SEQUENCE: 102

Gly Ile Ser Trp Asn Gly Gly Ser Met Gly Tyr Ala Ala Ser Val Lys
1               5                   10                  15

Gly

<210> SEQ ID NO 103
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 104"

<400> SEQUENCE: 103

Glu Lys Gly Pro Gly Leu Thr Gly Ser Thr Ala Asp Tyr Tyr Gly Leu
1               5                   10                  15

Asp Val

<210> SEQ ID NO 104
<211> LENGTH: 127
<212> TYPE: PRT
<213> ORGANISM: Homo sapiens
<220> FEATURE:
<221> NAME/KEY: source
<223> OTHER INFORMATION: /note="VH 1.21"

<400> SEQUENCE: 104

Glu Val Gln Leu Val Glu Ser Gly Gly Gly Leu Val Gln Pro Gly Arg
```

```
                1               5                   10                  15
            Ser Leu Arg Leu Ser Cys Ala Ala Ser Gly Phe Thr Phe Asp Asp Tyr
                                20                  25                  30

Ala Met His Trp Val Arg Gln Ala Pro Gly Lys Asp Leu Glu Trp Val
                    35                  40                  45

Ser Gly Ile Ser Trp Asn Gly Gly Ser Met Gly Tyr Ala Ala Ser Val
                50                  55                  60

Lys Gly Arg Phe Thr Ile Ser Arg Asp Asn Ala Lys Asn Ser Leu Tyr
            65                  70                  75                  80

Leu Gln Met Asn Ser Leu Arg Ala Glu Asp Thr Ala Leu Tyr Tyr Cys
                            85                  90                  95

Val Arg Glu Lys Gly Pro Gly Leu Thr Gly Ser Thr Ala Asp Tyr Tyr
                        100                 105                 110

Gly Leu Asp Val Trp Gly Gln Gly Thr Met Val Thr Val Ser Ser
                    115                 120                 125

<210> SEQ ID NO 105
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 108"

<400> SEQUENCE: 105

Asp Tyr Ala Met His
1               5

<210> SEQ ID NO 106
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 108"

<400> SEQUENCE: 106

Gly Ile Ser Trp Asn Gly Gly Ser Met Gly Tyr Ala Ala Ser Val Lys
1               5                   10                  15

Gly

<210> SEQ ID NO 107
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 108"

<400> SEQUENCE: 107

Glu Lys Gly Pro Gly Leu Thr Gly Ser Thr Ala Asp Tyr Tyr Gly Leu
1               5                   10                  15

Asp Ala

<210> SEQ ID NO 108
<211> LENGTH: 127
<212> TYPE: PRT
<213> ORGANISM: Homo sapiens
<220> FEATURE:
<221> NAME/KEY: source
<223> OTHER INFORMATION: /note="VH 1.22"

<400> SEQUENCE: 108
```

```
Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Gly Ser Met Gly Tyr Ala Ala Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125
```

<210> SEQ ID NO 109
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 112"

<400> SEQUENCE: 109

```
Asp Tyr Ala Met His
1               5
```

<210> SEQ ID NO 110
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 112"

<400> SEQUENCE: 110

```
Gly Ile Ser Trp Asn Ser Gly Ser Met Gly Tyr Ala Ala Ser Val Lys
1               5                   10                  15

Gly
```

<210> SEQ ID NO 111
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 112"

<400> SEQUENCE: 111

```
Glu Lys Gly Pro Gly Leu Thr Gly Ser Thr Ala Asp Tyr Tyr Gly Leu
1               5                   10                  15

Asp Val
```

<210> SEQ ID NO 112
<211> LENGTH: 127
<212> TYPE: PRT
<213> ORGANISM: Homo sapiens
<220> FEATURE:
<221> NAME/KEY: source
<223> OTHER INFORMATION: /note="VH 1.23"

<400> SEQUENCE: 112

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Ser Gly Ser Met Gly Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Val Trp Gly Gln Gly Thr Met Val Thr Val Ser Ser
        115                 120                 125

<210> SEQ ID NO 113
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 116"

<400> SEQUENCE: 113

Asp Tyr Ala Met His
1               5

<210> SEQ ID NO 114
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 116"

<400> SEQUENCE: 114

Gly Ile Ser Trp Asn Ser Gly Ser Met Gly Tyr Ala Ala Ser Val Lys
1               5                   10                  15

Gly

<210> SEQ ID NO 115
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 116"

<400> SEQUENCE: 115

Glu Lys Gly Pro Gly Leu Thr Gly Ser Thr Ala Asp Tyr Tyr Gly Leu
1               5                   10                  15

Asp Ala

<210> SEQ ID NO 116
<211> LENGTH: 127
<212> TYPE: PRT
<213> ORGANISM: Homo sapiens
<220> FEATURE:

```
<221> NAME/KEY: source
<223> OTHER INFORMATION: /note="VH 1.24"

<400> SEQUENCE: 116

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Ser Gly Ser Met Gly Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 117
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 120"

<400> SEQUENCE: 117

Asp Tyr Ala Met His
1               5

<210> SEQ ID NO 118
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 120"

<400> SEQUENCE: 118

Gly Ile Ser Trp Asn Gly Gly Ser Gln Gly Tyr Ala Ala Ser Val Lys
1               5                   10                  15

Gly

<210> SEQ ID NO 119
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 120"

<400> SEQUENCE: 119

Glu Lys Gly Pro Gly Leu Thr Gly Ser Thr Ala Asp Tyr Tyr Gly Leu
1               5                   10                  15

Asp Ala

<210> SEQ ID NO 120
<211> LENGTH: 127
<212> TYPE: PRT
```

<213> ORGANISM: Homo sapiens
<220> FEATURE:
<221> NAME/KEY: source
<223> OTHER INFORMATION: /note="VH 1.25"

<400> SEQUENCE: 120

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Gly Gly Ser Gln Gly Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 121
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 124"

<400> SEQUENCE: 121

Asp Tyr Ala Met His
1               5

<210> SEQ ID NO 122
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 124"

<400> SEQUENCE: 122

Gly Ile Ser Trp Asn Gly Gly Ser Met Gly Tyr Ala Asp Ser Val Lys
1               5                   10                  15

Gly

<210> SEQ ID NO 123
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 124"

<400> SEQUENCE: 123

Glu Lys Gly Pro Gly Leu Thr Gly Ser Thr Ala Asp Tyr Tyr Gly Leu
1               5                   10                  15

Asp Ala

<210> SEQ ID NO 124

```
<211> LENGTH: 127
<212> TYPE: PRT
<213> ORGANISM: Homo sapiens
<220> FEATURE:
<221> NAME/KEY: source
<223> OTHER INFORMATION: /note="VH 1.26"

<400> SEQUENCE: 124
```

Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Gly Gly Ser Met Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

```
<210> SEQ ID NO 125
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 128"

<400> SEQUENCE: 125
```

Asp Tyr Ala Met His
1               5

```
<210> SEQ ID NO 126
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 128"

<400> SEQUENCE: 126
```

Gly Ile Ser Trp Asn Gly Gly Ser Arg Gly Tyr Ala Ala Ser Val Lys
1               5                   10                  15

Gly

```
<210> SEQ ID NO 127
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 128"

<400> SEQUENCE: 127
```

Glu Lys Gly Pro Gly Leu Thr Gly Ser Thr Ala Asp Tyr Tyr Gly Leu
1               5                   10                  15

Asp Ala

<210> SEQ ID NO 128
<211> LENGTH: 127
<212> TYPE: PRT
<213> ORGANISM: Homo sapiens
<220> FEATURE:
<221> NAME/KEY: source
<223> OTHER INFORMATION: /note="VH 1.27"

<400> SEQUENCE: 128

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Gly Ser Arg Gly Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 129
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 132"

<400> SEQUENCE: 129

Asp Tyr Ala Met His
1               5

<210> SEQ ID NO 130
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 132"

<400> SEQUENCE: 130

Gly Ile Ser Trp Asn Ala Gly Ser Met Gly Tyr Ala Ala Ser Val Lys
1               5                   10                  15

Gly

<210> SEQ ID NO 131
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 132"

<400> SEQUENCE: 131

Glu Lys Gly Pro Gly Leu Thr Gly Ser Thr Ala Asp Tyr Tyr Gly Leu
1               5                   10                  15

Asp Ala

```
<210> SEQ ID NO 132
<211> LENGTH: 127
<212> TYPE: PRT
<213> ORGANISM: Homo sapiens
<220> FEATURE:
<221> NAME/KEY: source
<223> OTHER INFORMATION: /note="VH 1.28"

<400> SEQUENCE: 132
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Ala Gly Ser Met Gly Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

```
<210> SEQ ID NO 133
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 136"

<400> SEQUENCE: 133
```

Asp Tyr Ala Met His
1               5

```
<210> SEQ ID NO 134
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 136"

<400> SEQUENCE: 134
```

Gly Ile Ser Trp Asn Ser Gly Ser Met Gly Tyr Ala Asp Ser Val Lys
1               5                   10                  15

Gly

```
<210> SEQ ID NO 135
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 136"

<400> SEQUENCE: 135
```

Glu Lys Gly Pro Gly Leu Thr Gly Ser Thr Ala Asp Tyr Tyr Gly Leu

-continued

```
1               5                   10                  15

Asp Val

<210> SEQ ID NO 136
<211> LENGTH: 127
<212> TYPE: PRT
<213> ORGANISM: Homo sapiens
<220> FEATURE:
<221> NAME/KEY: source
<223> OTHER INFORMATION: /note="VH 1.29"

<400> SEQUENCE: 136

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Ser Gly Ser Met Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Val Trp Gly Gln Gly Thr Met Val Thr Val Ser Ser
        115                 120                 125

<210> SEQ ID NO 137
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 140"

<400> SEQUENCE: 137

Asp Tyr Ala Gly His
1               5

<210> SEQ ID NO 138
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 140"

<400> SEQUENCE: 138

Gly Ile Ser Trp Asn Gly Gly Ser Met Gly Tyr Ala Ala Ser Val Lys
1               5                   10                  15

Gly

<210> SEQ ID NO 139
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 140"

<400> SEQUENCE: 139
```

Glu Lys Gly Pro Gly Leu Thr Gly Ser Thr Ala Asp Tyr Tyr Gly Leu
1               5                   10                  15

Asp Ala

<210> SEQ ID NO 140
<211> LENGTH: 127
<212> TYPE: PRT
<213> ORGANISM: Homo sapiens
<220> FEATURE:
<221> NAME/KEY: source
<223> OTHER INFORMATION: /note="VH 1.30"

<400> SEQUENCE: 140

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Gly His Trp Val Arg Gln Ala Pro Gly Lys Asp Leu Glu Trp Val
        35                  40                  45

Ser Gly Ile Ser Trp Asn Gly Gly Ser Met Gly Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 141
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 144"

<400> SEQUENCE: 141

Asp Tyr Ala Leu His
1               5

<210> SEQ ID NO 142
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 144"

<400> SEQUENCE: 142

Gly Ile Ser Trp Asn Gly Gly Ser Met Gly Tyr Ala Ala Ser Val Lys
1               5                   10                  15

Gly

<210> SEQ ID NO 143
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 144"

<400> SEQUENCE: 143

Glu Lys Gly Pro Gly Leu Thr Gly Ser Thr Ala Asp Tyr Tyr Gly Leu
1               5                   10                  15

Asp Ala

<210> SEQ ID NO 144
<211> LENGTH: 127
<212> TYPE: PRT
<213> ORGANISM: Homo sapiens
<220> FEATURE:
<221> NAME/KEY: source
<223> OTHER INFORMATION: /note="VH 1.31"

<400> SEQUENCE: 144

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Asp Leu Glu Trp Val
        35                  40                  45

Ser Gly Ile Ser Trp Asn Gly Gly Ser Met Gly Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 145
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 148"

<400> SEQUENCE: 145

Asp Tyr Ala Met His
1               5

<210> SEQ ID NO 146
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 148"

<400> SEQUENCE: 146

Gly Ile Ser Trp Asn Ser Gly Ser Met Gly Tyr Ala Asp Ser Val Lys
1               5                   10                  15

Gly

<210> SEQ ID NO 147
<211> LENGTH: 18
<212> TYPE: PRT
<213> ORGANISM: Homo sapiens
<220> FEATURE:

```
<221> NAME/KEY: source
<223> OTHER INFORMATION: /note="CDR3 sequence of SEQ ID NO: 148"

<400> SEQUENCE: 147

Glu Lys Gly Pro Gly Leu Thr Gly Ser Thr Ala Asp Tyr Tyr Gly Leu
1               5                   10                  15

Asp Ala

<210> SEQ ID NO 148
<211> LENGTH: 127
<212> TYPE: PRT
<213> ORGANISM: Homo sapiens
<220> FEATURE:
<221> NAME/KEY: source
<223> OTHER INFORMATION: /note="VH 1.32"

<400> SEQUENCE: 148

Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Ser Gly Ser Met Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 149
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 152"

<400> SEQUENCE: 149

Asp Tyr Ala Met His
1               5

<210> SEQ ID NO 150
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 152"

<400> SEQUENCE: 150

Gly Ile Ser Trp Asn Gly Gly Ser Tyr Gly Tyr Ala Asp Ser Val Lys
1               5                   10                  15

Gly

<210> SEQ ID NO 151
<211> LENGTH: 18
<212> TYPE: PRT
```

```
<213> ORGANISM: Homo sapiens
<220> FEATURE:
<221> NAME/KEY: source
<223> OTHER INFORMATION: /note="CDR3 sequence of SEQ ID NO: 152"

<400> SEQUENCE: 151

Glu Lys Gly Pro Gly Leu Thr Gly Ser Thr Ala Asp Tyr Tyr Gly Leu
1               5                   10                  15

Asp Ala

<210> SEQ ID NO 152
<211> LENGTH: 127
<212> TYPE: PRT
<213> ORGANISM: Homo sapiens
<220> FEATURE:
<221> NAME/KEY: source
<223> OTHER INFORMATION: /note="VH 1.33"

<400> SEQUENCE: 152

Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Gly Ser Tyr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 153
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 156"

<400> SEQUENCE: 153

Asp Tyr Ala Met His
1               5

<210> SEQ ID NO 154
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 156"

<400> SEQUENCE: 154

Gly Ile Ser Trp Asn Gly Gly Ser Gln Gly Tyr Ala Asp Ser Val Lys
1               5                   10                  15

Gly

<210> SEQ ID NO 155
```

```
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 156"

<400> SEQUENCE: 155

Glu Lys Gly Pro Gly Leu Thr Gly Ser Thr Ala Asp Tyr Tyr Gly Leu
1               5                   10                  15

Asp Ala

<210> SEQ ID NO 156
<211> LENGTH: 127
<212> TYPE: PRT
<213> ORGANISM: Homo sapiens
<220> FEATURE:
<221> NAME/KEY: source
<223> OTHER INFORMATION: /note="VH 1.34"

<400> SEQUENCE: 156

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Gly Ser Gln Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 157
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 160"

<400> SEQUENCE: 157

Asp Tyr Ala Met His
1               5

<210> SEQ ID NO 158
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 160"

<400> SEQUENCE: 158

Gly Ile Ser Trp Asn Gly Gly Ser Lys Gly Tyr Ala Asp Ser Val Lys
1               5                   10                  15

Gly
```

```
<210> SEQ ID NO 159
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 160"

<400> SEQUENCE: 159

Glu Lys Gly Pro Gly Leu Thr Gly Ser Thr Ala Asp Tyr Tyr Gly Leu
1               5                   10                  15

Asp Ala

<210> SEQ ID NO 160
<211> LENGTH: 127
<212> TYPE: PRT
<213> ORGANISM: Homo sapiens
<220> FEATURE:
<221> NAME/KEY: source
<223> OTHER INFORMATION: /note="VH 1.35"

<400> SEQUENCE: 160

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Gly Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 161
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 164"

<400> SEQUENCE: 161

Asp Tyr Ala Met His
1               5

<210> SEQ ID NO 162
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 164"

<400> SEQUENCE: 162

Gly Ile Ser Trp Asn Ala Gly Ser Met Gly Tyr Ala Asp Ser Val Lys
1               5                   10                  15
```

Gly

<210> SEQ ID NO 163
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 164"

<400> SEQUENCE: 163

Glu Lys Gly Pro Gly Leu Thr Gly Ser Thr Ala Asp Tyr Tyr Gly Leu
1               5                   10                  15

Asp Ala

<210> SEQ ID NO 164
<211> LENGTH: 127
<212> TYPE: PRT
<213> ORGANISM: Homo sapiens
<220> FEATURE:
<221> NAME/KEY: source
<223> OTHER INFORMATION: /note="VH 1.36"

<400> SEQUENCE: 164

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Asp Leu Glu Trp Val
        35                  40                  45

Ser Gly Ile Ser Trp Asn Ala Gly Ser Met Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 165
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 168"

<400> SEQUENCE: 165

Asp Tyr Ala Phe His
1               5

<210> SEQ ID NO 166
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 168"

<400> SEQUENCE: 166

Gly Ile Ser Trp Asn Gly Gly Ser Met Gly Tyr Ala Asp Ser Val Lys

-continued

```
1               5                   10                  15
Gly

<210> SEQ ID NO 167
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 168"

<400> SEQUENCE: 167

Glu Lys Gly Pro Gly Leu Thr Gly Ser Thr Ala Asp Tyr Tyr Gly Leu
1               5                   10                  15

Asp Ala

<210> SEQ ID NO 168
<211> LENGTH: 127
<212> TYPE: PRT
<213> ORGANISM: Homo sapiens
<220> FEATURE:
<221> NAME/KEY: source
<223> OTHER INFORMATION: /note="VH 1.37"

<400> SEQUENCE: 168

Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Phe His Trp Val Arg Gln Ala Pro Gly Lys Asp Leu Glu Trp Val
            35                  40                  45

Ser Gly Ile Ser Trp Asn Gly Gly Ser Met Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 169
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 172"

<400> SEQUENCE: 169

Asp Tyr Ala Leu His
1               5

<210> SEQ ID NO 170
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 172"

<400> SEQUENCE: 170
```

```
Gly Ile Ser Trp Asn Gly Gly Ser Met Gly Tyr Ala Asp Ser Val Lys
1               5                   10                  15

Gly
```

<210> SEQ ID NO 171
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 172"

<400> SEQUENCE: 171

```
Glu Lys Gly Pro Gly Leu Thr Gly Ser Thr Ala Asp Tyr Tyr Gly Leu
1               5                   10                  15

Asp Ala
```

<210> SEQ ID NO 172
<211> LENGTH: 127
<212> TYPE: PRT
<213> ORGANISM: Homo sapiens
<220> FEATURE:
<221> NAME/KEY: source
<223> OTHER INFORMATION: /note="VH 1.38"

<400> SEQUENCE: 172

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Asp Leu Glu Trp Val
        35                  40                  45

Ser Gly Ile Ser Trp Asn Gly Gly Ser Met Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125
```

<210> SEQ ID NO 173
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 176"

<400> SEQUENCE: 173

```
Asp Tyr Ala Leu His
1               5
```

<210> SEQ ID NO 174
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 176"

-continued

```
<400> SEQUENCE: 174

Gly Ile Ser Trp Asn Gly Gly Ser Tyr Gly Tyr Ala Asp Ser Val Lys
1               5                   10                  15
Gly

<210> SEQ ID NO 175
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 176"

<400> SEQUENCE: 175

Glu Lys Gly Pro Gly Leu Thr Gly Ser Thr Ala Asp Tyr Tyr Gly Leu
1               5                   10                  15
Asp Ala

<210> SEQ ID NO 176
<211> LENGTH: 127
<212> TYPE: PRT
<213> ORGANISM: Homo sapiens
<220> FEATURE:
<221> NAME/KEY: source
<223> OTHER INFORMATION: /note="VH 1.39"

<400> SEQUENCE: 176

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Asp Leu Glu Trp Val
        35                  40                  45

Ser Gly Ile Ser Trp Asn Gly Gly Ser Tyr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 177
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 180"

<400> SEQUENCE: 177

Asp Tyr Ala Leu His
1               5

<210> SEQ ID NO 178
<211> LENGTH: 17
<212> TYPE: PRT
<213> ORGANISM: Homo sapiens
<220> FEATURE:
```

<221> NAME/KEY: source
<223> OTHER INFORMATION: /note="CDR2 sequence of SEQ ID NO: 180"

<400> SEQUENCE: 178

Gly Ile Ser Trp Asn Gly Gly Ser Gln Gly Tyr Ala Asp Ser Val Lys
1               5                   10                  15
Gly

<210> SEQ ID NO 179
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 180"

<400> SEQUENCE: 179

Glu Lys Gly Pro Gly Leu Thr Gly Ser Thr Ala Asp Tyr Tyr Gly Leu
1               5                   10                  15
Asp Ala

<210> SEQ ID NO 180
<211> LENGTH: 127
<212> TYPE: PRT
<213> ORGANISM: Homo sapiens
<220> FEATURE:
<221> NAME/KEY: source
<223> OTHER INFORMATION: /note="VH 1.40"

<400> SEQUENCE: 180

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Asp Leu Glu Trp Val
        35                  40                  45

Ser Gly Ile Ser Trp Asn Gly Gly Ser Gln Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 181
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 184"

<400> SEQUENCE: 181

Asp Tyr Ala Phe His
1               5

<210> SEQ ID NO 182
<211> LENGTH: 17
<212> TYPE: PRT

-continued

```
<213> ORGANISM: Homo sapiens
<220> FEATURE:
<221> NAME/KEY: source
<223> OTHER INFORMATION: /note="CDR2 sequence of SEQ ID NO: 184"

<400> SEQUENCE: 182

Gly Ile Ser Trp Asn Gly Gly Ser Tyr Gly Tyr Ala Asp Ser Val Lys
1               5                   10                  15

Gly

<210> SEQ ID NO 183
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 184"

<400> SEQUENCE: 183

Glu Lys Gly Pro Gly Leu Thr Gly Ser Thr Ala Asp Tyr Tyr Gly Leu
1               5                   10                  15

Asp Ala

<210> SEQ ID NO 184
<211> LENGTH: 127
<212> TYPE: PRT
<213> ORGANISM: Homo sapiens
<220> FEATURE:
<221> NAME/KEY: source
<223> OTHER INFORMATION: /note="VH 1.41"

<400> SEQUENCE: 184

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Phe His Trp Val Arg Gln Ala Pro Gly Lys Asp Leu Glu Trp Val
        35                  40                  45

Ser Gly Ile Ser Trp Asn Gly Gly Ser Tyr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 185
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 188"

<400> SEQUENCE: 185

Asp Tyr Ala Phe His
1               5

<210> SEQ ID NO 186
```

```
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 188"

<400> SEQUENCE: 186

Gly Ile Ser Trp Asn Gly Gly Ser Gln Gly Tyr Ala Asp Ser Val Lys
1               5                   10                  15

Gly

<210> SEQ ID NO 187
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 188"

<400> SEQUENCE: 187

Glu Lys Gly Pro Gly Leu Thr Gly Ser Thr Ala Asp Tyr Tyr Gly Leu
1               5                   10                  15

Asp Ala

<210> SEQ ID NO 188
<211> LENGTH: 127
<212> TYPE: PRT
<213> ORGANISM: Homo sapiens
<220> FEATURE:
<221> NAME/KEY: source
<223> OTHER INFORMATION: /note="VH 1.42"

<400> SEQUENCE: 188

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Phe His Trp Val Arg Gln Ala Pro Gly Lys Asp Leu Glu Trp Val
            35                  40                  45

Ser Gly Ile Ser Trp Asn Gly Gly Ser Gln Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 189
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 192"

<400> SEQUENCE: 189

Asp Tyr Ala Phe His
1               5
```

```
<210> SEQ ID NO 190
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 192"

<400> SEQUENCE: 190

Gly Ile Ser Trp Asn Ala Gly Ser Tyr Gly Tyr Ala Asp Ser Val Lys
1               5                   10                  15

Gly

<210> SEQ ID NO 191
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 192"

<400> SEQUENCE: 191

Glu Lys Gly Pro Gly Leu Thr Gly Ser Thr Ala Asp Tyr Tyr Gly Leu
1               5                   10                  15

Asp Ala

<210> SEQ ID NO 192
<211> LENGTH: 127
<212> TYPE: PRT
<213> ORGANISM: Homo sapiens
<220> FEATURE:
<221> NAME/KEY: source
<223> OTHER INFORMATION: /note="VH 1.43"

<400> SEQUENCE: 192

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Phe His Trp Val Arg Gln Ala Pro Gly Lys Asp Leu Glu Trp Val
            35                  40                  45

Ser Gly Ile Ser Trp Asn Ala Gly Ser Tyr Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 193
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 196"

<400> SEQUENCE: 193

Asp Tyr Ala Leu His
```

```
<210> SEQ ID NO 194
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 196"

<400> SEQUENCE: 194

Gly Ile Ser Trp Asn Ser Gly Ser Tyr Gly Tyr Ala Asp Ser Val Lys
1               5                   10                  15

Gly

<210> SEQ ID NO 195
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 196"

<400> SEQUENCE: 195

Glu Lys Gly Pro Gly Leu Thr Gly Ser Thr Ala Asp Tyr Tyr Gly Leu
1               5                   10                  15

Asp Ala

<210> SEQ ID NO 196
<211> LENGTH: 127
<212> TYPE: PRT
<213> ORGANISM: Homo sapiens
<220> FEATURE:
<221> NAME/KEY: source
<223> OTHER INFORMATION: /note="VH 1.44"

<400> SEQUENCE: 196

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Asp Leu Glu Trp Val
        35                  40                  45

Ser Gly Ile Ser Trp Asn Ser Gly Ser Tyr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 197
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 200"

<400> SEQUENCE: 197
```

Asp Tyr Ala Leu His
1               5

<210> SEQ ID NO 198
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 200"

<400> SEQUENCE: 198

Gly Ile Ser Trp Asn Ala Gly Ser Gln Gly Tyr Ala Asp Ser Val Lys
1               5                   10                  15

Gly

<210> SEQ ID NO 199
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 200"

<400> SEQUENCE: 199

Glu Lys Gly Pro Gly Leu Thr Gly Ser Thr Ala Asp Tyr Tyr Gly Leu
1               5                   10                  15

Asp Ala

<210> SEQ ID NO 200
<211> LENGTH: 127
<212> TYPE: PRT
<213> ORGANISM: Homo sapiens
<220> FEATURE:
<221> NAME/KEY: source
<223> OTHER INFORMATION: /note="VH 1.45"

<400> SEQUENCE: 200

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Asp Leu Glu Trp Val
        35                  40                  45

Ser Gly Ile Ser Trp Asn Ala Gly Ser Gln Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 201
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 204"

<400> SEQUENCE: 201

Asp Tyr Ala Leu His
1               5

<210> SEQ ID NO 202
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 204"

<400> SEQUENCE: 202

Gly Ile Ser Trp Asn Ala Gly Ser Tyr Gly Tyr Ala Asp Ser Val Lys
1               5                   10                  15

Gly

<210> SEQ ID NO 203
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 204"

<400> SEQUENCE: 203

Glu Lys Gly Pro Gly Leu Thr Gly Ser Thr Ala Asp Tyr Tyr Gly Leu
1               5                   10                  15

Asp Ala

<210> SEQ ID NO 204
<211> LENGTH: 127
<212> TYPE: PRT
<213> ORGANISM: Homo sapiens
<220> FEATURE:
<221> NAME/KEY: source
<223> OTHER INFORMATION: /note="VH 1.46"

<400> SEQUENCE: 204

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Asp Leu Glu Trp Val
        35                  40                  45

Ser Gly Ile Ser Trp Asn Ala Gly Ser Tyr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 205
<211> LENGTH: 5
<212> TYPE: PRT
<213> ORGANISM: Homo sapiens
<220> FEATURE:

```
<221> NAME/KEY: source
<223> OTHER INFORMATION: /note="CDR1 sequence of SEQ ID NO: 208"

<400> SEQUENCE: 205

Asp Tyr Ala Phe His
1               5

<210> SEQ ID NO 206
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 208"

<400> SEQUENCE: 206

Gly Ile Ser Trp Asn Ser Gly Ser Tyr Gly Tyr Ala Asp Ser Val Lys
1               5                   10                  15

Gly

<210> SEQ ID NO 207
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 208"

<400> SEQUENCE: 207

Glu Lys Gly Pro Gly Leu Thr Gly Ser Thr Ala Asp Tyr Tyr Gly Leu
1               5                   10                  15

Asp Ala

<210> SEQ ID NO 208
<211> LENGTH: 127
<212> TYPE: PRT
<213> ORGANISM: Homo sapiens
<220> FEATURE:
<221> NAME/KEY: source
<223> OTHER INFORMATION: /note="VH 1.47"

<400> SEQUENCE: 208

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Phe His Trp Val Arg Gln Ala Pro Gly Lys Asp Leu Glu Trp Val
            35                  40                  45

Ser Gly Ile Ser Trp Asn Ser Gly Ser Tyr Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 209
<211> LENGTH: 5
<212> TYPE: PRT
```

-continued

```
<213> ORGANISM: Homo sapiens
<220> FEATURE:
<221> NAME/KEY: source
<223> OTHER INFORMATION: /note="CDR1 sequence of SEQ ID NO: 212"

<400> SEQUENCE: 209

Asp Tyr Ala Leu His
1               5

<210> SEQ ID NO 210
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 212"

<400> SEQUENCE: 210

Gly Ile Ser Trp Asn Ser Gly Ser Gln Gly Tyr Ala Asp Ser Val Lys
1               5                   10                  15

Gly

<210> SEQ ID NO 211
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 212"

<400> SEQUENCE: 211

Glu Lys Gly Pro Gly Leu Thr Gly Ser Thr Ala Asp Tyr Tyr Gly Leu
1               5                   10                  15

Asp Ala

<210> SEQ ID NO 212
<211> LENGTH: 127
<212> TYPE: PRT
<213> ORGANISM: Homo sapiens
<220> FEATURE:
<221> NAME/KEY: source
<223> OTHER INFORMATION: /note="VH 1.48"

<400> SEQUENCE: 212

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Asp Leu Glu Trp Val
        35                  40                  45

Ser Gly Ile Ser Trp Asn Ser Gly Ser Gln Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125

<210> SEQ ID NO 213
```

```
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 216"

<400> SEQUENCE: 213

Asp Tyr Ala Phe His
1               5

<210> SEQ ID NO 214
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 216"

<400> SEQUENCE: 214

Gly Ile Ser Trp Asn Ser Gly Ser Gln Gly Tyr Ala Asp Ser Val Lys
1               5                   10                  15

Gly

<210> SEQ ID NO 215
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 216"

<400> SEQUENCE: 215

Glu Lys Gly Pro Gly Leu Thr Gly Ser Thr Ala Asp Tyr Tyr Gly Leu
1               5                   10                  15

Asp Ala

<210> SEQ ID NO 216
<211> LENGTH: 127
<212> TYPE: PRT
<213> ORGANISM: Homo sapiens
<220> FEATURE:
<221> NAME/KEY: source
<223> OTHER INFORMATION: /note="VH 1.49"

<400> SEQUENCE: 216

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Phe His Trp Val Arg Gln Ala Pro Gly Lys Asp Leu Glu Trp Val
        35                  40                  45

Ser Gly Ile Ser Trp Asn Ser Gly Ser Gln Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser
        115                 120                 125
```

<210> SEQ ID NO 217
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 220"

<400> SEQUENCE: 217

Asp Tyr Ala Phe His
1               5

<210> SEQ ID NO 218
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 220"

<400> SEQUENCE: 218

Gly Ile Ser Trp Asn Ala Gly Ser Gln Gly Tyr Ala Asp Ser Val Lys
1               5                   10                  15

Gly

<210> SEQ ID NO 219
<211> LENGTH: 18
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 220"

<400> SEQUENCE: 219

Glu Lys Gly Pro Gly Leu Thr Gly Ser Thr Ala Asp Tyr Tyr Gly Leu
1               5                   10                  15

Asp Ala

<210> SEQ ID NO 220
<211> LENGTH: 127
<212> TYPE: PRT
<213> ORGANISM: Homo sapiens
<220> FEATURE:
<221> NAME/KEY: source
<223> OTHER INFORMATION: /note="VH 1.50"

<400> SEQUENCE: 220

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Phe His Trp Val Arg Gln Ala Pro Gly Lys Asp Leu Glu Trp Val
        35                  40                  45

Ser Gly Ile Ser Trp Asn Ala Gly Ser Gln Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Glu Lys Gly Pro Gly Leu Thr Gly Ser Thr Ala Asp Tyr Tyr
            100                 105                 110

Gly Leu Asp Ala Trp Gly Gln Gly Thr Met Val Thr Val Ser Ser

<210> SEQ ID NO 221
<211> LENGTH: 381
<212> TYPE: DNA
<213> ORGANISM: Homo sapiens
<220> FEATURE:
<221> NAME/KEY: source
<223> OTHER INFORMATION: /note="VH 1.21"

<400> SEQUENCE: 221

| | | | | | |
|---|---|---|---|---|---|
| gaggtgcagc | tggtggagtc | tgggggaggc | ttggtacagc | ctggcaggtc | cctgagactc | 60 |
| tcctgtgcag | cctctggatt | cacctttgac | gattatgcca | tgcactgggt | ccggcaagct | 120 |
| ccagggaagg | acctggagtg | gtctcaggt | attagttgga | atggtggtag | catgggctac | 180 |
| gcggcctctg | tgaagggccg | attcaccatc | tccagagaca | acgccaagaa | ctccctgtat | 240 |
| ctgcaaatga | acagtctgag | agctgaggac | acggccttgt | attattgtgt | aagagaaaag | 300 |
| gggcccggct | taactggaag | tacggccgat | tactacggtt | tggacgtctg | gggccaaggg | 360 |
| accatggtca | ccgtctcctc | a | | | | 381 |

<210> SEQ ID NO 222
<211> LENGTH: 381
<212> TYPE: DNA
<213> ORGANISM: Homo sapiens
<220> FEATURE:
<221> NAME/KEY: source
<223> OTHER INFORMATION: /note="VH 1.22"

<400> SEQUENCE: 222

| | | | | | |
|---|---|---|---|---|---|
| gaggtgcagc | tggtggagtc | tgggggaggc | ttggtacagc | ctggcaggtc | cctgagactc | 60 |
| tcctgtgcag | cctctggatt | cacctttgac | gattatgcca | tgcactgggt | ccggcaagct | 120 |
| ccagggaagg | acctggagtg | gtctcaggt | attagttgga | atggtggtag | catgggctac | 180 |
| gcggcctctg | tgaagggccg | attcaccatc | tccagagaca | acgccaagaa | ctccctgtat | 240 |
| ctgcaaatga | acagtctgag | agctgaggac | acggccttgt | attattgtgt | aagagaaaag | 300 |
| gggcccggct | taactggaag | tacggccgat | tactacggtt | tggacgcctg | gggccaaggg | 360 |
| accatggtca | ccgtctcctc | a | | | | 381 |

<210> SEQ ID NO 223
<211> LENGTH: 381
<212> TYPE: DNA
<213> ORGANISM: Homo sapiens
<220> FEATURE:
<221> NAME/KEY: source
<223> OTHER INFORMATION: /note="VH 1.23"

<400> SEQUENCE: 223

| | | | | | |
|---|---|---|---|---|---|
| gaggtgcagc | tggtggagtc | tgggggaggc | ttggtacagc | ctggcaggtc | cctgagactc | 60 |
| tcctgtgcag | cctctggatt | cacctttgac | gattatgcca | tgcactgggt | ccggcaagct | 120 |
| ccagggaagg | acctggagtg | gtctcaggt | attagttgga | atagtggtag | catgggctac | 180 |
| gcggcctctg | tgaagggccg | attcaccatc | tccagagaca | acgccaagaa | ctccctgtat | 240 |
| ctgcaaatga | acagtctgag | agctgaggac | acggccttgt | attattgtgt | aagagaaaag | 300 |
| gggcccggct | taactggaag | tacggccgat | tactacggtt | tggacgtctg | gggccaaggg | 360 |
| accatggtca | ccgtctcctc | a | | | | 381 |

<210> SEQ ID NO 224

```
<211> LENGTH: 381
<212> TYPE: DNA
<213> ORGANISM: Homo sapiens
<220> FEATURE:
<221> NAME/KEY: source
<223> OTHER INFORMATION: /note="VH 1.24"

<400> SEQUENCE: 224
gaggtgcagc tggtggagtc tgggggaggc ttggtacagc ctggcaggtc cctgagactc      60
tcctgtgcag cctctggatt caccttttgac gattatgcca tgcactgggt ccggcaagct    120
ccagggaagg acctggagtg ggtctcaggt attagttgga atagtggtag catgggctac    180
gcggcctctg tgaagggccg attcaccatc tccagagaca cgccaagaa ctccctgtat     240 ctgcaaatga acagtctgag agctgaggac acggccttgt attattgtgt aagagaaaag    300
gggcccggct taactggaag tacgccgat tactacggtt tggacgcctg gggccaaggg     360
accatggtca ccgtctcctc a                                               381

<210> SEQ ID NO 225
<211> LENGTH: 381
<212> TYPE: DNA
<213> ORGANISM: Homo sapiens
<220> FEATURE:
<221> NAME/KEY: source
<223> OTHER INFORMATION: /note="VH 1.25"

<400> SEQUENCE: 225
gaggtgcagc tggtggagtc tgggggaggc ttggtacagc ctggcaggtc cctgagactc      60
tcctgtgcag cctctggatt caccttttgac gattatgcca tgcactgggt ccggcaagct    120
ccagggaagg acctggagtg ggtctcaggt attagttgga atggtggtag ccagggctac    180
gcggcctctg tgaagggccg attcaccatc tccagagaca cgccaagaa ctccctgtat     240 ctgcaaatga acagtctgag agctgaggac acggccttgt attattgtgt aagagaaaag    300
gggcccggct taactggaag tacgccgat tactacggtt tggacgcctg gggccaaggg     360
accatggtca ccgtctcctc a                                               381

<210> SEQ ID NO 226
<211> LENGTH: 381
<212> TYPE: DNA
<213> ORGANISM: Homo sapiens
<220> FEATURE:
<221> NAME/KEY: source
<223> OTHER INFORMATION: /note="VH 1.26"

<400> SEQUENCE: 226
gaggtgcagc tggtggagtc tgggggaggc ttggtacagc ctggcaggtc cctgagactc      60
tcctgtgcag cctctggatt caccttttgac gattatgcca tgcactgggt ccggcaagct    120
ccagggaagg acctggagtg ggtctcaggt attagttgga atggtggtag catgggctac    180
gcggactctg tgaagggccg attcaccatc tccagagaca cgccaagaa ctccctgtat     240 ctgcaaatga acagtctgag agctgaggac acggccttgt attattgtgt aagagaaaag    300
gggcccggct taactggaag tacgccgat tactacggtt tggacgcctg gggccaaggg     360
accatggtca ccgtctcctc a                                               381

<210> SEQ ID NO 227
<211> LENGTH: 381
<212> TYPE: DNA
<213> ORGANISM: Homo sapiens
<220> FEATURE:
```

<221> NAME/KEY: source
<223> OTHER INFORMATION: /note="VH 1.27"

<400> SEQUENCE: 227

```
gaggtgcagc tggtggagtc tgggggaggc ttggtacagc ctggcaggtc cctgagactc    60
tcctgtgcag cctctggatt cacctttgac gattatgcca tgcactgggt ccggcaagct   120
ccagggaagg acctggagtg ggtctcaggt attagttgga atggtggtag caggggctac   180
gcggcctctg tgaagggccg attcaccatc tccagagaca cgccaagaa ctccctgtat    240
ctgcaaatga acagtctgag agctgaggac acggccttgt attattgtgt aagagaaaag   300
gggcccggct taactggaag tacgccgat tactacggtt tggacgcctg gggccaaggg    360
accatggtca ccgtctcctc a                                             381
```

<210> SEQ ID NO 228
<211> LENGTH: 381
<212> TYPE: DNA
<213> ORGANISM: Homo sapiens
<220> FEATURE:
<221> NAME/KEY: source
<223> OTHER INFORMATION: /note="VH 1.28"

<400> SEQUENCE: 228

```
gaggtgcagc tggtggagtc tgggggaggc ttggtacagc ctggcaggtc cctgagactc    60
tcctgtgcag cctctggatt cacctttgac gattatgcca tgcactgggt ccggcaagct   120
ccagggaagg acctggagtg ggtctcaggt attagttgga atgcgggtag catgggctac   180
gcggcctctg tgaagggccg attcaccatc tccagagaca cgccaagaa ctccctgtat    240
ctgcaaatga acagtctgag agctgaggac acggccttgt attattgtgt aagagaaaag   300
gggcccggct taactggaag tacgccgat tactacggtt tggacgcctg gggccaaggg    360
accatggtca ccgtctcctc a                                             381
```

<210> SEQ ID NO 229
<211> LENGTH: 381
<212> TYPE: DNA
<213> ORGANISM: Homo sapiens
<220> FEATURE:
<221> NAME/KEY: source
<223> OTHER INFORMATION: /note="VH 1.29"

<400> SEQUENCE: 229

```
gaggtgcagc tggtggagtc tgggggaggc ttggtacagc ctggcaggtc cctgagactc    60
tcctgtgcag cctctggatt cacctttgac gattatgcca tgcactgggt ccggcaagct   120
ccagggaagg acctggagtg ggtctcaggt attagttgga atagtggtag catgggctac   180
gcggactctg tgaagggccg attcaccatc tccagagaca cgccaagaa ctccctgtat    240
ctgcaaatga acagtctgag agctgaggac acggccttgt attattgtgt aagagaaaag   300
gggcccggct taactggaag tacgccgat tactacggtt tggacgtctg gggccaaggg    360
accatggtca ccgtctcctc a                                             381
```

<210> SEQ ID NO 230
<211> LENGTH: 381
<212> TYPE: DNA
<213> ORGANISM: Homo sapiens
<220> FEATURE:
<221> NAME/KEY: source
<223> OTHER INFORMATION: /note="VH 1.30"

<400> SEQUENCE: 230
gaggtgcagc tggtggagtc tggggaggc ttggtacagc ctggcaggtc cctgagactc      60
tcctgtgcag cctctggatt cacctttgac gattatgccg gcactgggt ccggcaagct     120 ccagggaagg acctgagtg gtctcaggt attagttgga atggtggtag catgggctac      180
gcggcctctg tgaagggccg attcaccatc tccagagaca cgccaagaa ctccctgtat     240 ctgcaaatga acagtctgag agctgaggac acggccttgt attattgtgt aagagaaaag    300
gggcccggct taactggaag tacgccgat tactacggtt tggacgcctg gggccaaggg     360
accatggtca ccgtctcctc a                                              381

```
<210> SEQ ID NO 231
<211> LENGTH: 381
<212> TYPE: DNA
<213> ORGANISM: Homo sapiens
<220> FEATURE:
<221> NAME/KEY: source
<223> OTHER INFORMATION: /note="VH 1.31"
```

<400> SEQUENCE: 231
gaggtgcagc tggtggagtc tggggaggc ttggtacagc ctggcaggtc cctgagactc      60
tcctgtgcag cctctggatt cacctttgac gattatgcct tgcactgggt ccggcaagct    120
ccagggaagg acctgagtg gtctcaggt attagttgga atggtggtag catgggctac      180
gcggcctctg tgaagggccg attcaccatc tccagagaca cgccaagaa ctccctgtat     240 ctgcaaatga acagtctgag agctgaggac acggccttgt attattgtgt aagagaaaag    300
gggcccggct taactggaag tacgccgat tactacggtt tggacgcctg gggccaaggg     360
accatggtca ccgtctcctc a                                              381

```
<210> SEQ ID NO 232
<211> LENGTH: 381
<212> TYPE: DNA
<213> ORGANISM: Homo sapiens
<220> FEATURE:
<221> NAME/KEY: source
<223> OTHER INFORMATION: /note="VH 1.32"
```

<400> SEQUENCE: 232
gaggtgcagc tggtggagtc tggggaggc ttggtacagc ctggcaggtc cctgagactc      60
tcctgtgcag cctctggatt cacctttgac gattatgcca tgcactggt ccggcaagct     120 ccagggaagg acctgagtg gtctcaggt attagttgga atagtggtag catgggctac      180
gcggactctg tgaagggccg attcaccatc tccagagaca cgccaagaa ctccctgtat     240 ctgcaaatga acagtctgag agctgaggac acggccttgt attattgtgt aagagaaaag    300
gggcccggct taactggaag tacgccgat tactacggtt tggacgcctg gggccaaggg     360
accatggtca ccgtctcctc a                                              381

```
<210> SEQ ID NO 233
<211> LENGTH: 381
<212> TYPE: DNA
<213> ORGANISM: Homo sapiens
<220> FEATURE:
<221> NAME/KEY: source
<223> OTHER INFORMATION: /note="VH 1.33"
```

<400> SEQUENCE: 233
gaggtgcagc tggtggagtc tggggaggc ttggtacagc ctggcaggtc cctgagactc      60
tcctgtgcag cctctggatt cacctttgac gattatgcca tgcactgggt ccggcaagct    120

```
ccagggaagg acctggagtg ggtctcaggt attagttgga atggtggtag ctacggctac    180
gcggactctg tgaagggccg attcaccatc tccagagaca cgccaagaa ctccctgtat     240 ctgcaaatga acagtctgag agctgaggac acggccttgt attattgtgt aagagaaaag    300
gggcccggct taactggaag tacgccgat tactacggtt tggacgcctg gggccaaggg    360
accatggtca ccgtctcctc a                                              381
```

```
<210> SEQ ID NO 234
<211> LENGTH: 381
<212> TYPE: DNA
<213> ORGANISM: Homo sapiens
<220> FEATURE:
<221> NAME/KEY: source
<223> OTHER INFORMATION: /note="VH 1.34"

<400> SEQUENCE: 234
gaggtgcagc tggtggagtc tgggggaggc ttggtacagc ctggcaggtc cctgagactc    60
tcctgtgcag cctctggatt caccttttgac gattatgcca tgcactgggt ccggcaagct   120
ccagggaagg acctggagtg ggtctcaggt attagttgga atggtggtag ccagggctac    180
gcggactctg tgaagggccg attcaccatc tccagagaca cgccaagaa ctccctgtat     240 ctgcaaatga acagtctgag agctgaggac acggccttgt attattgtgt aagagaaaag    300
gggcccggct taactggaag tacgccgat tactacggtt tggacgcctg gggccaaggg    360
accatggtca ccgtctcctc a                                              381
```

```
<210> SEQ ID NO 235
<211> LENGTH: 381
<212> TYPE: DNA
<213> ORGANISM: Homo sapiens
<220> FEATURE:
<221> NAME/KEY: source
<223> OTHER INFORMATION: /note="VH 1.35"

<400> SEQUENCE: 235
gaggtgcagc tggtggagtc tgggggaggc ttggtacagc ctggcaggtc cctgagactc    60
tcctgtgcag cctctggatt caccttttgac gattatgcca tgcactgggt ccggcaagct   120
ccagggaagg acctggagtg ggtctcaggt attagttgga atggtggtag caagggctac    180
gcggactctg tgaagggccg attcaccatc tccagagaca cgccaagaa ctccctgtat     240 ctgcaaatga acagtctgag agctgaggac acggccttgt attattgtgt aagagaaaag    300
gggcccggct taactggaag tacgccgat tactacggtt tggacgcctg gggccaaggg    360
accatggtca ccgtctcctc a                                              381
```

```
<210> SEQ ID NO 236
<211> LENGTH: 381
<212> TYPE: DNA
<213> ORGANISM: Homo sapiens
<220> FEATURE:
<221> NAME/KEY: source
<223> OTHER INFORMATION: /note="VH 1.36"

<400> SEQUENCE: 236
gaggtgcagc tggtggagtc tgggggaggc ttggtacagc ctggcaggtc cctgagactc    60
tcctgtgcag cctctggatt caccttttgac gattatgcca tgcactgggt ccggcaagct   120
ccagggaagg acctggagtg ggtctcaggt attagttgga atgcgggtag catgggctac    180
gcggactctg tgaagggccg attcaccatc tccagagaca cgccaagaa ctccctgtat     240
```

-continued

| | |
|---|---|
| ctgcaaatga acagtctgag agctgaggac acggccttgt attattgtgt aagagaaaag | 300 |
| gggcccggct taactggaag tacggccgat tactacggtt tggacgcctg gggccaaggg | 360 |
| accatggtca ccgtctcctc a | 381 |

<210> SEQ ID NO 237
<211> LENGTH: 381
<212> TYPE: DNA
<213> ORGANISM: Homo sapiens
<220> FEATURE:
<221> NAME/KEY: source
<223> OTHER INFORMATION: /note="VH 1.37"

<400> SEQUENCE: 237

| | |
|---|---|
| gaggtgcagc tggtggagtc tgggggaggc ttggtacagc ctggcaggtc cctgagactc | 60 |
| tcctgtgcag cctctggatt caccttTgac gattatgcct ccactgggt ccggcaagct | 120 |
| ccagggaagg acctggagtg ggtctcaggt attagttgga atggtggtag catgggctac | 180 |
| gcggactctg tgaagggccg attcaccatc tccagagaca acgccaagaa ctccctgtat | 240 |
| ctgcaaatga acagtctgag agctgaggac acggccttgt attattgtgt aagagaaaag | 300 |
| gggcccggct taactggaag tacggccgat tactacggtt tggacgcctg gggccaaggg | 360 |
| accatggtca ccgtctcctc a | 381 |

<210> SEQ ID NO 238
<211> LENGTH: 381
<212> TYPE: DNA
<213> ORGANISM: Homo sapiens
<220> FEATURE:
<221> NAME/KEY: source
<223> OTHER INFORMATION: /note="VH 1.38"

<400> SEQUENCE: 238

| | |
|---|---|
| gaggtgcagc tggtggagtc tgggggaggc ttggtacagc ctggcaggtc cctgagactc | 60 |
| tcctgtgcag cctctggatt caccttTgac gattatgccc tccactgggt ccggcaagct | 120 |
| ccagggaagg acctggagtg ggtctcaggt attagttgga atggtggtag catgggctac | 180 |
| gcggactctg tgaagggccg attcaccatc tccagagaca acgccaagaa ctccctgtat | 240 |
| ctgcaaatga acagtctgag agctgaggac acggccttgt attattgtgt aagagaaaag | 300 |
| gggcccggct taactggaag tacggccgat tactacggtt tggacgcctg gggccaaggg | 360 |
| accatggtca ccgtctcctc a | 381 |

<210> SEQ ID NO 239
<211> LENGTH: 381
<212> TYPE: DNA
<213> ORGANISM: Homo sapiens
<220> FEATURE:
<221> NAME/KEY: source
<223> OTHER INFORMATION: /note="VH 1.39"

<400> SEQUENCE: 239

| | |
|---|---|
| gaggtgcagc tggtggagtc tgggggaggc ttggtacagc ctggcaggtc cctgagactc | 60 |
| tcctgtgcag cctctggatt caccttTgac gattatgccc tacactgggt ccggcaagct | 120 |
| ccagggaagg acctggagtg ggtctcaggt attagttgga atggtggtag ctacggctac | 180 |
| gcggactctg tgaagggccg attcaccatc tccagagaca acgccaagaa ctccctgtat | 240 |
| ctgcaaatga acagtctgag agctgaggac acggccttgt attattgtgt aagagaaaag | 300 |
| gggcccggct taactggaag tacggccgat tactacggtt tggacgcctg gggccaaggg | 360 |

```
accatggtca ccgtctcctc a                                          381

<210> SEQ ID NO 240
<211> LENGTH: 381
<212> TYPE: DNA
<213> ORGANISM: Homo sapiens
<220> FEATURE:
<221> NAME/KEY: source
<223> OTHER INFORMATION: /note="VH 1.40"

<400> SEQUENCE: 240
gaggtgcagc tggtggagtc tgggggaggc ttggtacagc ctggcaggtc cctgagactc    60
tcctgtgcag cctctggatt cacctttgac gattatgccc tacactgggt ccggcaagct   120
ccagggaagg acctggagtg ggtctcaggt attagttgga atggtggtag ccagggctac   180
gcggactctg tgaagggccg attcaccatc tccagagaca acgccaagaa ctccctgtat   240
ctgcaaatga acagtctgag agctgaggac acggccttgt attattgtgt aagagaaaag   300
gggcccggct taactggaag tacggccgat tactacggtt tggacgcctg gggccaaggg   360
accatggtca ccgtctcctc a                                          381

<210> SEQ ID NO 241
<211> LENGTH: 381
<212> TYPE: DNA
<213> ORGANISM: Homo sapiens
<220> FEATURE:
<221> NAME/KEY: source
<223> OTHER INFORMATION: /note="VH 1.41"

<400> SEQUENCE: 241
gaggtgcagc tggtggagtc tgggggaggc ttggtacagc ctggcaggtc cctgagactc    60
tcctgtgcag cctctggatt cacctttgac gattatgcct ccactgggt ccggcaagct    120 ccagggaagg acctggagtg ggtctcaggt attagttgga atggtggtag ctacggctac   180
gcggactctg tgaagggccg attcaccatc tccagagaca acgccaagaa ctccctgtat   240
ctgcaaatga acagtctgag agctgaggac acggccttgt attattgtgt aagagaaaag   300
gggcccggct taactggaag tacggccgat tactacggtt tggacgcctg gggccaaggg   360
accatggtca ccgtctcctc a                                          381

<210> SEQ ID NO 242
<211> LENGTH: 381
<212> TYPE: DNA
<213> ORGANISM: Homo sapiens
<220> FEATURE:
<221> NAME/KEY: source
<223> OTHER INFORMATION: /note="VH 1.42"

<400> SEQUENCE: 242
gaggtgcagc tggtggagtc tgggggaggc ttggtacagc ctggcaggtc cctgagactc    60
tcctgtgcag cctctggatt cacctttgac gattatgcct ccactgggt ccggcaagct    120 ccagggaagg acctggagtg ggtctcaggt attagttgga atggtggtag ccagggctac   180
gcggactctg tgaagggccg attcaccatc tccagagaca acgccaagaa ctccctgtat   240
ctgcaaatga acagtctgag agctgaggac acggccttgt attattgtgt aagagaaaag   300
gggcccggct taactggaag tacggccgat tactacggtt tggacgcctg gggccaaggg   360
accatggtca ccgtctcctc a                                          381
```

```
<210> SEQ ID NO 243
<211> LENGTH: 381
<212> TYPE: DNA
<213> ORGANISM: Homo sapiens
<220> FEATURE:
<221> NAME/KEY: source
<223> OTHER INFORMATION: /note="VH 1.43"

<400> SEQUENCE: 243
gaggtgcagc tggtggagtc tgggggaggc ttggtacagc ctggcaggtc cctgagactc      60
tcctgtgcag cctctggatt cacctttgac gattatgcct ccactgggt ccggcaagct     120 ccagggaagg acctggagtg ggtctcaggt attagttgga atgctggtag ctacggctac    180
gcggactctg tgaagggccg attcaccatc tccagagaca acgccaagaa ctccctgtat    240
ctgcaaatga acagtctgag agctgaggac acggccttgt attattgtgt aagagaaaag    300
gggcccggct taactggaag tacggccgat tactacggtt tggacgcctg gggccaaggg    360
accatggtca ccgtctcctc a                                                381

<210> SEQ ID NO 244
<211> LENGTH: 381
<212> TYPE: DNA
<213> ORGANISM: Homo sapiens
<220> FEATURE:
<221> NAME/KEY: source
<223> OTHER INFORMATION: /note="VH 1.44"

<400> SEQUENCE: 244
gaggtgcagc tggtggagtc tgggggaggc ttggtacagc ctggcaggtc cctgagactc      60
tcctgtgcag cctctggatt cacctttgac gattatgccc tacactgggt ccggcaagct    120
ccagggaagg acctggagtg ggtctcaggt attagttgga atagtggtag ctacggctac    180
gcggactctg tgaagggccg attcaccatc tccagagaca acgccaagaa ctccctgtat    240
ctgcaaatga acagtctgag agctgaggac acggccttgt attattgtgt aagagaaaag    300
gggcccggct taactggaag tacggccgat tactacggtt tggacgcctg gggccaaggg    360
accatggtca ccgtctcctc a                                                381

<210> SEQ ID NO 245
<211> LENGTH: 381
<212> TYPE: DNA
<213> ORGANISM: Homo sapiens
<220> FEATURE:
<221> NAME/KEY: source
<223> OTHER INFORMATION: /note="VH 1.45"

<400> SEQUENCE: 245
gaggtgcagc tggtggagtc tgggggaggc ttggtacagc ctggcaggtc cctgagactc      60
tcctgtgcag cctctggatt cacctttgac gattatgccc tacactgggt ccggcaagct    120
ccagggaagg acctggagtg ggtctcaggt attagttgga atgctggtag ccagggctac    180
gcggactctg tgaagggccg attcaccatc tccagagaca acgccaagaa ctccctgtat    240
ctgcaaatga acagtctgag agctgaggac acggccttgt attattgtgt aagagaaaag    300
gggcccggct taactggaag tacggccgat tactacggtt tggacgcctg gggccaaggg    360
accatggtca ccgtctcctc a                                                381

<210> SEQ ID NO 246
<211> LENGTH: 381
<212> TYPE: DNA
<213> ORGANISM: Homo sapiens
```

```
<220> FEATURE:
<221> NAME/KEY: source
<223> OTHER INFORMATION: /note="VH 1.46"

<400> SEQUENCE: 246
gaggtgcagc tggtggagtc tgggggaggc ttggtacagc ctggcaggtc cctgagactc      60
tcctgtgcag cctctggatt cacctttgac gattatgccc tacactgggt ccggcaagct     120
ccagggaagg acctggagtg ggtctcaggt attagttgga atgctggtag ctacggctac     180
gcggactctg tgaagggccg attcaccatc tccagagaca acgccaagaa ctccctgtat     240
ctgcaaatga acagtctgag agctgaggac acggccttgt attattgtgt aagagaaaag     300
gggcccggct aactggaagt acggccgatt actacggtt tggacgcctg gggccaaggg      360
accatggtca ccgtctcctc a                                               381

<210> SEQ ID NO 247
<211> LENGTH: 381
<212> TYPE: DNA
<213> ORGANISM: Homo sapiens
<220> FEATURE:
<221> NAME/KEY: source
<223> OTHER INFORMATION: /note="VH 1.47"

<400> SEQUENCE: 247
gaggtgcagc tggtggagtc tgggggaggc ttggtacagc ctggcaggtc cctgagactc      60
tcctgtgcag cctctggatt cacctttgac gattatgcct ccactgggt ccggcaagct      120 ccagggaagg acctggagtg ggtctcaggt attagttgga atagtggtag ctacggctac     180
gcggactctg tgaagggccg attcaccatc tccagagaca acgccaagaa ctccctgtat     240
ctgcaaatga acagtctgag agctgaggac acggccttgt attattgtgt aagagaaaag     300
gggcccggct aactggaagt acggccgatt actacggtt tggacgcctg gggccaaggg      360
accatggtca ccgtctcctc a                                               381

<210> SEQ ID NO 248
<211> LENGTH: 381
<212> TYPE: DNA
<213> ORGANISM: Homo sapiens
<220> FEATURE:
<221> NAME/KEY: source
<223> OTHER INFORMATION: /note="VH 1.48"

<400> SEQUENCE: 248
gaggtgcagc tggtggagtc tgggggaggc ttggtacagc ctggcaggtc cctgagactc      60
tcctgtgcag cctctggatt cacctttgac gattatgccc tacactgggt ccggcaagct     120
ccagggaagg acctggagtg ggtctcaggt attagttgga atagtggtag ccagggctac     180
gcggactctg tgaagggccg attcaccatc tccagagaca acgccaagaa ctccctgtat     240
ctgcaaatga acagtctgag agctgaggac acggccttgt attattgtgt aagagaaaag     300
gggcccggct aactggaagt acggccgatt actacggtt tggacgcctg gggccaaggg      360
accatggtca ccgtctcctc a                                               381

<210> SEQ ID NO 249
<211> LENGTH: 381
<212> TYPE: DNA
<213> ORGANISM: Homo sapiens
<220> FEATURE:
<221> NAME/KEY: source
<223> OTHER INFORMATION: /note="VH 1.49"
```

-continued

```
<400> SEQUENCE: 249
gaggtgcagc tggtggagtc tgggggaggc ttggtacagc ctggcaggtc cctgagactc    60
tcctgtgcag cctctggatt cacctttgac gattatgcct ccactgggt ccggcaagct    120 ccagggaagg acctggagtg ggtctcaggt attagttgga atagtggtag ccagggctac   180
gcggactctg tgaagggccg attcaccatc tccagagaca acgccaagaa ctccctgtat   240
ctgcaaatga acagtctgag agctgaggac acggccttgt attattgtgt aagagaaaag   300
gggcccggct taactggaag tacggccgat tactacggtt tggacgcctg gggccaaggg   360
accatggtca ccgtctcctc a                                             381

<210> SEQ ID NO 250
<211> LENGTH: 381
<212> TYPE: DNA
<213> ORGANISM: Homo sapiens
<220> FEATURE:
<221> NAME/KEY: source
<223> OTHER INFORMATION: /note="VH 1.50"

<400> SEQUENCE: 250
gaggtgcagc tggtggagtc tgggggaggc ttggtacagc ctggcaggtc cctgagactc    60
tcctgtgcag cctctggatt cacctttgac gattatgcct ccactgggt ccggcaagct    120 ccagggaagg acctggagtg ggtctcaggt attagttgga atgctggtag ccagggctac   180
gcggactctg tgaagggccg attcaccatc tccagagaca acgccaagaa ctccctgtat   240
ctgcaaatga acagtctgag agctgaggac acggccttgt attattgtgt aagagaaaag   300
gggcccggct taactggaag tacggccgat tactacggtt tggacgcctg gggccaaggg   360
accatggtca ccgtctcctc a                                             381

<210> SEQ ID NO 251
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 254"

<400> SEQUENCE: 251

Asp Tyr Ala Met Ser
1               5

<210> SEQ ID NO 252
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 254"

<400> SEQUENCE: 252

Gly Ile Thr Trp Asn Gly Gly Ser Thr Gly Tyr Ala Asp Ser Val Lys
1               5                   10                  15

Asp

<210> SEQ ID NO 253
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 254"
```

<400> SEQUENCE: 253

Asp Lys Tyr Ser Tyr Ala Trp Ser Tyr Asp Gly Phe Asp Ile
1               5                   10

<210> SEQ ID NO 254
<211> LENGTH: 123
<212> TYPE: PRT
<213> ORGANISM: Homo sapiens
<220> FEATURE:
<221> NAME/KEY: source
<223> OTHER INFORMATION: /note="VH 2.1"

<400> SEQUENCE: 254

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 255
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 258"

<400> SEQUENCE: 255

Asp Tyr Gly Met Ser
1               5

<210> SEQ ID NO 256
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 258"

<400> SEQUENCE: 256

Gly Ile Ser Arg Asn Gly Gly Ser Ala Gly Tyr Ser Asp Ser Ala Lys
1               5                   10                  15

Asp

<210> SEQ ID NO 257
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 258"

<400> SEQUENCE: 257

Glu Lys Tyr Ser Ser Gly Trp Ser Tyr Asp Asp Phe Asp Ile
1               5                   10

<210> SEQ ID NO 258
<211> LENGTH: 123
<212> TYPE: PRT
<213> ORGANISM: Homo sapiens
<220> FEATURE:
<221> NAME/KEY: source
<223> OTHER INFORMATION: /note="VH 2.2"

<400> SEQUENCE: 258

Glu Val Gln Leu Leu Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Pro Pro Gly Lys Gly Leu Glu Trp Val
        35                  40                  45

Ser Gly Ile Ser Arg Asn Gly Gly Ser Ala Gly Tyr Ser Asp Ser Ala
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Met Tyr Tyr Cys
                85                  90                  95

Ala Arg Glu Lys Tyr Ser Ser Gly Trp Ser Tyr Asp Asp Phe Asp Ile
            100                 105                 110

Trp Gly Gln Gly Thr Met Val Thr Val Ser Ser
        115                 120

<210> SEQ ID NO 259
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 262"

<400> SEQUENCE: 259

Asp Tyr Gly Met Ser
1               5

<210> SEQ ID NO 260
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 262"

<400> SEQUENCE: 260

Gly Ile Ser Arg Asn Gly Gly Ser Ala Gly Tyr Ser Asp Ser Ala Lys
1               5                   10                  15

Asp

<210> SEQ ID NO 261
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 262"

<400> SEQUENCE: 261

Glu Lys Tyr Ser Ser Gly Trp Ser Tyr Asp Asp Phe Asp Ile
1               5                   10

<210> SEQ ID NO 262
<211> LENGTH: 123
<212> TYPE: PRT
<213> ORGANISM: Homo sapiens
<220> FEATURE:
<221> NAME/KEY: source
<223> OTHER INFORMATION: /note="VH 2.3"

<400> SEQUENCE: 262

Gln Val Gln Leu Val Glu Ser Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Ser Pro Gly Lys Gly Leu Glu Trp Val
            35                  40                  45

Ser Gly Ile Ser Arg Asn Gly Gly Ser Ala Gly Tyr Ser Asp Ser Ala
        50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Met Tyr Tyr Cys
                85                  90                  95

Ala Arg Glu Lys Tyr Ser Ser Gly Trp Ser Tyr Asp Asp Phe Asp Ile
            100                 105                 110

Trp Gly Gln Gly Thr Met Val Thr Val Ser Ser
        115                 120

<210> SEQ ID NO 263
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 266"

<400> SEQUENCE: 263

Asp Tyr Gly Met Ser
1               5

<210> SEQ ID NO 264
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 266"

<400> SEQUENCE: 264

Gly Ile Ser Arg Asn Gly Gly Ser Ala Gly Tyr Ser Asp Ser Ala Lys
1               5                   10                  15

Asp

<210> SEQ ID NO 265
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 266"

<400> SEQUENCE: 265

Glu Lys Tyr Ser Ser Gly Trp Ser Tyr Asp Asp Phe Asp Ile
1               5                   10

<210> SEQ ID NO 266
<211> LENGTH: 123
<212> TYPE: PRT
<213> ORGANISM: Homo sapiens
<220> FEATURE:
<221> NAME/KEY: source
<223> OTHER INFORMATION: /note="VH 2.4"

<400> SEQUENCE: 266

Gln Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Pro Pro Gly Lys Gly Leu Glu Trp Val
            35                  40                  45

Ser Gly Ile Ser Arg Asn Gly Gly Ser Ala Gly Tyr Ser Asp Ser Ala
        50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Met Tyr Tyr Cys
                85                  90                  95

Ala Arg Glu Lys Tyr Ser Ser Gly Trp Ser Tyr Asp Asp Phe Asp Ile
                100                 105                 110

Trp Gly Gln Gly Thr Met Val Thr Val Ser Ser
            115                 120

<210> SEQ ID NO 267
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 270"

<400> SEQUENCE: 267

Asp Tyr Gly Met Ser
1               5

<210> SEQ ID NO 268
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 270"

<400> SEQUENCE: 268

Gly Ile Ser Arg Asn Gly Gly Ser Ala Gly Tyr Ser Asp Ser Ala Lys
1               5                   10                  15

Asp

<210> SEQ ID NO 269
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 270"

<400> SEQUENCE: 269

Glu Lys Tyr Ser Ser Gly Trp Ser Tyr Asp Asp Phe Asp Ile
1               5                   10

<210> SEQ ID NO 270
<211> LENGTH: 123
<212> TYPE: PRT
<213> ORGANISM: Homo sapiens
<220> FEATURE:
<221> NAME/KEY: source
<223> OTHER INFORMATION: /note="VH 2.5"

<400> SEQUENCE: 270

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Pro Pro Gly Lys Gly Leu Glu Trp Val
        35                  40                  45

Ser Gly Ile Ser Arg Asn Gly Gly Ser Ala Gly Tyr Ser Asp Ser Ala
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Met Tyr Tyr Cys
                85                  90                  95

Ala Arg Glu Lys Tyr Ser Ser Gly Trp Ser Tyr Asp Asp Phe Asp Ile
            100                 105                 110

Trp Gly Gln Gly Thr Met Val Thr Val Ser Ser
        115                 120

<210> SEQ ID NO 271
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 274"

<400> SEQUENCE: 271

Asp Tyr Gly Met Ser
1               5

<210> SEQ ID NO 272
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 274"

<400> SEQUENCE: 272

Gly Ile Ser Arg Asn Gly Gly Ser Thr Gly Tyr Ala Asp Ser Val Lys
1               5                   10                  15

Asp

<210> SEQ ID NO 273
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 274"

<400> SEQUENCE: 273

Asp Pro Tyr Ser Ser Gly Trp Ser Tyr Asp Ser Phe Asp Ile
1               5                   10

<210> SEQ ID NO 274
<211> LENGTH: 123
<212> TYPE: PRT
<213> ORGANISM: Homo sapiens
<220> FEATURE:
<221> NAME/KEY: source
<223> OTHER INFORMATION: /note="VH 2.6"

<400> SEQUENCE: 274

Gln Val Gln Leu Val Glu Ser Gly Gly Val Val Arg Leu Gly Gly
1               5                   10                  15

Ser Leu Arg Leu Ser Cys Ala Ala Ser Gly Phe Ser Phe Val Asp Tyr
            20                  25                  30

Gly Met Ser Trp Val Arg Gln Ala Pro Gly Gln Gly Leu Glu Trp Val
        35                  40                  45

Ser Gly Ile Ser Arg Asn Gly Gly Ser Thr Gly Tyr Ala Asp Ser Val
    50                  55                  60

Lys Asp Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Asp Pro Tyr Ser Ser Gly Trp Ser Tyr Asp Ser Phe Asp Ile
            100                 105                 110

Trp Gly Gln Gly Thr Met Val Thr Val Ser Ser
        115                 120

<210> SEQ ID NO 275
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 278"

<400> SEQUENCE: 275

Asp Tyr Gly Met Ser
1               5

<210> SEQ ID NO 276
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 278"

<400> SEQUENCE: 276

Gly Ile Ser Arg Asn Gly Gly Ser Thr Gly Tyr Thr Ala Ser Val Lys
1               5                   10                  15

Asp

<210> SEQ ID NO 277
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 278"

<400> SEQUENCE: 277

Glu Lys Tyr Ser Ser Gly Trp Ser Tyr Asp Asp Phe Asp Ile
1               5                   10

<210> SEQ ID NO 278
<211> LENGTH: 123
<212> TYPE: PRT
<213> ORGANISM: Homo sapiens
<220> FEATURE:
<221> NAME/KEY: source
<223> OTHER INFORMATION: /note="VH 2.7"

<400> SEQUENCE: 278

Gln Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
            35                  40                  45

Ser Gly Ile Ser Arg Asn Gly Gly Ser Thr Gly Tyr Thr Ala Ser Val
        50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Met Tyr Tyr Cys
                85                  90                  95

Ala Arg Glu Lys Tyr Ser Ser Gly Trp Ser Tyr Asp Asp Phe Asp Ile
            100                 105                 110

Trp Gly Gln Gly Thr Met Val Thr Val Ser Ser
        115                 120

<210> SEQ ID NO 279
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 282"

<400> SEQUENCE: 279

Asp Tyr Ala Met Ser
1               5

<210> SEQ ID NO 280
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 282"

<400> SEQUENCE: 280

Gly Ile Ser Trp Asn Gly Gly Ser Ala Gly Tyr Ala Asp Ser Val Lys
1               5                   10                  15

Asp

<210> SEQ ID NO 281
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 282"

<400> SEQUENCE: 281

Asp Pro His Ser Ser Ala Trp Ser Tyr Asp Ala Phe Asp Ile
1               5                   10

<210> SEQ ID NO 282
<211> LENGTH: 123
<212> TYPE: PRT
<213> ORGANISM: Homo sapiens
<220> FEATURE:
<221> NAME/KEY: source
<223> OTHER INFORMATION: /note="VH 2.8"

<400> SEQUENCE: 282

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Ser Trp Asn Gly Gly Ser Ala Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Pro His Ser Ser Ala Trp Ser Tyr Asp Ala Phe Asp Ile
            100                 105                 110

Trp Gly Gln Gly Thr Met Val Thr Val Ser Ser
        115                 120

<210> SEQ ID NO 283
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 286"

<400> SEQUENCE: 283

Asp Tyr Ala Met Ser
1               5

<210> SEQ ID NO 284
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 286"

<400> SEQUENCE: 284

Gly Ile Ser Trp Asn Gly Gly Ser Lys Gly Tyr Ala Asp Ser Val Lys
1               5                   10                  15

Asp

<210> SEQ ID NO 285
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 286"

<400> SEQUENCE: 285

Asp Pro Tyr Ser Gly Ala Trp Ser Tyr Asp Ala Phe Asp Ile
1               5                   10

<210> SEQ ID NO 286
<211> LENGTH: 123
<212> TYPE: PRT
<213> ORGANISM: Homo sapiens
<220> FEATURE:
<221> NAME/KEY: source
<223> OTHER INFORMATION: /note="VH 2.9"

<400> SEQUENCE: 286

Gln Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Ser Trp Asn Gly Gly Ser Lys Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Pro Tyr Ser Gly Ala Trp Ser Tyr Asp Ala Phe Asp Ile
            100                 105                 110

Trp Gly Gln Gly Thr Met Val Thr Val Ser Ser
        115                 120

<210> SEQ ID NO 287
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 290"

<400> SEQUENCE: 287

Asp Tyr Ala Met Ser
1               5

<210> SEQ ID NO 288
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 290"

<400> SEQUENCE: 288

Gly Ile Ser Trp Asn Gly Gly Ser Thr Gly Tyr Ala Asp Ser Val Lys
1               5                   10                  15

Asp

<210> SEQ ID NO 289
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 290"

<400> SEQUENCE: 289

Asp Pro Tyr Ser Gly Ala Trp Ser Tyr Asp Ala Phe Asp Ile
1               5                   10

<210> SEQ ID NO 290
<211> LENGTH: 123
<212> TYPE: PRT
<213> ORGANISM: Homo sapiens
<220> FEATURE:
<221> NAME/KEY: source
<223> OTHER INFORMATION: /note="VH 2.10"

<400> SEQUENCE: 290

Gln Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Ala Met Ser Trp Val Arg Gln Ala Pro Gly Lys Gly Leu Glu Trp Val
            35                  40                  45

Ser Gly Ile Ser Trp Asn Gly Gly Ser Thr Gly Tyr Ala Asp Ser Val
        50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Pro Tyr Ser Gly Ala Trp Ser Tyr Asp Ala Phe Asp Ile
            100                 105                 110

Trp Gly Gln Gly Thr Met Val Thr Val Ser Ser
        115                 120

<210> SEQ ID NO 291
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 294"

<400> SEQUENCE: 291

Asn Tyr Ala Met Ser
1               5

<210> SEQ ID NO 292
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 294"

<400> SEQUENCE: 292

Gly Ile Thr Trp Asn Gly Gly Ser Thr Gly Tyr Ala Asp Ser Val Lys
1               5                   10                  15

Asp

<210> SEQ ID NO 293
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 294"

<400> SEQUENCE: 293

Asp Lys Tyr Ser Tyr Ala Trp Ser Tyr Asp Thr Phe Asp Ile
1               5                   10

<210> SEQ ID NO 294
<211> LENGTH: 123
<212> TYPE: PRT
<213> ORGANISM: Homo sapiens
<220> FEATURE:
<221> NAME/KEY: source
<223> OTHER INFORMATION: /note="VH 2.11"

<400> SEQUENCE: 294

Gln Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asn Tyr
            20                  25                  30

Ala Met Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Tyr Ser Tyr Ala Trp Ser Tyr Asp Thr Phe Asp Ile
            100                 105                 110

Arg Gly Gln Gly Thr Met Val Thr Val Ser Ser
        115                 120

<210> SEQ ID NO 295
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 298"

<400> SEQUENCE: 295

Asp Tyr Ala Met Ser
1               5

<210> SEQ ID NO 296
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 298"

<400> SEQUENCE: 296

Gly Ile Thr Trp Asn Ala Gly Ser Thr Gly Tyr Ala Asp Ser Val Lys
1               5                   10                  15

Gly

<210> SEQ ID NO 297
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 298"

<400> SEQUENCE: 297

Asp Lys Tyr Ser Tyr Ala Trp Ser Tyr Asp Asp Phe Asp Ile
1               5                   10

<210> SEQ ID NO 298
<211> LENGTH: 123
<212> TYPE: PRT
<213> ORGANISM: Homo sapiens
<220> FEATURE:
<221> NAME/KEY: source
<223> OTHER INFORMATION: /note="VH 2.12"

<400> SEQUENCE: 298

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Asn Ala Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Asp Phe Asp Ile
            100                 105                 110

Trp Gly Gln Gly Thr Met Val Thr Val Ser Ser
        115                 120

<210> SEQ ID NO 299
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 302"

<400> SEQUENCE: 299

Asp Tyr Ala Met Ser
1               5

<210> SEQ ID NO 300
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 302"

<400> SEQUENCE: 300

Gly Ile Thr Trp Asn Arg Gly Ser Thr Gly Tyr Ala Asp Ser Val Lys
1               5                   10                  15

Gly

<210> SEQ ID NO 301
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 302"

<400> SEQUENCE: 301

Asp Lys Tyr Ser Tyr Ala Trp Ser Tyr Asp Asp Phe Asp Ile
1               5                   10

<210> SEQ ID NO 302
<211> LENGTH: 123
<212> TYPE: PRT
<213> ORGANISM: Homo sapiens
<220> FEATURE:
<221> NAME/KEY: source
<223> OTHER INFORMATION: /note="VH 2.13"

<400> SEQUENCE: 302

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Asn Arg Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Asp Phe Asp Ile
            100                 105                 110

Trp Gly Gln Gly Thr Met Val Thr Val Ser Ser
        115                 120

<210> SEQ ID NO 303
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 306"

<400> SEQUENCE: 303

Asp Tyr Ala Phe Ser
1               5

<210> SEQ ID NO 304
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 306"

<400> SEQUENCE: 304

Gly Ile Thr Trp Asn Gly Gly Ser Thr Gly Tyr Ala Asp Ser Val Lys
1               5                   10                  15

Gly

<210> SEQ ID NO 305
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 306"

<400> SEQUENCE: 305

Asp Lys Tyr Ser Tyr Ala Trp Ser Tyr Asp Gly Phe Asp Ile
1               5                   10

<210> SEQ ID NO 306
<211> LENGTH: 123
<212> TYPE: PRT
<213> ORGANISM: Homo sapiens
<220> FEATURE:
<221> NAME/KEY: source
<223> OTHER INFORMATION: /note="VH 2.14"

<400> SEQUENCE: 306

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Phe Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 307
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 310"

<400> SEQUENCE: 307

Asp Tyr Ala Gln Ser
1               5

<210> SEQ ID NO 308
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 310"

<400> SEQUENCE: 308

Gly Ile Thr Trp Asn Gly Gly Ser Thr Gly Tyr Ala Asp Ser Val Lys
1               5                   10                  15

Gly

<210> SEQ ID NO 309
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 310"

<400> SEQUENCE: 309

Asp Lys Tyr Ser Tyr Ala Trp Ser Tyr Asp Gly Phe Asp Ile
1               5                   10

<210> SEQ ID NO 310
<211> LENGTH: 123
<212> TYPE: PRT
<213> ORGANISM: Homo sapiens
<220> FEATURE:
<221> NAME/KEY: source
<223> OTHER INFORMATION: /note="VH 2.15"

<400> SEQUENCE: 310

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Gln Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 311
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 314"

<400> SEQUENCE: 311

Asp Tyr Ala Asn Ser
1               5

<210> SEQ ID NO 312
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 314"

<400> SEQUENCE: 312

Gly Ile Thr Trp Asn Gly Gly Ser Thr Gly Tyr Ala Asp Ser Val Lys
1               5                   10                  15

Gly

<210> SEQ ID NO 313
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 314"

```
<400> SEQUENCE: 313

Asp Lys Tyr Ser Tyr Ala Trp Ser Tyr Asp Gly Phe Asp Ile
1               5                   10

<210> SEQ ID NO 314
<211> LENGTH: 123
<212> TYPE: PRT
<213> ORGANISM: Homo sapiens
<220> FEATURE:
<221> NAME/KEY: source
<223> OTHER INFORMATION: /note="VH 2.16"

<400> SEQUENCE: 314

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Asn Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 315
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 318"

<400> SEQUENCE: 315

Asp Tyr Ala Gly Ser
1               5

<210> SEQ ID NO 316
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 318"

<400> SEQUENCE: 316

Gly Ile Thr Trp Asn Gly Gly Ser Thr Gly Tyr Ala Asp Ser Val Lys
1               5                   10                  15

Gly

<210> SEQ ID NO 317
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 318"
```

<400> SEQUENCE: 317

Asp Lys Tyr Ser Tyr Ala Trp Ser Tyr Asp Gly Phe Asp Ile
1               5                   10

<210> SEQ ID NO 318
<211> LENGTH: 123
<212> TYPE: PRT
<213> ORGANISM: Homo sapiens
<220> FEATURE:
<221> NAME/KEY: source
<223> OTHER INFORMATION: /note="VH 2.17"

<400> SEQUENCE: 318

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Gly Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 319
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 322"

<400> SEQUENCE: 319

Asp Tyr Ala Glu Ser
1               5

<210> SEQ ID NO 320
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 322"

<400> SEQUENCE: 320

Gly Ile Thr Trp Asn Gly Gly Ser Thr Gly Tyr Ala Asp Ser Val Lys
1               5                   10                  15

Gly

<210> SEQ ID NO 321
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 322"

<400> SEQUENCE: 321

Asp Lys Tyr Ser Tyr Ala Trp Ser Tyr Asp Gly Phe Asp Ile
1               5                   10

<210> SEQ ID NO 322
<211> LENGTH: 123
<212> TYPE: PRT
<213> ORGANISM: Homo sapiens
<220> FEATURE:
<221> NAME/KEY: source
<223> OTHER INFORMATION: /note="VH 2.18"

<400> SEQUENCE: 322

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Glu Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 323
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 326"

<400> SEQUENCE: 323

Asp Tyr Ala Trp Ser
1               5

<210> SEQ ID NO 324
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 326"

<400> SEQUENCE: 324

Gly Ile Thr Trp Asn Gly Gly Ser Thr Gly Tyr Ala Asp Ser Val Lys
1               5                   10                  15

Gly

<210> SEQ ID NO 325
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 326"

<400> SEQUENCE: 325

Asp Lys Tyr Ser Tyr Ala Trp Ser Tyr Asp Gly Phe Asp Ile
1               5                   10

<210> SEQ ID NO 326
<211> LENGTH: 123
<212> TYPE: PRT
<213> ORGANISM: Homo sapiens
<220> FEATURE:
<221> NAME/KEY: source
<223> OTHER INFORMATION: /note="VH 2.19"

<400> SEQUENCE: 326

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Trp Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 327
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 330"

<400> SEQUENCE: 327

Asp Tyr Ala Val Ser
1               5

<210> SEQ ID NO 328
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 330"

<400> SEQUENCE: 328

Gly Ile Thr Trp Asn Gly Gly Ser Thr Gly Tyr Ala Asp Ser Val Lys
1               5                   10                  15

Gly

<210> SEQ ID NO 329
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 330"

<400> SEQUENCE: 329

Asp Lys Tyr Ser Tyr Ala Trp Ser Tyr Asp Gly Phe Asp Ile
1               5                   10

<210> SEQ ID NO 330
<211> LENGTH: 123
<212> TYPE: PRT
<213> ORGANISM: Homo sapiens
<220> FEATURE:
<221> NAME/KEY: source
<223> OTHER INFORMATION: /note="VH 2.20"

<400> SEQUENCE: 330

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Val Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 331
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 334"

<400> SEQUENCE: 331

Asp Tyr Ala Leu Ser
1               5

<210> SEQ ID NO 332
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 334"

<400> SEQUENCE: 332

Gly Ile Thr Trp Asn Gly Gly Ser Thr Gly Tyr Ala Asp Ser Val Lys
1               5                   10                  15

Gly

<210> SEQ ID NO 333
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 334"

```
<400> SEQUENCE: 333

Asp Lys Tyr Ser Tyr Ala Trp Ser Tyr Asp Gly Phe Asp Ile
1               5                   10

<210> SEQ ID NO 334
<211> LENGTH: 123
<212> TYPE: PRT
<213> ORGANISM: Homo sapiens
<220> FEATURE:
<221> NAME/KEY: source
<223> OTHER INFORMATION: /note="VH 2.21"

<400> SEQUENCE: 334

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Leu Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 335
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 338"

<400> SEQUENCE: 335

Asp Tyr Ala Ser Ser
1               5

<210> SEQ ID NO 336
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 338"

<400> SEQUENCE: 336

Gly Ile Thr Trp Asn Gly Gly Ser Thr Gly Tyr Ala Asp Ser Val Lys
1               5                   10                  15

Gly

<210> SEQ ID NO 337
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 338"
```

<400> SEQUENCE: 337

Asp Lys Tyr Ser Tyr Ala Trp Ser Tyr Asp Gly Phe Asp Ile
1               5                   10

<210> SEQ ID NO 338
<211> LENGTH: 123
<212> TYPE: PRT
<213> ORGANISM: Homo sapiens
<220> FEATURE:
<221> NAME/KEY: source
<223> OTHER INFORMATION: /note="VH 2.22"

<400> SEQUENCE: 338

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Ser Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 339
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 342"

<400> SEQUENCE: 339

Asp Tyr Ala Arg Ser
1               5

<210> SEQ ID NO 340
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 342"

<400> SEQUENCE: 340

Gly Ile Thr Trp Asn Gly Gly Ser Thr Gly Tyr Ala Asp Ser Val Lys
1               5                   10                  15

Gly

<210> SEQ ID NO 341
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 342"

<400> SEQUENCE: 341

Asp Lys Tyr Ser Tyr Ala Trp Ser Tyr Asp Gly Phe Asp Ile
1               5                   10

<210> SEQ ID NO 342
<211> LENGTH: 123
<212> TYPE: PRT
<213> ORGANISM: Homo sapiens
<220> FEATURE:
<221> NAME/KEY: source
<223> OTHER INFORMATION: /note="VH 2.23"

<400> SEQUENCE: 342

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Arg Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 343
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 346"

<400> SEQUENCE: 343

Asp Tyr Ala Met Ser
1               5

<210> SEQ ID NO 344
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 346"

<400> SEQUENCE: 344

Gly Ile Thr Trp Asn Ser Gly Ser Thr Gly Tyr Ala Asp Ser Val Lys
1               5                   10                  15

Asp

<210> SEQ ID NO 345
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 346"

<400> SEQUENCE: 345

Asp Lys Tyr Ser Tyr Ala Trp Ser Tyr Asp Asp Phe Asp Ile
1               5                   10

<210> SEQ ID NO 346
<211> LENGTH: 123
<212> TYPE: PRT
<213> ORGANISM: Homo sapiens
<220> FEATURE:
<221> NAME/KEY: source
<223> OTHER INFORMATION: /note="VH 2.24"

<400> SEQUENCE: 346

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Asn Ser Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Asp Phe Asp Ile
            100                 105                 110

Trp Gly Gln Gly Thr Met Val Thr Val Ser Ser
        115                 120

<210> SEQ ID NO 347
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 350"

<400> SEQUENCE: 347

Asp Tyr Ala Met Ser
1               5

<210> SEQ ID NO 348
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 350"

<400> SEQUENCE: 348

Gly Ile Thr Trp Asn Gln Gly Ser Thr Gly Tyr Ala Asp Ser Val Lys
1               5                   10                  15

Asp

<210> SEQ ID NO 349
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 350"

-continued

<400> SEQUENCE: 349

Asp Lys Tyr Ser Tyr Ala Trp Ser Tyr Asp Asp Phe Asp Ile
1               5                   10

<210> SEQ ID NO 350
<211> LENGTH: 123
<212> TYPE: PRT
<213> ORGANISM: Homo sapiens
<220> FEATURE:
<221> NAME/KEY: source
<223> OTHER INFORMATION: /note="VH 2.25"

<400> SEQUENCE: 350

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Asn Gln Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Asp Phe Asp Ile
            100                 105                 110

Trp Gly Gln Gly Thr Met Val Thr Val Ser Ser
        115                 120

<210> SEQ ID NO 351
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 354"

<400> SEQUENCE: 351

Asp Tyr Ala Met Ser
1               5

<210> SEQ ID NO 352
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 354"

<400> SEQUENCE: 352

Gly Ile Thr Trp Asn His Gly Ser Thr Gly Tyr Ala Asp Ser Val Lys
1               5                   10                  15

Asp

<210> SEQ ID NO 353
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 354"

<400> SEQUENCE: 353

Asp Lys Tyr Ser Tyr Ala Trp Ser Tyr Asp Val Phe Asp Ile
1               5                   10

<210> SEQ ID NO 354
<211> LENGTH: 123
<212> TYPE: PRT
<213> ORGANISM: Homo sapiens
<220> FEATURE:
<221> NAME/KEY: source
<223> OTHER INFORMATION: /note="VH 2.26"

<400> SEQUENCE: 354

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Asn His Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Val Phe Asp Ile
            100                 105                 110

Trp Gly Gln Gly Thr Met Val Thr Val Ser Ser
        115                 120

<210> SEQ ID NO 355
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 358"

<400> SEQUENCE: 355

Asp Tyr Ala Met Ser
1               5

<210> SEQ ID NO 356
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 358"

<400> SEQUENCE: 356

Gly Ile Thr Trp Asn Ala Gly Ser Thr Gly Tyr Ala Asp Ser Val Lys
1               5                   10                  15

Asp

<210> SEQ ID NO 357
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 358"

<400> SEQUENCE: 357

Asp Lys Tyr Ser Tyr Ala Trp Ser Tyr Asp Asp Phe Asp Ile
1               5                   10

<210> SEQ ID NO 358
<211> LENGTH: 123
<212> TYPE: PRT
<213> ORGANISM: Homo sapiens
<220> FEATURE:
<221> NAME/KEY: source
<223> OTHER INFORMATION: /note="VH 2.27"

<400> SEQUENCE: 358

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Asn Ala Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Asp Phe Asp Ile
            100                 105                 110

Trp Gly Gln Gly Thr Met Val Thr Val Ser Ser
        115                 120

<210> SEQ ID NO 359
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 362"

<400> SEQUENCE: 359

Asp Tyr Ala Met Ser
1               5

<210> SEQ ID NO 360
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 362"

<400> SEQUENCE: 360

Gly Ile Thr Trp Asn Gly Gly Ser Thr Gly Tyr Ala Asp Ser Val Lys
1               5                   10                  15

Gly

<210> SEQ ID NO 361
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 362"

<400> SEQUENCE: 361

Asp Lys Tyr Ser Tyr Ala Trp Ser Tyr Asp Val Phe Asp Ile
1               5                   10

<210> SEQ ID NO 362
<211> LENGTH: 123
<212> TYPE: PRT
<213> ORGANISM: Homo sapiens
<220> FEATURE:
<221> NAME/KEY: source
<223> OTHER INFORMATION: /note="VH 2.28"

<400> SEQUENCE: 362

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Val Phe Asp Ile
            100                 105                 110

Trp Gly Gln Gly Thr Met Val Thr Val Ser Ser
        115                 120

<210> SEQ ID NO 363
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 366"

<400> SEQUENCE: 363

Asp Tyr Ala Met Ser
1               5

<210> SEQ ID NO 364
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 366"

<400> SEQUENCE: 364

Gly Ile Thr Trp Asn Gly Gly Ser Thr Gly Tyr Ala Asp Ser Val Lys
1               5                   10                  15

Gly

<210> SEQ ID NO 365
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 366"

<400> SEQUENCE: 365

Asp Lys Tyr Ser Tyr Ala Trp Ser Tyr Asp Asp Phe Asp Ile
1               5                   10

<210> SEQ ID NO 366
<211> LENGTH: 123
<212> TYPE: PRT
<213> ORGANISM: Homo sapiens
<220> FEATURE:
<221> NAME/KEY: source
<223> OTHER INFORMATION: /note="VH 2.29"

<400> SEQUENCE: 366

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Asp Phe Asp Ile
            100                 105                 110

Trp Gly Gln Gly Thr Met Val Thr Val Ser Ser
        115                 120

<210> SEQ ID NO 367
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 370"

<400> SEQUENCE: 367

Asp Tyr Ala Met Ser
1               5

<210> SEQ ID NO 368
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 370"

<400> SEQUENCE: 368

Gly Ile Thr Trp Asn Lys Gly Ser Thr Gly Tyr Ala Asp Ser Val Lys
1               5                   10                  15

Asp

<210> SEQ ID NO 369
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 370"

<400> SEQUENCE: 369

Asp Lys Tyr Ser Tyr Ala Trp Ser Tyr Asp Asp Phe Asp Ile
1               5                   10

<210> SEQ ID NO 370
<211> LENGTH: 123
<212> TYPE: PRT
<213> ORGANISM: Homo sapiens
<220> FEATURE:
<221> NAME/KEY: source
<223> OTHER INFORMATION: /note="VH 2.30"

<400> SEQUENCE: 370

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Ala Met Ser Trp Val Arg Gln Ala Pro Gly Lys Gly Leu Glu Trp Val
            35                  40                  45

Ser Gly Ile Thr Trp Asn Lys Gly Ser Thr Gly Tyr Ala Asp Ser Val
        50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Asp Phe Asp Ile
            100                 105                 110

Trp Gly Gln Gly Thr Met Val Thr Val Ser Ser
        115                 120

<210> SEQ ID NO 371
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 374"

<400> SEQUENCE: 371

Asp Tyr Ala Met Ser
1               5

<210> SEQ ID NO 372
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 374"

<400> SEQUENCE: 372

Gly Ile Thr Trp Asn Arg Gly Ser Thr Gly Tyr Ala Asp Ser Val Lys
1               5                   10                  15

Asp

<210> SEQ ID NO 373
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 374"

<400> SEQUENCE: 373

Asp Lys Tyr Ser Tyr Ala Trp Ser Tyr Asp Asp Phe Asp Ile
1               5                   10

<210> SEQ ID NO 374
<211> LENGTH: 123
<212> TYPE: PRT
<213> ORGANISM: Homo sapiens
<220> FEATURE:
<221> NAME/KEY: source
<223> OTHER INFORMATION: /note="VH 2.31"

<400> SEQUENCE: 374

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Asn Arg Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Asp Phe Asp Ile
            100                 105                 110

Trp Gly Gln Gly Thr Met Val Thr Val Ser Ser
        115                 120

<210> SEQ ID NO 375
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 378"

<400> SEQUENCE: 375

Asp Tyr Ala Ile Ser
1               5

<210> SEQ ID NO 376
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 378"

<400> SEQUENCE: 376

Gly Ile Thr Trp Asn Gly Gly Ser Thr Gly Tyr Ala Asp Ser Val Lys
1               5                   10                  15

Asp

<210> SEQ ID NO 377
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 378"

<400> SEQUENCE: 377

Asp Lys Tyr Ser Tyr Ala Trp Ser Tyr Asp Gly Phe Asp Ile
1               5                   10

<210> SEQ ID NO 378
<211> LENGTH: 123
<212> TYPE: PRT
<213> ORGANISM: Homo sapiens
<220> FEATURE:
<221> NAME/KEY: source
<223> OTHER INFORMATION: /note="VH 2.32"

<400> SEQUENCE: 378

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Ala Ile Ser Trp Val Arg Gln Ala Pro Gly Lys Gly Leu Glu Trp Val
            35                  40                  45

Ser Gly Ile Thr Trp Asn Gly Gly Ser Thr Gly Tyr Ala Asp Ser Val
        50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 379
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 382"

<400> SEQUENCE: 379

Asp Tyr Ala Thr Ser
1               5

<210> SEQ ID NO 380
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 382"

<400> SEQUENCE: 380

Gly Ile Thr Trp Asn Gly Gly Ser Thr Gly Tyr Ala Asp Ser Val Lys
1               5                   10                  15

Asp

<210> SEQ ID NO 381
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 382"

<400> SEQUENCE: 381

Asp Lys Tyr Ser Tyr Ala Trp Ser Tyr Asp Gly Phe Asp Ile
1               5                   10

<210> SEQ ID NO 382
<211> LENGTH: 123
<212> TYPE: PRT
<213> ORGANISM: Homo sapiens
<220> FEATURE:
<221> NAME/KEY: source
<223> OTHER INFORMATION: /note="VH 2.33"

<400> SEQUENCE: 382

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Thr Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 383
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 386"

<400> SEQUENCE: 383

Asp Tyr Ala Asn Ser
1               5

<210> SEQ ID NO 384
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 386"

<400> SEQUENCE: 384

Gly Ile Thr Trp Asn Gly Gly Ser Thr Gly Tyr Ala Asp Ser Val Lys
1               5                   10                  15

Asp

<210> SEQ ID NO 385
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 386"

<400> SEQUENCE: 385

Asp Lys Tyr Ser Tyr Ala Trp Ser Tyr Asp Gly Phe Asp Ile
1               5                   10

<210> SEQ ID NO 386
<211> LENGTH: 123
<212> TYPE: PRT
<213> ORGANISM: Homo sapiens
<220> FEATURE:
<221> NAME/KEY: source
<223> OTHER INFORMATION: /note="VH 2.34"

<400> SEQUENCE: 386

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Asn Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 387
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 390"

<400> SEQUENCE: 387

Asp Tyr Ala Asp Ser
1               5

<210> SEQ ID NO 388
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 390"

<400> SEQUENCE: 388

Gly Ile Thr Trp Asn Gly Gly Ser Thr Gly Tyr Ala Asp Ser Val Lys
1               5                   10                  15

Asp

<210> SEQ ID NO 389
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 390"

<400> SEQUENCE: 389

Asp Lys Tyr Ser Tyr Ala Trp Ser Tyr Asp Gly Phe Asp Ile
1               5                   10

<210> SEQ ID NO 390
<211> LENGTH: 123
<212> TYPE: PRT
<213> ORGANISM: Homo sapiens
<220> FEATURE:
<221> NAME/KEY: source
<223> OTHER INFORMATION: /note="VH 2.35"

<400> SEQUENCE: 390

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Asp Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 391
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 394"

<400> SEQUENCE: 391

Asp Tyr Ala Ser Ser
1               5

<210> SEQ ID NO 392
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 394"

<400> SEQUENCE: 392

Gly Ile Thr Trp Asn Gly Gly Ser Thr Gly Tyr Ala Asp Ser Val Lys
1               5                   10                  15

Asp

<210> SEQ ID NO 393
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 394"

```
<400> SEQUENCE: 393

Asp Lys Tyr Ser Tyr Ala Trp Ser Tyr Asp Gly Phe Asp Ile
1               5                   10

<210> SEQ ID NO 394
<211> LENGTH: 123
<212> TYPE: PRT
<213> ORGANISM: Homo sapiens
<220> FEATURE:
<221> NAME/KEY: source
<223> OTHER INFORMATION: /note="VH 2.36"

<400> SEQUENCE: 394

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Ser Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 395
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 398"

<400> SEQUENCE: 395

Asp Tyr Ala Leu Ser
1               5

<210> SEQ ID NO 396
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 398"

<400> SEQUENCE: 396

Gly Ile Thr Trp Asn Gly Gly Ser Thr Gly Tyr Ala Asp Ser Val Lys
1               5                   10                  15

Asp

<210> SEQ ID NO 397
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 398"
```

<400> SEQUENCE: 397

Asp Lys Tyr Ser Tyr Ala Trp Ser Tyr Asp Gly Phe Asp Ile
1               5                   10

<210> SEQ ID NO 398
<211> LENGTH: 123
<212> TYPE: PRT
<213> ORGANISM: Homo sapiens
<220> FEATURE:
<221> NAME/KEY: source
<223> OTHER INFORMATION: /note="VH 2.37"

<400> SEQUENCE: 398

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Leu Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 399
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 402"

<400> SEQUENCE: 399

Asp Tyr Ala Gly Ser
1               5

<210> SEQ ID NO 400
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 402"

<400> SEQUENCE: 400

Gly Ile Thr Trp Asn Gly Gly Ser Thr Gly Tyr Ala Asp Ser Val Lys
1               5                   10                  15

Asp

<210> SEQ ID NO 401
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 402"

<400> SEQUENCE: 401

Asp Lys Tyr Ser Tyr Ala Trp Ser Tyr Asp Gly Phe Asp Ile
1               5                   10

<210> SEQ ID NO 402
<211> LENGTH: 123
<212> TYPE: PRT
<213> ORGANISM: Homo sapiens
<220> FEATURE:
<221> NAME/KEY: source
<223> OTHER INFORMATION: /note="VH 2.38"

<400> SEQUENCE: 402

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Ala Gly Ser Trp Val Arg Gln Ala Pro Gly Lys Gly Leu Glu Trp Val
            35                  40                  45

Ser Gly Ile Thr Trp Asn Gly Gly Ser Thr Gly Tyr Ala Asp Ser Val
        50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 403
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 406"

<400> SEQUENCE: 403

Asp Tyr Ala Glu Ser
1               5

<210> SEQ ID NO 404
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 406"

<400> SEQUENCE: 404

Gly Ile Thr Trp Asn Gly Gly Ser Thr Gly Tyr Ala Asp Ser Val Lys
1               5                   10                  15

Asp

<210> SEQ ID NO 405
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 406"

<400> SEQUENCE: 405

Asp Lys Tyr Ser Tyr Ala Trp Ser Tyr Asp Gly Phe Asp Ile
1               5                   10

<210> SEQ ID NO 406
<211> LENGTH: 123
<212> TYPE: PRT
<213> ORGANISM: Homo sapiens
<220> FEATURE:
<221> NAME/KEY: source
<223> OTHER INFORMATION: /note="VH 2.39"

<400> SEQUENCE: 406

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Ala Glu Ser Trp Val Arg Gln Ala Pro Gly Lys Gly Leu Glu Trp Val
            35                  40                  45

Ser Gly Ile Thr Trp Asn Gly Gly Ser Thr Gly Tyr Ala Asp Ser Val
        50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 407
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 410"

<400> SEQUENCE: 407

Asp Tyr Ala Trp Ser
1               5

<210> SEQ ID NO 408
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 410"

<400> SEQUENCE: 408

Gly Ile Thr Trp Asn Gly Gly Ser Thr Gly Tyr Ala Asp Ser Val Lys
1               5                   10                  15

Asp

<210> SEQ ID NO 409
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 410"

<400> SEQUENCE: 409

Asp Lys Tyr Ser Tyr Ala Trp Ser Tyr Asp Gly Phe Asp Ile
1               5                   10

<210> SEQ ID NO 410
<211> LENGTH: 123
<212> TYPE: PRT
<213> ORGANISM: Homo sapiens
<220> FEATURE:
<221> NAME/KEY: source
<223> OTHER INFORMATION: /note="VH 2.40"

<400> SEQUENCE: 410

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Trp Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 411
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 414"

<400> SEQUENCE: 411

Asp Tyr Ala Arg Ser
1               5

<210> SEQ ID NO 412
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 414"

<400> SEQUENCE: 412

Gly Ile Thr Trp Asn Gly Gly Ser Thr Gly Tyr Ala Asp Ser Val Lys
1               5                   10                  15

Asp

<210> SEQ ID NO 413
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 414"

```
<400> SEQUENCE: 413

Asp Lys Tyr Ser Tyr Ala Trp Ser Tyr Asp Gly Phe Asp Ile
1               5                   10

<210> SEQ ID NO 414
<211> LENGTH: 123
<212> TYPE: PRT
<213> ORGANISM: Homo sapiens
<220> FEATURE:
<221> NAME/KEY: source
<223> OTHER INFORMATION: /note="VH 2.41"

<400> SEQUENCE: 414

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Arg Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 415
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 418"

<400> SEQUENCE: 415

Asp Tyr Ala Phe Ser
1               5

<210> SEQ ID NO 416
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 418"

<400> SEQUENCE: 416

Gly Ile Thr Trp Asn Gly Gly Ser Thr Gly Tyr Ala Asp Ser Val Lys
1               5                   10                  15

Asp

<210> SEQ ID NO 417
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 418"
```

<400> SEQUENCE: 417

Asp Lys Tyr Ser Tyr Ala Trp Ser Tyr Asp Gly Phe Asp Ile
1               5                   10

<210> SEQ ID NO 418
<211> LENGTH: 123
<212> TYPE: PRT
<213> ORGANISM: Homo sapiens
<220> FEATURE:
<221> NAME/KEY: source
<223> OTHER INFORMATION: /note="VH 2.42"

<400> SEQUENCE: 418

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Phe Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 419
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 422"

<400> SEQUENCE: 419

Asp Tyr Ala Val Ser
1               5

<210> SEQ ID NO 420
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 422"

<400> SEQUENCE: 420

Gly Ile Thr Trp Asn Gly Gly Ser Thr Gly Tyr Ala Asp Ser Val Lys
1               5                   10                  15

Asp

<210> SEQ ID NO 421
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 422"

```
<400> SEQUENCE: 421

Asp Lys Tyr Ser Tyr Ala Trp Ser Tyr Asp Gly Phe Asp Ile
1               5                   10

<210> SEQ ID NO 422
<211> LENGTH: 123
<212> TYPE: PRT
<213> ORGANISM: Homo sapiens
<220> FEATURE:
<221> NAME/KEY: source
<223> OTHER INFORMATION: /note="VH 2.43"

<400> SEQUENCE: 422

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Val Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 423
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 426"

<400> SEQUENCE: 423

Asp Tyr Ala Met Ser
1               5

<210> SEQ ID NO 424
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 426"

<400> SEQUENCE: 424

Gly Ile Thr Trp Thr Gly Gly Ser Thr Gly Tyr Ala Asp Ser Val Lys
1               5                   10                  15

Asp

<210> SEQ ID NO 425
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 426"
```

<400> SEQUENCE: 425

Asp Lys Tyr Ser Tyr Ala Trp Ser Tyr Asp Gly Phe Asp Ile
1               5                   10

<210> SEQ ID NO 426
<211> LENGTH: 123
<212> TYPE: PRT
<213> ORGANISM: Homo sapiens
<220> FEATURE:
<221> NAME/KEY: source
<223> OTHER INFORMATION: /note="VH 2.44"

<400> SEQUENCE: 426

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Thr Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 427
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 430"

<400> SEQUENCE: 427

Asp Tyr Ala Met Ser
1               5

<210> SEQ ID NO 428
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 430"

<400> SEQUENCE: 428

Gly Ile Thr Trp Ser Gly Gly Ser Thr Gly Tyr Ala Asp Ser Val Lys
1               5                   10                  15

Asp

<210> SEQ ID NO 429
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 430"

<400> SEQUENCE: 429

Asp Lys Tyr Ser Tyr Ala Trp Ser Tyr Asp Gly Phe Asp Ile
1               5                   10

<210> SEQ ID NO 430
<211> LENGTH: 123
<212> TYPE: PRT
<213> ORGANISM: Homo sapiens
<220> FEATURE:
<221> NAME/KEY: source
<223> OTHER INFORMATION: /note="VH 2.45"

<400> SEQUENCE: 430

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Ser Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 431
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 434"

<400> SEQUENCE: 431

Asp Tyr Ala Met Ser
1               5

<210> SEQ ID NO 432
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 434"

<400> SEQUENCE: 432

Gly Ile Thr Trp Pro Gly Gly Ser Thr Gly Tyr Ala Asp Ser Val Lys
1               5                   10                  15

Asp

<210> SEQ ID NO 433
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 434"

<400> SEQUENCE: 433

Asp Lys Tyr Ser Tyr Ala Trp Ser Tyr Asp Gly Phe Asp Ile
1               5                   10

<210> SEQ ID NO 434
<211> LENGTH: 123
<212> TYPE: PRT
<213> ORGANISM: Homo sapiens
<220> FEATURE:
<221> NAME/KEY: source
<223> OTHER INFORMATION: /note="VH 2.46"

<400> SEQUENCE: 434

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Pro Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 435
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 438"

<400> SEQUENCE: 435

Asp Tyr Ala Met Ser
1               5

<210> SEQ ID NO 436
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 438"

<400> SEQUENCE: 436

Gly Ile Thr Trp Ile Gly Gly Ser Thr Gly Tyr Ala Asp Ser Val Lys
1               5                   10                  15

Asp

<210> SEQ ID NO 437
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 438"

<400> SEQUENCE: 437

Asp Lys Tyr Ser Tyr Ala Trp Ser Tyr Asp Gly Phe Asp Ile
1               5                   10

<210> SEQ ID NO 438
<211> LENGTH: 123
<212> TYPE: PRT
<213> ORGANISM: Homo sapiens
<220> FEATURE:
<221> NAME/KEY: source
<223> OTHER INFORMATION: /note="VH 2.47"

<400> SEQUENCE: 438

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Ile Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 439
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 442"

<400> SEQUENCE: 439

Asp Tyr Ala Met Ser
1               5

<210> SEQ ID NO 440
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 442"

<400> SEQUENCE: 440

Gly Ile Thr Trp Leu Gly Gly Ser Thr Gly Tyr Ala Asp Ser Val Lys
1               5                   10                  15

Asp

<210> SEQ ID NO 441
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 442"

<400> SEQUENCE: 441

Asp Lys Tyr Ser Tyr Ala Trp Ser Tyr Asp Gly Phe Asp Ile
1               5                   10

<210> SEQ ID NO 442
<211> LENGTH: 123
<212> TYPE: PRT
<213> ORGANISM: Homo sapiens
<220> FEATURE:
<221> NAME/KEY: source
<223> OTHER INFORMATION: /note="VH 2.48"

<400> SEQUENCE: 442

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Leu Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 443
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 446"

<400> SEQUENCE: 443

Asp Tyr Ala Met Ser
1               5

<210> SEQ ID NO 444
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 446"

<400> SEQUENCE: 444

Gly Ile Thr Trp Asn Gly Gly Ser Thr Gly Tyr Ala Asp Ser Val Lys
1               5                   10                  15

Gly

<210> SEQ ID NO 445
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 446"

<400> SEQUENCE: 445

Asp Lys Tyr Ser Tyr Ala Trp Ser Tyr Asp Gly Phe Asp Ile
1               5                   10

<210> SEQ ID NO 446
<211> LENGTH: 123
<212> TYPE: PRT
<213> ORGANISM: Homo sapiens
<220> FEATURE:
<221> NAME/KEY: source
<223> OTHER INFORMATION: /note="VH 2.49"

<400> SEQUENCE: 446

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 447
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 450"

<400> SEQUENCE: 447

Asp Tyr Ala Met Ser
1               5

<210> SEQ ID NO 448
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 450"

<400> SEQUENCE: 448

Gly Ile Thr Trp Lys Gly Gly Ser Thr Gly Tyr Ala Asp Ser Val Lys
1               5                   10                  15

Asp

<210> SEQ ID NO 449
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 450"

<400> SEQUENCE: 449

Asp Lys Tyr Ser Tyr Ala Trp Ser Tyr Asp Gly Phe Asp Ile
1               5                   10

<210> SEQ ID NO 450
<211> LENGTH: 123
<212> TYPE: PRT
<213> ORGANISM: Homo sapiens
<220> FEATURE:
<221> NAME/KEY: source
<223> OTHER INFORMATION: /note="VH 2.50"

<400> SEQUENCE: 450

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Ala Met Ser Trp Val Arg Gln Ala Pro Gly Lys Gly Leu Glu Trp Val
            35                  40                  45

Ser Gly Ile Thr Trp Lys Gly Gly Ser Thr Gly Tyr Ala Asp Ser Val
        50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 451
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 454"

<400> SEQUENCE: 451

Asp Tyr Ala Met Ser
1               5

<210> SEQ ID NO 452
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 454"

<400> SEQUENCE: 452

Gly Ile Thr Trp Arg Gly Gly Ser Thr Gly Tyr Ala Asp Ser Val Lys
1               5                   10                  15

Asp

<210> SEQ ID NO 453
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 454"

<400> SEQUENCE: 453

Asp Lys Tyr Ser Tyr Ala Trp Ser Tyr Asp Gly Phe Asp Ile
1               5                   10

<210> SEQ ID NO 454
<211> LENGTH: 123
<212> TYPE: PRT
<213> ORGANISM: Homo sapiens
<220> FEATURE:
<221> NAME/KEY: source
<223> OTHER INFORMATION: /note="VH 2.51"

<400> SEQUENCE: 454

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Arg Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Gly Phe Asp Ile
            100                 105                 110

Trp Gly Gln Gly Thr Met Val Thr Val Ser Ser
        115                 120

<210> SEQ ID NO 455
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 458"

<400> SEQUENCE: 455

Asp Tyr Ala Met Ser
1               5

<210> SEQ ID NO 456
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 458"

<400> SEQUENCE: 456

Gly Ile Thr Trp Asn Gly Gly Ser Thr Gly Tyr Ala Asp Ser Val Lys
1               5                   10                  15

Asp

<210> SEQ ID NO 457
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 458"

<400> SEQUENCE: 457

Asp Lys Tyr Ser Tyr Ala Trp Ser Tyr Asp Val Phe Asp Ile
1               5                   10

<210> SEQ ID NO 458
<211> LENGTH: 123
<212> TYPE: PRT
<213> ORGANISM: Homo sapiens
<220> FEATURE:
<221> NAME/KEY: source
<223> OTHER INFORMATION: /note="VH 2.52"

<400> SEQUENCE: 458

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Ala Met Ser Trp Val Arg Gln Ala Pro Gly Lys Gly Leu Glu Trp Val
            35                  40                  45

Ser Gly Ile Thr Trp Asn Gly Gly Ser Thr Gly Tyr Ala Asp Ser Val
        50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Val Phe Asp Ile
            100                 105                 110

Trp Gly Gln Gly Thr Met Val Thr Val Ser Ser
        115                 120

<210> SEQ ID NO 459
<211> LENGTH: 5
<212> TYPE: PRT
<213> ORGANISM: Homo sapiens
<220> FEATURE:
<221> NAME/KEY: source
<223> OTHER INFORMATION: /note="CDR1 sequence of SEQ ID NO: 462"

<400> SEQUENCE: 459

Asp Tyr Ala Met Ser
1               5

<210> SEQ ID NO 460
<211> LENGTH: 17
<212> TYPE: PRT
<213> ORGANISM: Homo sapiens
<220> FEATURE:
<221> NAME/KEY: source
<223> OTHER INFORMATION: /note="CDR2 sequence of SEQ ID NO: 462"

<400> SEQUENCE: 460

Gly Ile Thr Trp Asn Gly Gly Ser Thr Gly Tyr Ala Asp Ser Val Lys
1               5                   10                  15

Asp

<210> SEQ ID NO 461
<211> LENGTH: 14
<212> TYPE: PRT
<213> ORGANISM: Homo sapiens
<220> FEATURE:
<221> NAME/KEY: source
<223> OTHER INFORMATION: /note="CDR3 sequence of SEQ ID NO: 462"

<400> SEQUENCE: 461

Asp Lys Tyr Ser Tyr Ala Trp Ser Tyr Asp Asp Phe Asp Ile
1               5                   10

<210> SEQ ID NO 462
<211> LENGTH: 123
<212> TYPE: PRT
<213> ORGANISM: Homo sapiens
<220> FEATURE:
<221> NAME/KEY: source
<223> OTHER INFORMATION: /note="VH 2.53"

<400> SEQUENCE: 462

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Thr Trp Asn Gly Gly Ser Thr Gly Tyr Ala Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Lys Tyr Ser Tyr Ala Trp Ser Tyr Asp Asp Phe Asp Ile
            100                 105                 110

Trp Gly Gln Gly Thr Met Val Thr Val Ser Ser
        115                 120

<210> SEQ ID NO 463
<211> LENGTH: 369
<212> TYPE: DNA
<213> ORGANISM: Homo sapiens
<220> FEATURE:
<221> NAME/KEY: source
<223> OTHER INFORMATION: /note="VH 2.1"

<400> SEQUENCE: 463
gaagtgcagc tggtggagtc tgggggaggt gtggtacggc ctgggggtc cctgagactc      60 tcctgtgcag cctctggatt cacctttgat gattatgcca tgagttgggt ccgccaagct    120
ccagggaagg gctggagtg gtctctggt attacttgga atggtggtag cacaggttat      180
gcagactctg tgaaggaccg attcaccatc tccagagaca cgccaagaa ctccctgtat    240 ctgcaaatga acagtctgag agccgaggac acggccttgt attactgtgt gagagacaag   300
tatagctatg cctggtctta tgatggtttt gatatctggg gccaagggac aatggtcact   360
gtctcctca                                                            369

<210> SEQ ID NO 464
<211> LENGTH: 369
<212> TYPE: DNA
<213> ORGANISM: Homo sapiens
<220> FEATURE:
<221> NAME/KEY: source
<223> OTHER INFORMATION: /note="VH 2.2"

<400> SEQUENCE: 464
gaggtgcagc tgttggagtc tgggggaggt gtggtgcggc cggggggtc cctgagactc      60

```
tcctgtgcag cctctggatt cacctttgat gattatggca tgagctgggt ccgccaacct    120
ccagggaagg ggctggagtg ggtctctggt ataagtagga atggtggtag cgcaggttat    180
tcagactctg cgaaggaccg atttaccatc tccagagaca acgccaagaa ctccctctat    240
ctgcaaatga acagtctgag agccgacgac acggccatgt attattgtgc gagagagaag    300
tatagcagtg gctggtccta tgatgatttt gatatctggg gccaagggac aatggtcacc    360
gtctcctca                                                            369

<210> SEQ ID NO 465
<211> LENGTH: 369
<212> TYPE: DNA
<213> ORGANISM: Homo sapiens
<220> FEATURE:
<221> NAME/KEY: source
<223> OTHER INFORMATION: /note="VH 2.3"

<400> SEQUENCE: 465
caggtgcagc tggtggagtc tgggggaggt gtggtgcggc ggggggggtc cctgagactc     60
tcctgtgcag cctctggatt cacctttgat gattatggca tgagctgggt ccgccaatct    120
ccagggaagg ggctggagtg ggtctctggt attagtagga atggtggtag cgcaggttat    180
tcagactctg cgaaggaccg atttaccatc tccagagaca acgccaagaa ctccctctat    240
ctgcaaatga acagtctgag agccgacgac acggccatgt attattgtgc gagagagaag    300
tatagcagtg gctggtccta tgatgatttt gatatctggg gccaagggac aatggtcacc    360
gtctcctca                                                            369

<210> SEQ ID NO 466
<211> LENGTH: 369
<212> TYPE: DNA
<213> ORGANISM: Homo sapiens
<220> FEATURE:
<221> NAME/KEY: source
<223> OTHER INFORMATION: /note="VH 2.4"

<400> SEQUENCE: 466
caggtgcagc tggtggagtc tgggggaggt gtggtgcggc ggggggggtc cctgagactc     60
tcctgtgcag cctctggatt cacctttgat gattatggca tgagctgggt ccgccaacct    120
ccagggaagg ggctggagtg ggtctctggt attagtagga atggtggtag cgcaggttat    180
tcagactctg cgaaagaccg atttaccatc tccagagaca acgccaagaa ctccctctat    240
ctgcaaatga acagtctgag agccgacgac acggccatgt attattgtgc gagagagaag    300
tatagcagtg gctggtccta tgatgatttt gatatctggg gccaagggac aatggtcact    360
gtctcttca                                                            369

<210> SEQ ID NO 467
<211> LENGTH: 369
<212> TYPE: DNA
<213> ORGANISM: Homo sapiens
<220> FEATURE:
<221> NAME/KEY: source
<223> OTHER INFORMATION: /note="VH 2.5"

<400> SEQUENCE: 467
gaagtgcagc tggtggagtc tgggggaggt gtggtgcggc ggggggggtc cctgagactc     60
tcctgtgcag cctctggatt cacctttgat gattatggca tgagctgggt ccgccaacct    120
ccagggaagg ggctggagtg ggtctctggt attagtagga atggtggtag cgcaggttat    180
```

```
tcagactctg cgaaggaccg atttaccatc tccagagaca acgccaagaa ctccctctat    240
ctgcaaatga acagtctgag agccgacgac acggccatgt attattgtgc gagagagaag    300
tatagcagtg gctggtccta tgatgatttt gatatctggg gccaagggac aatggtcact    360
gtctcctca                                                            369

<210> SEQ ID NO 468
<211> LENGTH: 369
<212> TYPE: DNA
<213> ORGANISM: Homo sapiens
<220> FEATURE:
<221> NAME/KEY: source
<223> OTHER INFORMATION: /note="VH 2.6"

<400> SEQUENCE: 468
caggtgcagc tggtggagtc tgggggaggt gtggtacggc ttgggggtc cctgagactc     60 tcctgtgcag cctctggatt cagctttgtt gattatggca tgagctgggt ccgacaagct    120
ccagggcagg gctggagtg gtctctggt attagtagga acgtggtag cacaggttat      180 gcagactctg tgaaggaccg attcaccatc tccagagaca acgccaagaa caccctgtat    240
ctgcaaatga acagtctgag agccgaggac acggccttgt attactgtgc gagagaccct    300
tatagcagtg gctggtccta tgattctttt gatatctggg gccaggggac aatggtcact    360
gtctcctca                                                            369

<210> SEQ ID NO 469
<211> LENGTH: 369
<212> TYPE: DNA
<213> ORGANISM: Homo sapiens
<220> FEATURE:
<221> NAME/KEY: source
<223> OTHER INFORMATION: /note="VH 2.7"

<400> SEQUENCE: 469
caggtgcagc tggtggagtc tgggggaggt gtggttcggc ctgggggtc cctgagactc     60 tcctgtgcag cctctggatt caccttgat gattatggca tgagctgggt ccgccaagct     120
ccagggaagg gactggagtg gtctctggt attagtcgga atggtggtag tacagggtat    180
acagcctctg tgaaggaccg attcaccatc tccagagaca acgccaagaa ctccctgtat    240
ctgcaaatga acagtctgag agccgacgac acagccatgt attactgtgc gcgagagaag    300
tatagcagtg gctggtccta tgatgacttt gatatctggg gccaagggac aatggtcacc    360
gtctcctca                                                            369

<210> SEQ ID NO 470
<211> LENGTH: 369
<212> TYPE: DNA
<213> ORGANISM: Homo sapiens
<220> FEATURE:
<221> NAME/KEY: source
<223> OTHER INFORMATION: /note="VH 2.8"

<400> SEQUENCE: 470
caggtgcagc tggtggagtc tgggggaggc ctggtccagc ctgggggtc cctgagactc     60 tcctgtgcag cctctggatt caccttgat gattatgcca tgagctgggt ccgccaagct     120
ccagggaagg gctggagtg gtctctggt attagttgga atggtggtag cgcaggttat    180
gcagactctg tgaaggaccg attcaccatc tccagagaca acgccaagaa ctccctgtat    240
ctgcaaatga acagtctgag agccgaggac acggccttgt attactgtgc gagagatccc    300
```

```
catagcagtg cctggtccta tgatgctttt gatatctggg gccaagggac aatggtcacc    360
gtctcttca                                                            369
```

<210> SEQ ID NO 471
<211> LENGTH: 369
<212> TYPE: DNA
<213> ORGANISM: Homo sapiens
<220> FEATURE:
<221> NAME/KEY: source
<223> OTHER INFORMATION: /note="VH 2.9"

<400> SEQUENCE: 471

```
caggtgcagc tggtggagtc tgggggaggt gtggtacggc ctgggggtc cctgagactc      60 tcctgtgcag cctccggatt cacctttgat gattatgcca tgagctgggt ccgccaagct    120
ccagggaagg gctggagtg gtctctggt attagttgga atggtggtag taaaggttat      180
gcagactctg tgaaggaccg attcaccatc tccagagaca acgccaagaa ctccctgtat    240
ctgcaaatga acagtctgag agccgaggac acggccttat attactgtgc gagagatccg    300
tatagcggtg cctggtccta tgatgctttt gatatctggg gccaagggac aatggtcact    360
gtctcctca                                                            369
```

<210> SEQ ID NO 472
<211> LENGTH: 369
<212> TYPE: DNA
<213> ORGANISM: Homo sapiens
<220> FEATURE:
<221> NAME/KEY: source
<223> OTHER INFORMATION: /note="VH 2.10"

<400> SEQUENCE: 472

```
caggtgcagc tggtggagtc tgggggaggt gtggtacggc ctgggggtc cctgagactc      60 tcctgtgcag cctctggatt cacctttgat gattatgcca tgagctgggt ccgccaagct    120
ccagggaagg gctggagtg gtctctggt attagttgga atggtggtag tacaggttat      180
gcagactctg tgaaggaccg attcaccatc tccagagaca acgccaagaa ctccctgtat    240
ctgcaaatga acagtctgag agccgaggac acggccttat attactgtgc gagagatccg    300
tatagcggtg cctggtccta tgatgctttt gatatctggg gccaagggac aatggtcact    360
gtctcttca                                                            369
```

<210> SEQ ID NO 473
<211> LENGTH: 369
<212> TYPE: DNA
<213> ORGANISM: Homo sapiens
<220> FEATURE:
<221> NAME/KEY: source
<223> OTHER INFORMATION: /note="VH 2.11"

<400> SEQUENCE: 473

```
caggtgcagc tggtggagtc tgggggaggt gtggtacggc ctgggggtc cctgagactc      60 tcctgtgcag cctctggatt cacctttgat aattatgcca tgagctgggt ccgccaagct    120
ccagggaagg gctggagtg gtctctggt attacttgga atggtggtag cacaggttat      180
gcagactctg tgaaggaccg attcaccatc tccagagaca acgccaagaa ctccctgtat    240
ctgcaaatga acagtctgag agccgaggac acggccttgt attactgtgc gagagacaag    300
tatagctatg cctggtctta tgatactttt gatatccggg gccaagggac aatggtcacc    360
gtctcttca                                                            369
```

<210> SEQ ID NO 474
<211> LENGTH: 369
<212> TYPE: DNA
<213> ORGANISM: Homo sapiens
<220> FEATURE:
<221> NAME/KEY: source
<223> OTHER INFORMATION: /note="VH 2.12"

<400> SEQUENCE: 474

```
gaggtgcagc tggtggagtc tgggggaggt gtggtacggc ctgggggtc cctgagactc        60 tcctgtgcag cctctggatt cacctttgat gattatgcca tgagttgggt ccgccaagct      120
ccagggaagg ggctggagtg ggtctctggt attacttgga atgccggtag cacaggttat      180
gcagactctg tgaagggccg attcaccatc tccagagaca acgccaagaa ctccctgtat      240
ctgcaaatga acagtctgag agccgaggac acggccttgt attactgtgt gagagacaag      300
tatagctatg cctggtctta tgatgatttt gatatctggg gccaagggac aatggtcacc      360
gtctcctca                                                               369
```

<210> SEQ ID NO 475
<211> LENGTH: 369
<212> TYPE: DNA
<213> ORGANISM: Homo sapiens
<220> FEATURE:
<221> NAME/KEY: source
<223> OTHER INFORMATION: /note="VH 2.13"

<400> SEQUENCE: 475

```
gaggtgcagc tggtggagtc tgggggaggt gtggtacggc ctgggggtc cctgagactc        60 tcctgtgcag cctctggatt cacctttgat gattatgcca tgagttgggt ccgccaagct      120
ccagggaagg ggctggagtg ggtctctggt attacttgga atcggggtag cacaggttat      180
gcagactctg tgaagggccg attcaccatc tccagagaca acgccaagaa ctccctgtat      240
ctgcaaatga acagtctgag agccgaggac acggccttgt attactgtgt gagagacaag      300
tatagctatg cctggtctta tgatgatttt gatatctggg gccaagggac aatggtcacc      360
gtctcctca                                                               369
```

<210> SEQ ID NO 476
<211> LENGTH: 369
<212> TYPE: DNA
<213> ORGANISM: Homo sapiens
<220> FEATURE:
<221> NAME/KEY: source
<223> OTHER INFORMATION: /note="VH 2.14"

<400> SEQUENCE: 476

```
gaggtgcagc tggtggagtc tgggggaggt gtggtacggc ctgggggtc cctgagactc        60 tcctgtgcag cctctggatt cacctttgat gattatgcct tcagttgggt ccgccaagct      120
ccagggaagg ggctggagtg ggtctctggt attacttgga atggtggtag cacaggttat      180
gcagactctg tgaagggccg attcaccatc tccagagaca acgccaagaa ctccctgtat      240
ctgcaaatga acagtctgag agccgaggac acggccttgt attactgtgt gagagacaag      300
tatagctatg cctggtctta tgatggtttt gatatctggg gccaagggac aatggtcacc      360
gtctcctca                                                               369
```

<210> SEQ ID NO 477
<211> LENGTH: 369
<212> TYPE: DNA

<213> ORGANISM: Homo sapiens
<220> FEATURE:
<221> NAME/KEY: source
<223> OTHER INFORMATION: /note="VH 2.15"

<400> SEQUENCE: 477

```
gaggtgcagc tggtggagtc tgggggaggt gtggtacggc ctggggggtc cctgagactc      60
tcctgtgcag cctctggatt cacctttgat gattatgccc agagttgggt ccgccaagct     120
ccagggaagg ggctggagtg ggtctctggt attacttgga atggtggtag cacaggttat     180
gcagactctg tgaagggccg attcaccatc tccagagaca acgccaagaa ctccctgtat     240
ctgcaaatga acagtctgag agccgaggac acggccttgt attactgtgt gagagacaag     300
tatagctatg cctggtctta tgatggtttt gatatctggg gccaagggac aatggtcacc     360
gtctcctca                                                             369
```

<210> SEQ ID NO 478
<211> LENGTH: 369
<212> TYPE: DNA
<213> ORGANISM: Homo sapiens
<220> FEATURE:
<221> NAME/KEY: source
<223> OTHER INFORMATION: /note="VH 2.16"

<400> SEQUENCE: 478

```
gaggtgcagc tggtggagtc tgggggaggt gtggtacggc ctggggggtc cctgagactc      60
tcctgtgcag cctctggatt cacctttgat gattatgcca acagttgggt ccgccaagct     120
ccagggaagg ggctggagtg ggtctctggt attacttgga atggtggtag cacaggttat     180
gcagactctg tgaagggccg attcaccatc tccagagaca acgccaagaa ctccctgtat     240
ctgcaaatga acagtctgag agccgaggac acggccttgt attactgtgt gagagacaag     300
tatagctatg cctggtctta tgatggtttt gatatctggg gccaagggac aatggtcacc     360
gtctcctca                                                             369
```

<210> SEQ ID NO 479
<211> LENGTH: 369
<212> TYPE: DNA
<213> ORGANISM: Homo sapiens
<220> FEATURE:
<221> NAME/KEY: source
<223> OTHER INFORMATION: /note="VH 2.17"

<400> SEQUENCE: 479

```
gaggtgcagc tggtggagtc tgggggaggt gtggtacggc ctggggggtc cctgagactc      60
tcctgtgcag cctctggatt cacctttgat gattatgccg ggagttgggt ccgccaagct     120
ccagggaagg ggctggagtg ggtctctggt attacttgga atggtggtag cacaggttat     180
gcagactctg tgaagggccg attcaccatc tccagagaca acgccaagaa ctccctgtat     240
ctgcaaatga acagtctgag agccgaggac acggccttgt attactgtgt gagagacaag     300
tatagctatg cctggtctta tgatggtttt gatatctggg gccaagggac aatggtcacc     360
gtctcctca                                                             369
```

<210> SEQ ID NO 480
<211> LENGTH: 369
<212> TYPE: DNA
<213> ORGANISM: Homo sapiens
<220> FEATURE:
<221> NAME/KEY: source
<223> OTHER INFORMATION: /note="VH 2.18"

<400> SEQUENCE: 480

```
gaggtgcagc tggtggagtc tgggggaggt gtggtacggc ctggggggtc cctgagactc    60
tcctgtgcag cctctggatt cacctttgat gattatgccg agagttgggt ccgccaagct   120
ccagggaagg ggctggagtg ggtctctggt attacttgga atggtggtag cacaggttat   180
gcagactctg tgaagggccg attcaccatc tccagagaca acgccaagaa ctccctgtat   240
ctgcaaatga acagtctgag agccgaggac acggccttgt attactgtgt gagagacaag   300
tatagctatg cctggtctta tgatggtttt gatatctggg gccaagggac aatggtcacc   360
gtctcctca                                                            369
```

<210> SEQ ID NO 481
<211> LENGTH: 369
<212> TYPE: DNA
<213> ORGANISM: Homo sapiens
<220> FEATURE:
<221> NAME/KEY: source
<223> OTHER INFORMATION: /note="VH 2.19"

<400> SEQUENCE: 481

```
gaggtgcagc tggtggagtc tgggggaggt gtggtacggc ctggggggtc cctgagactc    60
tcctgtgcag cctctggatt cacctttgat gattatgcct ggagttgggt ccgccaagct   120
ccagggaagg ggctggagtg ggtctctggt attacttgga atggtggtag cacaggttat   180
gcagactctg tgaagggccg attcaccatc tccagagaca acgccaagaa ctccctgtat   240
ctgcaaatga acagtctgag agccgaggac acggccttgt attactgtgt gagagacaag   300
tatagctatg cctggtctta tgatggtttt gatatctggg gccaagggac aatggtcacc   360
gtctcctca                                                            369
```

<210> SEQ ID NO 482
<211> LENGTH: 369
<212> TYPE: DNA
<213> ORGANISM: Homo sapiens
<220> FEATURE:
<221> NAME/KEY: source
<223> OTHER INFORMATION: /note="VH 2.20"

<400> SEQUENCE: 482

```
gaggtgcagc tggtggagtc tgggggaggt gtggtacggc ctggggggtc cctgagactc    60
tcctgtgcag cctctggatt cacctttgat gattatgccg tcagttgggt ccgccaagct   120
ccagggaagg ggctggagtg ggtctctggt attacttgga atggtggtag cacaggttat   180
gcagactctg tgaagggccg attcaccatc tccagagaca acgccaagaa ctccctgtat   240
ctgcaaatga acagtctgag agccgaggac acggccttgt attactgtgt gagagacaag   300
tatagctatg cctggtctta tgatggtttt gatatctggg gccaagggac aatggtcacc   360
gtctcctca                                                            369
```

<210> SEQ ID NO 483
<211> LENGTH: 369
<212> TYPE: DNA
<213> ORGANISM: Homo sapiens
<220> FEATURE:
<221> NAME/KEY: source
<223> OTHER INFORMATION: /note="VH 2.21"

<400> SEQUENCE: 483

```
gaggtgcagc tggtggagtc tgggggaggt gtggtacggc ctggggggtc cctgagactc    60
```

```
tcctgtgcag cctctggatt cacctttgat gattatgcct tgagttgggt ccgccaagct      120
ccagggaagg ggctggagtg gtctctggt attacttgga atggtggtag cacaggttat       180
gcagactctg tgaagggccg attcaccatc tccagagaca acgccaagaa ctccctgtat      240
ctgcaaatga acagtctgag agccgaggac acggccttgt attactgtgt gagagacaag      300
tatagctatg cctggtctta tgatggtttt gatatctggg gccaagggac aatggtcacc      360
gtctcctca                                                              369
```

```
<210> SEQ ID NO 484
<211> LENGTH: 369
<212> TYPE: DNA
<213> ORGANISM: Homo sapiens
<220> FEATURE:
<221> NAME/KEY: source
<223> OTHER INFORMATION: /note="VH 2.22"

<400> SEQUENCE: 484
gaggtgcagc tggtggagtc tgggggaggt gtggtacggc ctgggggtc cctgagactc        60 tcctgtgcag cctctggatt cacctttgat gattatgcca gcagttgggt ccgccaagct      120
ccagggaagg ggctggagtg gtctctggt attacttgga atggtggtag cacaggttat       180
gcagactctg tgaagggccg attcaccatc tccagagaca acgccaagaa ctccctgtat      240
ctgcaaatga acagtctgag agccgaggac acggccttgt attactgtgt gagagacaag      300
tatagctatg cctggtctta tgatggtttt gatatctggg gccaagggac aatggtcacc      360
gtctcctca                                                              369
```

```
<210> SEQ ID NO 485
<211> LENGTH: 369
<212> TYPE: DNA
<213> ORGANISM: Homo sapiens
<220> FEATURE:
<221> NAME/KEY: source
<223> OTHER INFORMATION: /note="VH 2.23"

<400> SEQUENCE: 485
gaggtgcagc tggtggagtc tgggggaggt gtggtacggc ctgggggtc cctgagactc        60 tcctgtgcag cctctggatt cacctttgat gattatgccc ggagttgggt ccgccaagct      120
ccagggaagg ggctggagtg gtctctggt attacttgga atggtggtag cacaggttat       180
gcagactctg tgaagggccg attcaccatc tccagagaca acgccaagaa ctccctgtat      240
ctgcaaatga acagtctgag agccgaggac acggccttgt attactgtgt gagagacaag      300
tatagctatg cctggtctta tgatggtttt gatatctggg gccaagggac aatggtcacc      360
gtctcctca                                                              369
```

```
<210> SEQ ID NO 486
<211> LENGTH: 369
<212> TYPE: DNA
<213> ORGANISM: Homo sapiens
<220> FEATURE:
<221> NAME/KEY: source
<223> OTHER INFORMATION: /note="VH 2.24"

<400> SEQUENCE: 486
gaggtgcagc tggtggagtc tgggggaggt gtggtacggc ctgggggtc cctgagactc        60 tcctgtgcag cctctggatt cacctttgat gattatgcca tgagttgggt ccgccaagct      120
ccagggaagg ggctggagtg gtctctggt attacttgga attcgggtag cacaggttat       180
```

```
gcagactctg tgaaggaccg attcaccatc tccagagaca acgccaagaa ctccctgtat    240
ctgcaaatga acagtctgag agccgaggac acggccttgt attactgtgt gagagacaag    300
tatagctatg cctggtctta tgatgatttt gatatctggg gccaagggac aatggtcacc    360
gtctcctca                                                            369
```

<210> SEQ ID NO 487
<211> LENGTH: 369
<212> TYPE: DNA
<213> ORGANISM: Homo sapiens
<220> FEATURE:
<221> NAME/KEY: source
<223> OTHER INFORMATION: /note="VH 2.25"

<400> SEQUENCE: 487

```
gaggtgcagc tggtggagtc tgggggaggt gtggtacggc ctgggggtc cctgagactc     60 tcctgtgcag cctctggatt cacctttgat gattatgcca tgagttgggt ccgccaagct    120
ccagggaagg ggctggagtg ggtctctggt attacttgga atcagggtag cacaggttat    180
gcagactctg tgaaggaccg attcaccatc tccagagaca acgccaagaa ctccctgtat    240
ctgcaaatga acagtctgag agccgaggac acggccttgt attactgtgt gagagacaag    300
tatagctatg cctggtctta tgatgatttt gatatctggg gccaagggac aatggtcacc    360
gtctcctca                                                            369
```

<210> SEQ ID NO 488
<211> LENGTH: 369
<212> TYPE: DNA
<213> ORGANISM: Homo sapiens
<220> FEATURE:
<221> NAME/KEY: source
<223> OTHER INFORMATION: /note="VH 2.26"

<400> SEQUENCE: 488

```
gaggtgcagc tggtggagtc tgggggaggt gtggtacggc ctgggggtc cctgagactc     60 tcctgtgcag cctctggatt cacctttgat gattatgcca tgagttgggt ccgccaagct    120
ccagggaagg ggctggagtg ggtctctggt attacttgga atcacggtag cacaggttat    180
gcagactctg tgaaggaccg attcaccatc tccagagaca acgccaagaa ctccctgtat    240
ctgcaaatga acagtctgag agccgaggac acggccttgt attactgtgt gagagacaag    300
tatagctatg cctggtctta tgatgtgttt gatatctggg gccaagggac aatggtcacc    360
gtctcctca                                                            369
```

<210> SEQ ID NO 489
<211> LENGTH: 369
<212> TYPE: DNA
<213> ORGANISM: Homo sapiens
<220> FEATURE:
<221> NAME/KEY: source
<223> OTHER INFORMATION: /note="VH 2.27"

<400> SEQUENCE: 489

```
gaggtgcagc tggtggagtc tgggggaggt gtggtacggc ctgggggtc cctgagactc     60 tcctgtgcag cctctggatt cacctttgat gattatgcca tgagttgggt ccgccaagct    120
ccagggaagg ggctggagtg ggtctctggt attacttgga atgccggtag cacaggttat    180
gcagactctg tgaaggaccg attcaccatc tccagagaca acgccaagaa ctccctgtat    240
ctgcaaatga acagtctgag agccgaggac acggccttgt attactgtgt gagagacaag    300
```

```
tatagctatg cctggtctta tgatgatttt gatatctggg gccaagggac aatggtcacc    360
gtctcctca                                                            369
```

<210> SEQ ID NO 490
<211> LENGTH: 369
<212> TYPE: DNA
<213> ORGANISM: Homo sapiens
<220> FEATURE:
<221> NAME/KEY: source
<223> OTHER INFORMATION: /note="VH 2.28"

<400> SEQUENCE: 490

```
gaggtgcagc tggtggagtc tgggggaggt gtggtacggc ctgggggtc cctgagactc     60 tcctgtgcag cctctggatt cacctttgat gattatgcca tgagttgggt ccgccaagct   120
ccagggaagg ggctggagtg ggtctctggt attacttgga atggtggtag cacaggttat   180
gcagactctg tgaagggccg attcaccatc tccagagaca cgccaagaa ctccctgtat    240 ctgcaaatga acagtctgag agccgaggac acggccttgt attactgtgt gagagacaag   300
tatagctatg cctggtctta tgatgtgttt gatatctggg gccaagggac aatggtcacc   360
gtctcctca                                                            369
```

<210> SEQ ID NO 491
<211> LENGTH: 369
<212> TYPE: DNA
<213> ORGANISM: Homo sapiens
<220> FEATURE:
<221> NAME/KEY: source
<223> OTHER INFORMATION: /note="VH 2.29"

<400> SEQUENCE: 491

```
gaggtgcagc tggtggagtc tgggggaggt gtggtacggc ctgggggtc cctgagactc     60 tcctgtgcag cctctggatt cacctttgat gattatgcca tgagttgggt ccgccaagct   120
ccagggaagg ggctggagtg ggtctctggt attacttgga atggtggtag cacaggttat   180
gcagactctg tgaagggccg attcaccatc tccagagaca cgccaagaa ctccctgtat    240 ctgcaaatga acagtctgag agccgaggac acggccttgt attactgtgt gagagacaag   300
tatagctatg cctggtctta tgatgatttt gatatctggg gccaagggac aatggtcacc   360
gtctcctca                                                            369
```

<210> SEQ ID NO 492
<211> LENGTH: 369
<212> TYPE: DNA
<213> ORGANISM: Homo sapiens
<220> FEATURE:
<221> NAME/KEY: source
<223> OTHER INFORMATION: /note="VH 2.30"

<400> SEQUENCE: 492

```
gaggtgcagc tggtggagtc tgggggaggt gtggtacggc ctgggggtc cctgagactc     60 tcctgtgcag cctctggatt cacctttgat gattatgcca tgagttgggt ccgccaagct   120
ccagggaagg ggctggagtg ggtctctggt attacttgga ataagggtag cacaggttat   180
gcagactctg tgaaggaccg attcaccatc tccagagaca cgccaagaa ctccctgtat    240 ctgcaaatga acagtctgag agccgaggac acggccttgt attactgtgt gagagacaag   300
tatagctatg cctggtctta tgatgatttt gatatctggg gccaagggac aatggtcacc   360
gtctcctca                                                            369
```

<210> SEQ ID NO 493
<211> LENGTH: 369
<212> TYPE: DNA
<213> ORGANISM: Homo sapiens
<220> FEATURE:
<221> NAME/KEY: source
<223> OTHER INFORMATION: /note="VH 2.31"

<400> SEQUENCE: 493
gaggtgcagc tggtggagtc tgggggaggt gtggtacggc ctgggggtc cctgagactc       60
tcctgtgcag cctctggatt cacctttgat gattatgcca tgagttgggt ccgccaagct     120
ccagggaagg ggctggagtg ggtctctggt attacttgga atcgcggtag cacaggttat     180
gcagactctg tgaaggaccg attcaccatc tccagagaca cgccaagaa ctccctgtat      240
ctgcaaatga acagtctgag agccgaggac acggccttgt attactgtgt gagagacaag     300
tatagctatg cctggtctta tgatgatttt gatatctggg gccaagggac aatggtcacc     360
gtctcctca                                                              369

<210> SEQ ID NO 494
<211> LENGTH: 369
<212> TYPE: DNA
<213> ORGANISM: Homo sapiens
<220> FEATURE:
<221> NAME/KEY: source
<223> OTHER INFORMATION: /note="VH 2.32"

<400> SEQUENCE: 494
gaggtgcagc tggtggagtc tgggggaggt gtggtacggc ctgggggtc cctgagactc       60
tcctgtgcag cctctggatt cacctttgat gattatgcca tcagttgggt ccgccaagct     120
ccagggaagg ggctggagtg ggtctctggt attacttgga atggtggtag cacaggttat     180
gcagactctg tgaaggaccg attcaccatc tccagagaca cgccaagaa ctccctgtat      240
ctgcaaatga acagtctgag agccgaggac acggccttgt attactgtgt gagagacaag     300
tatagctatg cctggtctta tgatggtttt gatatctggg gccaagggac aatggtcacc     360
gtctcctca                                                              369

<210> SEQ ID NO 495
<211> LENGTH: 369
<212> TYPE: DNA
<213> ORGANISM: Homo sapiens
<220> FEATURE:
<221> NAME/KEY: source
<223> OTHER INFORMATION: /note="VH 2.33"

<400> SEQUENCE: 495
gaggtgcagc tggtggagtc tgggggaggt gtggtacggc ctgggggtc cctgagactc       60
tcctgtgcag cctctggatt cacctttgat gattatgcca ccagttgggt ccgccaagct     120
ccagggaagg ggctggagtg ggtctctggt attacttgga atggtggtag cacaggttat     180
gcagactctg tgaaggaccg attcaccatc tccagagaca cgccaagaa ctccctgtat      240
ctgcaaatga acagtctgag agccgaggac acggccttgt attactgtgt gagagacaag     300
tatagctatg cctggtctta tgatggtttt gatatctggg gccaagggac aatggtcacc     360
gtctcctca                                                              369

<210> SEQ ID NO 496
<211> LENGTH: 369

```
<212> TYPE: DNA
<213> ORGANISM: Homo sapiens
<220> FEATURE:
<221> NAME/KEY: source
<223> OTHER INFORMATION: /note="VH 2.34"

<400> SEQUENCE: 496
gaggtgcagc tggtggagtc tggggggaggt gtggtacggc ctgggggggtc cctgagactc      60 tcctgtgcag cctctggatt cacctttgat gattatgcca acagttgggt ccgccaagct     120
ccagggaagg ggctggagtg ggtctctggt attacttgga atggtggtag cacaggttat     180
gcagactctg tgaaggaccg attcaccatc tccagagaca acgccaagaa ctccctgtat     240
ctgcaaatga acagtctgag agccgaggac acggccttgt attactgtgt gagagacaag     300
tatagctatg cctggtctta tgatggtttt gatatctggg gccaagggac aatggtcacc     360
gtctcctca                                                             369

<210> SEQ ID NO 497
<211> LENGTH: 369
<212> TYPE: DNA
<213> ORGANISM: Homo sapiens
<220> FEATURE:
<221> NAME/KEY: source
<223> OTHER INFORMATION: /note="VH 2.35"

<400> SEQUENCE: 497
gaggtgcagc tggtggagtc tggggggaggt gtggtacggc ctgggggggtc cctgagactc      60 tcctgtgcag cctctggatt cacctttgat gattatgccg acagttgggt ccgccaagct     120
ccagggaagg ggctggagtg ggtctctggt attacttgga atggtggtag cacaggttat     180
gcagactctg tgaaggaccg attcaccatc tccagagaca acgccaagaa ctccctgtat     240
ctgcaaatga acagtctgag agccgaggac acggccttgt attactgtgt gagagacaag     300
tatagctatg cctggtctta tgatggtttt gatatctggg gccaagggac aatggtcacc     360
gtctcctca                                                             369

<210> SEQ ID NO 498
<211> LENGTH: 369
<212> TYPE: DNA
<213> ORGANISM: Homo sapiens
<220> FEATURE:
<221> NAME/KEY: source
<223> OTHER INFORMATION: /note="VH 2.36"

<400> SEQUENCE: 498
gaggtgcagc tggtggagtc tggggggaggt gtggtacggc ctgggggggtc cctgagactc      60 tcctgtgcag cctctggatt cacctttgat gattatgcca gcagttgggt ccgccaagct     120
ccagggaagg ggctggagtg ggtctctggt attacttgga atggtggtag cacaggttat     180
gcagactctg tgaaggaccg attcaccatc tccagagaca acgccaagaa ctccctgtat     240
ctgcaaatga acagtctgag agccgaggac acggccttgt attactgtgt gagagacaag     300
tatagctatg cctggtctta tgatggtttt gatatctggg gccaagggac aatggtcacc     360
gtctcctca                                                             369

<210> SEQ ID NO 499
<211> LENGTH: 369
<212> TYPE: DNA
<213> ORGANISM: Homo sapiens
<220> FEATURE:
<221> NAME/KEY: source
```

<223> OTHER INFORMATION: /note="VH 2.37"

<400> SEQUENCE: 499

```
gaggtgcagc tggtggagtc tggggggaggt gtggtacggc ctgggggggtc cctgagactc      60
tcctgtgcag cctctggatt cacctttgat gattatgccc tcagttgggt ccgccaagct     120
ccagggaagg ggctggagtg ggtctctggt attacttgga atggtggtag cacaggttat     180
gcagactctg tgaaggaccg attcaccatc tccagagaca cgccaagaa ctccctgtat      240
ctgcaaatga acagtctgag agccgaggac acggccttgt attactgtgt gagagacaag     300
tatagctatg cctggtctta tgatggtttt gatatctggg gccaagggac aatggtcacc     360
gtctcctca                                                             369
```

<210> SEQ ID NO 500
<211> LENGTH: 369
<212> TYPE: DNA
<213> ORGANISM: Homo sapiens
<220> FEATURE:
<221> NAME/KEY: source
<223> OTHER INFORMATION: /note="VH 2.38"

<400> SEQUENCE: 500

```
gaggtgcagc tggtggagtc tggggggaggt gtggtacggc ctgggggggtc cctgagactc      60
tcctgtgcag cctctggatt cacctttgat gattatgccg ggagttgggt ccgccaagct     120
ccagggaagg ggctggagtg ggtctctggt attacttgga atggtggtag cacaggttat     180
gcagactctg tgaaggaccg attcaccatc tccagagaca cgccaagaa ctccctgtat      240
ctgcaaatga acagtctgag agccgaggac acggccttgt attactgtgt gagagacaag     300
tatagctatg cctggtctta tgatggtttt gatatctggg gccaagggac aatggtcacc     360
gtctcctca                                                             369
```

<210> SEQ ID NO 501
<211> LENGTH: 369
<212> TYPE: DNA
<213> ORGANISM: Homo sapiens
<220> FEATURE:
<221> NAME/KEY: source
<223> OTHER INFORMATION: /note="VH 2.39"

<400> SEQUENCE: 501

```
gaggtgcagc tggtggagtc tggggggaggt gtggtacggc ctgggggggtc cctgagactc      60
tcctgtgcag cctctggatt cacctttgat gattatgccg agagttgggt ccgccaagct     120
ccagggaagg ggctggagtg ggtctctggt attacttgga atggtggtag cacaggttat     180
gcagactctg tgaaggaccg attcaccatc tccagagaca cgccaagaa ctccctgtat      240
ctgcaaatga acagtctgag agccgaggac acggccttgt attactgtgt gagagacaag     300
tatagctatg cctggtctta tgatggtttt gatatctggg gccaagggac aatggtcacc     360
gtctcctca                                                             369
```

<210> SEQ ID NO 502
<211> LENGTH: 369
<212> TYPE: DNA
<213> ORGANISM: Homo sapiens
<220> FEATURE:
<221> NAME/KEY: source
<223> OTHER INFORMATION: /note="VH 2.40"

<400> SEQUENCE: 502

```
gaggtgcagc tggtggagtc tgggggaggt gtggtacggc ctgggggggtc cctgagactc    60 tcctgtgcag cctctggatt cacctttgat gattatgcct ggagttgggt ccgccaagct   120
ccagggaagg ggctggagtg ggtctctggt attacttgga atggtggtag cacaggttat   180
gcagactctg tgaaggaccg attcaccatc tccagagaca acgccaagaa ctccctgtat   240
ctgcaaatga acagtctgag agccgaggac acggccttgt attactgtgt gagagacaag   300
tatagctatg cctggtctta tgatggtttt gatatctggg gccaagggac aatggtcacc   360
gtctcctca                                                           369

<210> SEQ ID NO 503
<211> LENGTH: 369
<212> TYPE: DNA
<213> ORGANISM: Homo sapiens
<220> FEATURE:
<221> NAME/KEY: source
<223> OTHER INFORMATION: /note="VH 2.41"

<400> SEQUENCE: 503
gaggtgcagc tggtggagtc tgggggaggt gtggtacggc ctgggggggtc cctgagactc    60 tcctgtgcag cctctggatt cacctttgat gattatgccc ggagttgggt ccgccaagct   120
ccagggaagg ggctggagtg ggtctctggt attacttgga atggtggtag cacaggttat   180
gcagactctg tgaaggaccg attcaccatc tccagagaca acgccaagaa ctccctgtat   240
ctgcaaatga acagtctgag agccgaggac acggccttgt attactgtgt gagagacaag   300
tatagctatg cctggtctta tgatggtttt gatatctggg gccaagggac aatggtcacc   360
gtctcctca                                                           369

<210> SEQ ID NO 504
<211> LENGTH: 369
<212> TYPE: DNA
<213> ORGANISM: Homo sapiens
<220> FEATURE:
<221> NAME/KEY: source
<223> OTHER INFORMATION: /note="VH 2.42"

<400> SEQUENCE: 504
gaggtgcagc tggtggagtc tgggggaggt gtggtacggc ctgggggggtc cctgagactc    60 tcctgtgcag cctctggatt cacctttgat gattatgcct tcagttgggt ccgccaagct   120
ccagggaagg ggctggagtg ggtctctggt attacttgga atggtggtag cacaggttat   180
gcagactctg tgaaggaccg attcaccatc tccagagaca acgccaagaa ctccctgtat   240
ctgcaaatga acagtctgag agccgaggac acggccttgt attactgtgt gagagacaag   300
tatagctatg cctggtctta tgatggtttt gatatctggg gccaagggac aatggtcacc   360
gtctcctca                                                           369

<210> SEQ ID NO 505
<211> LENGTH: 369
<212> TYPE: DNA
<213> ORGANISM: Homo sapiens
<220> FEATURE:
<221> NAME/KEY: source
<223> OTHER INFORMATION: /note="VH 2.43"

<400> SEQUENCE: 505
gaggtgcagc tggtggagtc tgggggaggt gtggtacggc ctgggggggtc cctgagactc    60 tcctgtgcag cctctggatt cacctttgat gattatgccg tgagttgggt ccgccaagct   120
```

```
ccagggaagg ggctggagtg ggtctctggt attacttgga atggtggtag cacaggttat    180
gcagactctg tgaaggaccg attcaccatc tccagagaca acgccaagaa ctccctgtat    240
ctgcaaatga acagtctgag agccgaggac acggccttgt attactgtgt gagagacaag    300
tatagctatg cctggtctta tgatggtttt gatatctggg gccaagggac aatggtcacc    360
gtctcctca                                                            369

<210> SEQ ID NO 506
<211> LENGTH: 369
<212> TYPE: DNA
<213> ORGANISM: Homo sapiens
<220> FEATURE:
<221> NAME/KEY: source
<223> OTHER INFORMATION: /note="VH 2.44"

<400> SEQUENCE: 506
gaggtgcagc tggtggagtc tgggggaggt gtggtacggc ctgggggtc cctgagactc      60 tcctgtgcag cctctggatt cacctttgat gattatgcca tgagttgggt ccgccaagct    120
ccagggaagg ggctggagtg ggtctctggt attacttgga ccggtggtag cacaggttat    180
gcagactctg tgaaggaccg attcaccatc tccagagaca acgccaagaa ctccctgtat    240
ctgcaaatga acagtctgag agccgaggac acggccttgt attactgtgt gagagacaag    300
tatagctatg cctggtctta tgatggtttt gatatctggg gccaagggac aatggtcacc    360
gtctcctca                                                            369

<210> SEQ ID NO 507
<211> LENGTH: 369
<212> TYPE: DNA
<213> ORGANISM: Homo sapiens
<220> FEATURE:
<221> NAME/KEY: source
<223> OTHER INFORMATION: /note="VH 2.45"

<400> SEQUENCE: 507
gaggtgcagc tggtggagtc tgggggaggt gtggtacggc ctgggggtc cctgagactc      60 tcctgtgcag cctctggatt cacctttgat gattatgcca tgagttgggt ccgccaagct    120
ccagggaagg ggctggagtg ggtctctggt attacttggt ccggtggtag cacaggttat    180
gcagactctg tgaaggaccg attcaccatc tccagagaca acgccaagaa ctccctgtat    240
ctgcaaatga acagtctgag agccgaggac acggccttgt attactgtgt gagagacaag    300
tatagctatg cctggtctta tgatggtttt gatatctggg gccaagggac aatggtcacc    360
gtctcctca                                                            369

<210> SEQ ID NO 508
<211> LENGTH: 369
<212> TYPE: DNA
<213> ORGANISM: Homo sapiens
<220> FEATURE:
<221> NAME/KEY: source
<223> OTHER INFORMATION: /note="VH 2.46"

<400> SEQUENCE: 508
gaggtgcagc tggtggagtc tgggggaggt gtggtacggc ctgggggtc cctgagactc      60 tcctgtgcag cctctggatt cacctttgat gattatgcca tgagttgggt ccgccaagct    120
ccagggaagg ggctggagtg ggtctctggt attacttggc ccggtggtag cacaggttat    180
gcagactctg tgaaggaccg attcaccatc tccagagaca acgccaagaa ctccctgtat    240
```

```
ctgcaaatga acagtctgag agccgaggac acggccttgt attactgtgt gagagacaag    300
tatagctatg cctggtctta tgatggtttt gatatctggg gccaagggac aatggtcacc    360
gtctcctca                                                            369

<210> SEQ ID NO 509
<211> LENGTH: 369
<212> TYPE: DNA
<213> ORGANISM: Homo sapiens
<220> FEATURE:
<221> NAME/KEY: source
<223> OTHER INFORMATION: /note="VH 2.47"

<400> SEQUENCE: 509
gaggtgcagc tggtggagtc tgggggaggt gtggtacggc ctgggggtc cctgagactc      60 tcctgtgcag cctctggatt cacctttgat gattatgcca tgagttgggt ccgccaagct    120
ccagggaagg ggctggagtg ggtctctggt attacttgga tcggtggtag cacaggttat    180
gcagactctg tgaaggaccg attcaccatc tccagagaca cgccaagaa ctccctgtat     240 ctgcaaatga acagtctgag agccgaggac acggccttgt attactgtgt gagagacaag    300
tatagctatg cctggtctta tgatggtttt gatatctggg gccaagggac aatggtcacc    360
gtctcctca                                                            369

<210> SEQ ID NO 510
<211> LENGTH: 369
<212> TYPE: DNA
<213> ORGANISM: Homo sapiens
<220> FEATURE:
<221> NAME/KEY: source
<223> OTHER INFORMATION: /note="VH 2.48"

<400> SEQUENCE: 510
gaggtgcagc tggtggagtc tgggggaggt gtggtacggc ctgggggtc cctgagactc      60 tcctgtgcag cctctggatt cacctttgat gattatgcca tgagttgggt ccgccaagct    120
ccagggaagg ggctggagtg ggtctctggt attacttggc tgggtggtag cacaggttat    180
gcagactctg tgaaggaccg attcaccatc tccagagaca cgccaagaa ctccctgtat     240 ctgcaaatga acagtctgag agccgaggac acggccttgt attactgtgt gagagacaag    300
tatagctatg cctggtctta tgatggtttt gatatctggg gccaagggac aatggtcacc    360
gtctcctca                                                            369

<210> SEQ ID NO 511
<211> LENGTH: 369
<212> TYPE: DNA
<213> ORGANISM: Homo sapiens
<220> FEATURE:
<221> NAME/KEY: source
<223> OTHER INFORMATION: /note="VH 2.49"

<400> SEQUENCE: 511
gaggtgcagc tggtggagtc tgggggaggt gtggtacggc ctgggggtc cctgagactc      60 tcctgtgcag cctctggatt cacctttgat gattatgcca tgagttgggt ccgccaagct    120
ccagggaagg ggctggagtg ggtctctggt attacttgga tggtggtag cacaggttat     180 gcagactctg tgaagggccg attcaccatc tccagagaca cgccaagaa ctccctgtat     240 ctgcaaatga acagtctgag agccgaggac acggccttgt attactgtgt gagagacaag    300
tatagctatg cctggtctta tgatggtttt gatatctggg gccaagggac aatggtcacc    360
```

```
gtctcctca                                                                369
```

<210> SEQ ID NO 512
<211> LENGTH: 369
<212> TYPE: DNA
<213> ORGANISM: Homo sapiens
<220> FEATURE:
<221> NAME/KEY: source
<223> OTHER INFORMATION: /note="VH 2.50"

<400> SEQUENCE: 512

```
gaggtgcagc tggtggagtc tgggggaggt gtggtacggc ctgggggttc cctgagactc     60
tcctgtgcag cctctggatt caccttttgat gattatgcca tgagttgggt ccgccaagct    120
ccagggaagg ggctggagtg ggtctctggt attacttgga agggtggtag cacaggttat    180
gcagactctg tgaaggaccg attcaccatc tccagagaca acgccaagaa ctccctgtat    240
ctgcaaatga acagtctgag agccgaggac acggccttgt attactgtgt gagagacaag    300
tatagctatg cctggtctta tgatggtttt gatatctggg gccaagggac aatggtcacc    360
gtctcctca                                                            369
```

<210> SEQ ID NO 513
<211> LENGTH: 369
<212> TYPE: DNA
<213> ORGANISM: Homo sapiens
<220> FEATURE:
<221> NAME/KEY: source
<223> OTHER INFORMATION: /note="VH 2.51"

<400> SEQUENCE: 513

```
gaggtgcagc tggtggagtc tgggggaggt gtggtacggc ctgggggtc cctgagactc      60
tcctgtgcag cctctggatt cacctttgat gattatgcca tgagttgggt ccgccaagct    120
ccagggaagg ggctggagtg ggtctctggt attacttggc ggggtggtag cacaggttat    180
gcagactctg tgaaggaccg attcaccatc tccagagaca acgccaagaa ctccctgtat    240
ctgcaaatga acagtctgag agccgaggac acggccttgt attactgtgt gagagacaag    300
tatagctatg cctggtctta tgatggtttt gatatctggg gccaagggac aatggtcacc    360
gtctcctca                                                            369
```

<210> SEQ ID NO 514
<211> LENGTH: 369
<212> TYPE: DNA
<213> ORGANISM: Homo sapiens
<220> FEATURE:
<221> NAME/KEY: source
<223> OTHER INFORMATION: /note="VH 2.52"

<400> SEQUENCE: 514

```
gaggtgcagc tggtggagtc tgggggaggt gtggtacggc ctgggggtc cctgagactc      60
tcctgtgcag cctctggatt cacctttgat gattatgcca tgagttgggt ccgccaagct    120
ccagggaagg ggctggagtg ggtctctggt attacttgga atggtggtag cacaggttat    180
gcagactctg tgaaggaccg attcaccatc tccagagaca acgccaagaa ctccctgtat    240
ctgcaaatga acagtctgag agccgaggac acggccttgt attactgtgt gagagacaag    300
tatagctatg cctggtctta tgatgtgttt gatatctggg gccaagggac aatggtcacc    360
gtctcctca                                                            369
```

<210> SEQ ID NO 515

<211> LENGTH: 369
<212> TYPE: DNA
<213> ORGANISM: Homo sapiens
<220> FEATURE:
<221> NAME/KEY: source
<223> OTHER INFORMATION: /note="VH 2.53"

<400> SEQUENCE: 515

```
gaggtgcagc tggtggagtc tgggggaggt gtggtacggc ctgggggtc cctgagactc        60
tcctgtgcag cctctggatt cacctttgat gattatgcca tgagttgggt ccgccaagct       120
ccagggaagg gctggagtg gtctctggt attacttgga atggtggtag cacaggttat         180
gcagactctg tgaaggaccg attcaccatc tccagagaca cgccaagaa ctccctgtat        240
ctgcaaatga acagtctgag agccgaggac acggccttgt attactgtgt gagagacaag       300
tatagctatg cctggtctta tgatgatttt gatatctggg gccaagggac aatggtcacc       360
gtctcctca                                                               369
```

<210> SEQ ID NO 516
<211> LENGTH: 5
<212> TYPE: PRT
<213> ORGANISM: Homo sapiens
<220> FEATURE:
<221> NAME/KEY: source
<223> OTHER INFORMATION: /note="Termination sequence of a human VH
    domain"

<400> SEQUENCE: 516

Val Thr Val Ser Ser
1               5

<210> SEQ ID NO 517
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic 6xHis tag"

<400> SEQUENCE: 517

His His His His His His
1               5

<210> SEQ ID NO 518
<211> LENGTH: 288
<212> TYPE: PRT
<213> ORGANISM: Homo sapiens
<220> FEATURE:
<221> NAME/KEY: source
<223> OTHER INFORMATION: /note="Wild type human PD-1 protein"

<400> SEQUENCE: 518

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

```
Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 519
<211> LENGTH: 14
<212> TYPE: PRT
<213> ORGANISM: Homo sapiens
<220> FEATURE:
<221> NAME/KEY: source
<223> OTHER INFORMATION: /note="Residues 102-115 of human PD-1"

<400> SEQUENCE: 519

Asn Gly Arg Asp Phe His Met Ser Val Val Arg Ala Arg Arg
1               5                   10

<210> SEQ ID NO 520
<211> LENGTH: 6
<212> TYPE: PRT
<213> ORGANISM: Homo sapiens
<220> FEATURE:
<221> NAME/KEY: source
<223> OTHER INFORMATION: /note="Binding motif in human PD-1"

<400> SEQUENCE: 520

Asn Pro Pro Thr Phe Ser
1               5

<210> SEQ ID NO 521
<211> LENGTH: 14
<212> TYPE: PRT
<213> ORGANISM: Homo sapiens
<220> FEATURE:
<221> NAME/KEY: source
<223> OTHER INFORMATION: /note="Binding motif in human PD-1"

<400> SEQUENCE: 521

Cys Ser Phe Ser Asn Thr Ser Glu Ser Phe Val Leu Asn Trp
```

-continued

```
<210> SEQ ID NO 522
<211> LENGTH: 10
<212> TYPE: PRT
<213> ORGANISM: Homo sapiens
<220> FEATURE:
<221> NAME/KEY: source
<223> OTHER INFORMATION: /note="Binding motif in human PD-1"

<400> SEQUENCE: 522

Pro Asn Gly Arg Asp Phe His Met Ser Val
1               5                   10

<210> SEQ ID NO 523
<211> LENGTH: 12
<212> TYPE: PRT
<213> ORGANISM: Homo sapiens
<220> FEATURE:
<221> NAME/KEY: source
<223> OTHER INFORMATION: /note="Binding motif in human PD-1"

<400> SEQUENCE: 523

Ser Glu Ser Phe Val Leu Asn Trp Tyr Arg Met Ser
1               5                   10

<210> SEQ ID NO 524
<211> LENGTH: 9
<212> TYPE: PRT
<213> ORGANISM: Homo sapiens
<220> FEATURE:
<221> NAME/KEY: source
<223> OTHER INFORMATION: /note="Binding motif in human PD-1"

<400> SEQUENCE: 524

Gly Gln Asp Cys Arg Phe Arg Val Thr
1               5

<210> SEQ ID NO 525
<211> LENGTH: 11
<212> TYPE: PRT
<213> ORGANISM: Homo sapiens
<220> FEATURE:
<221> NAME/KEY: source
<223> OTHER INFORMATION: /note="Binding motif in human PD-1"

<400> SEQUENCE: 525

Arg Asp Phe His Met Ser Val Val Arg Ala Arg
1               5                   10

<210> SEQ ID NO 526
<211> LENGTH: 7
<212> TYPE: PRT
<213> ORGANISM: Homo sapiens
<220> FEATURE:
<221> NAME/KEY: source
<223> OTHER INFORMATION: /note="Binding motif in human PD-1"

<400> SEQUENCE: 526

Arg Asp Phe His Met Ser Val
1               5

<210> SEQ ID NO 527
<211> LENGTH: 14
<212> TYPE: PRT
<213> ORGANISM: Mus sp.
<220> FEATURE:
<221> NAME/KEY: source
```

```
<223> OTHER INFORMATION: /note="Murine PD-1"

<400> SEQUENCE: 527

Asn Arg His Asp Phe His Met Asn Ile Leu Asp Thr Arg Arg
1               5                   10

<210> SEQ ID NO 528
<211> LENGTH: 125
<212> TYPE: PRT
<213> ORGANISM: Homo sapiens

<400> SEQUENCE: 528

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 529
<211> LENGTH: 125
<212> TYPE: PRT
<213> ORGANISM: Homo sapiens

<400> SEQUENCE: 529

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125
```